Figure 2:
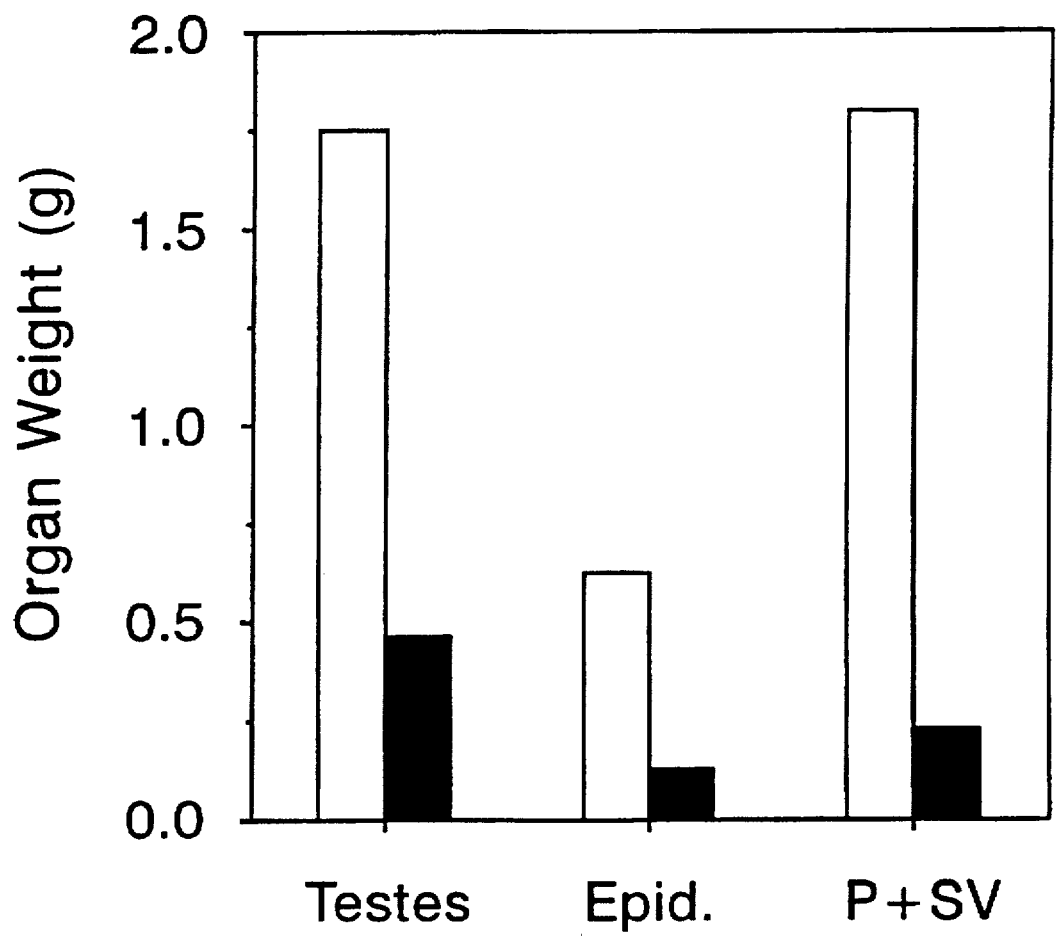

US005759551A

United States Patent [19]

Ladd et al.

[11] Patent Number: 5,759,551

[45] Date of Patent: Jun. 2, 1998

[54] IMMUNOGENIC LHRH PEPTIDE CONSTRUCTS AND SYNTHETIC UNIVERSAL IMMUNE STIMULATORS FOR VACCINES

[75] Inventors: Anna Efim Ladd, Brooklyn; Chang Yi Wang, Cold Spring Harbor; Timothy Joseph Zamb, Stony Brook, all of N.Y.

[73] Assignee: United Biomedical, Inc., Hauppauge, N.Y.

[21] Appl. No.: 446,692

[22] PCT Filed: Apr. 28, 1994

[86] PCT No.: PCT/US94/04832

§ 371 Date: Dec. 26, 1995

§ 102(e) Date: Dec. 26, 1995

[87] PCT Pub. No.: WO94/25060

PCT Pub. Date: Nov. 10, 1994

Related U.S. Application Data

[62] Division of Ser. No. 488,351, Jun. 7, 1995.

[51] Int. Cl.$^6$ .................... A61K 39/00; A61K 39/29
[52] U.S. Cl. .................... 424/198.1; 424/185.1; 424/227.1; 514/841; 514/843
[58] Field of Search .................... 424/198.1, 227.1, 424/185.1; 514/841, 843

[56] References Cited

U.S. PATENT DOCUMENTS

| | | | |
|---|---|---|---|
| 4,377,574 | 3/1983 | Rivier et al. | 424/177 |
| 4,608,251 | 8/1986 | Mia | 424/85 |
| 4,613,586 | 9/1986 | Barchas et al. | 514/13 |
| 4,975,420 | 12/1990 | Silversides et al. | 514/15 |
| 5,023,077 | 6/1991 | Gevas et al. | 424/88 |
| 5,212,288 | 5/1993 | Nestor, Jr. et al. | 530/324 |
| 5,324,512 | 6/1994 | Ladd et al. | 424/88 |

FOREIGN PATENT DOCUMENTS

| | | |
|---|---|---|
| 0 301 850 | 2/1989 | European Pat. Off. |
| 0 343 460 | 11/1989 | European Pat. Off. |
| 0 403 312 | 12/1990 | European Pat. Off. |
| 0 427 347 | 5/1991 | European Pat. Off. |
| 0427341 | 5/1991 | European Pat. Off. |
| 0 429 816 | 6/1991 | European Pat. Off. |
| 0 429 816 A1 | 6/1991 | European Pat. Off. |
| 0 471 177 A2 | 2/1992 | European Pat. Off. |
| 0 578293 | 1/1994 | European Pat. Off. |
| WO 87/07896 | 12/1987 | WIPO |
| 8906974 | 8/1989 | WIPO |
| PCT/US89/00388 | 8/1989 | WIPO |
| 9011298 | 10/1990 | WIPO |
| WO 91/17768 | 11/1991 | WIPO |
| PCT/AU91/00429 | 4/1992 | WIPO |
| PCT/US92/00776 | 8/1992 | WIPO |
| PCT/AU92/00194 | 11/1992 | WIPO |
| PCT/US92/03616 | 11/1992 | WIPO |
| PCT/US92/07218 | 3/1993 | WIPO |
| PCT/US92/08370 | 4/1994 | WIPO |

OTHER PUBLICATIONS

Leong et al. (1991) "Mapping and Topographic Localization of Epitopes of the *Yersinia pseudotuberculosis* Invasin Protein" *Infection and Immunity* 59(10):3424–3433.

Jayashankar et al. (1989) "Semisynthetic Anti–LHRH Vaccine Causing Atrophy of the Prostate" *The Prostate* 14:3–11.

Partidos et al. (1991) "Immune Responses in Mice Following Immunization with Chimeric Synthetic Peptides Representing B and T Cell Epitopes of Measles Virus Proteins" *J. of Gen. Virol.* 72:1293–1299.

Ladd et al. (1990) "Active Immunization Against LHRH:1. Effects of Conjugation Site and Dose" *Am. J. Reproduct. Immunol.* 22:56–63.

Cornette et al. (1989) "Identification of T–Cell Epitopes and Use in Construction of Synthetic Vaccines" *Methods in Enzymol.* 178:611–634.

Wiesmuller et al. (1989) "Novel Low–Molecular Weight Synthetic Vaccine Against Foot–and–Mouth Disease Containing a Potent B–Cell and Macrophage Activator" *Vaccine* 7:29–33.

Talwar (1985) "Immunobiology of Gonadotropin–Releasing Hormone" *J. Steroid Biochem* 23:795–800.

Wiesmuller et al. (1992) "Solid Phase Peptide Synthesis Of Lipopeptide Vaccines Eliciting Epitope–Specific B–, T–helper and T–killer Cell Response" *Int. J. Peptide Protein Res.* 40:255–260.

(List continued on next page.)

*Primary Examiner*—Lynette F. Smith
*Attorney, Agent, or Firm*—Morgan & Finnegan, LLP

[57] ABSTRACT

This invention relates to immunogenic luteinizing hormone releasing hormone (LHRH) peptides that lead to suppression of LHRH activity in males or females. When male rats are immunized with these peptides, serum testosterone drops and androgen-dependent organs atrophy significantly. These peptides are useful for inducing infertility and for treating prostatic hyperplasia, androgen-dependent carcinoma, prostatic carcinoma and testicular carcinoma in males. In females, the peptides are useful for treating endometriosis, benign uterine tumors, recurrent functional ovarian cysts and (severe) premenstrual syndrome as well as prevention or treatment of estrogen-dependent breast cancer. The subject peptides contain a helper T cell epitope and have LHRH at the C terminus. The helper T cell epitope aids in stimulating the immune response against LHRH. The peptides, optionally contain an invasin domain which acts as a general immune stimulator. In another aspect this invention relates to immunogenic synthetic peptides having an invasin domain, a helper T cell epitope and a peptide hapten and methods of using these peptides to treat disease or provide protective immunity. The peptide haptens of the invention include LHRH, amylin, gastrin, gastrin releasing peptide, IgE CH4 peptide, Chlamydia MOMP peptides, HIV V3 peptides and Plasmodium berghei.

15 Claims, 37 Drawing Sheets

OTHER PUBLICATIONS

Kumer et al. (1990) "Amino Acid Variations At a Single Residue In an Autoimmune Peptide Profoundly Affect Its Properties: T–cell Activation, Major Histocompatibility Complex Binding, and Ability To Block Experimental Allergic Ancephalomyelitis" *Pro. Nat'l. Acad. Sci. U.S.A.* 87:1337–1341.

Milich (1990) "Synthetic Peptides: Prospects for Vaccine Development" *Seminar in Immunology* 2:307–315.

Lowell et al. (1988) "Peptides Bound To proteosomes Via Hydrophobic Feet Become Highly Immunogenic Without Adjuvants" *J. of Experimental Medicine* 167:658–663.

Wiesmuller et al. (1992) "Solid Phase Peptide Synthesis Of Lipopeptide Vaccines Eliciting Epitope–Specific B–, T–helper and T–killer Cell Response" *Int. J. Peptide Protein Res.* 40:255–260.

Ladd et al. (1988) "Active Immunization Against Gonadotropin–Releasing Hormone Combined With Androgen Supplementation Is a Promising Antifertility Vaccine For Males" *American J. of Reproductive Immunology & Microbiology* 17:121–127.

Kironde et al. (1991) "Towards the Design Of Heterovalent Anti–Malaria Vaccines: A Hybrid Immunogen Capable Of Eliciting Immune Responses To Epitopes of Circumsporozoite Antigens From Two Different Species Of The Malaria Parasite, Plasmodium" *Immunonology (England)* 74:323–328.

Etlinger et al. (1990) Use Of Prior Vaccinations For The Development Of New Vaccines *Science* 249:423–425.

Cooper et al. (1987) "Purification and Characterization of a Peptide Form Amyloid–Rich Pancreases of Type 2 Diabetic Patients" *PNAS* 84(23):8628–8632.

Cooper et al. (1988) "Amylin Found In Amyloid Deposits In Human Type 2 Diabetes Mellitus May Be a Hormone That Regulates Glycogen Metabolism In Skeletal Muscle" *Medical Science* 85:7763–7766.

Shaw et al. (1993) "Influence of the T–Helper Epitope On the Titre and Affinity Of Antibodies To B–Cell Epitopes After Co–Immunization" *Molecular Immunology* 30(11):961–968.

Sad et al. (1992) "Bypass of Carrier–Induced Epitope–Specific Suppression Using a T–Helper Epitope" *Immunology* 76:599–603.

Panina–Bordignon et al. (1989) "Universally Immunogenic T Cell Epitopes: Promiscuous Binding to Human MHC Class II and Promiscuous Recognition by T Cells" *J. Immunol.* 19:2237–2242.

Demotz et al. (1989) "Delineation of Several De–Restricted Tetanus Toxin T Cell Epitopes" *J. Immunol.* 142:394–402.

Ennis et al. (1993) "Very Late Antigen 4–Dependent Adhesion and Costimulation of Resting Human T Cells by the Bacterial β1 Integrin Ligand Invasin" *J. Exp. Med.* 177:207–212.

Partidos et al. (1990) "Prediction and Identification of a T Cell Epitope in the Fusion Protein of Measles Virus Immunodominant in Mice and Humans" *J. Gen. Virol.* 71:2099–2105.

Partidos et al. (1992) "Antibody Responses to Non–Immunogenic Synthetic Peptides Induced by Co–Immunization with Immunogenic Peptides" *Immunol.* 77:262–266.

Greenstein et al. (1992) "A Universal T Cell Epitope–Containing Peptide From Hepatitis B Surface Antigen Can Enhance Antibody Specific for HIV gp120" *J. Immunol.* 148:3970–3977.

Brett et al. (1993) "The Invasin Protein of Yersina spp. Provides Co–Stimulatory Activity to Human T Cells through Interaction with β–1 Integrins" *Eur. J. Immunol.* 23:1608–1614.

Giri et al. (1991) "Prostatic Hypoplasia in Bonnet Monkeys following Active Immunization with Semisynthetic Anti–L–HRH Vaccine" *Exper. Mole. Pathol.* 54:255–264.

Chong et al. (1992) "Identification of T–and B–Cell Epitopes of the S2 and S3 Subunits of Pertussis Toxin by Use of Synthetic Peptides" *Infect. Immunity* 6011:4640–4647.

Remy et al. (1993) "Suppression of Fertility in Male Mice by Immunization Against LH Receptor" *J. Reproduct. Immunol.* 25:63–79.

Ladd et al. (1989) "Effects of Long–term Immunization against LHRH and Androgen Treatment on Gonadol Function" *J. Reproduct. Immunol.* 15:85–101.

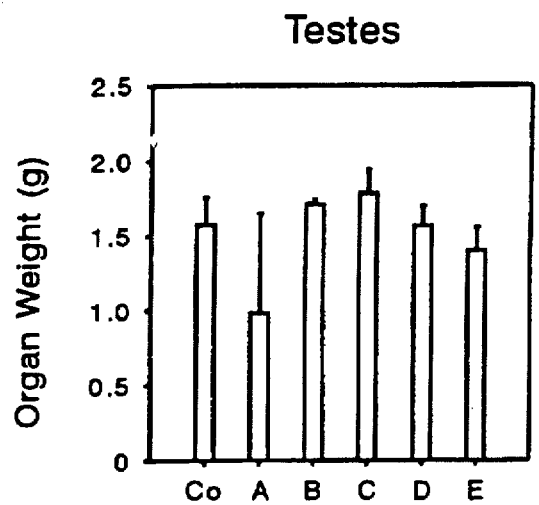
Fig. 1A
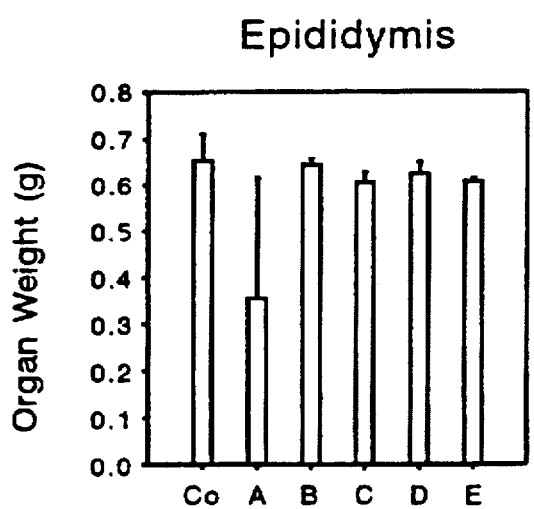
Fig. 1B
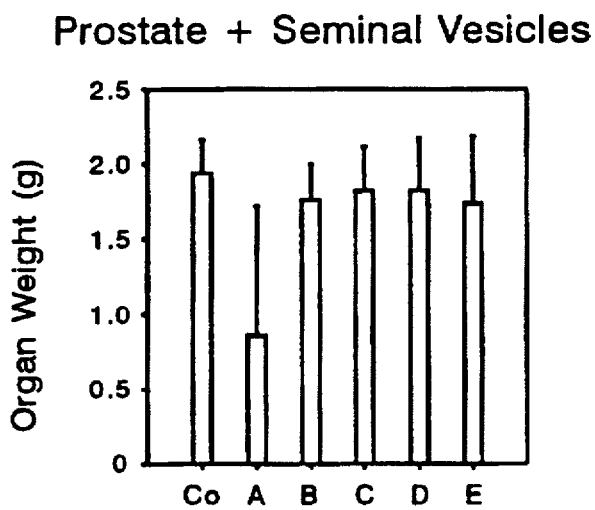
Fig. 1C
Fig. 1

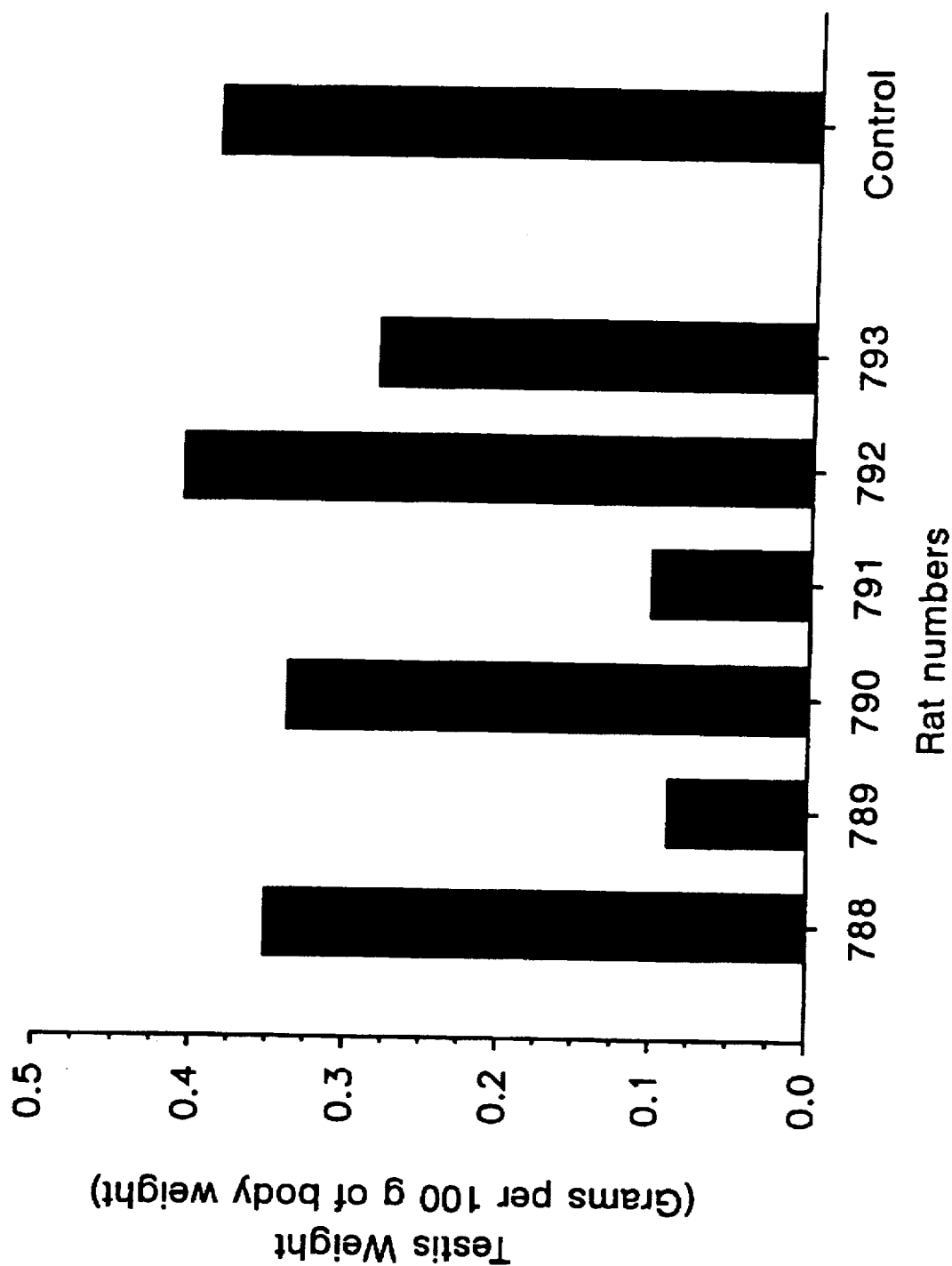

IMMUNOGENIC LHRH PEPTIDE CONSTRUCTS AND SYNTHETIC UNIVERSAL IMMUNE STIMULATORS FOR VACCINES

This is a divisional application of application Ser. No. 08/488,351, filed Jun. 7, 1995; and is the national stage application of PCT/US94/04832, filed Apr. 27, 1994; which is in turn a continuation-in-part application of application Ser. No. 08/229,275, filed Apr. 14, 1994, now abandoned, which is in turn a continuation-in-part application of application Ser. No. 08/057,166, filed Apr. 27, 1993, now abandoned.

This invention relates to immunogenic luteinizing hormone releasing hormone (LHRH) peptides that lead to functional suppression of LHRH levels in males or females. When male rats are immunized with these peptides, serum testosterone drops and androgen-dependent organs atrophy significantly. These peptides are useful for inducing infertility and for treating prostatic hyperplasia, androgen-dependent carcinoma, prostatic carcinoma and testicular carcinoma in males. In females, the peptides are useful for treating endometriosis, benign uterine tumors, recurrent functional ovarian cysts and (severe) premenstrual syndrome as well as prevention or treatment of estrogen-dependent breast cancer. The subject peptides contain a helper T cell epitope (Th epitope) and have LHRH at the C terminus. The helper T cell epitope aids in stimulating the immune response against LHRH. The peptides, optionally, contain an invasin domain which acts as a general immune stimulator.

In another aspect this invention relates to immunogenic synthetic peptides having an invasin domain, a helper T cell epitope and a peptide hapten and methods of using these peptides to treat disease or provide protective immunity. The peptide haptens of the invention include LHRH, amylin, gastrin, gastrin releasing peptide, IgE CH4 peptides, Chlamydia MOMP peptides, HIV V3 peptides and Plasmodium berghei peptides.

Prostate cancer is the third leading cause of death in men and the most common malignancy in men over the age of 70 years. The number of new prostate cancer cases has risen steadily over the past 20 years, with the expectation that more than 4 million men over the age of 75 may develop clinically detectable prostate cancer in the early 21st century [Perez et al. (1985) in *Cancer Principles and Practice of Oncology.* Vol. 9 (DeVita et al., eds.) J. B. Lippincott Company, Philadelphia, Pa., pp. 1023-48; Chodak et al. (1990) *Current Concepts in Prostate Cancer Diagnosis and Management,* 26th Annual Meeting, American Society of Clinical Oncology. Unfortunately, at the time of diagnosis about 40-50% of the patients with newly diagnosed prostate cancer will have advanced disease (stage D), with a median survival time of approximately 2.4 years [Torty (1988) Adv. Onc. 4:15). Consequently, the therapies developed to combat this disease should demonstrate efficacy as rapidly as possible.

The classical treatment for advanced prostate cancer has been surgical orchiectomy, i.e. castration, developed by Huggins and others in the early 1940s [Huggins et al. (1941) Cancer Res. 1:293-297]. This procedure reduces serum testosterone by 95%, causes measurable tumor regression in approximately 45% of patients, and disease stabilization in an additional 40% of patients. At least temporary stabilization of advanced prostatic disease, including improvement of urinary tract symptoms and reduction of pain, occurs in about 70% of patients (Klein (1979) N. Engl. J. Med. 300:824-33]. While such treatments are effective, particularly when combined with estrogen therapy, the associated psychological trauma is unacceptable to some patients.

Over 95% of testosterone production originates in the testes. Testosterone production in the Leydig cells of the testes is controlled by pituitary secretion of luteinizing hormone (LH). The secretion of LH together with follicle stimulating hormone (FSH), in turn is controlled by the pulsatile release of LHRH from the hypothalamus [See, for example, Paulsen (1974) in *Textbook of Endocrinology* (Williams, ed.) Saunders, Philadelphia, Pa., pp. 323–367).

Attempts to block LHRH, to reduce testosterone effect on androgen-dependent organs, e.g. prostate, or to block other parts of this pathway have provided therapeutic alternative treatments for prostate cancer, including treatment with estrogens or LHRH analogs. Unfortunately, therapeutic doses of estrogens can cause significant side effects such as cardiovascular mortality, gynecomastia, nausea, sodium retention, and impotence [Blackard (1975) Can. Chem. Rep. 59:225-7]. Treatment with LHRH analogs, such as Leuprolide or goserelin, causes eventual decline of serum testosterone; however, the associated initial rise of serum LH and FSH levels (450 and 250 per cent, respectively), leads to a painful condition known as the "flare up phenomena" in which a temporary increase in serum testosterone and other symptoms occur (Crawford et al. (1991) Urol. Clin. N.A. 18:55-633. In addition LHRH analog therapy can cause gastrointestinal upset and hot flushes.

Active immunization against LHRH has long been known to exert multiple effects, including decreasing serum and pituitary LH and FSH, reducing serum testosterone, suppressing spermatogenesis and causing reversible atrophy of the gonads and accessory sex organs. (See, for example, Fraser et al. (1974) J. Endocrinol. 63:399–405; Giri et al. (1991) Exp. Molec. Pathol. 54:255–264; Ladd et al. (1989) J. Reprod. Immunol. 15:85-101; and references cited therein].

Immune intervention of the androgen hormone cascade can also be used in the treatment of endometriosis in women.

This disease is the second leading cause of infertility in females after infection-induced infertility. The ectopic development and maintenance of endometrial tissues outside the uterine musculature is mediated by estrogen. Since LHRH regulates the production of FSH by the anterior pituitary which in turn regulates the production of estrogen by the ovaries, blocking the action of LHRH is another therapy for this disease. Thus by analogy to prostate cancer, estrogen-driven tumors of the breast should also be responsive to LHRH immunotherapy.

In addition to providing treatment for a number of important diseases in both men and women, regulation of the androgen hormone cascade through immunologic intervention provides a means of regulating fertility in both sexes. Since LHRH controls both testosterone production, which regulates the development of sperm, and estrogen production, which causes the ripening of ova, immunological blocking of LHRH action results in reversible infertility. Moreover, LHRH-based immunotherapy provides a means for reversible contraception in male and female companion animals (e.g. dogs, cats, horses and rabbits) as well as mitigating undesirable androgen-driven behavior such as heat, territorial marking and aggression. Lastly, immunological castration (e.g. antibody-based inhibition of LHRH action) has application in the meat animal industry. Males are not processed into prime cuts of meat because of the offensive aroma and taste associated with their flesh as a result of circulating testosterone (e.g. boar taint). Since mechanical castration of male food animals is no longer considered humane. immunological castration provides an acceptable alternative to this practice.

Several immunogenic forms of LHRH have been tested. For example, LHRH has been combined with adjuvants or conjugated with protein to enhance immunopotency. However, these adjuvants have been unsuitable for human use, and protein carriers are too expensive for large scale use.

Further, effective immunization with LHRH depends on the conjugation site between LHRH and the carrier. Conjugation of the carrier protein (diphtheria toxin or tetanus toxoid) to the amino terminus of LHRH provided a more effective vaccine for immunization and contraception relative to formulations having the carrier protein at other conjugation sites on LHRH (Ladd et al. (1990) Am. J. Reprod. Immunol. 22:56-63).

Moreover, protein linkage to LHRH is problematic because the majority of immune responses are directed to the carrier rather than to LHRH (the mass of the toxin molecule(s) is much greater than that of LHRH). This phenomenon leads to carrier-induced immune suppression. Because the majority of cancer or endometriosis patients have been previously immunized with diphtheria and tetanus vaccines as part of mandatory immunization programs, antibody and/or suppressor T cell responses directed to tetanus or diphtheria toxin components of the vaccines can interfere with the subsequent immune responses to toxin-linked LHRH immunogens.

Accordingly, an immune enhancer that is suitable for human use, inexpensive and capable of stimulating an early and strong immune response to LHRH has been sought. Likewise this immune enhancer should avoid carrier-induced suppression. Hence, it has been found that peptides containing particular structural arrangements of a Th epitope alone or linked to an invasin domain (as an immune enhancer) and LHRH (as immunogen) are effective in stimulating the production of antibodies against LHRH.

The present invention relates to peptides, preferably synthetic peptides, which are capable of inducing antibodies against LHRH that lead to the suppression of LHRH levels in males or females. The subject peptides are useful for inducing infertility and for treating prostatic hyperplasia, androgen-dependent carcinoma, prostatic carcinoma, testicular carcinoma, endometriosis, benign uterine tumors, recurrent functional ovarian cysts (severe) premenstrual syndrome or for prevention or treating estrogen-dependent breast cancer. In particular, peptides of this invention have a Th epitope and carboxyl-terminal LHRH, or a peptide analog of LHRH. These peptides are effective as immunogens and therapeutics. The peptides of this invention are capable of reducing serum testosterone to levels comparable to those obtained by orchiectomy (castration) and of causing reversible atrophy of the testes, prostate and other androgen- or estrogen-dependent sex organs. Optionally, the peptides have an invasin domain as an immune stimulator.

Another aspect of this invention provides a vaccine composition comprising an immunologically effective amount of a peptide in accordance with this invention and one or more pharmaceutically acceptable carriers. Such vaccine compositions are useful in the induction of infertility or the treatment of prostatic hyperplasia, androgen-dependent carcinoma, prostatic carcinoma, testicular carcinoma, endometriosis, benign uterine tumors, recurrent functional ovarian cysts and/or (severe) premenstrual syndrome as well as for prevention or treatment of estrogen-dependent breast cancer.

A further aspect of the invention relates to a method for suppressing activity of circulating LHRH levels in a mammal by administering one or more of the subject peptides to the mammal for a time and under conditions sufficient to induce functional antibodies directed against said LHRH. Suppression of LHRH activity is useful to treat prostatic hyperplasia, androgen-dependent carcinoma, prostatic carcinoma, testicular carcinoma, endometriosis, benign uterine tumors, recurrent functional ovarian cysts or (severe) premenstrual syndrome, or to prevent or treat estrogen-dependent breast cancer. More particularly, the invention provides a method for inducing infertility in a mammal by administering the subject vaccine compositions to the mammal for a time and under conditions to produce an infertile state in the mammal. Similarly, this invention relates to a method for treating androgen-dependent carcinoma by administering the subject vaccine compositions to the mammal for a time and under conditions to effect regression or prevent growth of the carcinoma.

Yet another aspect of the invention relates to an immunogenic synthetic peptide of about 30 to about 90 amino acids which contains an immunostimulatory invasin domain, a helper T cell (Th) epitope and a peptide hapten. These three elements of the peptide can be covalently joined in any order provided that either the immunoreactivity of the peptide hapten is substantially preserved or that immunoreactivity to a self-peptide can be generated. The peptide haptens of the invention include self-peptides LHRH, amylin, gastrin (gastrin$_{34}$ and gastrin$_{17}$), gastrin releasing peptide and a peptide derived from the CH4 domain of the IgE molecule as well as peptides from Chlamydia trachomitis, human immunodeficiency virus, Plasmodium berghei, or any other B cell epitope (such as from pathogenic organisms) or a CTL (cytotoxic T cell)-generating epitope. Further these peptides have one or more amino terminal $(A)_n$ groups, where A is an amino acid, a-NH$_2$, tripalmitoyl cysteine or a fatty acid and n is from 1 to about 10. The three elements of the subject peptides can be separated by a $(B)_o$ spacer group, where B is independently any amino acid and o is from 0 to about 10.

When the peptide hapten is amylin or an immunogenic analog thereof, the peptide can be formulated into a vaccine and administered for the treatment of non-insulin dependent diabetes. This treatment causes a reduction in circulating amylin levels and/or reduction in blood glucose levels.

When the peptide hapten is gastrin$_{34}$, gastrin$_{17}$, or an immunogenic analog thereof, the peptide can be formulated into a vaccine and administered for the treatment of peptic ulcers or gastrin releasing peptide-stimulated tumors. This treatment causes a reduction of gastrin levels and thereby acid secretion.

When the peptide hapten is gastrin releasing peptide or an immunogenic analog thereof, the peptide can be formulated into a vaccine and administered for the treatment of peptic ulcers, gastrin-stimulated tumors or lung cancer. This treatment causes reduction of gastrin releasing peptide levels.

When the peptide hapten is derived from the CH4 domain of IgE (SEQ ID NO:79) or an immunogenic analog thereof, the peptide can be formulated into a vaccine and administered for the treatment of allergy. This treatment causes a reduction in histamine levels or blocks IgE-mediated activation of mast cells or basophils.

When the peptide hapten is a variable domain (VDI–IV) of Chlamydia trachomatis major outer membrane protein (MOMP) or an immunogenic analog thereof, the peptide can be formulated into a vaccine and administered for immunization against Chlamydia trachomitis and production of neutralizing antibodies thereto.

When the peptide hapten is an HIV V3 principal neutralizing domain or an immunogenic analog thereof, the peptide can be formulated into a vaccine and administered for the treatment of acquired immune deficiency syndrome (AIDS), or prevention of HIV infection by the elicitation of neutralizing antibodies against HIV.

FIG. 1 graphically illustrates the average androgen-dependent organ weights (g) obtained 8 or 11 weeks after immunization of rats (n=5) with Peptides A-E. Panel A provides testes weight; Panel B provides epididymis weight; Panel C provides prostate plus associated seminal vesicles weight. Organ weights were obtained at 11 weeks for Peptides A-C and at 8 weeks for Peptides D and E. The average weight of the organs in control animals (n=8) is indicated by "Co".

FIG. 2 shows the relative androgen-dependent organ weights (g) in the responder (solid bars) and non-responder (open bars) animals immunized with Peptide A. Abbreviations: Epid., epididymis; P+SV, prostate and seminal vesicles.

FIG. 3 graphically depicts the correlation between testes weight (g) and serum anti-LHRH antibody levels (nmole/L) as determined in a radioimmunoassay (RIA) after immunization with Peptide A.

FIG. 4 is a photograph illustrating the size of androgen-dependent organs in controls or animals treated with a Peptide F.

FIG. 5 graphically depicts levels of anti-LHRH specific antibody produced in rats following immunization with an immunogenic LHRH construct designated as HBSAg $T_h$: LHRH (peptide A). Eight sexually mature Sprague-Dawley male rats per group were given 100 μg or 500 μg of peptide A by intramuscular administration. The antigen was formulated in Freund's complete adjuvant and given at week 0, and in incomplete Freund's adjuvant and administered at weeks 3 and 6. LHRH-specific antibody as reported in this and subsequent figures was determined by standard radioimmunoassay and expressed as the mean value in nanomoles of total LHRH antibody per liter of serum. The control group was given unmodified LHRH in Freund's adjuvant using the same immunization schedule.

FIG. 6 graphically depicts serum testosterone levels in rats following administration of peptide A as described in FIG. 5. Testosterone as reported in this and subsequent figures was measured in the serum samples used for determining the LHRH-specific antibody titers. Serum testosterone was measured by radioimmunoassay, and expressed as the mean value in nanomoles of testosterone per liter of serum.

FIG. 7 graphically depicts testis weights of animals given peptide A as described in FIG. 5. At 11 weeks following the commencement of the experiment described in the legend to FIG. 5, animals were sacrificed and the relevant organs dissected and weighed. Testis weights are expressed as the mean value in grams of organ weight per 100 grams of body weight. HypoX designates hypophysectomized rats. Group 1 animals were immunized with Freund's adjuvant without antigen, using an identical schedule to the experimental groups.

FIG. 8 graphically depicts prostate and seminal vesicle weights of animals given peptide A as described in FIG. 5. Prostate and seminal vesicles were weighed together and their collective weight expressed as the mean value in grams of tissue per 100 grams of body weight. HypoX designates hypophysectomized rats. Group 1 animals were immunized with Freund's adjuvant without antigen, using an identical schedule to the experimental groups.

FIG. 9 graphically depicts levels of anti-LHRH specific antibody produced in rats following immunization with an immunogenic LHRH construct designated as HBSAg $T_h$: GG : LHRH (peptide 18). Six sexually mature Sprague-Dawley male rats per group were given 100 μg of peptide 18 by subcutaneous administration. The antigen was formulated in Freund's complete adjuvant and given at week 0, and in incomplete Freund's adjuvant and administered at weeks 3 and 6. The control group was given unmodified LHRH in Freund's adjuvant using the same immunization schedule.

FIG. 10 graphically depicts levels of anti-LHRH specific antibody produced in rats following immunization with HBsAg $T_h$: LHRH (peptide A). Six sexually mature Sprague-Dawley male rats per group were given 100 μg peptide A by subcutaneous administration. The antigen was formulated in Freund's complete adjuvant and given at week 0, and in incomplete Freund's adjuvant and administered at weeks 3 and 6. The control group was given unmodified LHRH in Freund's adjuvant using the same immunization schedule.

FIG. 11 graphically depicts serum testosterone levels in rats following administration of peptide 18 in Freund's adjuvant. The experimental design is that described in the legend to FIG. 9.

FIG. 12 graphically depicts serum testosterone levels in rats following administration of peptide A. The experimental design is that described in the legend to FIG. 10.

FIG. 13 graphically depicts prostate and seminal vesicle weights of animals given peptide 18. The experimental protocol is described in the legend to FIG. 9. Prostate and seminal vesicles were weighed together and their collective weight expressed as the mean value in grams of tissue per 100 grams of body weight. Control animals were immunized with Freund's adjuvant without antigen, using an identical schedule to the experimental groups.

FIG. 14 graphically depicts levels of anti-LHRH specific antibody produced in rats following immunization with MV $F_1$ $T_h$: LHRH (peptide 19). Peptide 19 consists of a segment of the F protein from measles virus linked to the amino terminus of LHRH. Six sexually mature Sprague-Dawley male rats per group were given peptide 19 equivalent to 100 μg of peptide A by subcutaneous administration. The antigen was formulated in Freund's complete adjuvant and given at week 0, and in incomplete Freund's adjuvant and administered at weeks 3 and 6. The control group was given unmodified LHRH in Freund's adjuvant using the same immunization schedule.

FIGS. **15*a* and 15*b* graphically depict serum testosterone levels in rats following administration of peptide 19. The experimental design is that described in the legend to FIG. 14. FIG. 15*a* shows data for animals which achieved serum testosterone levels below the castration threshold, whereas FIG. 15*b*** shows data for animals which did not achieve castration levels of testosterone by week 8.

FIG. 16 graphically depicts testis weights of animals given peptide 19. At 10 weeks following the commencement of the experiment described in the legend to FIG. 14, animals were sacrificed and the relevant organs dissected and weighed. Testis weights are expressed as the mean value in grams of organ weight per 100 grams of body weight. Control animals were immunized with Freund's adjuvant without antigen, using an identical schedule to the experimental groups.

FIG. 17 graphically depicts prostate and seminal vesicle weights of animals given peptide 19. The experimental protocol is described in the legend to FIG. 14. Prostate and seminal vesicles were weighed together and their collective weight expressed as the mean value in grams of tissue per 100 grams of body weight. Control animals were immunized with Freund's adjuvant without antigen, using an identical schedule to the experimental groups.

Figure 18:
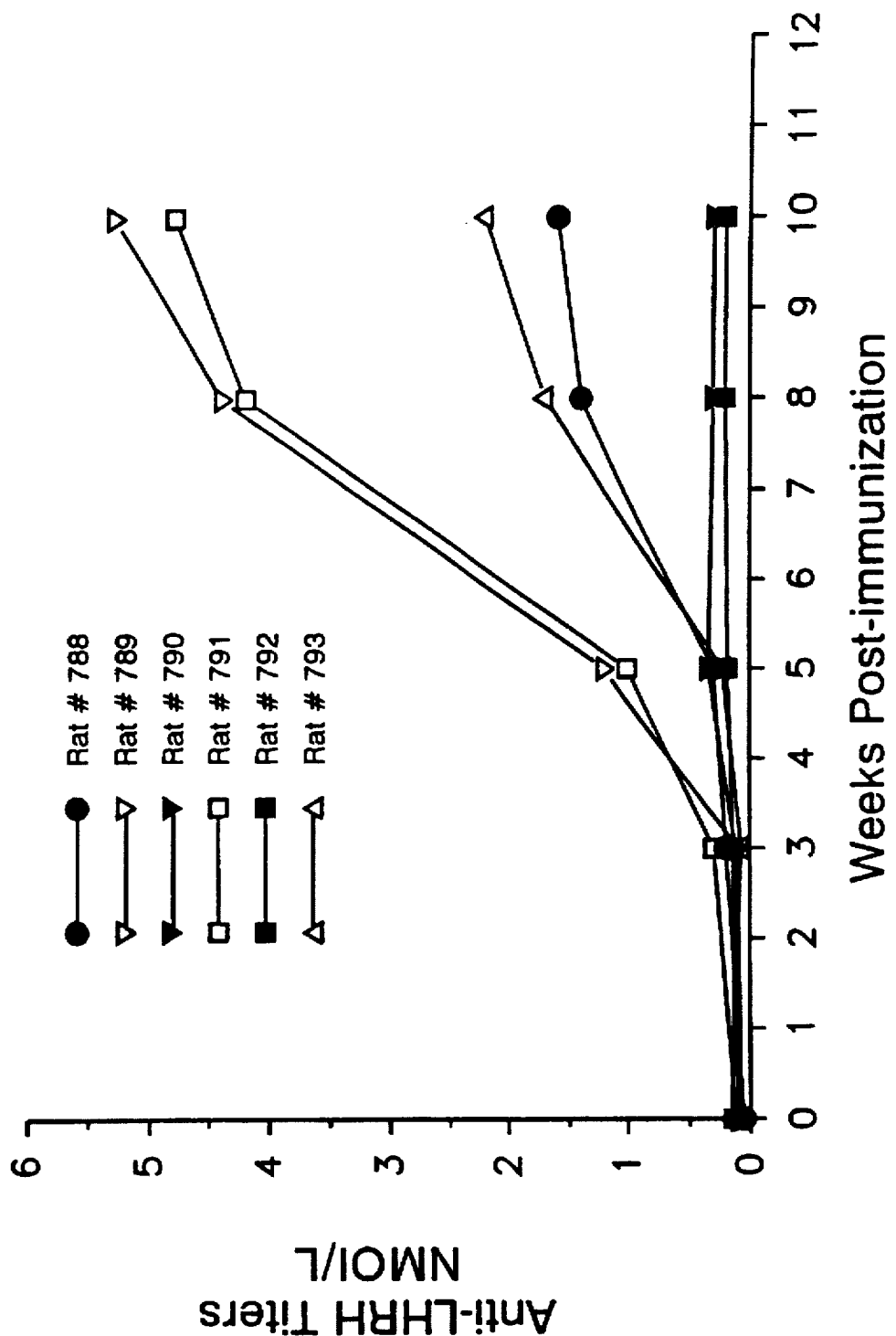

FIG. 18 graphically depicts anti-LHRH specific antibody produced in rats following immunization with PT $Th^2$: LHRH (peptide K, Seq ID No:16). Peptide K consists of a segment of pertussis toxin linked to the amino terminus of LHRH. Six sexually mature Sprague-Dawley male rats per group were given peptide K equivalent to 100 µg of peptide A by subcutaneous administration. The antigen was formulated in Freund's complete adjuvant and given at week 0, and in incomplete Freund's adjuvant and administered at weeks 3 and 6. The control group was given unmodified LHRH in Freund's adjuvant using the same immunization schedule.

Figure 19A:
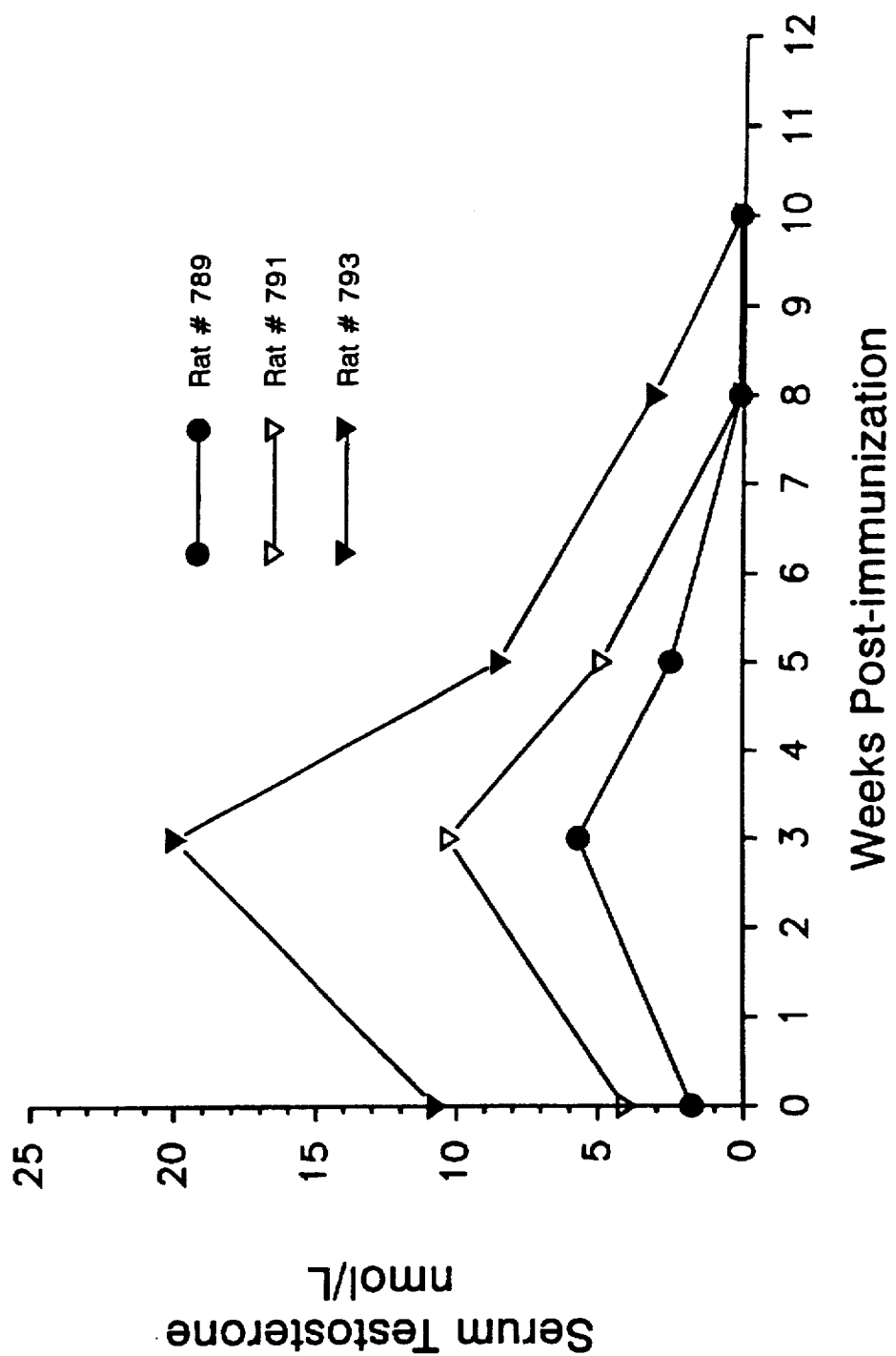
Figure 19B:
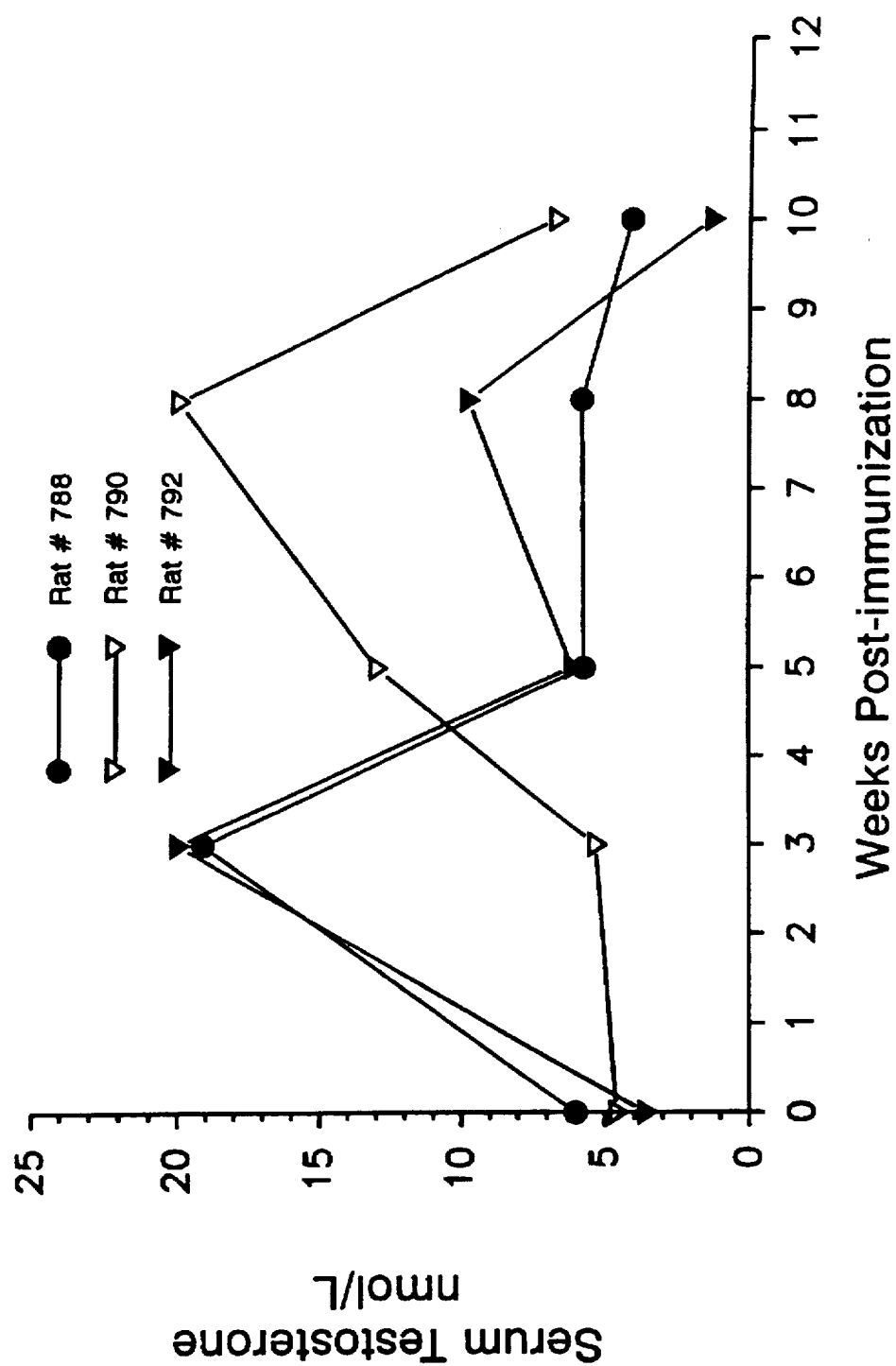

FIG. 19A and 19B graphically depicts serum testosterone levels in rats following administration of peptide K. The experimental design is that described in the legend to FIG. 18. FIG. 19A shows data for animals which achieved serum testosterone levels below the castration threshold, whereas FIG. 19B shows data for animals which did not achieve castration levels of testosterone by week 8.

FIG. 20 graphically depicts testis weights of animals given peptide K. At 10 weeks following the commencement of the experiment described in the legend to FIG. 18, animals were sacrificed and the relevant organs dissected and weighed. Testis weights are expressed as the mean value in grams of organ weight per 100 grams of body weight. Control animals were immunized with Freund's adjuvant without antigen, using an identical schedule to the experimental groups.

Figure 21:
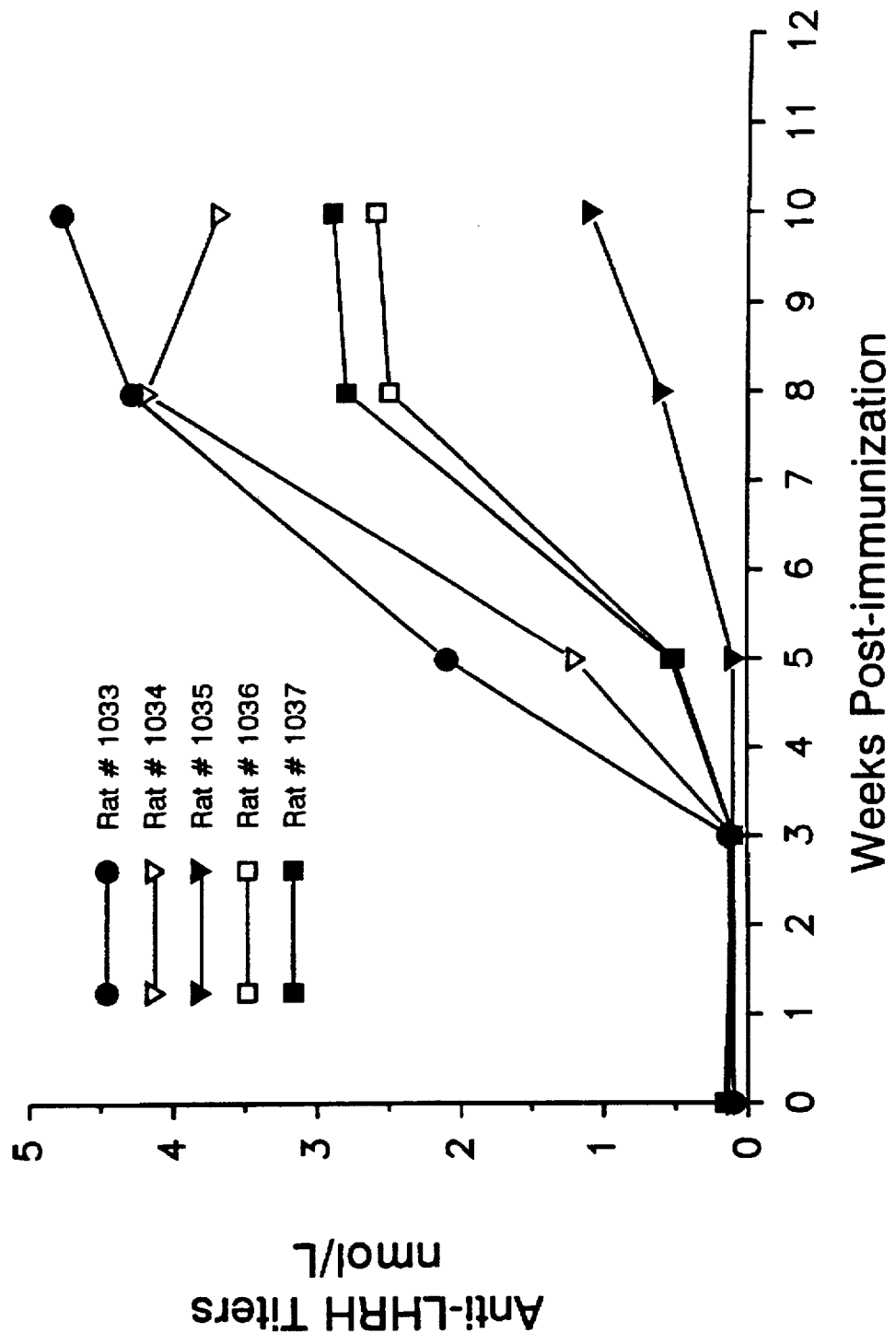

FIG. 21 graphically depicts levels of anti-LHRH specific antibody produced in rats following immunization with an immunogenic LHRH construct designated as $TT_1T_h$: LHRH (peptide H). Five sexually mature Sprague-Dawley male rats per group were given 100 µg of peptide H by subcutaneous administration. The antigen was formulated in Freund's complete adjuvant and given at week 0, and in incomplete Freund's adjuvant and administered at weeks 3 and 6. The control group was given unmodified LHRH on alum using the same immution schedule.

Figure 22:
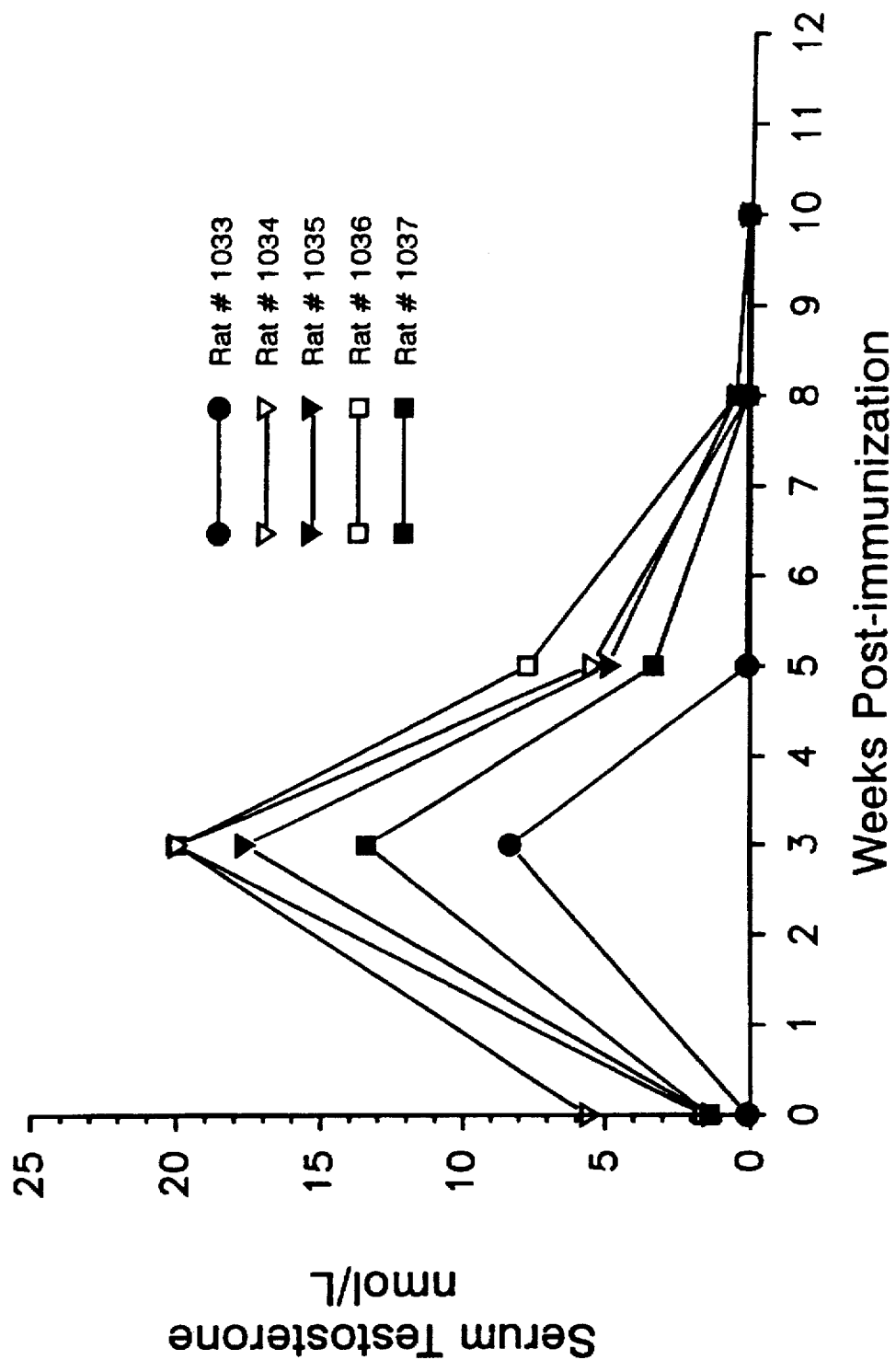

FIG. 22 graphically depicts serum testosterone levels in rats following administration of peptide H. The experimental design is that described in the legend to FIG. 21.

Figure 23:
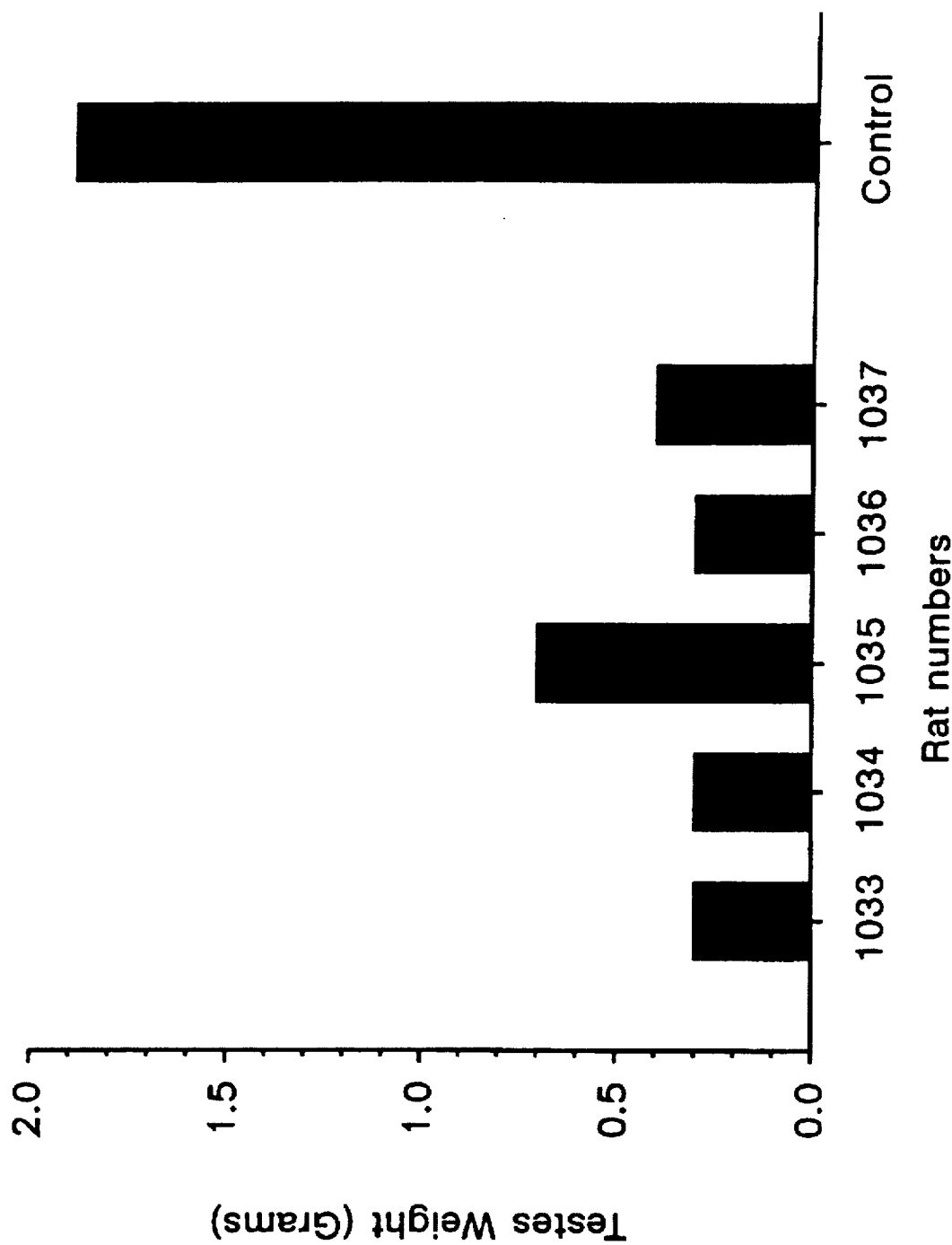

FIG. 23 graphically depicts testis weights of animals given peptide H. At 10 weeks following the commencement of the experiment described in the legend to FIG. 21, animals were sacrificed and the relevant organs dissected and weighed. Testis weights are expressed as the mean value in grams of organ weight per 100 grams of body weight. Control animals were immunized with alum adjuvant without antigen, using an identical schedule to the experimental groups.

Figure 24:
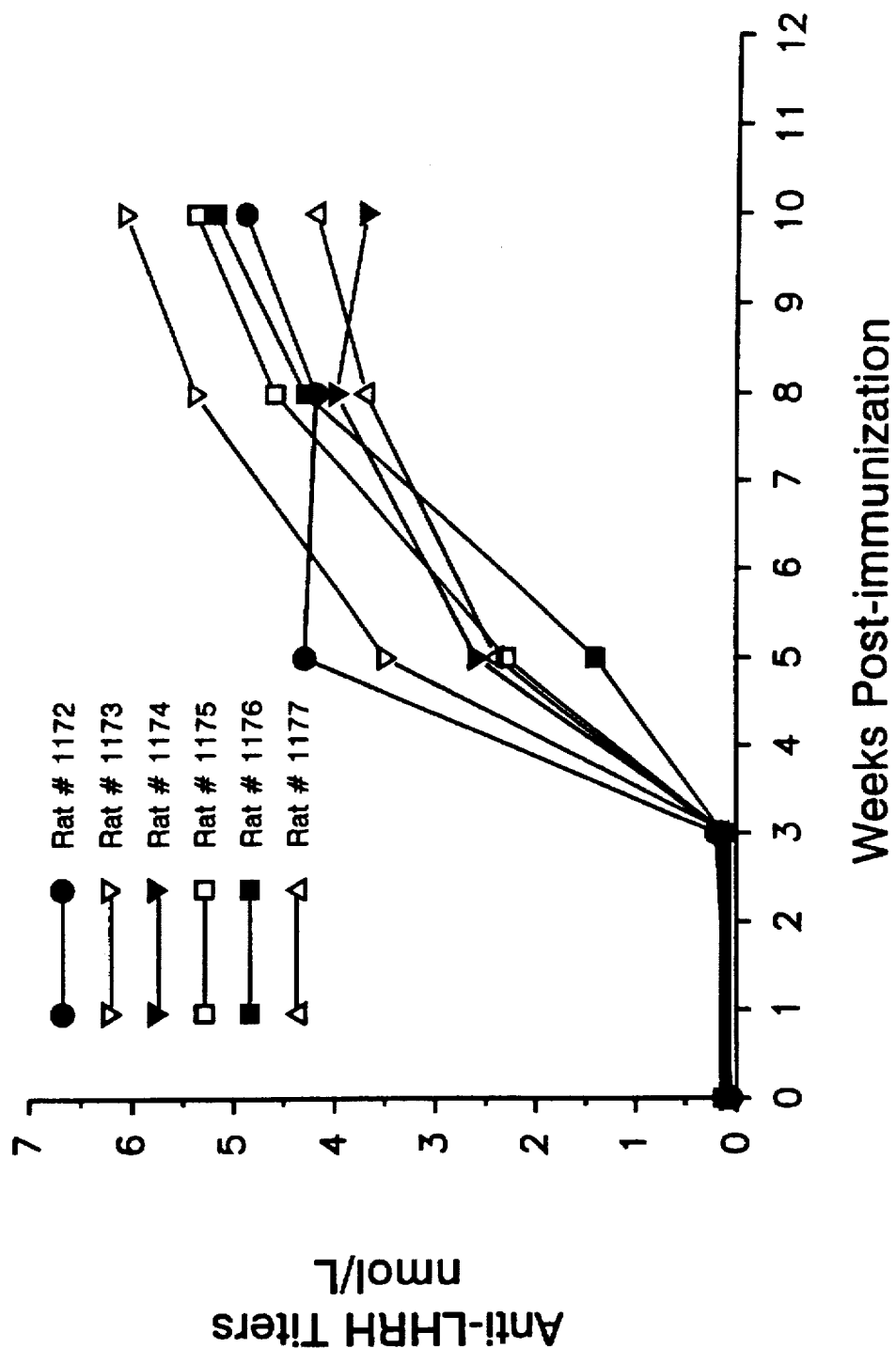

FIG. 24 graphically depicts levels of anti-LHRH specific antibody produced by immunization with a prototype immunogen cocktail formulated with Freund's adjuvant. Equimolar amounts of $HB_sT_h$:LHRH+$MV_{F1}T_h$: LHRH+ $PT_2T_h$:LHRH+$TT_1T_h$:LHRH were mixed and formulated in Freund's adjuvant. Six sexually mature Sprague-Dawley male rats were given a molar equivalent of the immunogen cocktail equal to 100 µg of peptide A in Freund's complete adjuvant at week 0 and in Freund's incomplete adjuvant at weeks 3 and 6. All immunizations were via the subcutaneous route.

Figure 25:
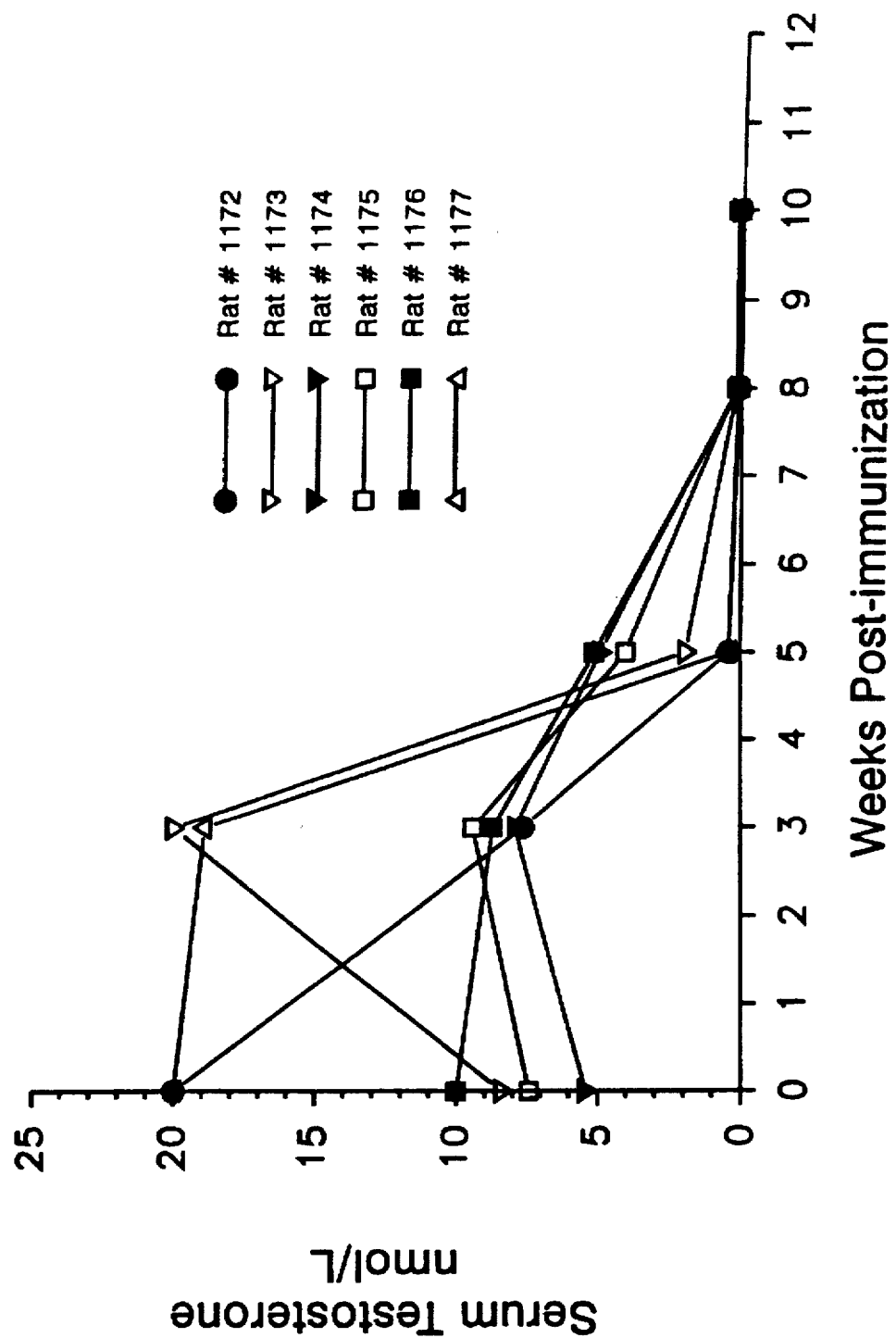

FIG. 25 graphically depicts serum testosterone levels in rats following administration of the prototype immunogen cocktail in Freund's adjuvant. The experimental design is that described in the legend to FIG. 24.

Figure 26:
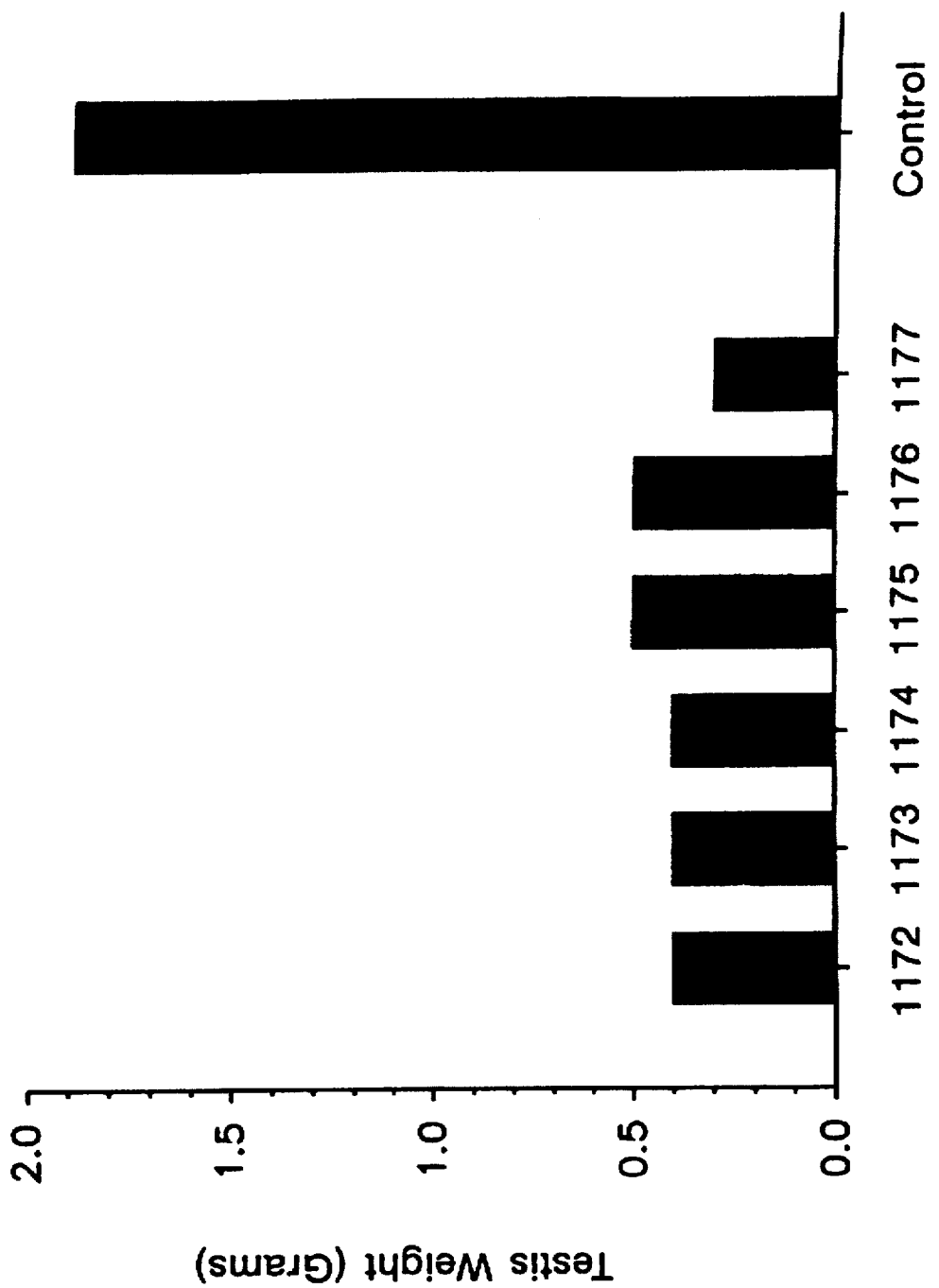

FIG. 26 graphically depicts testis weights of animals given the prototype immunogen cocktail in Freund's adjuvant. At 10 weeks following the commencement of the experiment described in the legend to FIG. 24, animals were sacrificed and the relevant organs dissected and weighed. Testis weights are expressed as the mean value in grams of organ weight per 100 grams of body weight. Control animals were immunized with Freund's adjuvant without antigen, using an identical schedule to the experimental groups.

Figure 27:
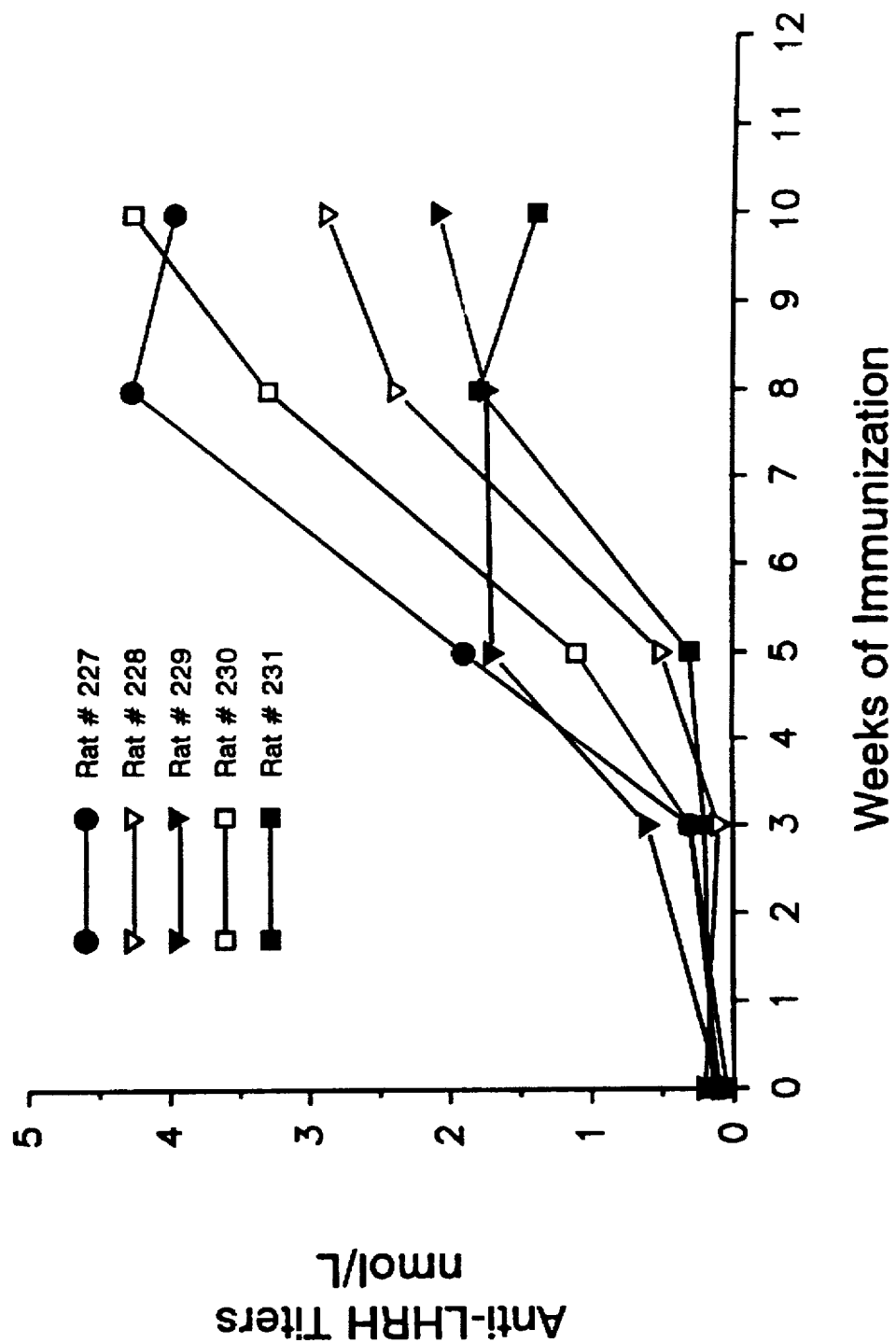

FIG. 27 graphically depicts levels of anti-LHRH specific antibody produced by immunization with a prototype immunogen cocktail. Equimolar amounts of $HB_sT_h$:LHRH+ $MV_{F1}T_h$:LHRH+$PT_2T_h$:LHRH+$TT_1T_h$:LHRH were mixed and formulated on alum. Six sexually mature Sprague-Dawley male rats per group were given a molar equivalent of the immunogen cocktail equal to 100 µg of peptide A by intramuscular administration at weeks 0, 3 and 6.

Figure 28:
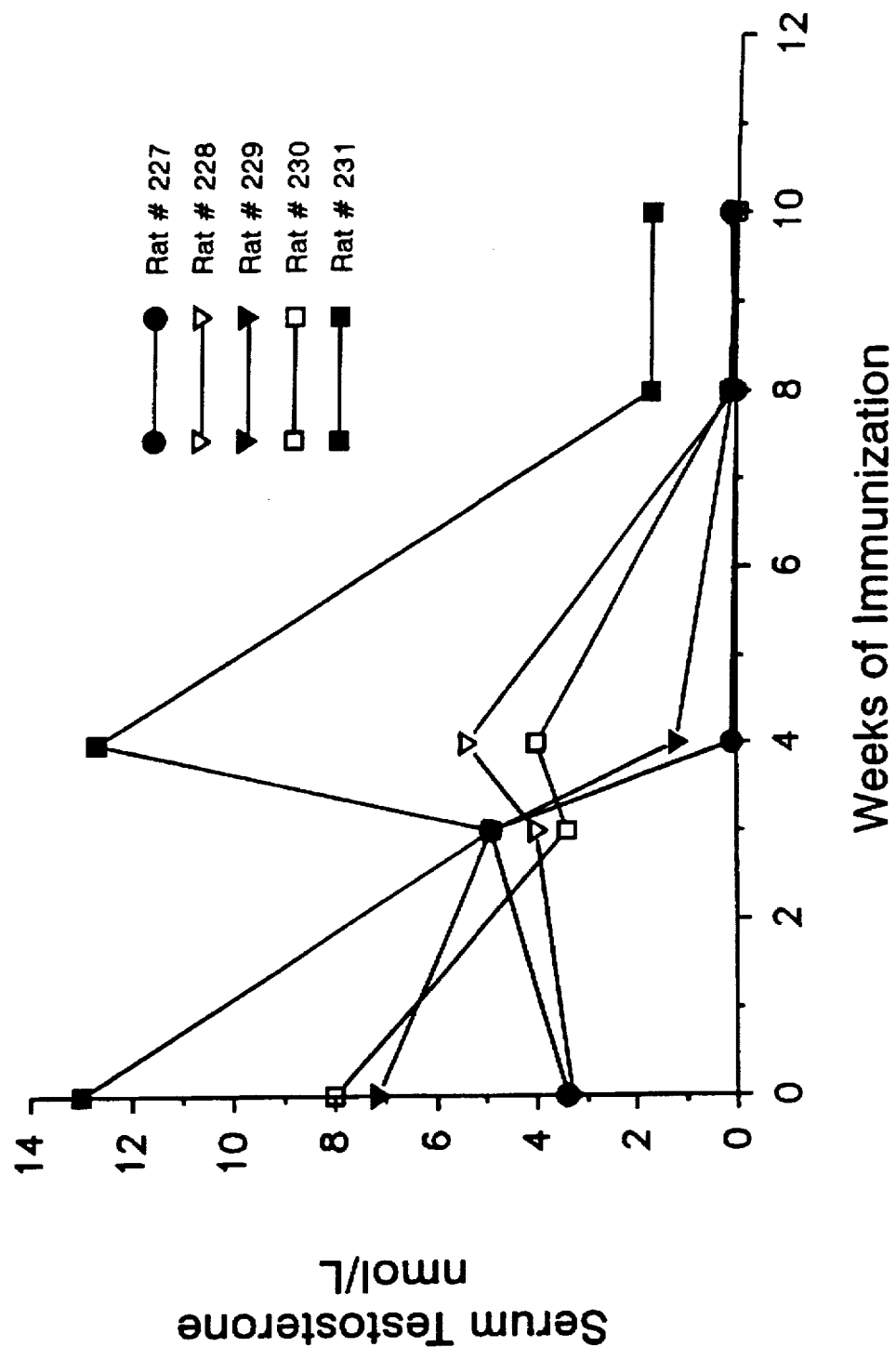

FIG. 28 graphically depicts serum testosterone levels in rats following administration of the prototype immunogen cocktail. The experimental design is that described in the legend to FIG. 27.

Figure 29:
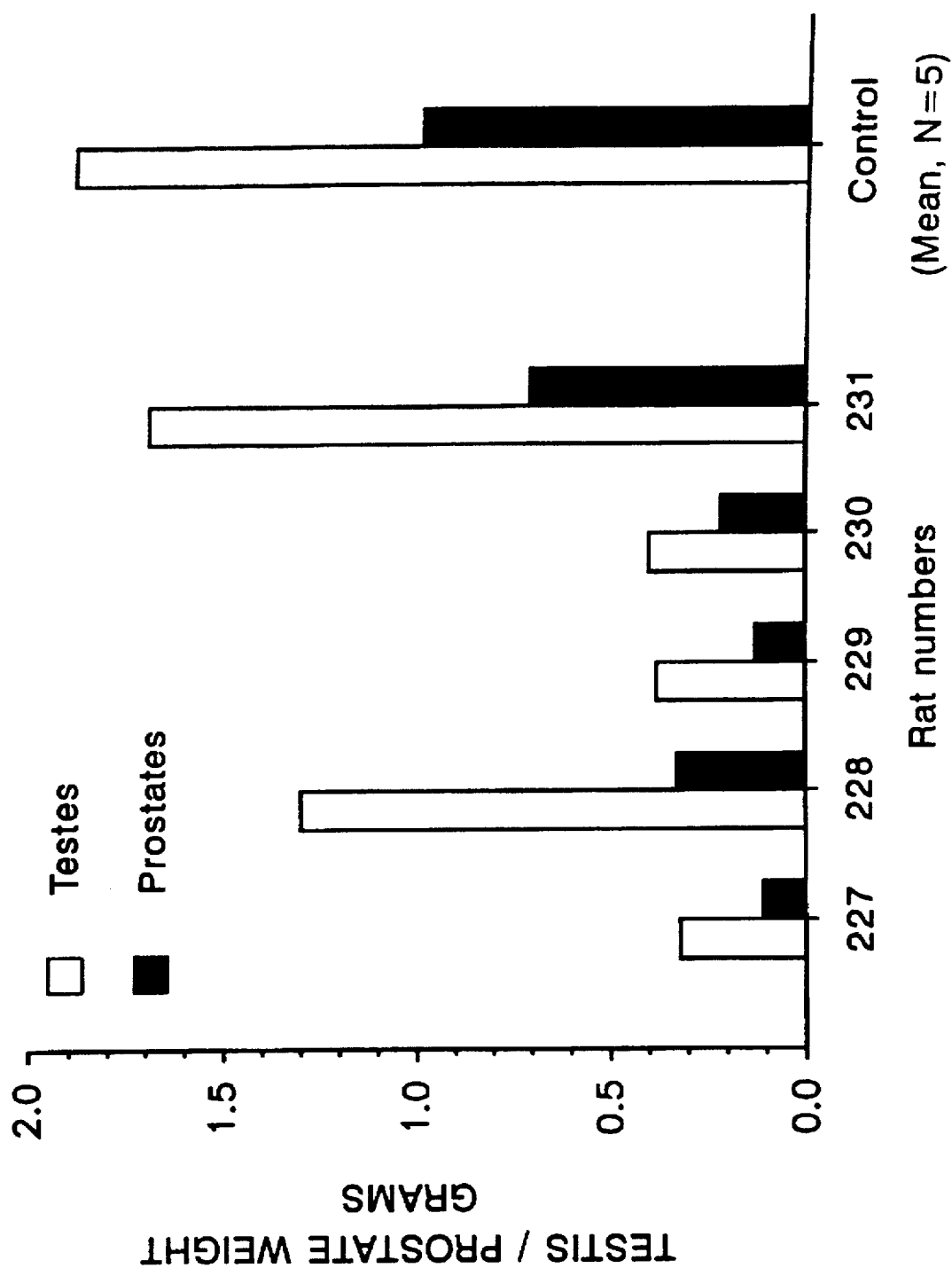

FIG. 29 graphically depicts testis weights of animals given the prototype immunogen cocktail. At 10 weeks following the commencement of the experiment described in the legend to FIG. 27, animals were sacrificed and the relevant organs dissected and weighed. Testis and prostate weights are expressed in grams. Control animals were immunized with alum adjuvant without antigen, using an identical schedule to the experimental groups.

Figure 30:
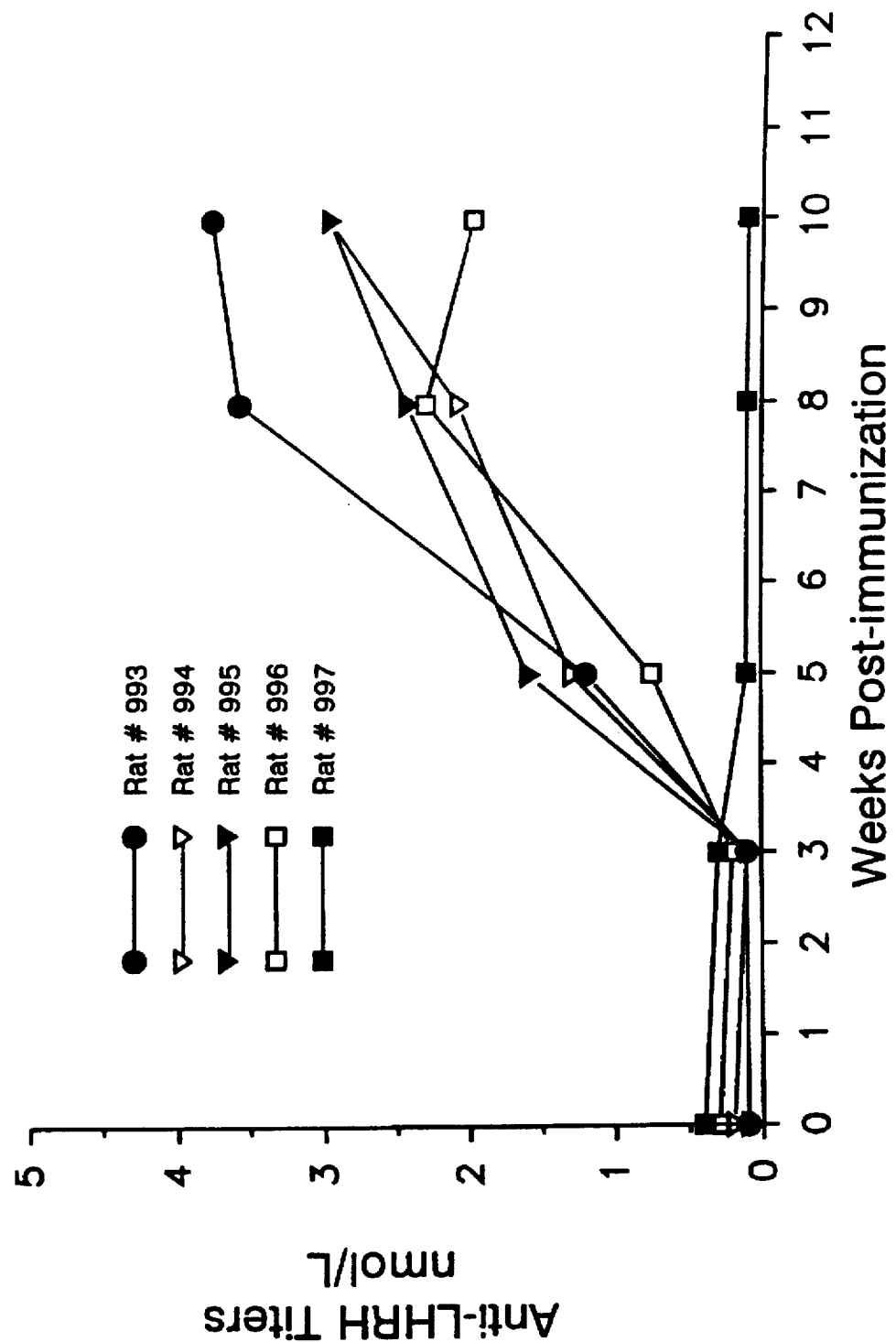

FIG. 30 graphically depicts levels of anti-LHRH specific antibody produced in rats following immunization with Inv: $HBsAgT_h$: LHRH (peptide 32). Peptide 32 consists of a segment of Yersenia adhesion molecule, Invasin, linked to a T cell helper epitope derived from the hepatitis B virus surface antigen linked to LHRH. Five sexually mature Sprague-Dawley male rats per group were given peptide 32 equivalent to 100 µg of peptide A by subcutaneous administration. The antigen was formulated on aluminum hydroxide and given at week 0, 3 and 6. The control group was given unmodified LHRH on alum using the same immunization schedule.

Figure 31:
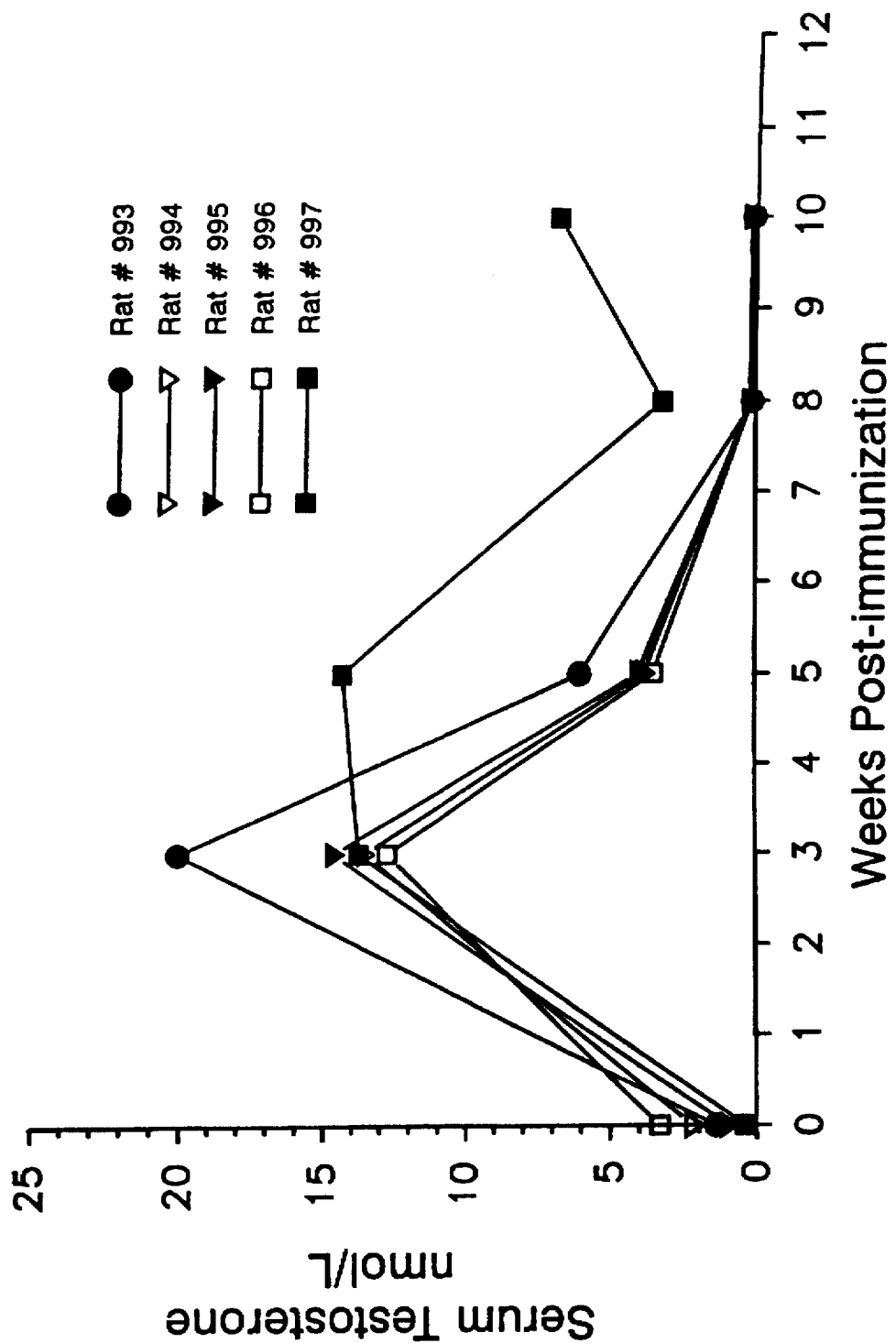

FIG. 31 graphically depicts serum testosterone levels in rats following administration of peptide 32. The experimental design is that described in the legend to FIG. 30.

Figure 32:
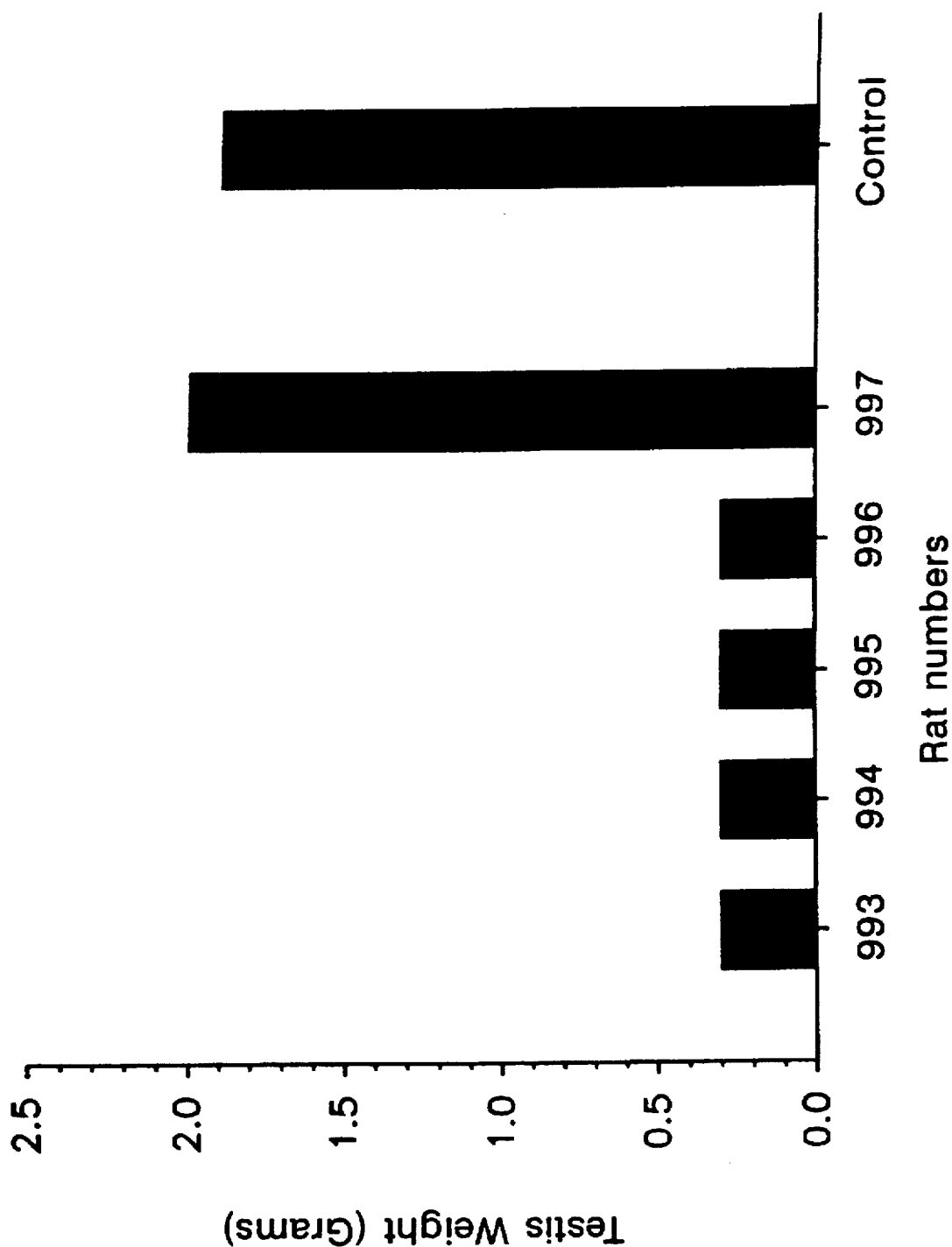

FIG. 32 graphically depicts testis weights of animals given peptide 32. At 10 weeks following the commencement of the experiment described in the legend to FIG. 30, animals were sacrificed and the relevant organs dissected and weighed. Testis weights are expressed as the mean value in grams of organ weight per 100 grams of body weight. Control animals were immunized with alum adjuvant without antigen, using an identical schedule to the experimental groups.

Figure 33:
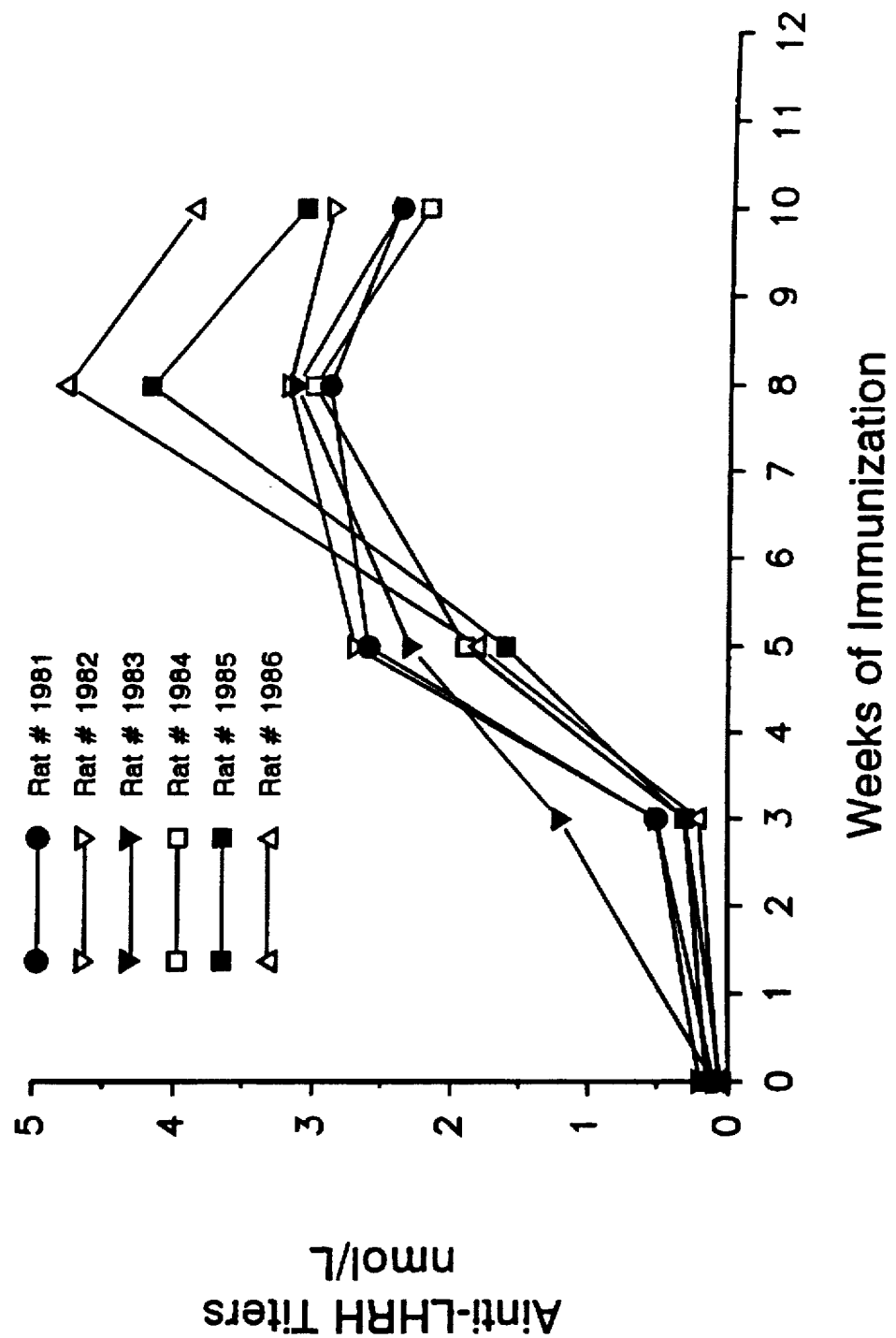

FIG. 33 graphically depicts levels of anti-LHRH specific antibody produced by immunization with a immunogen cocktail containing peptide H. Equimolar amounts of Inv:$HB_sT_h$:LHRH+$MV_{F1}T_h$:LHRH+$PT_2T_h$:LHRH+ $TT_1T_h$:LHRH were mixed and formulated on alum. Five sexually mature Sprague-Dawley male rats per group were given a molar equivalent of the immunogen cocktail equal to 100 µg of peptide A by intramuscular administration at weeks 0, 3 an 6.

Figure 34:
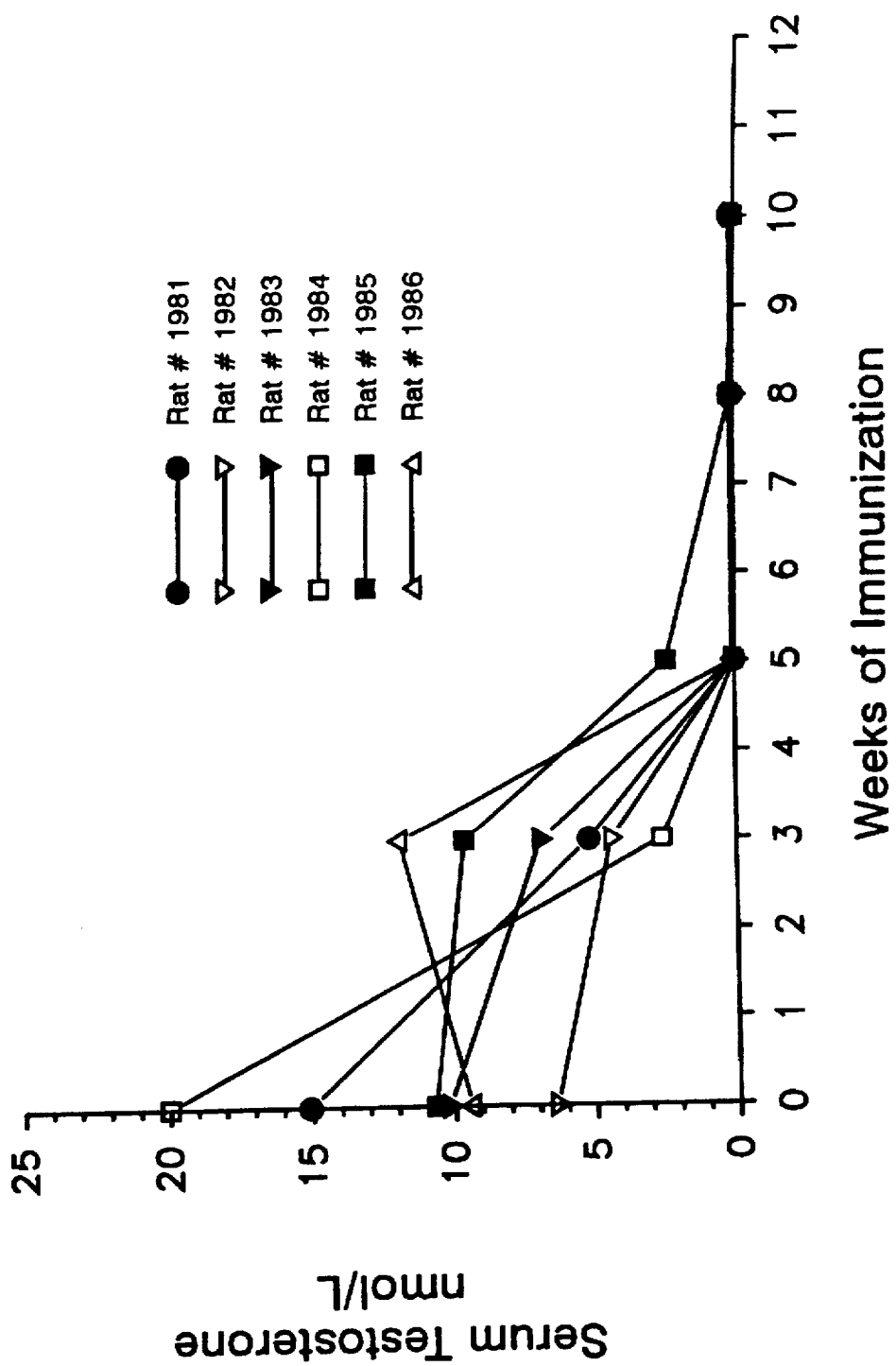

FIG. 34 graphically depicts serum testosterone levels in rats following administration of the prototype immunogen cocktail. The experimental design is that described in the legend to FIG. 33.

Figure 35:
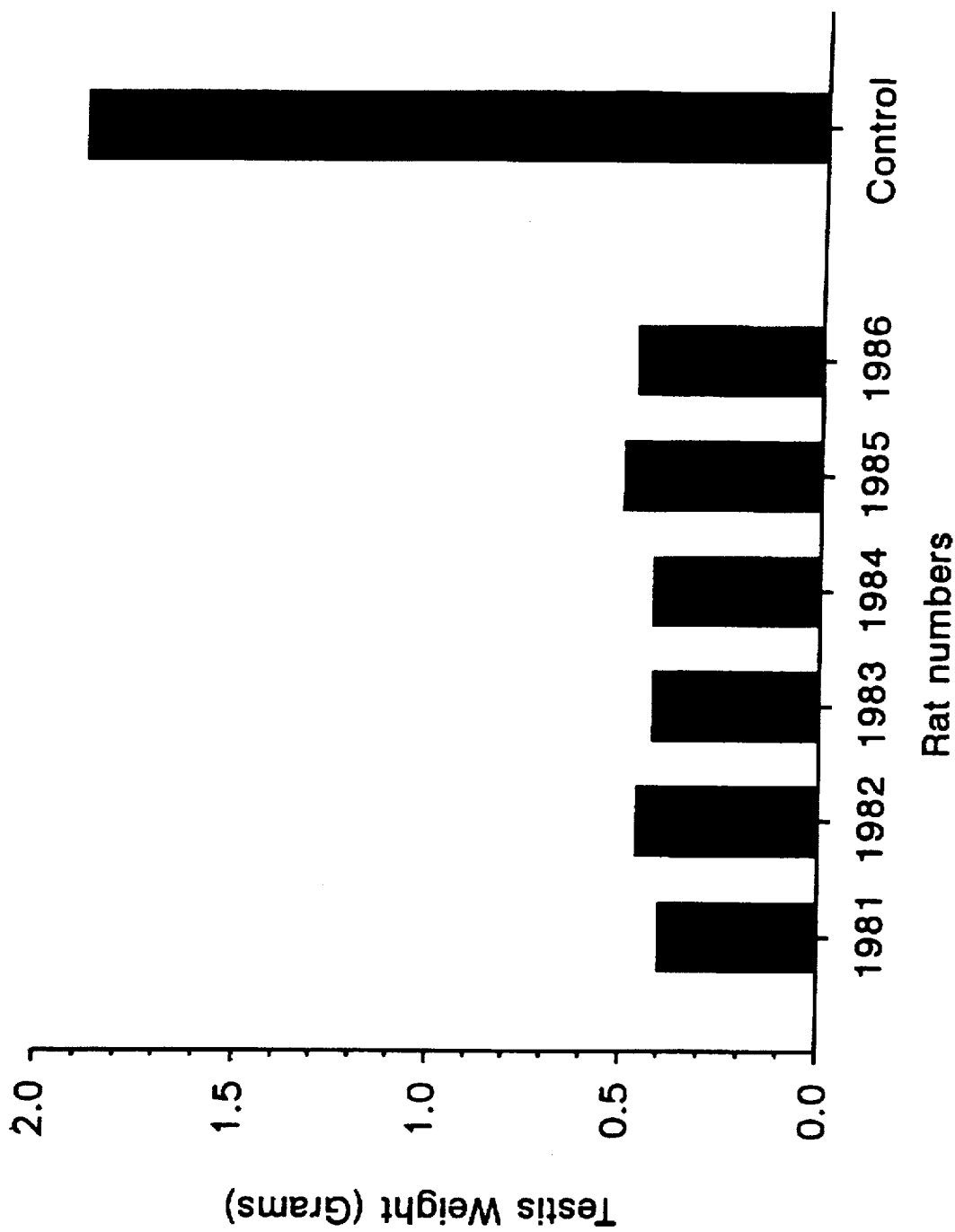

FIG. 35 graphically depicts testis weights of animals given the prototype immunogen cocktail. At 10 weeks following the commencement of the experiment described in the legend to FIG. 33, animals were sacrificed and the relevant organs dissected and weighed. Testis weights are expressed in grams. Control animals were immunized with alum adjuvant without antigen, using an identical schedule to the experimental groups.

The present invention relates to peptides, preferably synthetic peptides, which are capable of inducing antibodies against LHRH, which antibodies lead to the suppression of active LHRH levels in males or females. For the present invention, the following factors contribute to the immuno-efficacy of the subject LHRH constructs. These factors, singly or in combination, are considered important aspects for preparing peptides in accordance with the present invention.

1. Addition of Promiscuous Helper T ($T_h$) Cell Epitopes. To evoke an efficient antibody response, immunogens must be presented in conjunction with major histocompatibility (MHC) class II antigens. The MHC class II antigens produced by antigen-presenting cells (APCS) bind to T cell epitopes present in the immunogen in a sequence specific manner. This MHC class II-immunogen complex is recognized by CD4+ lymphocytes ($T_h$ cells), which cause the proliferation of specific B cells capable of recognizing a B cell epitope from the presented immunogen and the production of B cell epitope-specific antibody by them. Since. LHRH is a self molecule, it does not possess any recognizable $T_h$ epitopes. Such epitopes can be provided by specific sequences derived from potent immunogens including tetanus toxin, pertussis toxin, the measles virus F protein and the hepatitis B virus surface antigen (HBsAg). The $T_h$ epitopes selected are, preferably, capable of eliciting helper T cell responses in large numbers of individuals expressing diverse MHC haplotypes. These epitopes function in many different individuals of a heterogeneous population and are considered to be promiscuous $T_h$ epitopes. Promiscuous $T_h$ epitopes provide an advantage of eliciting potent LHRH antibody responses in most members of genetically diverse population groups.

Thus, the helper epitopes of this invention are selected not only for a capacity to cause immune responses in most members of a given population, but also for a capacity to cause memory/recall responses. The vast majority of human patients receiving LHRH immunotherapy will already have been immunized with the pediatric vaccines (i.e., measles+mumps+rubella and diphtheria+pertussis+tetanus vaccines) and, possibly, the newer hepatitis B virus vaccine. These patients have therefore been previously exposed to more than one of the $T_h$ epitopes present in the immunogen mixture. Prior exposure to a $T_h$ epitope through immunization with the standard vaccines should establish $T_h$ cell clones which can immediately proliferate upon administration of the LHRH immunotherapy (i.e. a recall response), thereby stimulating rapid B cell responses to LHRH. In addition, the $T_h$ epitopes avoid any pathogen-specific B cell and/or suppressor T cell epitopes which could lead to carrier-induced immune suppression, a problem encountered when toxin molecules are used to elicit helper T cell responses.

2. Addition of Spacer Residues Between Immunogenic Elements. Immunogenicity can be improved through the addition of spacer residues (e.g. Gly-Gly) between the promiscuous $T_h$ epitope and LHRH. In addition to physically separating the $T_h$ epitope from the B cell epitope (i.e., LHRH), the glycine residues can disrupt any artificial secondary structures created by the joining of the $T_h$ epitope with LHRH—and thereby eliminate interference between the T and/or B cell responses. The conformational separation between the helper epitope and the antibody eliciting domain thus permits more efficient interactions between the presented immunogen and the appropriate $T_h$ and B cells.

3. Mixing of $T_h$ Epitope-modified Immunogens to Cause Broad-spectrum Efficacy. The $T_h$ epitopes of the invention are promiscuous but not universal. This characteristic means that the $T_h$ epitopes are reactive in a large segment of an outbred population expressing different MHC antigens (reactive in 50 to 90% of the population), but not in all members of that population. To provide a comprehensive, approaching universal, immune reactivity for the LHRH immunotherapeutic construct, a combination of LHRH constructs with different $T_h$ epitopes can be prepared. For example, a combination of four $T_h$ epitope: LHRH constructs, including promiscuous $T_h$ epitopes from tetanus and pertussis toxins, measles virus F protein and from the HBsAg is particularly effective. On an equimolar basis, this mixture is more broadly effective than any single immunogen in the mixture.

4. Production of $T_h$ Epitope Libraries. In another embodiment the $T_h$ epitope can be a structured synthetic antigen library (SSAL) as described in U.S. Ser. No. 143, 412, filed Oct. 26, 1993, which is incorporated herein by reference. This technology can be used as another, and perhaps, a more efficient means to obtain universal immune reactivity (as opposed to mixing promiscuous helper epitope constructs). An SSAL is composed of an ordered set of from 2 to several trillion different, but related, peptides made simultaneously in a single, automated peptide synthesis. The sequences of the peptides within a library are defined by a set of peptides or protein domains which share common structural and/ or functional properties. The order within any SSAL is provided by invariant amino acid residues which define the core sequence of the library. The core sequence is determined by aligning the primary amino acid sequences of a related family of epitopes, identifying the invariant loci within the alignment and the specific amino acid residues present at each invariant position. The SSAL is then synthesized with conserved amino acid residues at the invariant positions as defined by the alignment. The degeneracy within the library is determined by the loci within the alignment that harbor different amino acid residues when the ordered epitopes are compared. The degree of degeneracy within an array is determined by the number of variant loci within the alignment and the number of different amino acids found at each variant locus.

Promiscuous $T_h$ epitopes are included in structured libraries since they often share common structural features as based upon similar landmark sequences. For example, promiscuous $T_h$ epitopes range in size from about 15 to about 30 residues. Amphipathic helices are a common feature of the $T_h$ epitopes. An amphipathic helix is defined by an alpha-helical structure with hydrophobic amino acid residues dominating one face of the helix, and charged and polar residues dominating the surrounding faces. $T_h$ epitopes frequently contain additional primary amino acid patterns such as: a Gly or a charged reside followed by two to three hydrophobic residues followed in turn by a charged or polar residue. This pattern defines Rothbard sequences. $T_h$ epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single $T_h$ epitope.

5. Covalent Addition of an Invasin Domain as an Adjuvant. The invasins of the pathogenic bacteria Yersinia spp. are outer membrane proteins which mediate entry of the bacteria into mammalian cells (Isberg and Leong, 1990, *Cell* 60:861). Invasion of cultured mammalian cells by the bacterium was demonstrated to require interaction between the Yersinia invasin molecule and several species of the β1 family of integrins present on the cultured cells (Tran Van Nhieu and Isberg, 1991, *J. Biol. Chem.* 266:24367). Since T lymphocytes are rich in β1 integrins (especially activated immune or memory T cells) the effects of invasin upon human T cell have been investigated (Brett et al., 1993, *Eur. J. Immunol.* 23:1608). It is thought that integrins facilitate the migration of immune T cells out of the blood vessels and through connective tissues to sites of antigenic challenge through their interaction with extracellular matrix proteins including fibronectin, laminin and collagen. The carboxyterminus of the invasin molecule was found to be costimulatory for naive human $CD^4+T$ cells in the presence of the non-specific mitogen, anti-CD3 antibody, causing marked proliferation and expression of cytokines. The specific invasin domain which interacts with the β1 integrins to cause this stimulation also was identified (Brett et al., 1993). Because of the demonstrated T cell co-stimulatory properties associated with this domain, it can be linked it to promiscuous $T_h$ epitope: LHRH constructs.

6. Covalent Addition of Pam$_3$Cys as an Adjuvant. Many of the outer membrane proteins of Gram-negative bacteria are both lipid-modified and very immunogenic. Because of the apparent correlation between covalent lipid linkage and immunogenicity, tripalmitoyl-S-glycerol cysteine (Pam$_3$Cys), a lipid common to bacterial membrane proteins, can be coupled to synthetic peptides representing either B cell of cytotoxic T cell epitopes. Because significant adjuvanting responses are elicited by this lipid linkage, lipid-modified promiscuous $T_h$ epitope: LHRH constructs can be prepared. Such lipid-modified constructs are more immunogenic than the unmodified version of the same peptide.

7. Selection of an Adjuvant/Emulsion Formulation to Maximize Antibody Responses. In addition to the significant adjuvanting properties associated with covalent modifications of the $T_h$ epitope: LHRH constructs (e.g the invasin domain and/or Pam$_3$Cys), addition of exogenous adjuvant/emulsion formulations which maximize immune responses to the LHRH immunotherapeutic immunogens have been investigated. The adjuvants and carriers that have been evaluated are those: (1) which have been successfully used in Phase I human trials; (2) based upon their lack of reactogenicity in preclinical safety studies, have the potential for approval for use in humans; or (3) have been approved for use in food and companion animals.

8. Microparticle Delivery of Modified Immunogens. Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher coglycolide concentrations degrade more rapidly); (2) particle size, (smaller particles degrade more rapidly than larger ones); and, (3) entrapment efficiency, (particles with higher concentrations of entrapped antigen degrade more rapidly than particle with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved [see, for example, U.S. Ser. No. 201,524, filed Feb. 25, 1994]. Moreover, delivery of promiscuous $T_h$ epitope: LHRH immunogens entrapped in microparticles can also provide improved efficacy when the microparticulate immunogen is mixed with an exogenous adjuvant/emulsion formulations.

The peptides of this invention have a helper T cell epitope (Th epitope) and carboxyl-terminal LHRH. Moreover, the subject peptides can have LHRH replaced by an immunogenic analog of LHRH.

The peptides of this invention are represented by the formula $$(A)_n-(Th)_m-(B)_o-LHRH$$

wherein A is independently an amino acid, α-NH$_2$, a tripalmitoyl cysteine group, a fatty acid, an invasin domain or an immunostimulatory analog of the corresponding invasin domain;

B is an amino acid;

each Th is independently a sequence of amino acids that comprises a helper T cell epitope or an immune enhancing analog or segment thereof;

LHRH is luteinizing hormone releasing hormone or an immunogenic analog thereof;

n is from 1 to about 10;

m is from 1 to about 4; and o is from 0 to about 10.

The peptides of the present invention have from about 20 to about 100 amino acid residues, preferably from about 20 to about 50 amino acid residues and more preferably from about 20 to about 35 amino acid residues. In another preferred embodiment, the peptide has from about 25 to about 40 amino acid residues.

When A is an amino acid, then it can be any non-naturally occurring amino acid or any naturally occurring amino acid. Non-naturally occuring amino acids include, but are not limited to, β-alanine, ornithine, norleucine, norvaline, hydroxyproline, thyroxine, gamma-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Moreover, when m is greater than one, and two or more of the A groups are amino acids, then each amino acid is independently the same or different.

When A is a tripalmitoyl cysteine (Pam$_3$ Cys) group it acts as an adjuvant by enhancing the immunostimulating properties of the Th epitope [Weismuller et al. (1992) Int. J. Peptide Res. 40:255–260 and references cited therein]. When A is a fatty acid it is usually located at the amino terminus of the peptide. Furthermore, when one of A is a fatty acid, then, there are 2 or 3 additional amino acids as A moieties. As used herein, fatty acids have a hydrocarbon chain length of 8 to 24 carbon atoms. The hydrocarbon chain can be saturated or unsaturated.

When A is an invasin domain it is an immunostimulatory epitope from the invasin protein of a Yersinia species. This invasin domain is also capable of interacting with the β1 integrin molecules present on T cells, particularly activated immune or memory T cells, as described above under point 5 in the Detailed Description of the Invention. In a preferred embodiment the invasin domain has the sequence:

Thr-Ala-Lys-Ser-Lys-Lys-Phe-Pro-Ser-Tyr-Thr-Ala-Ser-Ile-Gly-Phe or is an immunostimulatory analog thereof from the corresponding region in another Yersinia species invasin protein. Such analogs thus have substitutions, deletions or insertions to accommodate strain to strain variation, provided that the analogs retain its immunostimulatory properties.

In one embodiment, n is four and A is α-NH₂, lysine, lysine and lysine in that order. In another embodiment n is one and A is α-NH₂. In yet another embodiment, m is four and A is α-NH₂, an invasin domain, glycine and glycine in that order.

The amino acids for B can be the naturally occurring amino acids or the non-naturally occurring amino acids as described above. Each B is independently the same or different. When B is lysine then a polymer can be formed. For example, if o is 7 and all seven B groups are lysine then a branching heptalysyl core (K₄K₂K or K core) is formed when peptide synthesis is performed without protection of the lysyl side chain ε-amino group. Peptides with a K core have eight branch arms, with each branch arm being identical and represented by the formula $(A)_n$—$(Th)_m$—$(B)_o$—. In addition, the amino acids of B can form a flexible hinge, or spacer, to enhance the immune response to the Th epitope and LHRH. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro, where Xaa is any amino acid, and preferably aspartic acid. An example of a spacer is provided by the sequence Gly-Gly.

Th is a sequence of amino acids (natural or non-natural amino acids) that comprises a Th epitope. A Th epitope can consist of a continuous or discontinuous epitope. Hence not every amino acid of Th is necessarily part of the epitope. Accordingly, Th epitopes, including analogs and segments of Th epitopes, are capable of enhancing or stimulating an immune response to LHRH. Immunodominant Th epitopes are broadly reactive in animal and human populations with widely divergent MHC types [Celis et al. (1988) J. Immunol. 140:1808-1815; Demotz et al. (1989) J. Immunol. 142:394-402; Chong et al. (1992) Infect. Immun. 60:4640-4647]. The Th domain of the subject peptides has from about 10 to about 50 amino acids and preferably from about 10 to about 30 amino acids. When multiple Th epitopes are present (i.e. n>2), then each Th epitope is independently the same or different.

Th epitope analogs include substitutions, deletions and insertions of from one to about 10 amino acid residues in the Th epitope. Th segments are contiguous portions of a Th epitope that are sufficient to enhance or stimulate an immune response to LHRH. An example of Th segments is a series of overlapping peptides that are derived from a single longer peptide.

Th epitopes of the present invention include hepatitis B surface antigen helper T cell epitopes (HB$_s$Th), pertussis toxin helper T cell epitopes (PT Th), tetanus toxin helper T cell epitopes (TT Th), measles virus F protein helper T cell epitopes (MV$_F$ Th), Chlamydia trachamates major outer membrane protein helper T cell epitopes (CT T$_h$), diphtheria toxin helper T cell epitopes (DT T$_h$), Plasmodium falciparum circumsporozoite helper T cell epitopes (PF T$_h$), Schistosoma mansoni triose phosphate isomerase helper T cell epitopes (SM T$_h$), Escherichia coli TraT helper T cell epitopes (TraT T$_h$) and immune-enhancing analogs and segments of any of these Th epitopes. Examples of Th epitope sequences are provided below:

| | |
|---|---|
| HB$_s$Th: | Phe—Phe—Leu—Leu—Thr—Arg—Ile—Leu—thr—Ile—Pro—Gln—Ser—Leu—Asp, SEQ ID NO:2 |
| PT₁Th: | Lys—Lys—Leu—Arg—Arg—Leu—Leu—Tyr—Met—Ile—Tyr—Met—Ser—Gly—Leu—Ala—Val—Arg—Val—His—Val—Ser—Lys—Glu—Glu—Gln—Tyr—Tyr—Asp—Tyr, SEQ ID NO:3 |
| TT₁Th: | Lys—Lys—Gln—Tyr—Ile—Lys—Ala—Asn—Ser—Lys—Phe—Ile—Gly—Ile—Thr—Glu—Leu, SEQ ID NO:4 |
| TT₂Th: | Lys—Lys—Phe—Asn—Asn—Phe—Thr—Val—Ser—Phe—Trp—Leu—Arg—Val—Pro—Lys—Val—Ser—Ala—Ser—His—Leu SEQ ID NO:5 |
| PT₁ₐTh: | Tyr—Met—Ser—Gly—Leu—Ala—Val—Arg—Val—His—Val—Ser—Lys—Glu—Glu, SEQ ID NO:6 |
| TT₃Th: | Tyr—Asp—Pro—Asn—Tyr—Leu—Arg—Thr—Asp—Ser—Asp—Lys—Asp—Arg—Phe—Leu—Gln—Thr—Met—Val—Lys—Leu—Phe—Asn—Arg—Ile—Lys, SEQ ID NO:7 |
| PT₂Th: | Gly—Ala—Tyr—Ala—Arg—Cys—Pro—Asn—Gly—Thr—Arg—Ala—Leu—Thr—Val—Ala—Glu—Leu—Arg—Gly—Asn—Ala—Glu—Leu SEQ ID NO:8. |
| MV$_{F1}$Th: | Leu—Ser—Glu—Ile—Lys—Gly—Val—Ile—Val—His—Arg—Leu—Glu—Gly—Val SEQ ID NO:9 |
| MV$_{F2}$T$_h$: | Gly—Ile—Leu—Glu—Ser—Arg—Gly—Ile—Lys—Ala—Arg—Ile—Thr—His—Val—Asp—Thr—Glu—Ser—Tyr SEQ ID NO:42 |
| TT₄T$_h$: | Trp—Val—Arg—Asp—Ile—Ile—Asp—Asp—Phe—Thr—Asn—Glu—Ser—Ser—Gln—Lys—Thr SEQ ID NO:43 |
| TT₅T$_h$: | Asp—Val—Ser—Thr—Ile—Val—Pro—Tyr—Ile—Gly—Pro—Ala—Leu—Asn—His—Val SEQ ID NO:44 |
| CTT$_h$: | Ala—Leu—Asn—Ile—Trp—Asp—Arg—Phe—Asp—Val—Phe—Cys—Thr—Leu—Gly—Ala—Thr—Thr—Gly—Tyr—Leu—Lys—Gly—Asn—Ser SEQ ID NO:45 |
| DT₁T$_h$: | Asp—Ser—Glu—Thr—Ala—Asp—Asn—Leu—Glu—Lys—Thr—Val—Ala—Ala—Leu—Ser—Ile—Leu—Pro—Gly—His—Gly—Cys SEQ ID NO:46 |

-continued

| | |
|---|---|
| DT₂Tₕ: | Glu—Glu—Ile—Val—Ala—Gln—Ser—Ile—Ala—Leu—Ser—Ser—Leu—Met—Val—Ala—Gln—Ala—Ile—Pro—Leu—Val—Gly—Glu—Leu—Val—Asp—Ile—Gly—Phe—Ala—Ala—Thr—Asn—Phe—Val—Glu—Ser—Cys SEQ ID NO:47 |
| PFTₕ: | Asp—His—Glu—Lys—Lys—His—Ala—Lys—Met—Glu—Lys—Ala—Ser—Ser—Val—Phe—Asn—Val—Val—Asn—Ser SEQ ID NO: 48 |
| SMTₕ: | Lys—Trp—Phe—Lys—Thr—Asn—Ala—Pro—Asn—Gly—Val—Asp—Glu—Lys—His—Arg—His SEQ ID NO:49 |
| TraT₁Tₕ: | Gly—Leu—Gln—Gly—Lys—Hfis—Ala—Asp—Ala—Val—Lys—Ala—Lys—Gly SEQ ID NO:50 |
| TraT₂Tₕ: | Gly—Leu—Ala—Ala—Gly—Leu—Val—Gly—Met—Ala—Ala—Asp—Ala—Met—Val—Glu—Asp—Val—Asn SEQ ID NO:51 |
| TraT₃Tₕ: | Ser—Thr—Glu—Thr—Gly—Asn—Gln—His—His—Tyr—Gln—Thr—Arg—Val—Val—Ser—Asn—Ala—Asn—Lys SEQ ID NO:52 |

In a preferred embodiment to Th epitope is HB$_s$Th, Pt$_2$Th or TT$_1$ Th or MV$_{F1}$T$_h$.

LHRH has the amino acid sequence Glu-His-Trp-Ser-TyrGly-Leu-Arg-Pro-Gly (SEQ ID NO:1). LHRH analogs according to the invention have a substitution, deletion, or insertion of from one to about four amino acid residues provided that the analog is capable of stimulating an immune response crossreactive with LHRH. For example, replacing the glycine residue at position six with a D-amino acid, preferably Dlysine, produces an immunogenic analog of LHRH (Jayashankar et al.). The substitutions and insertions can be accomplished with natural or non-natural amino acids as defined herein.

Accordingly, peptides of this invention are Peptide A (SEQ ID NO:10; Table 1), Peptides F-L (SEQ ID NOS:11–17; Table 4) and Peptides 18-41 (SEQ ID NOS:18–41; Table 5). Preferred peptides include Peptide A, Peptide F and Peptide H. More preferred peptides include peptides 18, 19, 32-35, H and K, and most preferably 19, 32, H and K.

The peptides of this invention can be made by synthetic chemical methods which are well known to the ordinarily skilled artisan. See, for example, Grant, ed. (1992) *Synthetic Peptides: A User's Guide*, W.H.Freeman & Co., New York, N.Y., pp. 382. Hence, peptides can be synthesized using the automated Merrifield techniques of solid phase synthesis with either t-Boc or F-moc chemistry on an Applied Biosystems Peptide Synthesizer Model 430A or 431. To synthesize a K core moiety, unprotected [Di(tBoc) or Di(Fmoc) -N$_\alpha$, N$^\epsilon$) lysine residues are used in place of lysine residues with a protected ε-amino group. To add Pam$_3$Cys, the lipoamino acid S-[2,3-Bis(palmitoyloxy)-(2R)-propyl-N-palmitoyl-(R)-cysteine (Pam$_3$cys) is synthesized by chemical methods. Pam$_3$Cys is coupled to a peptide by solid-phase synthesis using Pam$_3$Cys-OH in the final coupling step to link the lipoamino acid to a resin-bound peptide chain. To improve the specificity of the final coupling reaction, the solid-phase peptide can be elongated with additional serine and lysine residues at the N-terminus.

After complete assembly of the desired peptide, the resin is treated according to standard procedures to cleave the peptide from the resin and deblock the protecting groups on the amino acid side chains. The free peptide is purified by HPLC and characterized biochemically, for example, by amino acid analysis or by sequencing. Purification and characterization methods for peptides are well known to one of ordinary skill in the art.

Alternatively, the longer linear peptides can be synthesized by well known recombinant DNA techniques. Any standard manual on DNA technology provides detailed protocols to produce the peptides of the invention. To construct a gene encoding a peptide of this invention, the amino acid sequence is reverse transcribed into a nucleic acid sequence, and preferably using optimized codon usage for the organism in which the gene will be expressed. Next, a synthetic gene is made, typically by synthesizing overlapping oligonucleotides which encode the peptide and any regulatory elements, if necessary. The synthetic gene is inserted in a suitable cloning vector and recombinants are obtained and characterized. The peptide is then expressed under suitable conditions appropriate for the selected expression system and host. The peptide is purified and characterized by standard methods.

The subject peptides can also be polymerized. Polymerization can be accomplished by reaction with dilute glutaraldehyde using routine methodology.

The efficacy of the peptides can be established and analyzed by injecting an animal, for example rats, and following the immune response to LHRH, the serum testosterone levels and palpating the testes. At the end of the experimental period the animal can be sacrificed and androgen-dependent organ weights obtained. Androgen-dependent organs include the testes, the epididymis, the prostate and the seminal vesicles. In a preferred method of measuring efficacy, the LHRH construct is formulated in alum and injected into rats. This method is detailed in the Examples.

Another aspect of this invention provides a vaccine composition comprising an immunologically-effective amount of one or more of the peptides of this invention and a pharmaceutically acceptable carrier. Such vaccine compositions are used in the methods of inducing infertility or treating prostatic hyperplasia, androgen-dependent carcinoma, prostatic carcinoma, testicular carcinoma, endometriosis, benign uterine tumors, recurrent functional ovarian cysts or (severe) premenstrual syndrome or prevention or treatment of estrogen-dependent breast tumors.

Accordingly, the subject peptides can be formulated as a vaccine composition using adjuvants, pharmaceutically-acceptable carriers or other ingredients routinely provided in vaccine compositions. Such formulations are readily determined by one of ordinary skill in the art and include formulations for immediate release and for sustained release, e.g., microencapsulation. The present vaccines can be administered by any convenient route including subcutaneous, oral, intramuscular, or other parenteral or enteral route. Similarly the vaccines can be administered as a single dose or divided into multiple doses for administration. Immunization schedules are readily determined by the ordinarily skilled artisan. For example, the adjuvants or emulsifiers that can be used in this invention include alum, incomplete Freund's adjuvant, liposyn, saponin, squalene, L121, emulsigen and ISA 720 as well as the other efficacious adjuvants and emulsifiers described in Tables 7–9. In a preferred embodiment, the adjuvants/emulsifiers are alum, incomplete Freund's adjuvant, a combination of liposyn and saponin, a combination of squalene and L121 or a combination of emulsigen and saponin.

The vaccine compositions of the instant invention contain an immunoeffective amount of one or more of the LHRH-containing peptides and a pharmaceutically acceptable carrier. Such compositions in dosage unit form can contain about 0.5 µg to about 1 mg of each peptide per kg body weight. When delivered in multiple doses, the dosage unit form is conveniently divided into the appropriate amounts per dosage.

Vaccines which contain cocktails of two or more of the subject peptides enhance immunoefficacy in a broader population and thus provide a better immune response against LHRH. For example, a cocktail of Peptides A, F and H is useful. A preferred cocktail includes Peptides 18, 19, K and H; another includes 32, 19, K and H. Other immunostimulatory synthetic peptide LHRH immunogens are arrived at through modification into lipopeptides so as to provide built-in adjuvanticity for potent vaccines. The immune response to synthetic peptide LHRH immunogens can be improved by delivery through entrapment in or on biodegradable microparticles of the type described by O'Hagan et al. (1991) Vaccine 9:768–771. The immunogens can be encapsulated with or without adjuvant, including covalently attached Pam$_3$Cys (see Example 15), and such microparticles can be administered with an immunostimulatory adjuvant such as Freund's Incomplete Adjuvant or alum. The microparticles function to potentiate immune responses to an immunogen and to provide time-controlled release for sustained or periodic responses, for oral administration, and for topical administration [O'Hagan et al.; Eldridge et al. (1991) Molec. Immunol. 28:287–294].

A further aspect of the invention relates to a method for reducing or suppressing activity of LHRH levels in a mammal by administering one or more of the subject peptides to the mammal for a time and under conditions sufficient to induce functional antibodies directed against said LHRH. Suppression of LHRH levels can be used to induce infertility via suppression of spermatogenesis or ovulation. Likewise, suppression of functional, circulating LHRH levels is effective to treat prostatic hyperplasia, androgen-dependent carcinoma, prostatic carcinoma, testicular carcinoma, endometriosis, benign uterine tumors, recurrent functional ovarian cysts or (severe) premenstrual syndrome or estrogen-dependent breast tumors (treatment of such breast tumors includes prevention thereof). In animals, suppression of circulating levels of functional LHRH is useful to reduce boar taint in pigs, to immunocastrate dogs and cats, and to geld stallions.

Serum LHRH can be measured by radioimmunoassay (RIA), enzyme-linked immunoadsorbent assay (EIA) or other convenient method. Antibodies against LHRH are measured by RIA (see Example 2) or EIA. Serum testosterone is measured by RIA. The vaccine dosage needed to reduce or suppress activity of LHRH can be determined by the ordinarily skilled artisan. Such compositions in dosage unit form can contain about 0.5 µg to about 1 mg of each peptide per kg body weight. When delivered in multiple doses, the dosage unit form is conveniently divided into the appropriate amounts per dosage.

More particularly, the invention provides a method for inducing infertility in a mammal by administering the subject vaccine compositions to the mammal or a farm animal for a time and under conditions to produce an infertile state in the mammal or the farm animal. As used herein an infertile state is that state which prevents conception. Infertility can be measured by methods known in the art, e.g. evaluation of spermatogenesis or ovulation, as well as by statistical modeling of experimental animal data. An indicator of infertility in males includes reduction of serum testosterone to near castration levels. Compositions in dosage unit form can contain about 0.5 µg to about 1 mg of each peptide per kg body weight. When delivered in multiple doses, the dosage unit form is conveniently divided into the appropriate amounts per dosage.

Similarly, this invention relates to a method for treating androgen-dependent carcinoma by administering the subject vaccine compositions to the mammal for a time and under conditions to effect regression of the carcinoma, or to prevent (further) growth of the carcinoma. Compositions in dosage unit form can contain about 0.5 µg to about 1 mg of each peptide per kg body weight. When delivered in multiple doses, the dosage unit form is conveniently divided into the appropriate amounts per dosage.

The identification and synthesis of peptides with a defined B-cell or a cytotoxic-T cell epitope and its immediate flanking sequences provides an essential component for the production of a synthetic peptide immunogen. However, additional required components, such as effective helper T cell epitopes, which must be present to provide the full range of immune responses necessary to elicit the desired biological effect, may not be included in such sequences. Addition of a universal synthetic immune stimulator to a poorly antigenic peptide immunogen provides an effective solution to this problem. A universal immune stimulator which when linked to any peptide or protein (i.e., the peptide hapten), containing either B cell and/or cytotoxic T lymphocyte (CTL) epitopes, causes potent immune responses to the coupled peptide or protein. The universal immune stimulator consists of a promiscuous helper T cell ($T_h$) epitope which elicits an immune response to the coupled peptide in members of a heterogeneous population expressing diverse HLA phenotypes (as hereinbefore defined) and an adjuvant peptide sequence from the invasin protein of Yersinia which is capable of specifically binding to CD4$^+$ and CD8$^+$ lymphocytes (as defined herein above). Further, the immune stimulator can have a lipid moiety or charged amino acid residues which act to increase the binding affinity of the immune stimulator for biological membranes. The target peptide hapten can be a self molecule and, therefore, not immunogenic without modification, such as LHRH, which following addition of the immune stimulator can be used in the treatment of cancer or other non-infectious diseases. similarly, the peptide hapten can be a B cell epitope representing neutralizing determinants or CTL epitope peptides from a viral, bacterial or a parasitic pathogen for use as a vaccine or an immunotherapy.

In order to provide maximum coverage, that is maximum immune responses in members of a genetically diverse population (e.g. as broad-based response as possible), synthetic peptides contain the invasin domain, a promiscuous Th epitope, and a B cell epitope (or a CTL epitope) can be mixed together and formulated with adjuvant and vaccine carrier. Alternatively, rather than peptide mixtures, peptide libraries (i.e. SSALs) which represent the promiscuous $T_h$ epitope and/or the B cell or CTL epitope are synthesized into the peptides of the invention and formulated for vaccine delivery. This technology, i.e. SSAL, provides a significant advantage in both simplifying the manufacture as well as improving the immunologic coverage provided relative to simple mixtures of peptides for use as immunogens.

The synthetic peptides of the invention are made by automated chemical synthesis as described above.

Specific peptide haptens of the present invention are described below together with diseases that can be ameliorated by immune responses to such peptides or immunotherapies provided by such peptides.

*Treatment of non-insulin dependent diabetes by Amylin based immunotherapy.* Amylin is a 37 amino acid residue peptide hormone produced by the β cells in the islets of Langerhans (Snake, et al 1988, *J. Biol. Chem.* 263:17243–17246). It is produced as an 89 amino acid prepropeptide, which is proteolytically cleaved to generate the mature active form of the molecule, that is amidated at the carboxy-terminus during the cleavage process (Cooper, et al., 1989, Biochim. Biophys. Acta. 1014: 247–258). A disulfide bridge is present between Cys 2 and Cys 7 of mature amylin. Both the carboxy-terminal amide residue and the disulfide bridge are required for full biologic activity (Cooper, et al., 1988, Proc. Natl. Acad. Sci. USA 85:7763–7766). Amylin is co-secreted with insulin from the pancreas and they, in conjunction, regulate glucose metabolism and the production of carbohydrate energy stores by a metabolic pathway known as the Cori cycle, which links striated muscle, the liver and adipose tissue. Insulin primarily drives the forward limb of this cycle, i.e. glucose uptake from the blood by striated muscle and its conversion into glycogen. Amylin primarily regulates the reverse limb, i.e. the promotion of muscle glycogen breakdown to lactate, which is the substrate for glyconeogenesis and glycogen production in the liver. The dominant action of amylin is to be a non-competitive antagonist of insulin in skeletal muscle and the liver, while insulin action in adipose tissue is unhindered by this peptide hormone.

Over-production of amylin is associated with noninsulin-dependent diabetes mellitus (NIDDM), and results in the deposition of amylin in β cells in the form of insoluble amyloid. Over 2% of the US population suffers from this condition, meaning that well over 5 million people are currently afflicted. Amyloid deposition in the pancreas is also a condition associated with aging, and the elderly having this condition may or may not express overt symptoms. High levels of amylin in the blood lead to a number of biological consequences, including: inhibition of glucose-stimulated insulin production by the pancreas; a decrease in the rate of insulin-stimulated glucose uptake and its incorporation into glycogen by striated muscle, i.e. insulin resistance resulting from a inhibition of glycogen synthetase activity; an increase in glycogenolysis by striated muscle mediated by the conversion of glycogen phosphorylase from an inactive to its active form; overcoming inhibition by insulin of glucose liberation by glucagon; increasing lactate release from striated muscle and its incorporation into glucose by the liver; and opposing inhibition by insulin of hepatic glucose output. Thus, the major feature of amylin over-expression (in addition to amyloid deposition) is the accumulation of high levels of glucose in the blood, which can lead to obesity as one sequela, since glucose uptake and formation of triglycerides by adipose tissue is not inhibited under conditions of amylin excess. The long-term consequences of chronic NIDDM is the reduction in function of the islet β cells through amyloid deposition, thus reducing the production of both functional amylin and insulin. Chronic NIDDM can result in persistent hypertension, ischemia, small vessel disease, blindness and increased incidence of systemic infection and limb loss.

In addition to its role in glucose metabolism, amylin mimics the effect of calcitonin gene releasing peptide (CGRP) by also acting as a vasodilator. For example, amylin elicits transient hypotension when administered intravenously. The two molecules share approximately 50% homology at the amino acid level. Each are 37 amino acid residues long, possess a disulfide bridge between cys 2 and cys 7, and are amidated at the carboxy-terminus. The disulfide bridge and the carboxy-terminal amidation are required for full biological activity of both amylin and CGRP. However, irrespective of their close similarity, CGRP is approximately 100 times more active in vasodilation than amylin. Amylin is also structurally related to the calcitonins. It shares some functions with these molecules as well. For example, when either is administered to the brain both suppress food intake, and both regulate bone resorption by osteoclasts and the levels of serum calcium. Again, however, calcitonin is at least an order of magnitude more efficient in these activities than amylin.

Specific examples are provided below for the linkage of a universal synthetic immune stimulator to amylin such that antibody responses are directed to this peptide hormone. Inhibition of the action of amylin by mounting selective immune responses to it causes the amelioration of the pathology associated with its overproduction, namely NIDDM.

*Treatment of peptide ulcer disease and cancers associated with an overproduction of Gastrin by Gastrin-based immunotherapy.* Gastrin is a well-characterized gastrointestinal hormone whose purification and chemical characterization was first achieved in 1964 (Gregory, et al., 1964, Nature 204: 931–933). Gastrin is first produced as a 101 amino acid long precursor molecule known as preprogastrin. Preprogastrin consists of the following segments, from the amino- to the carboxy- terminus: a 21 amino acid long signal sequence, a 33 residue long intervening peptide, the 34 residue long "big gastrin" molecule, Gastrin$_{34}$, followed by a 9 residue sequence at the carboxy-terminus. The signal sequence is cleaved from the body of preprogastrin during its entrance into the endoplasmic reticulum to yield progastrin. A trypsin-like cleavage then removes the intervening peptide from the amino-terminus of progastrin, and the 6 carboxy-terminal residues are also cleaved by a similar process (Shields and Blobell, 1978, J. Biol. Chem. 253:3753–3756). The remaining peptide, termed glycine-extended gastrin possesses the sequence -Gly-Arg-Arg at the carboxy-terminal end. These three residues are then removed, and the carboxy-terminal residue Phe of big gastrin, or Gastrin$_{34}$, is amidated (Eipper, et al., 1985, 116:2497–2504). Finally, the carboxy-terminal 17 amino acid residues are cleaved to yield Gastrin$_{17}$ (Dockray, et al., 1975, Nature 243:770–772). Approximately one-half of the processed gastrin 34 and 17 molecules found in the antrum and duodenum are sulfated at the unique tyrosine residue (Andersen, 1984, Scand. J. Clin. Lab. Invest. Suppl. 168:5-24).

Gastrin has several important functions, the two most important being stimulation of gastric acid secretion and stimulation of the growth of cells in the gastrointestinal tract. The hormone exists in at least two molecular forms, "G$_{34}$" and "G$_{17}$", (see Table 11, Seq ID Nos. 69 and 74 respectively), termed according to the number of amino acid ("AA") residues in each molecule as described above.

Although G$_{34}$ and G$_{17}$ are thought to be equipotent on a molar basis as stimulators of acid release, G$_{34}$ is more probably responsible for the stimulation of growth of the gastrointestinal mucosa and the maintenance of the basal acidity of the stomach. G$_{34}$ is the principal form present during interdigestive periods. $G_{34}$ has a serum half life approximately six times as long as $G_{17}$ (40 minutes versus 6 minutes) and is produced in both the stomach and the duodenum. Alternatively, $G_{17}$ is the primary agent of gastrin-stimulated acid secretion following meals, which accounts for roughly 60%–70% of the gastrin-mediated acid release.

Gastric acid is produced in a specialized stomach cell, the parietal cell. Parietal cells can be stimulated to secrete acid by acetylcholine, histamine and gastrin, upon the activation to specific receptors on the surfaces of parietal cells binding with each of these compounds. Among these stimulators, the most potent is Gastrin$_{17}$.

Excessive secretion of stomach acid has been known to be a central factor in peptic ulcer disease, which exists in two forms, duodenal ulcers and gastric ulcers. Antacid preparations are a commonly used method of treatment for ulcers. Antacid treatments merely neutralize stomach acid after it is produced and are insufficiently therapeutic because of failure to affect the source of acid production.

Current approaches to the control and cure of peptic ulcers center upon devising drugs that inhibit the ability of one or more of the stimulator compounds to evoke acid production or secretion. The most effective group of drugs developed for this application have been the H2 antagonists (e.g. Tagamet and Zantac) which block the histamine H2 receptors on gastric parietal cells and inhibit acid secretion. These drugs, however, require relatively large doses on a daily basis and may induce several undesirable side effects. In those cases where H2 antagonists have healed ulcers, relapses occur in almost 100% of the treated individuals within a year of discontinuation of treatment. No successful chemical antagonists have been identified to inhibit the action of the peptide hormone gastrin.

Besides being the most potent stimulator of acid secretion by parietal cells, gastrin also promotes the growth of colon carcinoma, gastric carcinoma and gastric carcinoids. Another peptide hormone structurally related to gastrin is Cholecystokinin (CCK). CCK stimulates the growth of pancreatic carcinomas and small cell lung cancers. Furthermore, certain cancers of the gastrointestinal tract, apudomas, are found to produce extremely large quantities of gastrin, while some tumors of the pituitary are also found to produce excessive amounts of CCK. Excessive gastrin production by apudomas stimulates hypertrophy of the acid secreting epithelium of the stomach, leading to excess stomach acid secretion, peptic ulcer, and neoplastic changes in the epithelium. Excessive chronic CCK stimulation of pancreatic cells has been demonstrated to induce pancreatic hypertrophy, hyperplasia and certain premalignant changes.

Current treatment for tumors stimulated by gastrin or by the related CCK and for tumors that produce gastrin or CCK consists primarily of surgical resection of the cancerous tissue. This approach is frequently unsuccessful or not appropriate; in many instances the tumors cannot be located or are present in anatomic sites that are inoperable. In most instances these tumors do not respond well to radiation or chemotherapy regimens. New treatments are urgently needed to supplement present procedures.

A therapeutic method of selectively neutralizing the biological activity of these gastrointestinal hormones (e.g., Gastrin$_{34}$, Gastrin$_{17}$ and CCK) would provide an effective means of controlling or preventing the pathologic changes resulting from excessive hormone production. Control of gastrin levels by anti-gastrin antibodies induced by either active immunization or passive administration of preformed antibodies is a logical approach for such gastrin-related disease intervention. Such attempts have been made by many over the past two decades without much success (Jaffe, B. M., et al., 1971, "Gastrin resistance following immunizations to the C-terminal tetrapeptide amide of gastrin. Surgery 69: 232–238; Jaffe, B. M., et al., 1970, "Inhibition of endogenous gastrin activity by antibodies to the carboxyl terminal tetrapeptide amide of gastrin", Gastroenterology 58: 151–156; Jaffe et al., 1969, "Inhibition of endogenous gastrin activity by incubation with antibodies to the C-terminal tetrapeptide of gastrin. Surgery 65: 5633–639 and Gevas, P. C. et al. EPO 380230 "Immunogens against gastrin peptides"), mostly due to the lack of site-directed gastrin reactivity and the poor immunogenicities of inadequately designed gastrin immunogens.

Specific examples are provided for the linkage of the universal synthetic immune stimulator to gastrin and its fragments such that selective antibody responses are elicited to various sites of this peptide hormone. These specific gastrin-reactive antibodies can selectively neutralize the biological activities of the hormone peptide and other pathological conditions. Specific inhibition or depletion of the gastrin by the generation of potent anti-gastrin and CCK crossreactive antibodies provides a method for the treatment of gastrin or CCK stimulated tumors and tumors that overproduce either hormone. The immunotherapeutic approach described in the present invention is non-invasive, does not require frequent repeated treatments, does not damage normal tissue and thus, has reduced side effects.

*Treatment of gastric ulcers, tumors and lung cancer by gastrin releasing peptide-based immunotherapy.* Gastrin Releasing Peptide (GRP) is a 27 amino acid residue hormone derived from a 138 amino acid residue long prepromolecule (Spindel, et al., 1986, Proc. Natl. Acad. Sci. USA 83:19 23). GRP is the mammalian homologue of amphibian bombesin (McDonald et al., 1979, Biochem. Biophys. Res. Commun. 90:227–233). It is a ubiquitous hormone found in the gastrointestinal tract, nervous system and pulmonary tract. Within the gastrointestinal tract, it regulates the production of gastrointestinal hormones, including Gastrin 34 and Gastrin 17 (McDonald, et al., 1983, Regul. Pept. 5:125–137). The same hormone, in the central nervous system, regulates hypothermia and hypoglycemia (Tache and Brown, 1982, Trends Neurosci. 5:431–433). GRP is present in the lung in pulmonary neuroendocrine cells (Moody, et al., 1981, Science 214:1246–1248) and it has been found to be an important marker for neuroendocrine cell hyperplasia (Aguayo, et al., 1989, J. Clin. Invest. 84:1105–1113). It is also a significant autocrine growth factor for small cell lung carcinomas, and is therefore an important target for intervention therapies for the treatment of lung cancer (Mulshine, et al., 1991, Oncology 5:25–33). Therefore, immune regulation of GRP through induction of antibodies to it, via immunization with a universal synthetic immune stimulator linked to the hormone, provides an effective therapy for gastric ulcers and tumors, as well as for lung cancer.

Specific examples are provided below for the linkage of the universal synthetic immune stimulator to GRP, and its fragments, such that antibody responses are generated to allow an effective GRP-based immunotherapy.

*Treatment of allergy by IgE-CH4 based immunotherapy.* Treatment of IgE-mediated allergic responses such as asthma and hay fever by desensitization or hyposensitization has been known and practiced since early in this century (Noon L. (1911) *Lancet*, i:1572–1573). Limitations to such an allergen-based immunotherapy include difficulties in identifying the allergen involved and the adverse reactions frequently caused by the use of the allergen once it is identified (World Health Organization and International Union of Immunological Societies Working Group Report: Current status of allergen immunotherapy. (1989) Lancet, i:259–261). Other treatments for the relief of allergies employs therapeutic compounds to block the cascade of cellular events that is responsible for allergic reactions. Unfortunately, anti-histamines block vary late in the cascade as to provide only delayed and partial relief, and corticosteroids act too early in the cascade to cause an undesirably broad immunosuppression. The results of using these two classes of compounds further point to the need in developing a treatment modality by inhibiting allergic responses at the level of IgE. This may be possible either by inhibiting its synthesis, such as is accomplished by the inconvenient desensitization method, or by blocking the stimulatory action of IgE on mast cells and basophils.

Stanworth et al. (Stanworth D. R., Kings M, Roy PD, et al. (1979) *Biochem. J.,* 180:665–668; Stanworth D. R. (1984) *Mol. Immunol.,* 21:1183–1190; Stanworth D. R., and Bint DS. (1986) *Mol. Immunol.,* 23:1231–1235, 1986; Bint DS, and Stanworth D. R. (1987) *Eur. J. Immunol.,* 17:437–440; Stanworth D.R. (1988) *Mol. Immunol.,* 25:1213–1215) reported the identification of a site located within the Fc CH4 region of human IgE that are involved in the immunological triggering process.

Stanworth et al. further demonstrated the feasibility of providing an immunotherapy to patients with IgE-mediated allergic reactions (Stanworth D. R., Jones VM, Lewin IV, and Nayyar S. (1990) *Lancet,* 336:1279–1281; Jones V, Lewin IV, Nayyar S, and Stanworth D. R. GB patent application No. 9013478.4) through the use of a peptide-based vaccine. More specifically, an IgE CH4 decapeptide with a sequence of LysThr-Lys-Gly-Ser-Gly-Phe-Phe-Val-Phe-NH$_2$ (SEQ ID NO:79), previously shown to approximate a conformational site on IgE involved in activation of the mast cells and basophils by IgE, was coupled to carrier proteins such as keyhole limpet hemocyanin (KLH) and used as an immunogen. Animal immune sera obtained from such immunizations were found to moderately reduce the decapeptide-induced histamine release from rat peritoneal mast cells in a titer-dependent fashion. Inhibitory activity by these immune sera was further confirmed by in vivo passive cutaneous anaphylaxis (PCA) tests under conditions of multiple allergen application.

A major deficiency of these prototype "IgE CH4 peptide" vaccines is weak immunogenicity, an inherent problem associated with almost all self-antigens. In the present invention, specific examples are provided for the linkage of the universal synthetic immune stimulator to the CH4 peptide of IgE such that potent antibodies directed to this activation site on IgE can be generated, which in turn block the stimulatory action of IgE on mast cells and basophils, thus resulting in an effective treatment of allergy.

*Other peptide haptens and treatments. Chlamydia trachomatis* is an obligate intracellular bacteria which infects the mucosal surfaces of the genital tract and the eye. There are fifteen relevant different serovars of *C. trachomatis* based upon serological reactivity. These serovars are grouped according to the major disease symptoms each is associated with: the eye disease or trachoma-associated group which includes serovars B, Ba, A and C; the sexually transmitted disease-associated group which includes serovars D, E, F, G, H, I, J & K; and, the lymphogranuloma venereum-associated serovars $L_1$, $L_2$ & $L_3$ (Murdin, et al., 1993, Infect. Immun. 61:4406–4414). Infection by C. trachomatis, by itself and in combination with *Neisseria gonorrhea,* is responsible for over one-half of the diagnosed cases of pelvic inflammatory disease (PID) of women or salpingitis. Each year, over one million women in the United States are diagnosed with PID, and infertility is the expected sequela in over 25% of the cases (Washington, et al., 1987, J. Am. Med. Assoc. 257:2070–2072). In addition to disease of the genital tract, *C. trachomatis* is the leading cause of preventable blindness (i.e. trachoma) in the world. Currently, over 10 million people have been permanently blinded by this condition (Su and Caldwell, 1992, J. Exp. Med. 175: 227–235).

The life cycle of C. trachomatis includes two alternative forms. The elementary body (EB) which is the extracellular, non-replicative, condensed, spore-like infectious form of the organism, and the reticulate body (RB) is the intracellular, vegetative form which produce EBs. The cycle of infection is initiated by attachment of EBs to cells of the permissive host. This process involves non-specific charge interactions followed by specific receptor-ligand binding between the EB and the host cell membrane. The charge interactions are mediated by the major outer membrane protein (MOMP) of Chlamydia, while the specific bacterial attachment protein (i.e. the protein involved in host cell receptor recognition) has not yet been identified (Stephens, 1993, Infect. Agents Dis. 1:279–293).

Following the initial acute stage of infection, during which EBs are shed, the disease progresses to a chronic pathology that is largely associated with cellular lymphoproliferative responses (Morrison et al. 1989, J. Exp. Med. 169:663–675; Morrison et al., 1989, J. Exp. Med. 170: 1271–1283; Taylor, et al., 1990, Infect. Immun. 58:3061–3063). Thus, most of the disease pathology is associated with the immune responses to chlamydial proteins and not replication of the pathogen per se. During this chronic phase, it is rare to isolate/identify EB or RB.

Vaccine design is targeted at interrupting EB attachment to permissive cells, since the RB is inaccessible and Chlamydia proteins are not expressed on the surfaces of infected cells. Therefore, the major outer membrane protein (MOMP) protein of EB has been heavily investigated. MOMP is the dominant immunogen on the surface of EBs, mediates EB attachment to cells, and antibodies to MOMP are not implicated with pathology. The immunodominant sites on MOMP consist of four surface exposed variable domains (VDI–IV) linked by invariant regions (Cheng, et al., 1992, Infect. Immun. 60:3428–3432). Antibodies elicited to MOMP, or to the specific critical variable domains of MOMP, can block the initial interaction of the EB with the membrane of the permissive host cell and prevent infection (Caldwell et al., 1987, Infect. Immun. 55: 93–98; Taylor, et al., 1988, Invest. Ophthalmol. Vis. Sci. 29:1847–1853; Su and Caldwell, 1991, Infect. Immun. 59:2843–2845). Therefore, a vaccine designed to maximize the immune responses to a wide range of the immunogenic variable domains of MOMP is anticipated to be broadly efficacious. This vaccine is provided by linking the universal synthetic immune stimulator to peptides which represent the MOMP variable domains.

The World Health Organization estimates that 14 million people are now infected with HIV-1. Moreover, WHO estimates that by the year 2000, 40 million persons will have contracted HIV-1 (Centers for Disease Control, 1991). The natural history of HIV infection suggests that virtually all HIV-infected persons will eventually progress from asymptomatic infection to the morbidity and mortality associated with AIDS. Despite global investments in prevention and education campaigns, HIV infection rates are still expanding in several regions of the world. From a public health perspective, the development of a safe and effective vaccine which protects from HIV infection and disease must be an international priority.

Several studies have demonstrated that neutralizing antibodies of sufficient titer which are directed against the V3 domain of gp120 protect chimpanzees from challenge with HIV-1 (Berman et al., 1990, Nature 345:622–625; Girard et al., 1991, Proc. Nat. Acad. Sci. U.S.A. 88:542–546; Emini et al., 1992, Nature 355:728–730). No other HIV-1 domain thus far identified is as effective as V3 in eliciting protective antibody responses, thus V3 is known as the principal neutralizing domain (PND). The V3 domain contains a linear stretch of amino acids that mediates critical events required for virus entry into permissive cells and to which virus neutralizing antibodies are directed. Therefore, a universal synthetic immune stimulator linked to a synthetic peptide sequence corresponding to the V3 PND can potentiate antibody responses to V3 and thus HIV. The example provided below describes a construct which is an important immunogen for inclusion in an effective HIV-1 vaccine.

The following examples further illustrate the invention.

EXAMPLE 1

Immunization of Rats with Linear and Octameric LHRH-containing peptides

A. Immunogen preparation: Peptides A–E (Table 1) and all other peptides were synthesized using the strategy of solid phase synthesis employing the standard F-moc chemistry performed on an Applied Biosystems Peptide Synthesizer Model 430A or 431 according to manufacturer's instructions. Di(Fmoc)—$\alpha$, $\epsilon$ $NH_2$ protected lysine was used, in doubling concentrations after each additional cycle of coupling, for synthesis of the heptalysyl core ($K_4K_2K$ or $K_{core}$). After complete assembly of the peptide, the resin was treated with TFA (trifluroacetic acid) according to standard procedures to cleave the peptide from the resin and deblock the protecting groups on amino acid side chains. The free peptide was then purified by HPLC and characterized biochemically by amino acid analysis.

The structure of the peptides from the amino terminus to the carboxyl terminus is as follows: Peptide A is a linear peptide with three domains: 3 lysine residues (3K), the hepatitis B surface antigen helper T cell epitope ($HB_sTh$ epitope) and LHRH. Peptide A is thus represented by 3K—$HB_sTh$—LHRH. Peptide B is an octameric peptide with each branch having two copies of LHRH. The branches are attached to a heptalysyl core that has a $HB_sTh$ epitope attached to its C terminal tail. Peptide B is thus represented by (LHRH—LHRH)$_8$—$K_{core}$—$HB_sTh$. Peptide C, represented by (LHRH—LHRH—LHRH)$_8$—$K_{core}$— $HB_sTh$, is similar to Peptide B except the branch has three copies of LHRH. Peptide D, (LHRH—$HB_sTh$)$_8$—$K_{core}$—AA, is an octameric peptide with each branch having one LHRH domain and one $HB_sTh$ domain. The branches are attached to a heptalysyl core with two alanine residues (AA) attached to its C-terminal lysine. Peptide E, (LHRH—LHRH—$HB_sTh$)$_8$—$K_{core}$—AA, is an octameric peptide with each branch having two LHRH domains and one $HB_sTh$ domain. The branches are attached to a heptalysyl core with two alanine residues attached to its C-terminal lysine. The actual sequences of these peptides are shown in Table 1.

For immunizations administered at weeks 0 and 2, 600 µg of each peptide was dissolved in 3 mL of an adjuvant solution of 0.2% Tween 80, 2.5% Pluronic L 121, 0.9% NaCl (TP). The solution was stored at 4° C. until use and vortexed for 3 to 5 min prior to injection. Each rat received 100 pg per injection in 0.5 ml. For the immunization administered at week 5 in Freunds' complete adjuvant, 4 mg of each peptide was dissolved in 2 mL of 0.9% NaCl and emulsified with an equal volume of Freunds' complete adjuvant. Each rat received 500 µg per injection.

B. Immunization schedule and serum collection: Sexually mature, male Sprague-Dawley rats (n=5) were immunized subcutaneously (s.c.). Booster injections were given s.c. at weeks 2 and 5. Blood was collected at weeks 3, 6, 7 and 11 for rats injected with Peptides A, B and C, or at weeks 3, 6, 7 and 8 for rats injected with Peptides D and E.

Blood collection from the middle caudal artery was performed by injecting the rats with 1 mL of sodium pentobarbital (64.8 mg/mL; Anthony Products Co., Accadia, CA) diluted 1 to 10 in 0.9% NaCl administered intraperitoneally. The tails were kept in 48° C.+0.5° C. water for 2 min and rapidly massaged with paper towels (i.e., milked). Blood was collected immediately into a 5 mL syringe outfitted with a 23 gauge needle. Typically, 3 to 4 mL of blood was obtained. The serum was collected by centrifugation for 25 min at 3000 rpm. The serum was aliquoted in 300 µL volumes and stored frozen until used for assays.

EXAMPLE 2

Immunogenic and Therapeutic Efficacy of Peptides A–E

A. Assay methods and organ weight determinations: The anti-LHRH titer in each serum sample was measured by RIA [Ladd et al. (1988) Am. J. Reprod. Immunol. 17:121–127]. Antisera were diluted 1:100 (V:V) in 1% bovine serum albumin (BSA), pH 7.4. An equal volume of diluted sera was added to 100 µL of [$^{125}$I]-LHRH diluted in 1% BSA to contain approximately 15000 cpm for 5.25 pg LHRH (New England Nuclear Company, Boston, Mass.). The solution was incubated overnight at room temperature and antibody-bound LHRH was precipitated with 400 µL of 25% polyethylene glycol (MW 8,000) in 0.01M phosphate-buffered saline (PBS), pH 7.6, and 200 µL of 5 mg/mL bovine gamma globulin in PBS. Antibody titers are expressed as nmol iodinated LHRH bound per liter of serum.

Serum testosterone levels were measured using an RIA kit from Diagnostic Products (Los Angeles, Calif.) according to manufacturer's instructions. The lower detection limit for testosterone ranged from 0.01 to 0.03 nmol/L. Each sample was analyzed in duplicate.

At 11 weeks (Peptides A–C) or 8 weeks (Peptides D and E) after the initial injection, the rats were sacrificed by overexposure to carbon dioxide. The maximum amount of trunk blood was collected. The androgen-dependent sex organs (testes, epididymis, prostate and seminal vesicles) were dissected from each rat, paper towel dried and weighed.

B. Results: Groups of five rats were immunized with Peptides A–E. During the course of the study, anti-LHRH titers and testosterone levels were monitored in each rat. At the end of the study the rats were sacrificed and the androgen-dependent organ weights were obtained. The anti-LHRH titer, testosterone level and testes weight for each rat at the time of sacrifice are shown in Table 2. A summary of this data is provided in Table 3 together with average weights of other androgen-dependent organs.

Rats immunized with Peptide A produced antibodies against LHRH as measured by the RIA. None of the rats immunized with the other peptides (e.g. B, C, D and E)

produced any significant antibody titers against LHRH. The average anti-LHRH titer (nmol/L) at week 11 (Peptides A–C), week 8 (Peptides D–E) and control rats are reported in Table 3. The average anti-LHRH titer for the 5 rats immunized with Peptide A was 1.94 nmol/L, whereas the rats from the remaining groups had titers ranging from 0.48 to 0.73 nmol/L. The average weights of androgen-dependent organs from these groups of animals are reported in Table 3 and depicted graphically in FIG. 1. Rats immunized with Peptide A showed a significant decrease (about 40%) in organ weights relative to the control animals.

The results indicate that the presence of LHRH at the C-terminus of the peptide is more effective at stimulating antibody production and the concomitant reduction of androgen-dependent organ weights. In this regard, Peptide A has a C-terminal LHRH domain, whereas non-effective Peptides B-E have N-terminal or internal copies of LHRH.

Figure 3:
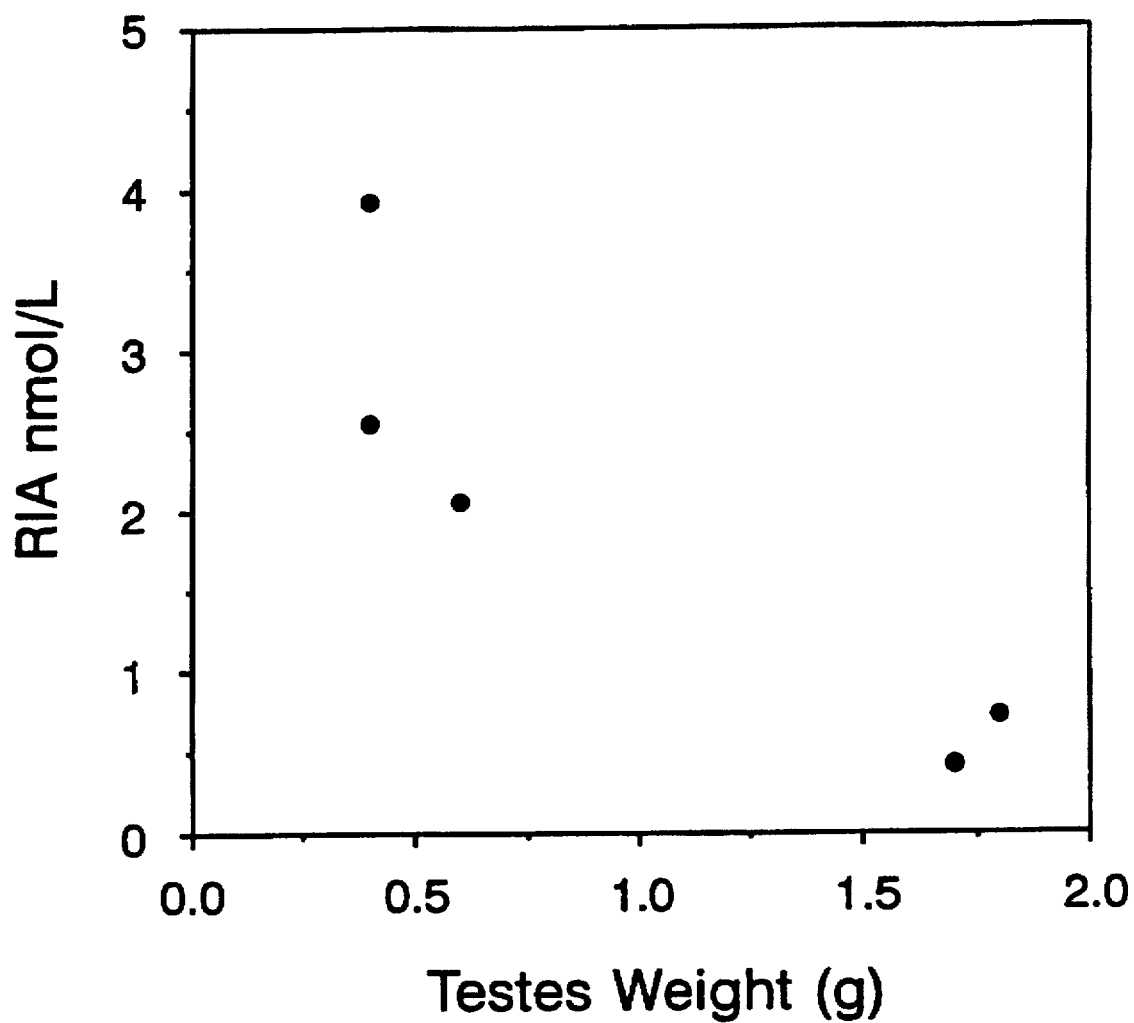

While the average reduction of androgen-dependent organ weights of the Peptide A rats relative to Peptide B-E rats and control rats was significant, this drop was attributed to dramatic reductions that occurred in three of the five animals. Hence, the group A rats were classified into responder and non-responders and the data reanalyzed. The average androgen-dependent organ weights of responders and non-responders depicted in FIG. 2 graphically illustrates the large difference between these two groups. Responder animals had undetectable levels of serum testosterone (Table 2). FIG. 3 shows the inverse relationship between anti-LHRH titers and testes organ weight. The relationship is similar for the other androgen-dependent organ weights.

EXAMPLE 3

Immunization with a Linear Peptide Containing a Pertussis Toxin Th Epitope

Figure 4:
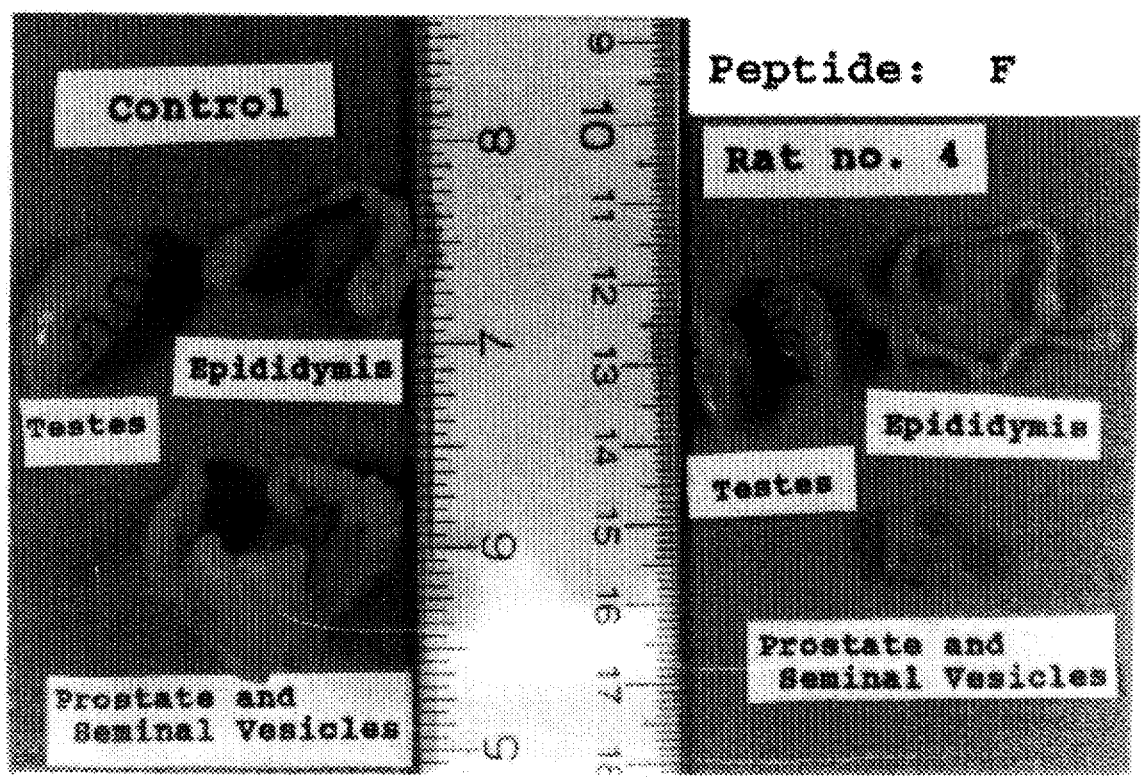

Peptide F (PT$_1$Th—LHRH; Table 4) was synthesized and purified as described in Example 1. The peptide was prepared for immunization as described in Example 1 except the adjuvant was 0.5% alum. Immunizations were administered s.c. to Sprague Dawley rats at weeks 0, 2 and 4. Determination of anti-LHRH titers, testosterone levels and androgen-dependent organ weights were obtained and analyzed as described in Example 2. Eleven weeks after the initial immunization, the testes, epididymis, prostate and seminal vesicles were significantly smaller than those obtained in control animals (FIG. 4).

EXAMPLE 4

Peptide Cocktails for Induction of anti-LHRH Response in Broad Populations

Mixtures of potent synthetic LHRH peptide immunogens are formulated in combinations to provide broadly potent vaccines. Peptides A, F and H (Table 1 and Table 4) are prepared as described in Example 1 and combined in a cocktail for immunization into sexually mature male rats at weeks 0, 3 and 6. The primary injection is in Freunds' complete adjuvant and the booster injections are in Freunds' incomplete adjuvant. Bleeds are done at weeks 0, 3, 6, 9 and 11. Animals are sacrificed at week 11 for organ weight determinations. The results are assayed and evaluated as described in Example 2.

EXAMPLE 5

Dose Dependence of Peptide A

Peptide A, 3K—HB$_s$T$_h$—LHRH, was synthesized as described in Example 1. This peptide was tested for efficacy in accordance with the experimental design set forth below:

Experimental Design

Immunogen: peptide A
Controls: unmodified LHRH & adjuvant groups
Dose: 100 or 500 µg per immunization
Route: intramuscular
Adjuvant: Freund's complete/incomplete
Schedule: week 0 (FCA), 3 and 6 weeks (IFA)
Species: 8 sexually mature Sprague-Dawley male rats/group
Assay: LHRH-specific antibody serum testosterone LH and FSH levels relative testis size by palpation
Necropsy: at 10 weeks determine testis weights prostate+ seminal vesicle weights epididymis weights

Results

Figure 5:
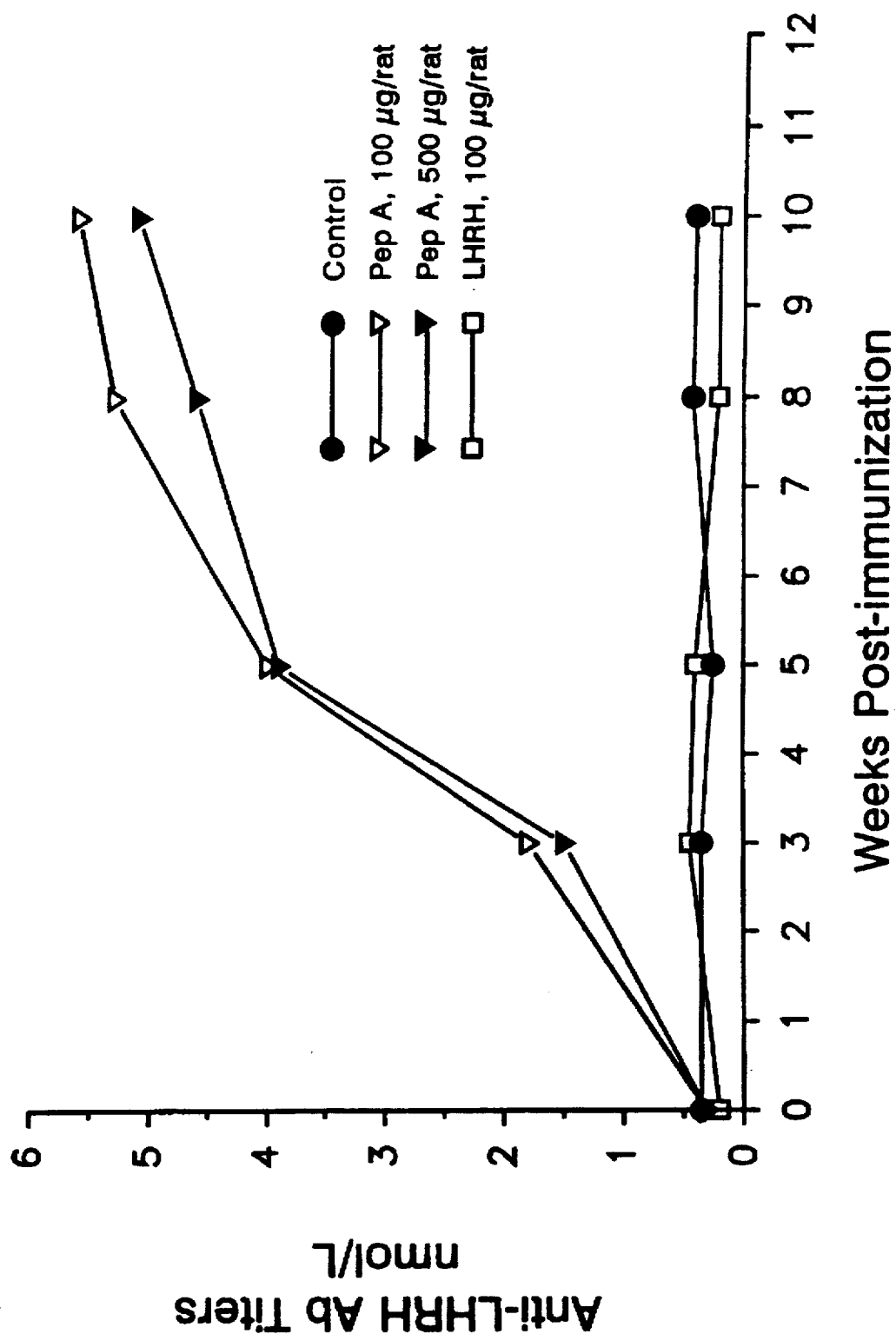
Figure 6:
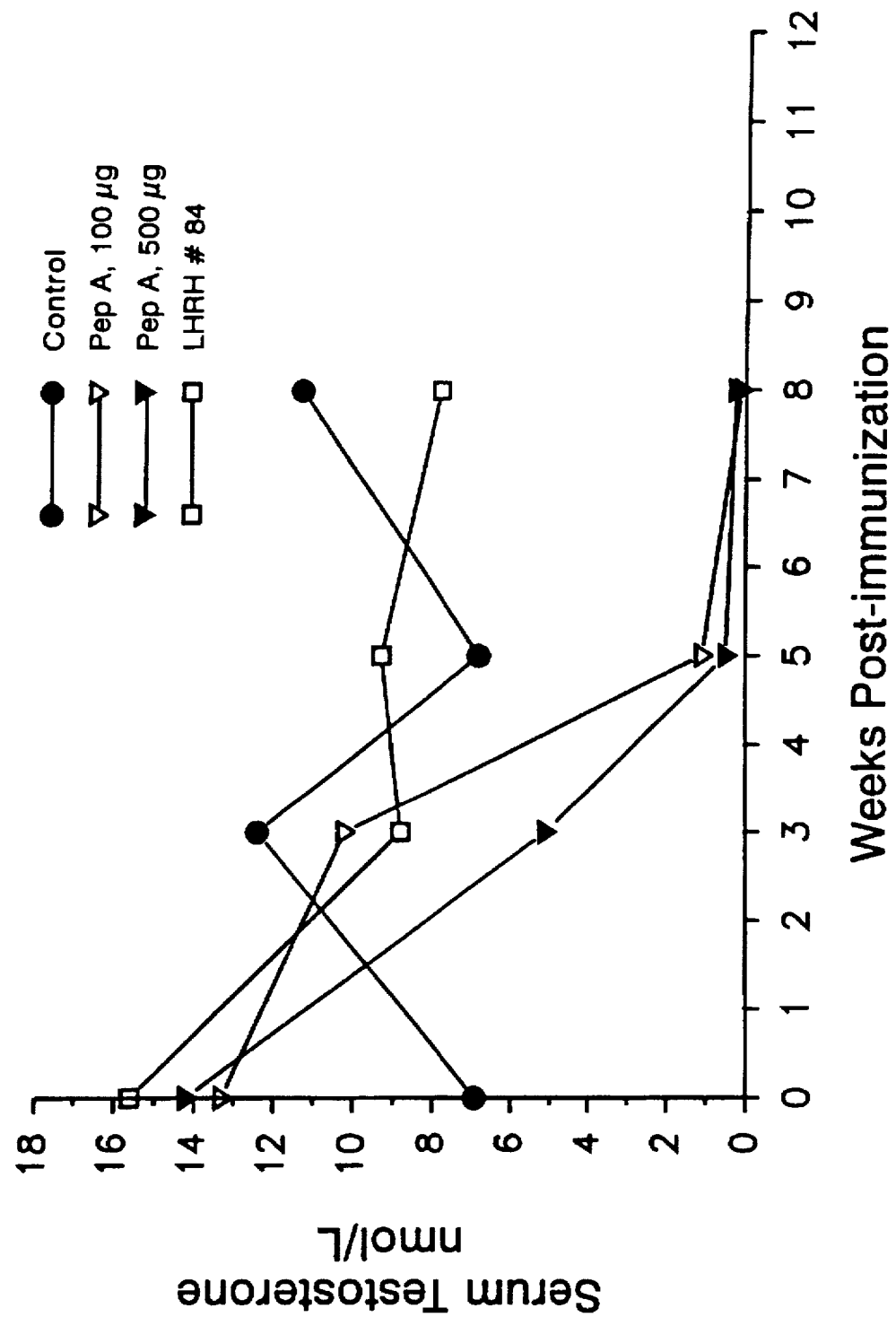
Figure 7:
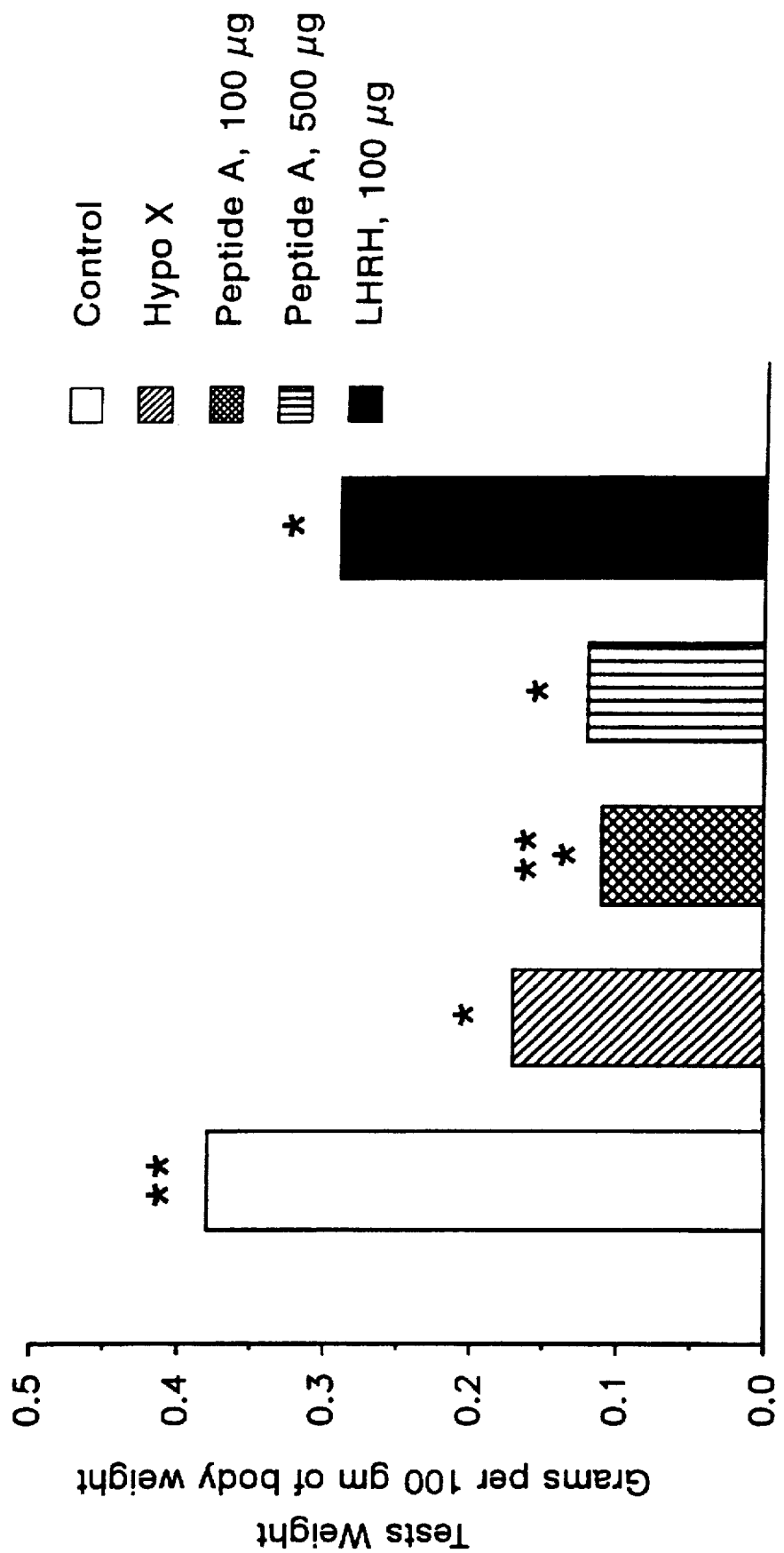
Figure 8:
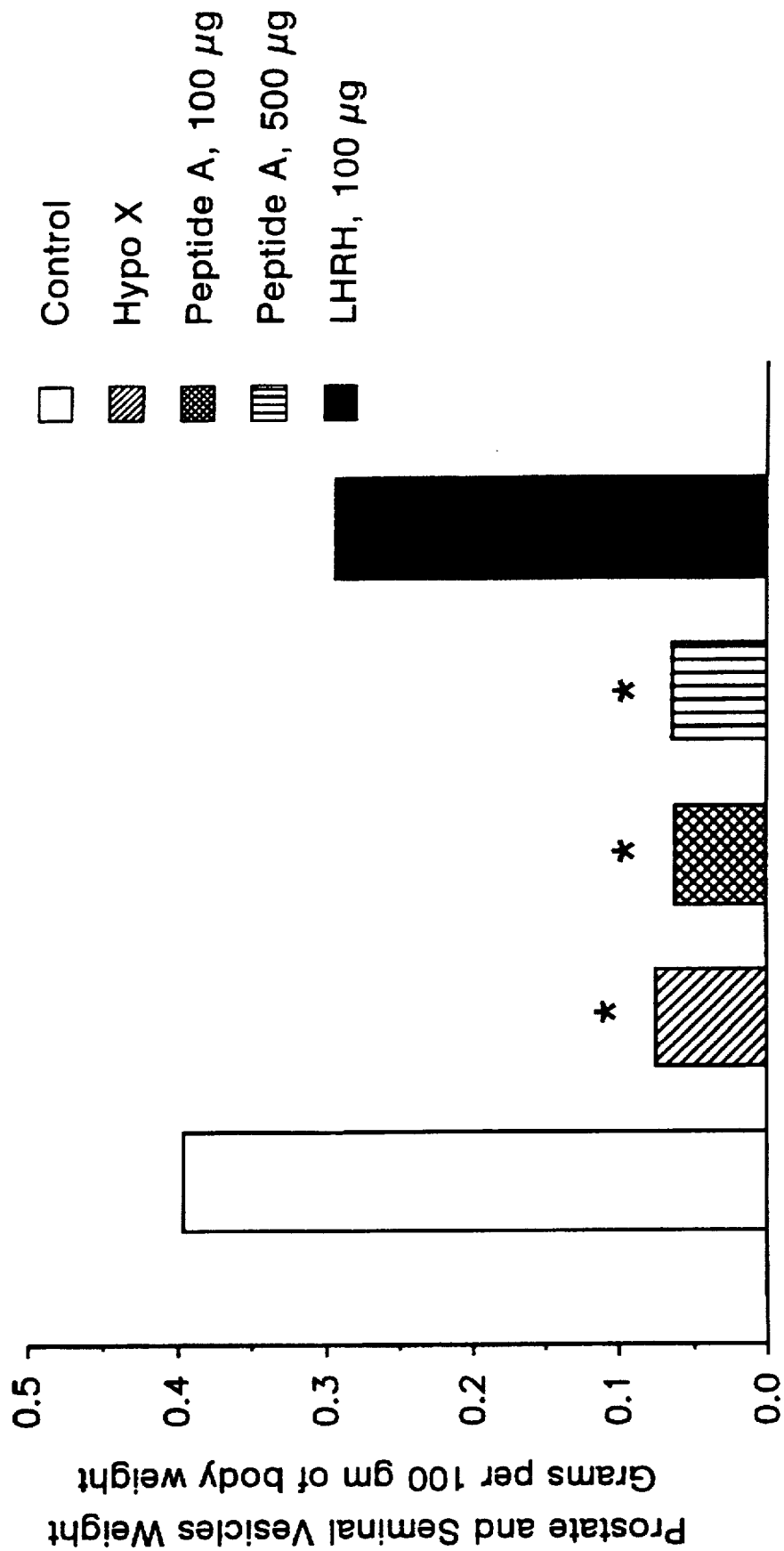

Blood samples were periodically withdrawn from the immunized and control rats. Sera from these samples were analyzed for the presence of peptide A-specific antibody, LHRH specific-antibody, and serum testosterone. At 10 weeks, the animals were sacrificed and relevant organs, including testis and prostate glands plus seminal vesicles were dissected and weighed. Hypophysectomized rats were included in the experiment as positive controls. By week 3 (the day of the first booster) measurable LHRH-specific antibody titers were observed and a significant increase in those titers was achieved through booster immunizations (FIG. 5). The antibody titers were measured by radioimmunoassay. These results indicate that the amount of antigen used was at saturating levels, since there were no significant differences between the responses elicited by either the 100 µg or 500 µg doses. FIG. 6 establishes a strong correlation between increases in serum antibody to LHRH and the reduction in serum testosterone (a concomitant dramatic decrease in both LH and FSH was also observed). By week 5 (post primary immunization), there was a ten-fold decrease in serum testosterone and by week 8, serum testosterone was at castration levels (less than 0.5 nmole/L) in all animals. FIG. 7 demonstrates the biological effect of reducing serum testosterone through LHRH immunization. The testes size of animals immunized with the 100 pg dose of peptide A was significantly reduced by the end of the experiment (week 10). Testis size reduction in these animals was even greater than the effect obtained through pituitary ablation (i.e. the hypophysectomized group). Although not tested through mating, the state of the testes (including histopathologic examination) indicated that every animal immunized with peptide A was functionally sterile before the end of the experiment. Prostate weights (FIG. 8) parallel the results obtained with the testes, i.e. peptide A immunization produced a significant atrophy of the prostate. By any measurement, no significant effect was observed through immunization with LHRH alone, demonstrating that linking promiscuous helper T cell epitopes to poor immunogens provides a means of stimulating a strong immune response to those immunogens.

Conclusions

1. The HBs T$_h$ epitope induced potent antibody responses to LHRH.

2. Antibody to peptide A efficiently neutralized LHRH activity in vaccinated animals.

3. LHRH inhibition was sufficient to reduce serum testosterone to castration levels.

4. Immunization with peptide A produced the desired biological effects, i.e. dramatic shrinkage of the prostate and testis.

EXAMPLE 5A

Identification and Testing of Additional

Efficacious Th: LHRH Constructs

The peptide A results have been reproduced consistently in a number of different studies with an aggregate efficiency (organ weight reduction used as the end-point) exceeding 95%. However, to establish a system that reliably measured the relative efficacy, or lack thereof, of different "$T_h$ epitope:LHRH" constructs, we modified the immunization protocol. The initial experiments with the LHRH constructs fell into two distinct groups when evaluated by the experimental protocol described in Example 5 (i.e. intramuscular administration of Freund's adjuvant formulations). The constructs either lacked efficacy and did not cause any significant organ weight reduction, or were totally effective and mimicked the results for peptide A, making it impossible to establish the rank order of the efficacious candidates. Thus, a simple modification of the protocol described above, i.e. subcutaneous as opposed to intramuscular administration of the candidate peptide formulations, allowed a determination of rank order. For example, subcutaneous administration of peptide A in FCA/IFA mitigated the responses to this peptide such that approximately 30%, as opposed to greater than 95%, of the animals responded sufficiently to cause shrinkage of their testes and prostates.

Accordingly, equimolar amounts of different $T_h$: LHRH constructs (equivalent to 100 µg of peptide A) were formulated as above, but administered subcutaneously at 0, 3 and 6 weeks. The sequences of the tested peptides are provided in Table 5 and the results from several different experiments are compiled in Table 6. In each study, peptide A was included as a positive control to normalize data between different experiments. As shown, peptides which elicited significant anti-LHRH antibody titers caused the serum testosterone levels of immunized animals to drop to below castration levels and caused significant reduction in testis weights. The results from the experiments conducted to produce Table 6 are provided in the following Examples.

EXAMPLE 6

Efficacy of Peptide 18, an HBsAg $T_h$ Epitope:

LHRH Construct Containing a Glycine Spacer

Peptide 18 is a 30 amino acid residue synthetic peptide which is organized in four linear domains, from the amino-to the carboxyl- terminus, as follows: 3 lysine residues ($K_3$), the hepatitis B virus helper epitope$_{19-33}$ (HBsAg $T_h$), a glycine spacer (GG), and LHRH. Peptide 18 is represented as $K_3$: HBsAg $T_h$: GG: LHRH. Thus, the structure of peptide 18 differs from peptide A simply by the addition of the Gly-Gly spacer sequence between the helper epitope and LHRH. The following describes analysis of the efficacy of peptide 18 when formulated in Freund's adjuvant and administered subcutaneously. The experimental design is the same as in Example 5 except as indicated otherwise.

Experimental Design

Immunogen: peptide A or peptide 18 (i.e., in separate groups)

Dose: 100 µg of peptide A, peptide 18 at molar equivalent to 100 µg of peptide A Route: subcutaneous Adjuvant: Freund's complete/incomplete Species: 6 sexually mature Sprague-Dawley male rats/group

Results

Figure 9:
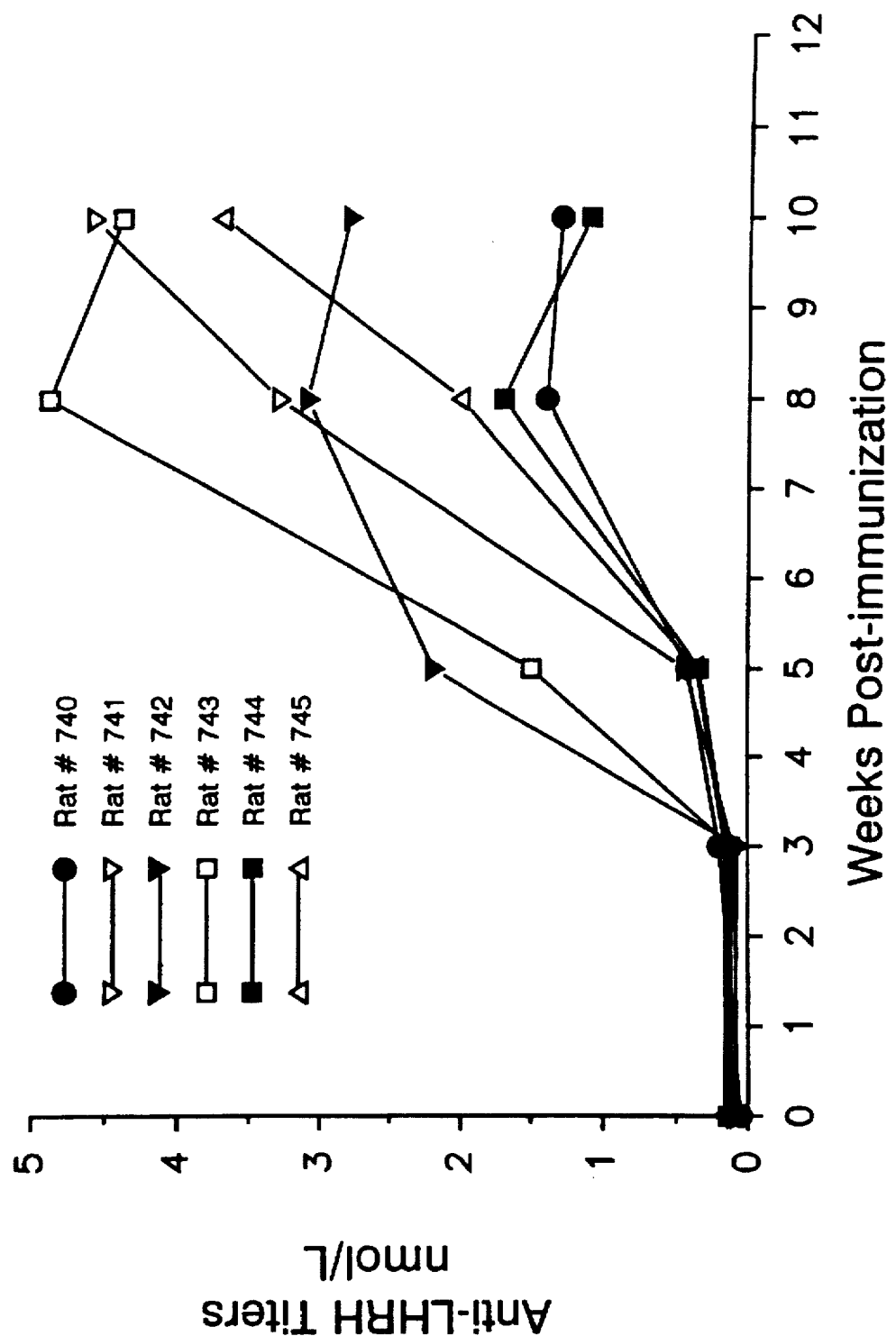
Figure 10:
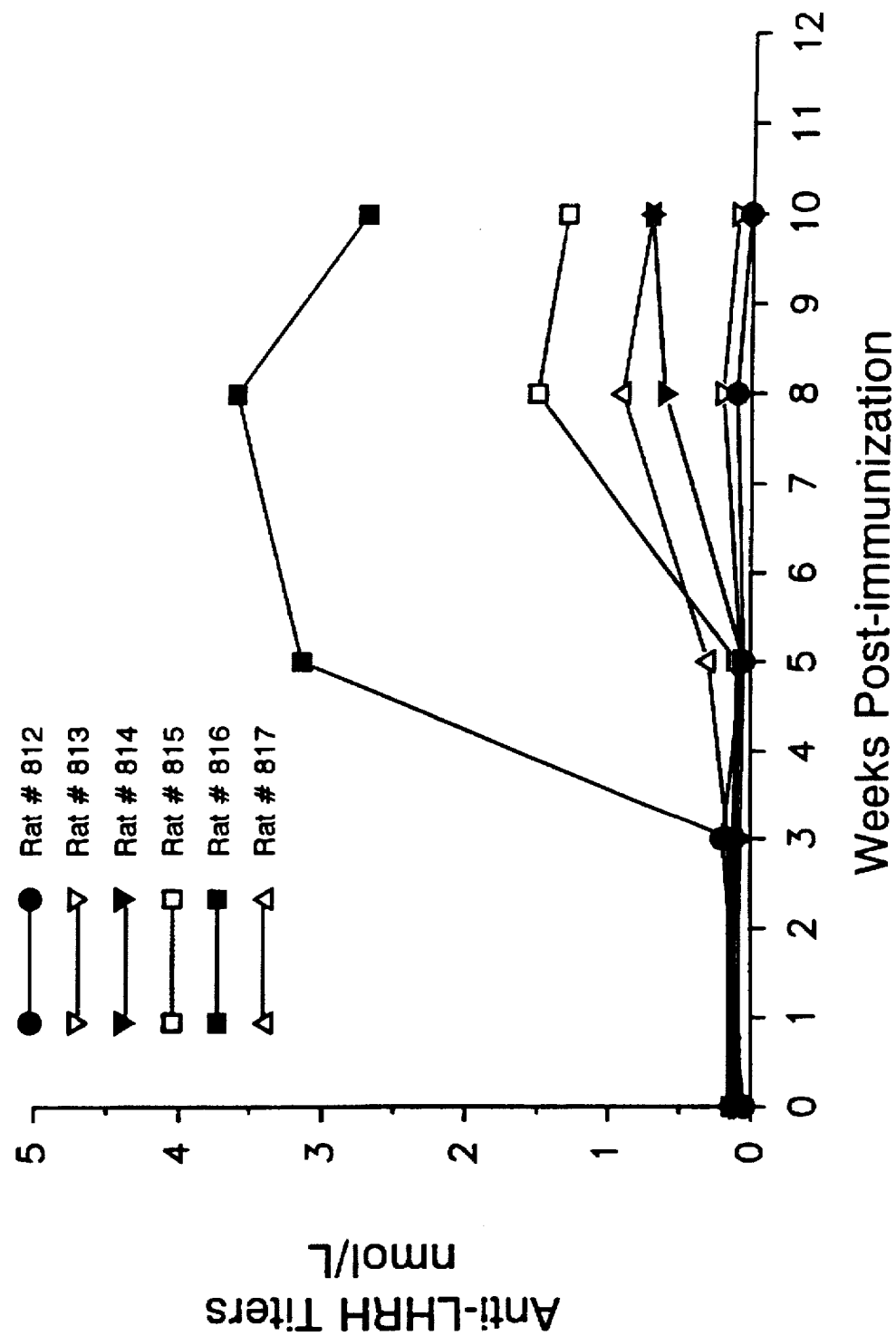
Figure 11:
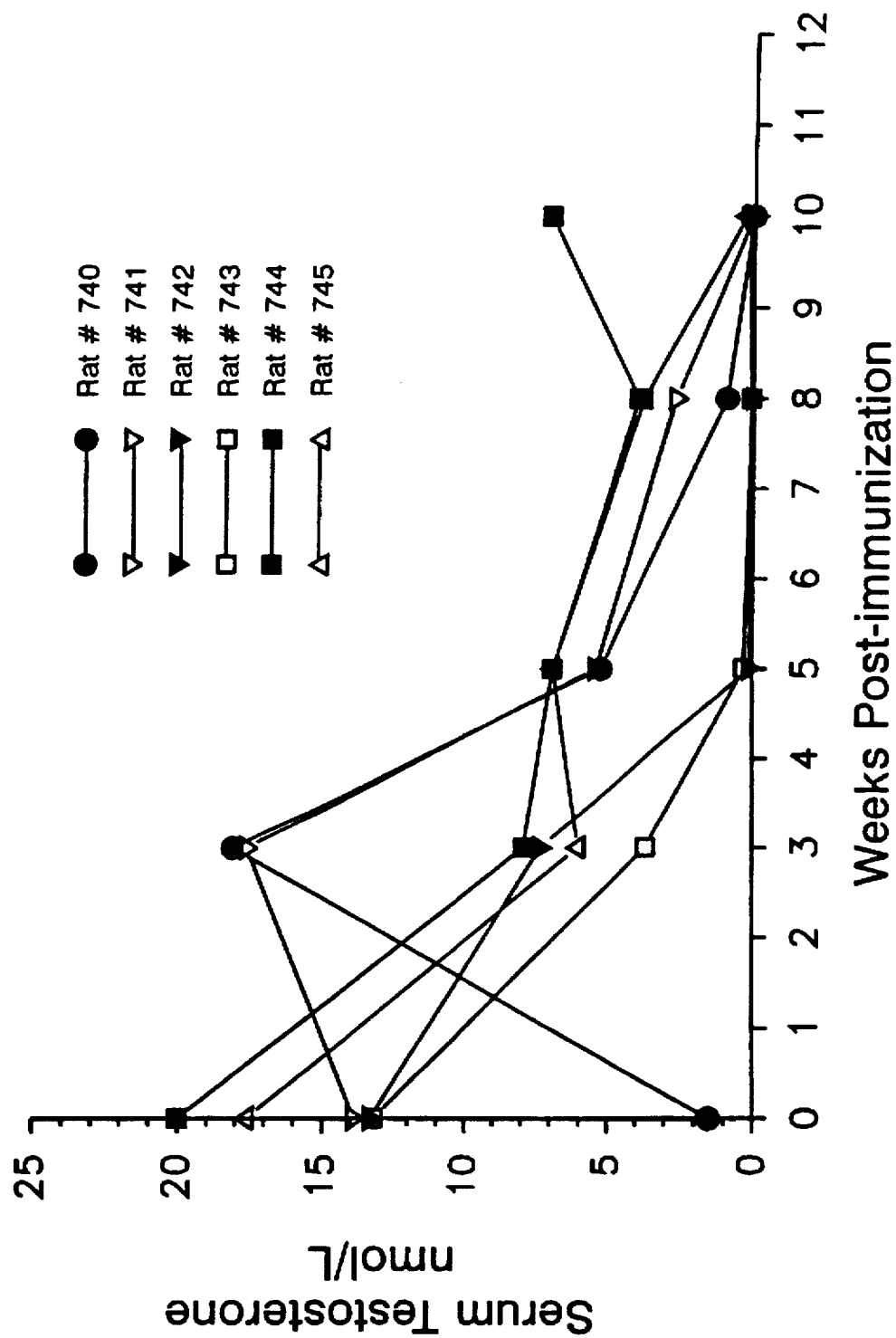
Figure 12:
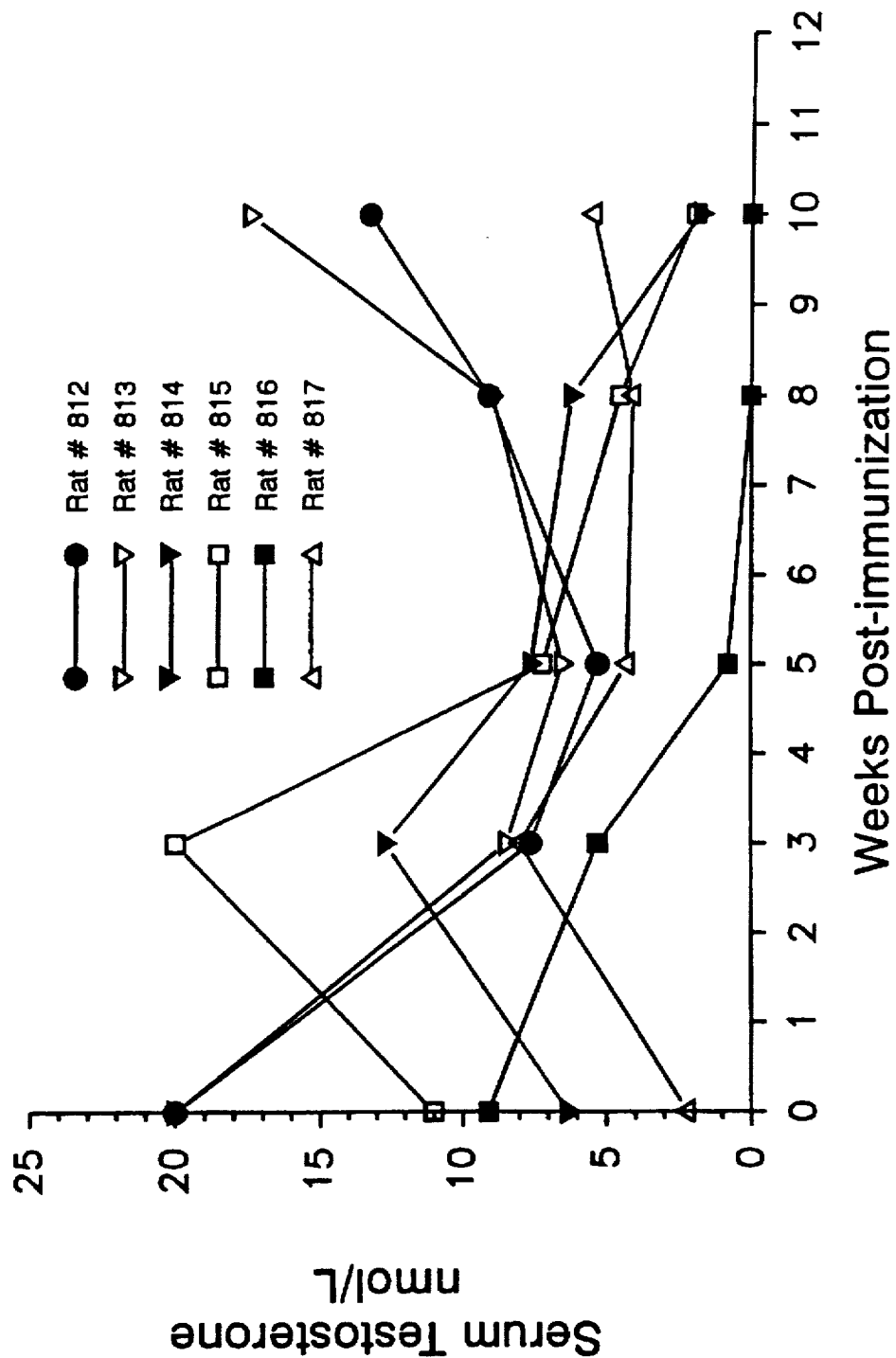
Figure 13:
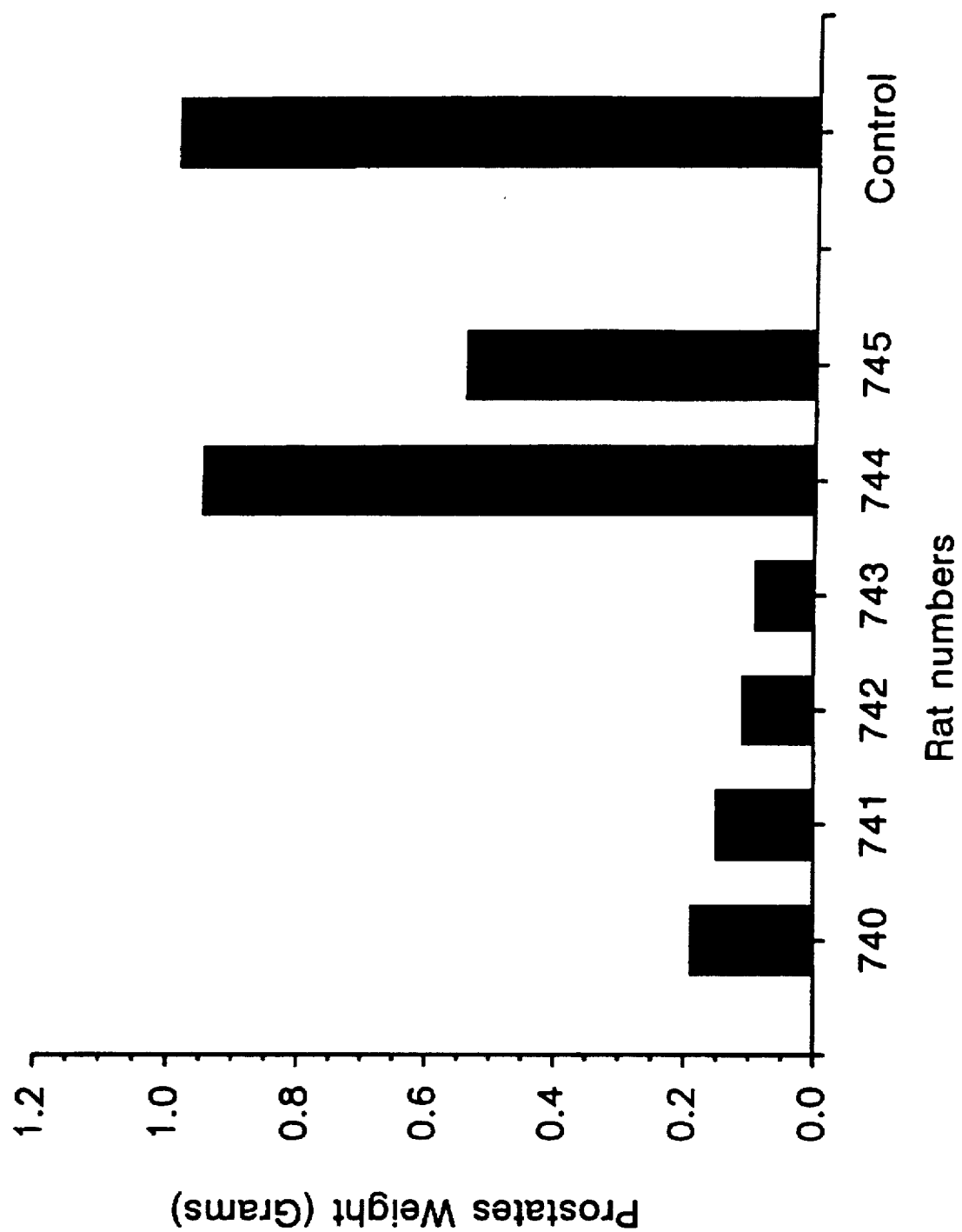

Two weeks following the second booster immunization (i.e. at 8 weeks), 6 of 6 animals receiving peptide 18 expressed anti-LHRH antibody titers greater than 1 nmole/L (FIG. 9). These high levels of antibodies were maintained in all animals until the termination of the experiment (week 10). In contrast, only 2 of 6 animals immunized with peptide A, expressed anti-LHRH antibody titers greater than 1 nmole/L by week 10 (FIG. 10). The differences in LHRH-specific antibody titers between the two groups were also reflected in the levels of circulating testosterone present in these animals. By week 10 (when animals were sacrificed), 5 of 6 animals receiving peptide 18 expressed serum testosterone at castration levels (FIG. 11), while 1 of 6 animals receiving peptide A had castration levels of this hormone (FIG. 12). Dissection of organs at week 10 demonstrated that 5 of 6 animals receiving peptide 18 had significantly atrophied prostate glands (FIG. 13), while only 1 of 6 animals receiving peptide A exhibited shrunken prostates.

Conclusions

1. Peptide 18 was effective in eliciting the desired biological responses, i.e. expression of LHRH-specific antibody, reduction in serum testosterone and relevant organ atrophy.

2. Insertion of the Gly-Gly spacer sequence between the $T_h$ epitope and LHRH improved the immune response to the peptide, as seen by comparison of the results from peptide 18 with those from peptide A.

EXAMPLE 7

Efficacy of Peptide 19, a Measles Virus

Promiscuous $T_h$ Epitope: LHRH Construct

A 15 residue domain from the measles virus (MV) F glycoprotein was linked to the LHRH sequence by automated synthesis to produce peptide 19. Peptide 19 is organized in three linear domains, from the amino- to the carboxyl-terminus, as follows: the measles virus helper epitope (MVF$_1$ $T_h$), a glycine spacer (GG) and LHRH. Peptide 19 is thus represented as MVF$_1$ $T_h$: GG: LHRH. This peptide was formulated in Freund's adjuvant and administered subcutaneously as described below. The experimental design is the same as in Example 5 except as indicated otherwise.

Experimental Design

Immunogen: peptide 19

Dose: molar equivalents to 100 µg of peptide A

Route: subcutaneous

Adjuvant: Freund's complete/incomplete

Species: 6 sexually mature Sprague-Dawley male rats/group

Results

Figure 14:
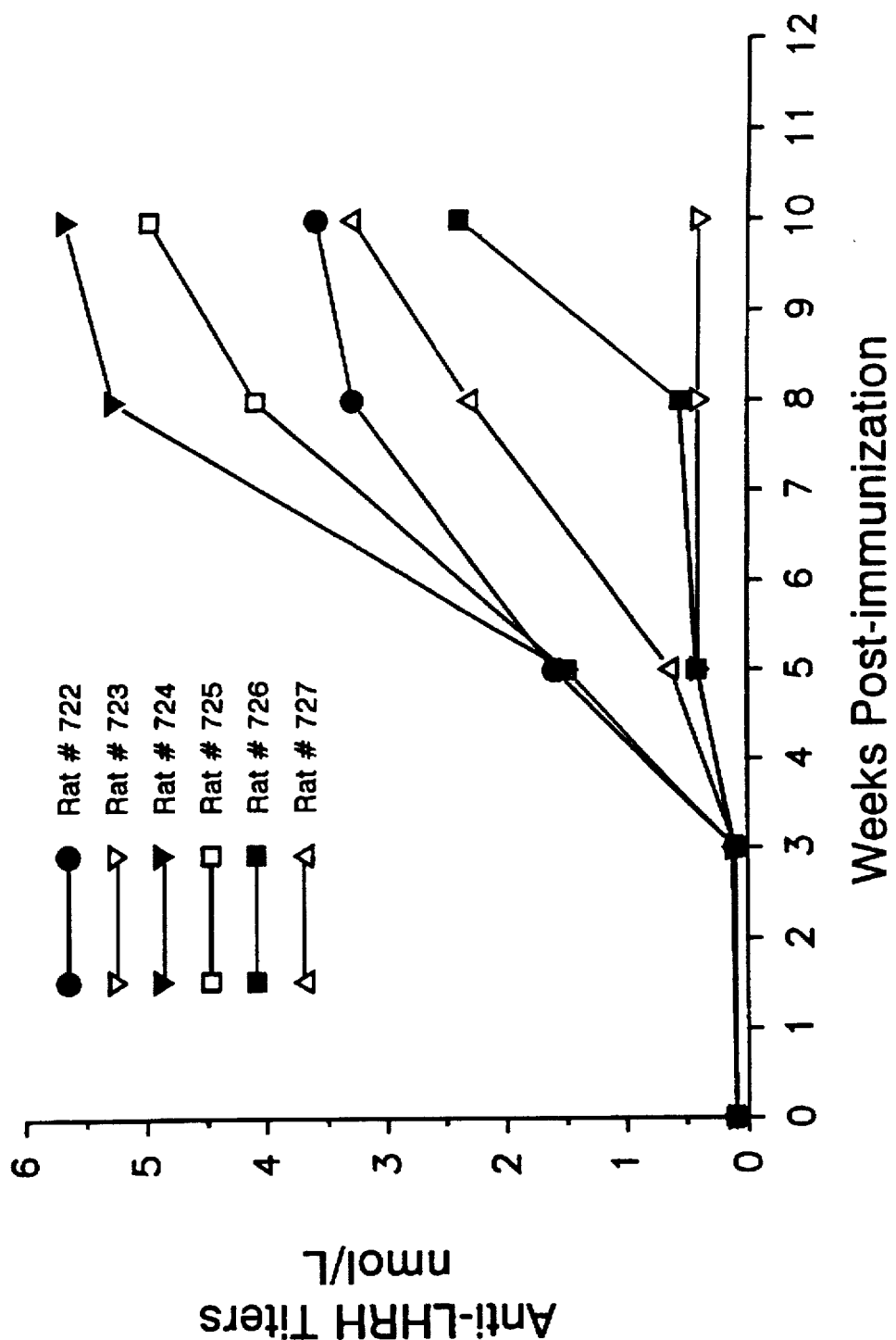
Figure 15A:
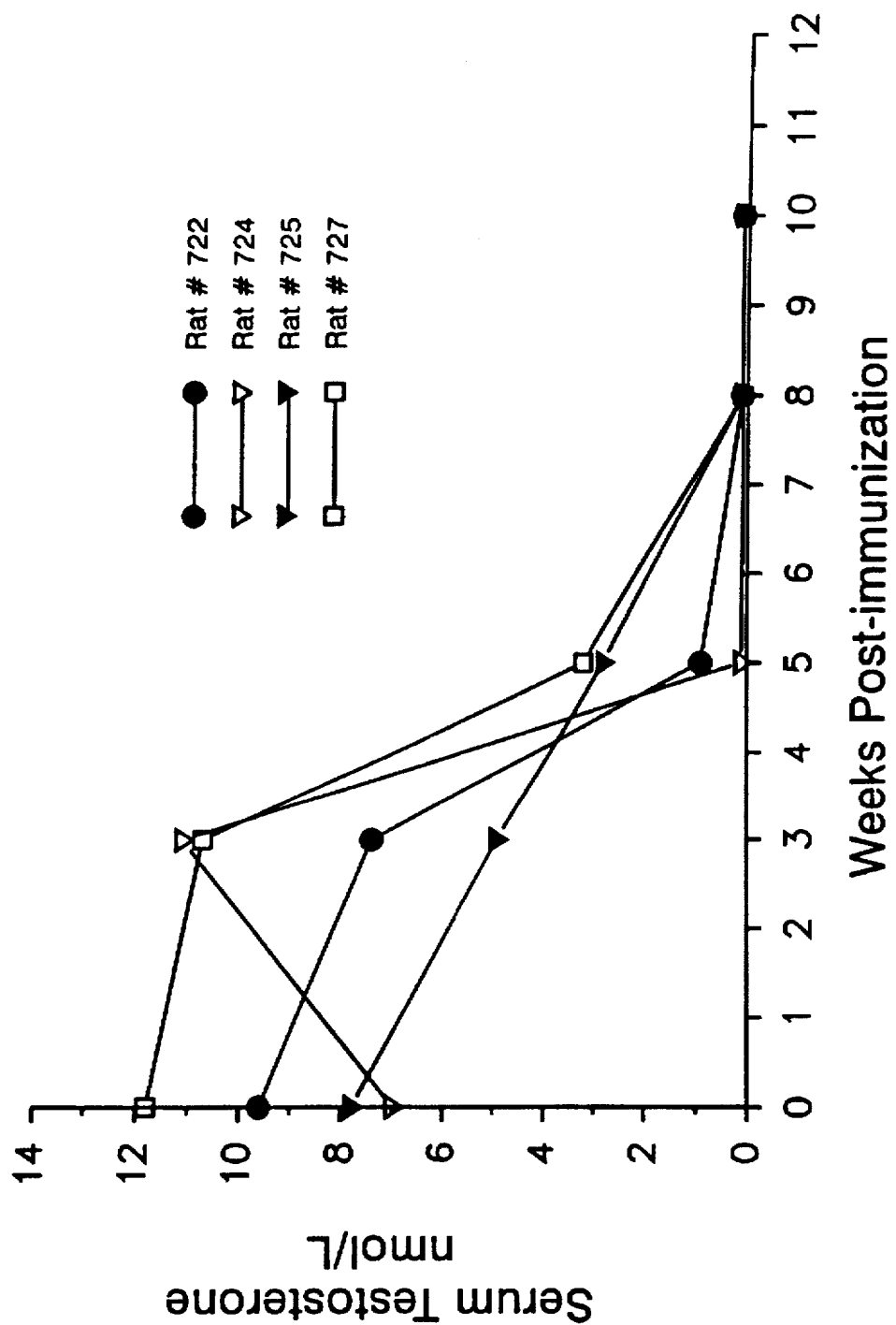
Figure 15B:
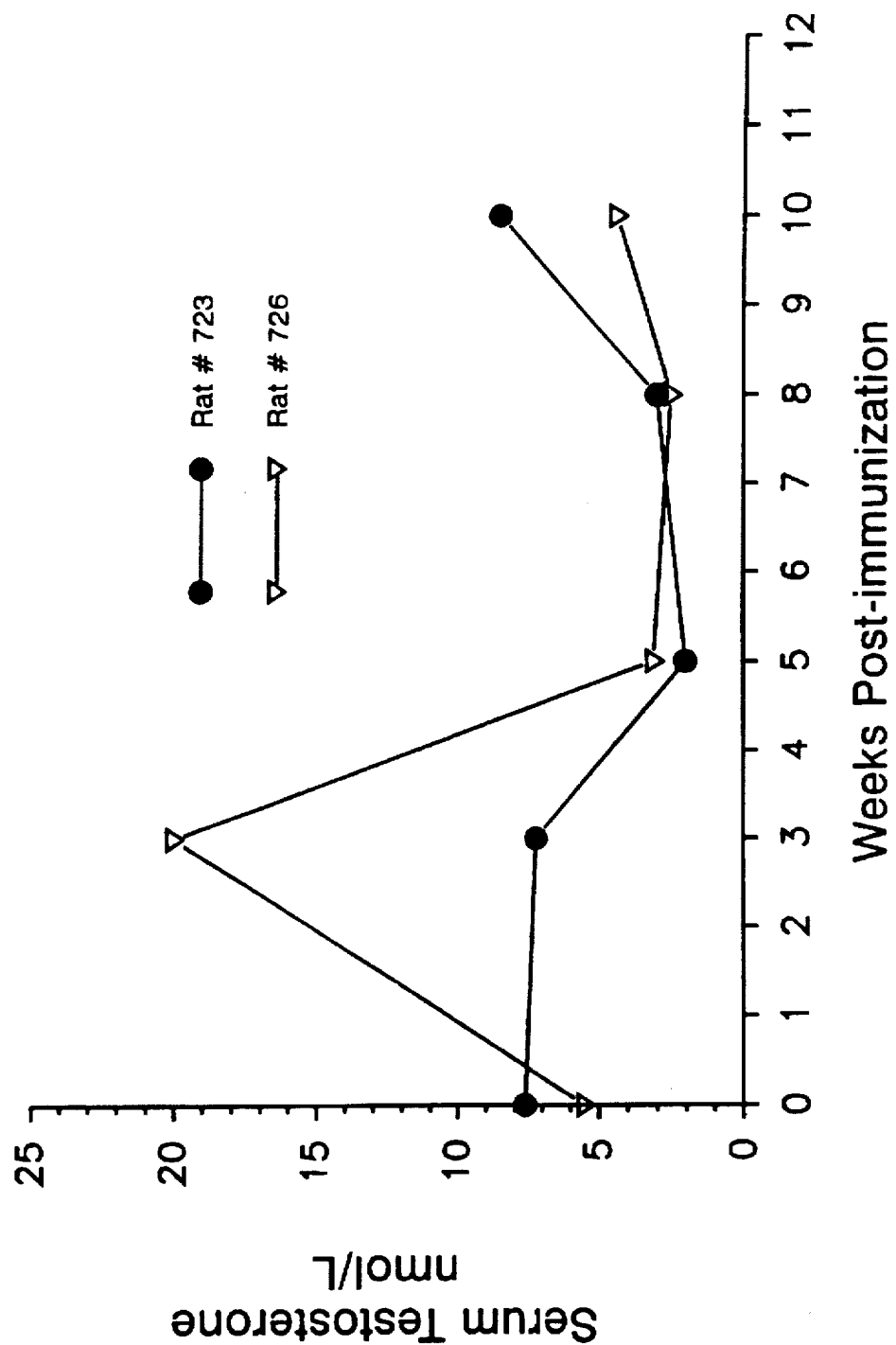
Figure 16:
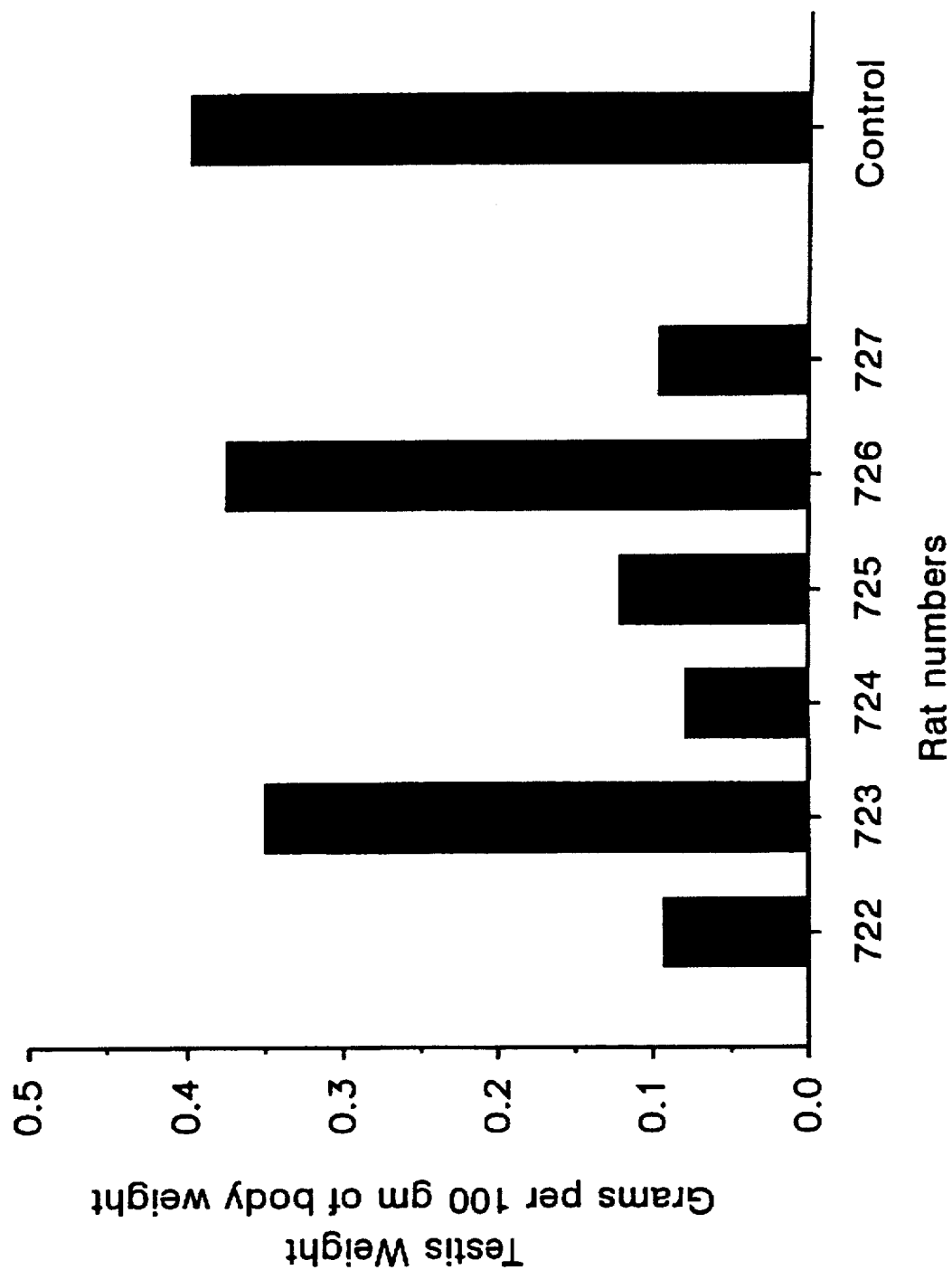
Figure 17:
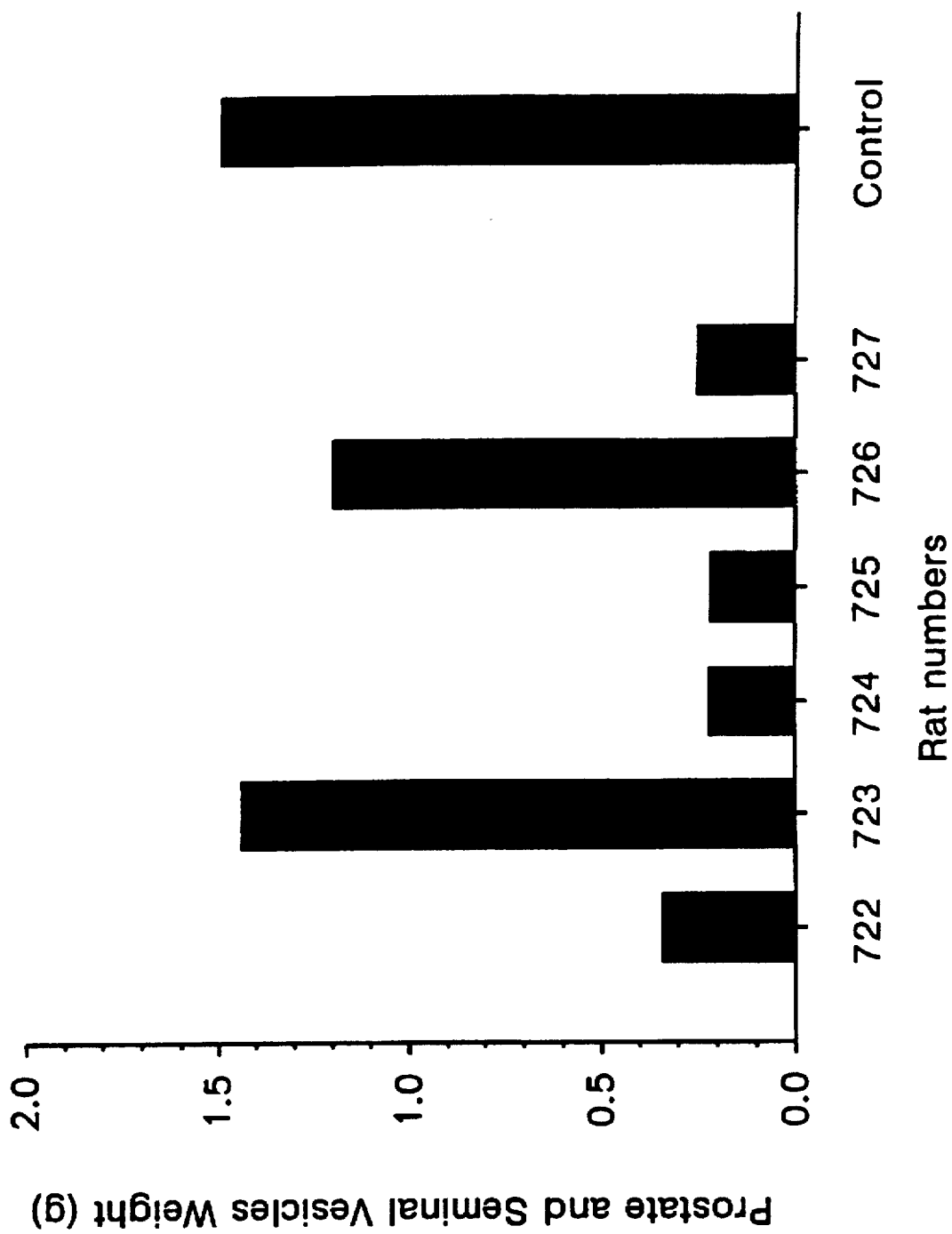

Two weeks following administration of the second booster immunization (at 8 wks), significant LHRH-specific antibody titers were observed in 4 of the 6 animals immunized (FIG. 14). There was a modest increase in the LHRH antibody titers between weeks 8 and 10, and in addition, one of the initially non-responding animals (rat #726) began to express significant anti-LHRH antibody during this period. FIG. 15 again demonstrates the strong positive correlation between the presence of significant LHRH antibodies and the reduction of serum testosterone. The four animals expressing anti-LHRH titers greater than 2 nmole/L at week 8 had serum testosterone levels below 0.5 nmole/L by week 8, and these levels were maintained through week 10 (FIG. 15a). The remaining animals which had lower LHRH antibody titers appeared to have reduced testosterone levels, but not to castration levels (FIG. 15b). The significant reduction in serum testosterone to below castration levels caused the expected severe atrophy of the testis as demonstrated by FIG. 16. An essentially identical result for prostate atrophy was observed as well (FIG. 17). For Peptide 19 greater than 65% of the animals tested exhibited castration levels of testosterone and severe atrophy of the testis and prostate gland (in this "modified" protocol. When given intramuscularly, according to the protocol in Example 5, greater than 95% of the animals exhibit relevant organ atrophy by 10 weeks. The accumulated data for peptide 19 show that LHRH antibody titers of greater than 2 nmole/L will cause serum testosterone to fall to castration levels (below 0.5 nmole/L) which results in atrophy of both the testis and prostate gland. LHRH-specific antibody titers must be elevated for 1–2 weeks for it to have the desired effect, namely organ atrophy. Based upon this, it is likely that rat #726 would have achieved castration levels of testosterone if the study was extended beyond 10 weeks duration.

Testis weight reduction is a logical endpoint for screening experiments because testis atrophy is an absolute predictor of prostate gland atrophy: Prostate shrinkage precedes reduction in testis weight (i.e., the prostate gland is heavily dependent upon testosterone for its maintenance, thus elimination of serum testosterone causes rapid prostate gland shrinkage, which is only then followed by testis atrophy); testis removal is trivial relative to the complicated dissection required for removal of the prostate and associated seminal vesicles; and, the simple form of the testis relative to the prostate and seminal vesicles make testis weight measurements more accurate.

Conclusions

1. Peptide 19 is efficacious (i.e. produces significant reduction in serum testosterone, plus testis and prostate weights) when administered with Freund's adjuvant.

2. Subcutaneous administration of the peptide formulation allows the means of ranking immunogen efficacy.

3. Peptide 19 has better efficacy than peptide A.

EXAMPLE 8

Efficacy of Peptide K, a Pertussis Toxin Promiscuous $T_h$ Epitope: LHRH Construct A 24 residue long $T_h$ epitope from pertussis toxin was linked to LHRH through automated synthesis, to form peptide K. This peptide is organized into two linear domains, from the amino- to the carboxyl- terminus, as follows: the pertussis toxin helper epitope $T_h2$ ($PT_2$ $T_h$), and LHRH. Peptide K is thus represented as $PT_2 T_h$: LHRH. This peptide was tested for efficacy using the same protocol as described for the analysis of peptides 18 and 19 (Examples 6 and 7, above). The experimental design is the same as in Example 5 except as indicated otherwise.

Experimental Design

Immunogen: peptide K

Dose: molar equivalent to 100 μg of peptide A
Route: subcutaneous
Adjuvant: Freund's complete/incomplete Species: 6 sexually mature Sprague-Dawley male rats/group Necropsy: at 10 weeks determine testis weights Results FIG. 18 describes the LHRH-specific antibody titers expressed in animals given peptide K subcutaneously. Two animals exhibited significant LHRH-specific antibody titers (greater than 4 nmole/L) by week 8, two intermediate levels (1.5–2.0 nmole/L) and two animals exhibited essentially no response. Again, there was the expected correlation of anti-LHRH titers with serum testosterone levels. The two animals with high antibody titers had serum testosterone at castration levels by week 8, which remained at that level until the termination of the experiment (FIG. 19a). Rat #793 expressed LHRH antibody titers of greater than 2 nmole/L at week 10 and had castration levels of testosterone at that point. Rat #791 which had LHRH antibody titers of 1.6 nmole/L measured at week 10 (FIG. 18) had testosterone levels approaching the limit for castration at that time (FIG. 19b). Animals expressing high levels of LHRH antibodies (FIG. 18) had significantly atrophied testes at 10 weeks (FIG. 20). Rat #791 showed some reduction in testis weights, and based on the kinetics of serum testosterone levels, it is very probable that organ atrophy would have been significant if necropsy was conducted after week 11.

The variability in the responses to peptide K most probably reflects genetic differences within the outbred rat population used for this study, and define differences between animals in their ability to effectively recognize the $T_h$ epitope contained within this LHRH construct. This result supports the use of mixtures of constructs, containing different promiscuous $T_h$ epitopes to produce uniform potent responses in populations expressing diverse HLA haplotypes.

Conclusions

1. Peptide K is efficacious (i.e. produces significant reduction in serum testosterone and testis weight size) when administered with Freund's adjuvant.

2. Subcutaneous administration of the peptide formulation provides the means of ranking immunogen efficacy.

3. Promiscuous $T_h$ constructs are capable of differing degrees of efficacy when viewed in genetically heterogeneous populations.

4. Peptide K has an efficacy approximates that achieved by peptide A.

EXAMPLE 9

Efficacy of Peptide H, a Tetanus Toxin Promiscuous $T_h$ Epitope: LHRH Construct A 27 amino acid long peptide, consisting of a 15 amino acid Th epitope from tetanus toxin located near the amino-terminus and followed by the LHRH sequence, was synthesized using the standard automated synthesis techniques. This peptide, peptide H, is organized in three linear domains, from the amino- to the carboxyl- terminus, as follows: 2 lysine residues ($K_2$), the tetanus toxin helper T cell epitope 1 ($TT_1$ $T_h$) and LHRH. Peptide H is thus represented as $K_2$: $TT_1$ $T_h$: LHRH. The following describes analysis of the efficacy of peptide H when formulated in Freund's adjuvant and administered subcutaneously. The experimental design is the same as in Example 5 except as indicated otherwise.

Experimental Design

Immunogen: peptide H

Dose: molar equivalent to 100 μg of peptide A

Route: subcutaneous

Adjuvant: Freund's complete/incomplete

Species: 5 sexually mature Sprague-Dawley male rats/group

Necropsy: at 10 weeks determine testis weights

Results

FIG. 17 demonstrates the capacity of peptide H to cause the production of LHRH-specific antibodies. By week 8 (two weeks after the second booster administration) 4 of 5 animals express anti-LHRH antibody titers greater than 2.0 nmole/L. By week 10, the fifth animal expressed LHRH antibodies to greater than 1.0 nmole/L. At week 8, there was a significant reduction in serum testosterone levels in all animals, and by week 10, serum testosterone was at castration levels in all animals (FIG. 22). At week 10, animals were sacrificed and the relevant organs weighed. Four of 5 rats exhibited dramatically atrophied testes (FIG. 23). The fifth animal, rat #103, exhibited significantly reduced testes, but were slightly larger than the testes from the other animals receiving peptide H. This correlates with the lower levels of anti-LHRH antibodies expressed by this animal (FIG. 21).

Conclusions

1. Peptide H is efficacious (i.e. produces significant reduction in serum testosterone, plus testis and prostate weights) when administered with Freund's adjuvant.

2. Subcutaneous administration of the peptide formulation provides the means of ranking immunogen efficacy.

3. Peptide H is significantly more efficacious than peptide A.

EXAMPLE 10

Immunogen Cocktail Administered in Freund's Adjuvant

Establishing the relative efficacies of the many different $T_h$ epitope: LHRH constructs (Examples 5–10; Table 6) permits selection of representative peptides for a cocktail of immunogens. Individual constructs carrying $T_h$ from measles virus F, hepatitis B surface antigen, tetanus toxin and pertussis toxin in the immunogen cocktail have demonstrated efficacy (Table 6) and are promiscuous, providing maximum coverage in a genetically diverse population. Moreover, because these $T_h$ epitopes are present in previously administered vaccines, they provide the potential for priming responses. The experiments below show the rapid atrophy of the relevant organs using a cocktail approach. The experimental design is the same as in Example 5 except as indicated otherwise.

Experimental Design

Immunogen: Cocktail (HBs $T_h$:LHRH+MV$_{F1}T_h$:LHRH+ PT$_2$ $_{Th}$:LHRH+TT$_1$T$_h$:LHRH)

Dose: molar equival of each, to equal 100 μg of peptide A

Route: subcutaneous

Adjuvant: Freund's complete/incomplete

Species: 6 sexually mature Sprague-Dawley male rats/group

Necropsy: at 10 weeks determine test weights

Results

The mixture of $T_h$: LHRH constructs was administered subcutaneously in Freund's adjuvant by the methods described in Examples 6–9, above. As demonstrated by FIG. 24, rapid and potent anti-LHRH antibody responses were observed in all animals. By week 5, i.e. two week safter the first booster immunization and prior to the second booster, 5 of 6 animals expressed LHRH specific antibody titers sufficient to reduce serum testosterone levels below that required for castration. Significant increase in antibody titers was achieved for all animals following the second booster immunization. Serum testosterone levels fell below the threshold required for castration between 5 and 8 weeks following the primary immunization and remained at these levels for the remainder of the experiment (FIG. 25). This marked decrease in serum testosterone caused significant atrophy in the testes for every animal measured at week 10 (FIG. 26). This experiment demonstrates the advantages provided by the cocktail of immunogens (compare FIG. 26 with FIGS. 16, 20 & 23). The desired endpoint is achieved in all animals as opposed to a few. In addition to the uniformity of responses, the rapidity of the responses and their intensity were enhanced when the cocktail was administered in lieu of the individual components (compare FIG. 24 with FIGS. 14, 18 & 21).

Conclusions

1. A cocktail of $T_h$: LHRH immunogens is more efficacious than any individual peptide within the mixture.

2. A cocktail of immunogens is fully effective (greater than 95% of the animals exhibiting the desired characteristics) in producing the desired effect, i.e. relevant organ atrophy.

EXAMPLE 11

Immunogen Cocktail Formulated on Alum

For a human prostate cancer therapy, it is necessary to achieve similar levels of organ weight reduction using a vaccine formulation acceptable for use in humans. Therefore, the efficacy of a cocktail of $T_h$: LHRH constructs adjuvanted with aluminum hydroxide was tested. The following is a summary of that experiment. The experimental design is the same as in Example 5 except as indicated otherwise.

Experimental Design

Immunogen: Cocktail (HBs $T_h$:LHRH+MV$_{F1}T_h$:LHRH+ PT$_2$ $T_h$:LHRH+TT$_1$T$_h$:LHRH)

Dose: 250 μg, molar equivalent of each

Route: intramuscular

Adjuvant: aluminum hydroxide

Schedule: week 0, 2 and 4 weeks

Species: 5 sexually mature Sprague-Dawley male rats/group

Necropsy: at 10 weeks determine tests weights

Results

At 8 weeks following the initiation of the experiment, significant LHRH-specific antibody titers were observed in all animals, three animals expressed titers above 2 nmole/L and two had titers between 1.5 and 2.0 nmole/L (FIG. 27). By week 10, 4 of 5 animals exhibited LHRH antibody titers above the 2 nmole/L. At this time, point 4 of 5 animals exhibited castration levels of serum testosterone (FIG. 28) and the same four animals had significantly atrophied prostate glands (FIG. 29). The fifth animal, #231, exhibited a marked, though incomplete, prostate weight reduction when compared to the other animals in the group. Its prostate weight is consistent with reduced, though measurable, levels of serum testosterone in this animal at the end of the experiment. This is the first report ever described where the desired biologic effect (namely, elimination of serum testosterone and significant prostate gland atrophy) was produced through immunization with LHRH constructs on alum. In all other cases thus far described in the literature, attempts to use alum with LHRH-based immunogens have failed, requiring the use of reactogenic formulations (e.g. Freund's adjuvant), to produce the desired effects.

The reduced efficacy of the alum-based formulation (FIG. 28), when compared to the same immunogen cocktail in Freund's adjuvant (FIG. 25), manifested as a delay in the timing of the desired responses. This is demonstrated by rat #228 (FIG. 29) which had an atrophied prostate gland, but normal testes weights at week 10. It is probable that this animal would have expressed shrunken testes if the experiment were to have continued beyond 10 weeks. In contrast, every animal receiving the Freund's adjuvant t-based formulation exhibited atrophied testes by week 10 (FIG. 26).

Conclusions

1. Mixing promiscuous $T_h$: LHRH synthetic peptide constructs provides an efficacious LHRH immunotherapeutic vaccine.

2. This immunogen cocktail can be formulated with alum (one of the very few and most safe adjuvants approved for human use) and obtain the required biological effects, i.e. atrophy of the relevant organs.

EXAMPLE 12

Efficacy of an Artificial $T_h$ Epitope SSAL: LHRH Construct

Peptide 38 (also represented as peptide SSAL1) is a peptide library in which a degenerate $T_h$ sequence, modeled after the measles virus $F_1$ $T_h$ epitope, is linked to LHRH. This peptide is organized in three linear domains, from the amino- to the carboxyl- terminus, as follows: the structured synthetic antigen library representing a synthetic helper T cell epitope (SSAL $T_h$), a glycine spacer (GG), and LHRH. Peptide 38 may therefore be represented as SSAL1 $T_h$: GG: LHRH, and is analogous to peptide 19 (i.e. MVF$_1$ $T_h$: GG: LHRH).

The sequence of peptide 38 is as provided in Table 5. Peptide SSAL1: SSAL $T_h$l:GG: LHRH (SSAL $T_h$1MVFI $T_h$ Derivative).

This peptide library is composed of a mixture of approximately $5.24 \times 10^5$ different sequences, where the precise measles virus $T_h$l epitope is represented in only one of these sequences. The Gly spacer and LHRH are invariant in the library sequences.

The degenerate helper T cell epitope present in peptide SSAL1 is modeled after a promiscuous helper T cell epitope identified from the F protein of measles virus represented by residues 288–302 of the F protein and has the following amino acid sequence, LSEIKGVIVHRLEGV. The library sequence was constructed using this sequence as a template. Charged residues Glu (E) and Asp (D) were added at position 1 to increase the charge surrounding the hydrophobic face of the amphipathic helical epitope. This face is made up of residues at positions 2, 5, 8, 9, 10, 13 and 16. The hydrophobic residues commonly associated with promiscuous epitopes were added at these positions. A Rothbard sequence is present at residues 6–10 in the prototype sequence and its character is maintained throughout all sequences within the library. Sequences obeying the 1, 4, 5, 8 rule begin at residue 5 of the prototype sequence and are maintained in all sequences as well.

Peptide 38 was prepared by chemical synthesis using standard techniques well known in the art such as the solid-phase synthetic route pioneered by Merrifield. The coupling of multiple amino acids at a given position is accomplished by providing a mixture of the desired amino acids at the appropriate ratios as indicated in the formula. For example, at positions 2, 5, 8, 9, 10, 13, and 15 from the N-terminus, an equimolar amount of protected $N^\alpha$-amino group, Leu (L), Ile(I), Val(V) and Phe(F), instead of a single protected amino acid, was used for each of the corresponding coupling steps. If necessary the ratio of amino acids in the mixture can be varied to account for different coupling efficiency of those amino acids. At the end of the synthesis, the peptide libraries were cleaved individually according to standard procedures to release the free peptide mixtures. The experimental design is the same as in Example 5 except as indicated otherwise.

Experimental Design

Immunogen: peptide 38 or peptide 19 (in separate groups)
Dose: 400 µg of each peptide
Route: intramuscular
Adjuvant: Incomplete Freund's
Schedule: week 0 (FCA), 3 and 6 weeks (IFA)
Species: 5 sexually mature Sprague-Dawley male rats/group
Necropsy: at 10 weeks determine testes weights Results Six weeks following the commencement of the experiment (i.e. 2 weeks after the first booster immunization and immediately prior to the second booster), 4 of 5 animals receiving peptide 38 expressed serum testosterone at castration levels. At 8 weeks, serum testosterone was at castration levels in 5 of 5 animals. Palpation of the testes at that time demonstrated that the 4 animals having negligible serum testosterone at week 6 also have atrophied organs. In contrast, only 1 of 5 animals immunized with peptide 19 expressed castration levels of serum testosterone by week 6, the remainder were in the normal range, and this number did not change by week 8. By week 8, the animal receiving peptide 19 which had negligible levels of testosterone at week 6, had atrophied testes by palpation.

Conclusions

1. The $T_h$ epitope library has shown significant efficacy by causing reduction of serum testosterone to castration levels in all animals receiving peptide 38.

2. The $T_h$ epitope library peptide has provided what a single peptide immunogen composed of a promiscuous $T_h$ epitope linked to LHRH cannot provide, i.e. comprehensive efficacy in all members of an outbred population.

EXAMPLE 13

Further Modification of the LHRH Immunogens to Amplify Antibody Induction: Addition of an Invasin Domain T cell activation can also be brought about by LHRH that is covalently linked to a specific fragment from the invasin protein of the pathogenic bacteria Yersinia spp. Peptide 32, in which a domain of the invasin protein is linked to the HBs $T_h$ epitope: LHRH construct (i.e. $Inv_{718-732}$+peptide 18) has been synthesized. Peptide 32 is organized in five linear domains, from the amino- to the carboxyl-terminus, as follows: the invasin T cell stimulator (Inv), a glycine spacer (GG), the hepatitis B surface antigen helper T cell epitope (HBsAg $T_h$l), a glycine spacer (GG), and LHRH. Peptide 32 is thus represented as: Inv: GG: HBsAg $T_h$l: GG: LHRH. The following provides a specific example of the significant efficacy imparted to the LHRH immunogen by the addition of the invasin domain. The experimental design is the same as in Example 5 except as indicated otherwise. Experimental Design:

Immunogen: peptide 32

Dose: 100 μg, per dose

Route: subcutaneous

Adjuvant: aluminum hydroxide

Species: 5 sexually mature Sprague-Dawley male rats/group

Necropsy: at 10 weeks determine tests weights

Results

FIG. 30 describes the LHRH-specific antibody titers produced in rats immunized with peptide 32. Significant titers were achieved after the first booster immunization (at 3 weeks) which continued to increase following the second booster immunization at 6 weeks. By week 8, 4 of 5 animals exhibited LHRH antibody titers above 2 nmole/L. Control animals immunized with an $Inv_{718-732}$: LHRH construct, lacking a $T_h$ epitope, did not produce any measurable LHRH-specific antibody. Serum testosterone levels (FIG. 31) fell precipitously in the animals responding to peptide 32, and by week 8, testosterone levels were below the threshold for castration. Serum testosterone in these animals remained unmeasurable for the remainder of the experiment. As demonstrated by FIG. 32, dramatic organ atrophy was achieved in the four responding animals. The testes of control animals immunized with peptide 18 (HBs $T_h$: GG: LHRH; lacking the invasin epitope) were unaffected at the end of this experiment (i.e. at week 10). This result is especially important since the invasin-containing LHRH peptide was formulated on alum and administered subcutaneously. Previous studies with LHRH linked to high molecular weight carrier molecules, e.g. tetanus and diphtheria toxins, required formulation with Freund's complete adjuvant or other reactogenic adjuvants to achieve any significant degree of efficacy.

Conclusions

1. The invasin fragment provides a significant improvement in the immune responses to $T_h$: LHRH constructs.

2. Alum was a sufficient adjuvant for peptide 32. 3. Peptide 32 is capable of causing organ atrophy.

EXAMPLE 14

Efficacy of an LHRH Immunogen Cocktail Containing Peptide 32

An experiment testing the efficacy of the cocktail of immunogens as described in Examples 10 and 11, was conducted except that the HBs $T_h$: GG: LHRH construct was replaced with peptide 32. The protocol for this example is identical to that used in Example 11. As above, animals received 100 μg of peptide on alum, administered at 0, 3 & 6 weeks. As demonstrated by FIG. 33, rapid and potent anti-LHRH antibody responses were produced in response to immunization with the Invasin fragment-containing cocktail when formulated on alum. By 8 weeks, 6 of 6 animals receiving the peptide 32-containing cocktail expressed serum testosterone levels (FIG. 34) below the castration threshold (i.e. less than 0.5 nmole/L). In contrast, 4 of 6 animals receiving an equivalent dose of peptide 32 alone on alum had castration levels of testosterone. These data suggest that any genetic variability associated with responses to the invasin fragment are overcome by its presentation in the cocktail containing the different $T_h$ constructs. FIG. 35 describes the testis weights at the end of the experiment (at 10 weeks). Five of 5 animals receiving the peptide 32-containing cocktail of immunogens exhibited significant organ atrophy and by histological examination were functionally sterile.

$Invasin_{718-732}$ linked to: HBs $T_h$:GG:LHRH generates peptide 32, to $MV_{F1}T_h$:GG:LHRH generates peptide 33, to $PT_2T_h$:GG:LHRH generates peptide 34, to $TT_1T_h$:GG:LHRH generates peptide 35, to $TT_4T_h$:GG:LHRH generates peptide 36, and to $TT_5T_h$:GG:LHRH generates peptide 37. Experiments designed to evaluate the efficacy of peptides 32–37, alone and in combination, are conducted in accordance with this and Example 13.

EXAMPLE 15

Improved Efficacy Provided to an LHRH Immunogen by the Covalent Linkage of $Pam_3Cys$ The HBsAg $T_h$: GG: LHRH peptide was further modified by the addition of the lipid moiety $Pam_3Cys$. The lipid residue was covalently linked to the amino-terminus of peptide 18 prior to its cleavage from the resin used for synthesis of the peptide. Therefore, this modified peptide is organized in four linear domains, from the amino- to the carboxyl-terminus, as follows: tripalmitoyl-S-glycerol cysteine ($Pam_3Cys$), the hepatitis B surface antigen promiscuous helper T cell epitope (HBsAg $T_h$), the glycine spacer (GG), and LHRH. This peptide is represented as follows: $Pam_3Cys$: HBsAg T: GG: LHRH. The lipid-modified peptide was formulated in the stable lipid emulsion, Liposyn (a mixture of emulsified soy bean and safflower oils) and administered subcutaneously to Sprague-Dawley rats. The dose used was the molar equivalent of 100 Mg of peptide 18 given at 0, 3 and 6 weeks. A second group of animals received unmodified peptide 18 in 100 Mg doses at 0, 3 and 6 weeks. 10 weeks following the initiation of the experiment, an ELISA assay was performed on sera from the immunized animals. 5 of 5 animals immunized with $Pam_3Cys$: HBsAg: GG: LHRH expressed significant anti-peptide 18 antibodies (OD>0.5 at a 1: 100 dilution). In contrast, none of the animals immunized with unmodified peptide 18 expressed antibodies to this level. Therefore, covalent lipid addition provides an effective means of potentiating immune responses.

EXAMPLE 16

Delivery of Peptide A in Microparticles

Efficient immune responses occur when an LHRH immunogen is entrapped microparticles of 10 μm or less were delivered subcutaneously or intramuscularly. These small microparticles were efficiently taken up by macrophages allowing for effective antigen presentation.

Microparticles containing peptide A were prepared with a poly(lactide-co-glycolide) copolymer as described in U.S. Series No. 201524, filed Feb. 25, 1994.

A sterile (water-in-oil)-in-water emulsion was prepared as follows: an aqueous solution of 1.5% w/w synthetic peptide A was prepared by passing the peptide solution through a sterile 0.2 μm filter. Polymer was dissolved in dichloromethane at a concentration of 4.0% w/w; 200 g of this solution was added to 20 g of peptide solution and mixed with a homogenizer (Model STD 1, Silverson Machiens, East Longmeadow, Mass., 1" tubular head, 13,000 rpm, 4 min). After the water-in-oil emulsion was formed, 600 g of a 10% w/w solution of polyvinyl alcohol was added thereto and mixed with a homogenizer (13,000 rpm, 6 min). A stable (water-in-oil)-in-water emulsion formed and was transferred to a 2 L filtration flask. The dichloromethane was evaporated with stirring by a magnetic stir bar for 16 h under ambient conditions. Sterile air was introduced into the evaporation flask through a 0.2 μm filter and a gas dispersion tube placed 4 cm above the emulsion. As the dichloromethane evaporated, it was removed from the flask by the stream of air vented through a side arm on the flask. The air/dichloromethane mixture was passed into a dry ice-acetone cold trap to condense the dichloromethane. The evaporation of the dichloromethane was complete after 16 h and discrete particles had formed. The particles were recovered from the polyvinyl alcohol solution by centrifugation, washing with sterile water and lyophilized for 24 hours to provide a dry powder. The particle size is less than 10 μm. Immune responses to microparticulate peptide A was evaluated in rats in an experiment described below and summarized in Table 7. The experimental design is the same as in Example 5 except as indicated otherwise.

Experimental Design:
Immunogen: peptide A (HBsAg $T_h$: LHRH, without spacer) in rapid-release microparticles (1: 1, polylactide:co-glycolide)
Dose: 100 μg of peptide A per dose
Route: subcutaneous
Adjuvant: the experimental variable
Species: 6 sexually mature Sprague-Dawley male rats/group
Necropsy: at 10 weeks determine testis weights Results Microparticulate peptide A caused significant LHRH-specific antibody production and dramatic atrophy of the testes in 2 of 6 immunized animals. When an equivalent dose of peptide A formulated on alum was administered in an identical manner, none of the animals exhibited significant organ weight reduction. Thus, microparticles were more efficient than alum in causing the desired effects, i.e. elevated LHRH-specific antibody titers, elimination of serum testosterone and organ atrophy. Microparticle delivery compares favorably with the efficacy exhibited by the delivery of soluble peptide A in Freund's adjuvant, which caused organ atrophy in 3 of 6 animals. By comparison, as demonstrated in Example 6, the simple addition of glycine spacer sequences (found in peptide 18) to the HBsAg $T_h$: LHRH construct significantly improved immunogenicity; 6 of 6 animals given peptide 18 in FCA/IFA had atrophied testes.

The effects of mixing peptide A loaded microparticles in various adjuvant/emulsion formulations was examined. As can be seen in Table 7, certain formulations including Liposyn+Saponin and Squalene+L121 (4 of 6 animals in each group had atrophied testes) appear to improve the immune responses elicited by microparticulate peptide A. Liposyn is a soy bean oil and safflower oil emulsion prepared for intravenous feeding of humans, saponin is a water soluble extract of Quil A, squalene is a metabolizable animal oil previously tested in humans as a vaccine carrier and L121 is a triblock polymer which has proven efficacious in human cancer therapy trials. 100% efficacy was achieved with peptide A-loaded microparticles formulated in Emulsigen +Saponin. Emulsigen is an adjuvant approved for use in food animals, and this formulation (i.e. immunogen cocktail in Emulsigen+saponin) can be used in a pet contraception vaccine or for the treatment of boar taint.

Polylactide-co-glycolyde microparticles containing an immunogen cocktail are formulated and tested for immune potency in accordance with this example.

EXAMPLE 17

Efficacy of $T_h$: LHRH Delivered in Emulsions $T_h$ epitope: LHRH immunogens have been identified and ranked in order of their effectiveness (Table 6) using a standard Freund's complete/incomplete immunization protocol. These results have permitted the selection of a number of different $T_h$ constructs for formulation into a cocktail of immunogens. This cocktail, coupled to alum, has demonstrated significant efficacy (Example 11). The addition of the invasin domain has enhanced the immunogenicity of the subject LHRH constructs, such that a single invasin epitope-bearing peptide demonstrates significant efficacy when administered on alum (Example 13). The invasin-containing construct also elicits exceptional and uniform responses when it is a component of an immunogen cocktail (Example 14).

In addition to microparticle delivery of immunotherapeutic immunogens in emulsion formulations, adjuvant/emulsion-based formulations of soluble immunogen have been evaluated. Again, peptide A was used to provide a means of comparing the relative efficacies of the different formulations. A representation of the different adjuvant/emulsion combinations that have been evaluated are listed in Table 8. Table 8 indicates which adjuvant/emulsion combinations are suitable for human or animal use. Some of the more reactogenic adjuvants (e.g. Freund's incomplete) approved for use in cancer patients were included. Animals were immunized at 0, 3 and 6 weeks with 100 μg of peptide A in the indicated formulations administered subcutaneously. Significant efficacy, as good or better than that achieved with Freund's complete adjuvant was obtained with some of these formulations, e.g. Emulsigen+L121 and ISA 720.

EXAMPLE 18

Efficacy of the Invasin Containing-peptide Cocktail in Unique Emulsion Formulations The adjuvant formulations which improved the efficacy of peptide A when compared to an alum-based formulation, e.g. IFA, ISA 720, ISA 51, Detox, Liposyn+Avridine, squalene+L121, MPL+TDE, Emulsigen+DDA, and Emulsigen+L121 were then used to prepare the peptide 32-containing cocktail described in Example 14. The results testing the effectiveness of these different formulations are summarized in Table 9. Significant efficacy (measured by serum testosterone levels below the threshold for castration at 8 weeks for 100% of the animals, and atrophied testes in 100% of the animals at week 10) was observed for several of the adjuvants. These findings demonstrate the power of combining a potent immunogen, namely a Th epitope: LHRH cocktail containing an Invasin domain with efficacious and safe emulsion formulations.

EXAMPLE 19

Efficacy of the Universal Synthetic Immune Stimulator-Amylin Constructs

Peptides 92 through 94 (peptide ID No:92–94) are synthesized using standard Fmoc synthesis procedures. Following purification by HPLC, the integrity and authenticity of the peptides are determined by mass-spectrophotometric analyses. The efficacy of each synthetic peptide construct is determined individually, and as a mixture of constructs, through immunization of laboratory animals using the Experimental Design:

Immunogen: peptides 92 through 94, individually peptides 92 through 94, in combination
Dose: molar equival. to 100 µg of peptide 92
Route: subcutaneous
Adjuvant: Freund's complete/ incomplete
Schedule: 0 weeks, peptide in Freund's complete 3 & 6 weeks, peptide in incomplete Freund's
Species: 5 female Sprague-Dawley rats per group
Control: one group, receiving adjuvant alone
Blood Samples: taken at 0, 3, 6 and 10 weeks post primary
Necropsy: at 10 weeks isolate pancreata Sera separated from blood samples withdrawn from immunized animals are tested for the presence of amylin-specific antibodies by standard ELISA assay. Full-length amylin peptide are used to coat the microtiter plates and serial dilutions of each serum sample is tested to determine titers. The capacity of amylin specific antibodies present in ELISA-positive sera to block amylin-mediated inhibition of glucose uptake is determined by the in situ assay for insulin stimulated glycogen synthesis described by Cooper et al. (1988, Proc. Natl. Acad. Sci. USA 85:7763–7766). Briefly, soleus muscle strips are prepared from fasting male Wistar rats and held in modified Krebs-Ringer bicarbonate buffer. Following a brief incubation (30 min.) the muscle strips are transferred to new buffer solutions containing $[U^{14}C]$ glucose and serial dilutions of full-length amylin peptide previously incubated with the ELISA-positive rat sera. Following a one hour incubation the amount of $[U^{14}C]$ glucose incorporated into glycogen in the muscle tissues is then determined. Control samples, amylin incubated in normal saline and amylin incubated in sera from adjuvant control animals, are also included. Antibodies capable of blocking the functional activity of amylin prevent amylin inhibition of insulin-stimulated glucose uptake by the muscle fibers.

At the completion of the experiment (i.e. at 10 weeks) the animals are sacrificed and their pancreata removed. Tissue sections from these organs are evaluated for the presence of amylin using a peptide hormone-specific immunohistochemical staining procedure (Westermark, et al., 1987, Diabetologia, 30:887–892). Those synthetic immunogens which significantly inhibit the function of amylin and block amylin deposition in islets cells are tested for efficacy in the rat model using adjuvants acceptable for use in humans.

EXAMPLE 20

Efficacy of the Universal Synthetic Immune Stimulator-Gastrin Constructs

Peptides 95 through 100 (peptide ID No:95–100) are synthesized using standard Fmoc synthesis procedures. Following purification by HPLC, the integrity and authenticity of the peptides are determined by mass-spectrophotometric analyses. The efficacy of each synthetic peptide construct is determined individually, and as a mixture of constructs, through immunization of laboratory animals using the Experimental Design:

Immunogen: peptides 95 through 100, individually peptides 95 through 100, in combination
Dose: molar equival. to 100 µg of peptide 95
Route: subcutaneous
Adjuvant: Freund's complete/ incomplete
Schedule: 0 weeks, peptide in Freund's complete 3 & 6 weeks, peptide in incomplete Freund's
Species: 5 female Sprague-Dawley rats per group
Control: one group, receiving adjuvant alone
Blood Samples: taken at 0, 3, 6 and 10 weeks post-primary immunization

Results

Blood samples are periodically withdrawn from the immunized and control rats. Sera processed from these samples are analyzed for the presence of $Gastrin_{17}$, $Gastrin_{34}$ and CCK specific-antibodies.

Two types of assays are used to detect anti-gastrin antibodies: a solid-phase enzyme linked immunosorbent assay (ELISA) and a liquid phase radioimmunoassay (RIA).

ELISA is used to screen for reactivity or cross-reactivity of antisera raised against $Gastrin_{34}$, $Gastrin_{17}$ and CCK. The RIA is used to quantitate the antibody levels in the serum from each immunized animal by reacting serum aliquots with each of these hormones for the determination of antigen binding capacity, expressed as pg hormone bound per microliter of antiserum (pg/µL).

The ELISA is conducted by coating polystyrene 96 well plates with 1 µg/mL of peptides $Gastrin_{34}$, $Gastrin_{17}$, or CCK. Serial dilutions of test antisera are used to determine the end-point titers of the sera.

In the RIA, 0.1, 1.0 or 10.0 µl aliquots of antiserum are incubated with $^{125}$I-labeled $Gastrin_{34}$, $Gastrin_{17}$ or CCK. The antisera are incubated with the labeled hormones for 2 hours, followed by precipitation of the hormone-antibody complexes with 25% polyethylene glycol. Antigen binding capacities for each antiserum are determined from the amount of the respective radioactive hormone precipitated.

The capacity of gastrin-reactive antibodies present in ELISA or RIA positive sera to neutralize the in vivo acid-stimulating activity of gastrin is determined using the perfused rat stomach method described in Gevas, P. C. et al EPO 380230, 1991. In brief, rats injected with gastrin or gastrin-anti-gastrin complex to induce acid secretion, are surgically prepared for collection of stomach secretions. Under general anesthesia and following tracheostomy, rats are cannulated via the esophagus and duodenum to allow continuous perfusion of the stomach with 0.9% saline. The stomach perfusate is collected periodically, and samples from each interval are titrated for acid content by neutralization with base (NaOH). Incremental and total acid input during the duration of the experiment and immediately after each treatment is determined.

The stomach acid outputs are calculated as the percent of maximal acid output=100×(An-Ab/Amax-Ab) where An=the acid produced over each sampling interval (as determined by titration with NaOH); Amax=the maximal interval release of stomach acid upon stimulation, and Ab=the baseline level of acid present at the time of a given stimulation.

The capacity of gastrin-reactive antibodies present in ELISA or RIA positive sera to neutralize the in vitro tumor stimulatory activity of gastrin is determined by the ability of immune sera to inhibit gastrin-induced proliferative response of a colon carcinoma cell line as measured by [$H^3$]-thymidine incorporation.

EXAMPLE 21

Efficacy of the Universal Synthetic Immune Stimulator-GRP Constructs

Peptides 101 through 102 (peptide ID No:101–102) are synthesized using standard Fmoc synthesis procedures. Following purification by HPLC, the integrity and authenticity of the peptides are determined by mass-spectrophotometric analyses. The efficacy of each synthetic peptide construct is determined individually, and as a mixture of constructs, through immunization of laboratory animals using the Experimental Design:

Immunogen: peptides 101 and 102, individually peptides 101 and 102, in combination Dose: molar equival. to 100 µg of peptide 101

Route: subcutaneous

Adjuvant: Freund's complete/incomplete

Schedule: 0 weeks, peptide in Freund's complete 3 & 6 weeks, peptide in incomplete Freund's Species: 5 female Sprague-Dawley rats per group Control: one group, receiving adjuvant alone Blood Samples: taken at 0, 3, 6 and 10 weeks post-primary immunization Sera separated from blood samples withdrawn from immunized animals are tested for the presence of Gastrin Releasing Peptide (GRP)-specific antibodies by standard ELISA assay. Full-length GRP peptide is used to coat the microtiter plates and serial dilutions of each serum sample are tested to determine titers.

The capacity of GRP-specific antibodies present in ELISA-positive sera to inhibit GRP-mediated induction of tumor growth is determined by the in vitro assay for ($H^3$) thymidine uptake by GRP-induced proliferative response of selected carcinoma cell lines.

EXAMPLE 22

Efficacy of the Universal Synthetic Immune Stimulator-IgE-CH4 Constructs

Peptides 103 and 104 (peptide ID No:103–104) are synthesized using standard Fmoc synthesis procedures. Following purification by HPLC, the integrity and authenticity of the peptides are determined by mass-spectrophotometric analyses. The efficacy of each synthetic peptide construct is determined individually, and as a mixture, through immunization of laboratory animals using the Experimental Design:

Immunogen: peptides 103 and 104, individually peptides 103 and 104, in combination Dose: molar equival. to 100 µg of peptide 103

Route: subcutaneous

Adjuvant: Freund's complete/incomplete

Schedule: 0 weeks, peptide in Freund's complete 3 & 6 weeks, peptide in incomplete Freund's Species: 5 female Sprague-Dawley rats per group Control: one group, receiving adjuvant alone Blood Samples: taken at 0, 3, 6 and 10 weeks post-primary Sera isolated from blood samples withdrawn from immunized animals are tested for the presence of IgE CH4-specific antibodies by standard ELISA assay. IgE CH4 peptide (SEQ ID NO:79) is used to coat the microtiter plates and serial dilutions of each serum sample are tested on them to determine titers.

The capacity of IgE-CH4 specific antibodies present in ELISA-positive sera to inhibit direct histamine release action of the IgE CH4 peptide on rat peritoneal mast cells is tested as described by Stanworth D. R. et al. (Lancet 1990, 336:1279–1281). These positive sera are further tested by in vivo assays to measure the capability of sera to inhibit the blueing reaction in the Rat Passive Cutaneous Anaphylaxis Assay, as described by Stanworth D. R. et al (Lancet 1990, 336:1279–1281).

EXAMPLE 23

Efficacy of the Universal Synthetic Immune Stimulator-Chlamydia trachomatis MOMP Constructs Peptides 105 through 114 (Peptides ID NO:105 through 114) were synthesized using standard Fmoc synthesis procedures. Each universal immune stimulator-C. trachomatis MOMP peptide construct was formulated, alone and in combination, and then injected into laboratory animals for the determination of relative immunogenicities, using the following Experimental Design:

Immunogen: peptides 105 through 114, individually peptides 105 through 114, in combination Dose: molar equival. to 100 µg of peptide 107

Route: intraperitoneal

Adjuvant: Freund's complete/incomplete

Schedule: 0 weeks, peptide in Freund's complete 3 and 10 weeks, peptide in incomplete Freund's Species: 5 female Dunkin-Hartley guinea pigs (450–500 grams) per group Control: one group receiving adjuvant alone Blood Samples: taken at 0, 5, 8 & 12 weeks Sera separated from blood samples withdrawn from the immunized animals are tested for the presence of MOMP variable domain specific antibodies by a standard ELISA assay. Individual microtiter plates are coated with synthetic peptides representing the MOMP variable domains I to IV, lacking the universal immune stimulator, each on separate plates. Serial dilutions of sera from each immunized animal are tested on them to determine anti-MOMP peptide antibody titers. ELISA positive sera are then tested for the capacity to bind to purified elementary bodies (EBs) representing each of the different C. trachomatis serovars (A through L3) coated on microtiter plates). EB binding positive sera are then tested for their capacity to block infectivity of permissive mammalian cells in culture by all relevant C. trachomatis serovars (Su, et al., 1990, Infect. Immun. 58;1017–1025). Those synthetic immunogens which demonstrate a significant ability to elicit C. trachomatis neutralizing antibodies are tested for efficacy in guinea pigs using adjuvants acceptable for use in humans. Peptides can be evaluated for a capacity to block infection in vivo using the mouse salpingitis model (Tuffrey et al., 1992, J. Gen. Microbiol. 138: 1707–1715) or the cynomolgus monkey eye challenge model (Taylor, et al., 1988, Invest. Opthalmol. Vis. Sci. 29:1847–1853).

EXAMPLE 24

Efficacy of the Universal Immune Stimulator-HIV-1 V3 PND Construct

Peptide 115 (SEQ ID No:115) was synthesized using standard Fmoc synthesis procedures. The efficacy of the construct in eliciting HIV-1 neutralizing antibodies in laboratory animals is determined according to the following:

Experimental Design

Immunogen: peptide
Dose: 100 μg per immunization
Route: subcutaneous
Adjuvant: Freund's complete/ incomplete
Schedule: 0 weeks, peptide in Freund's complete 4 weeks, peptide in incomplete Freund's
Species: 5 female Dunkin-Hartley guinea pigs (450–500 grams) per group
Control: one group receiving adjuvant alone
Blood Samples: taken at 0, 4, & 8 weeks Sera separated from blood samples withdrawn from the immunized animals are tested for the presence of anti-V3 PND antibodies by a standard ELISA assay. The monomeric version of the V3 PND not linked to the synthetic immune stimulator is used to coat the ELISA microtiter plates, and serial dilutions of each serum sample are tested on them to determine ELISA titers. Positive samples are evaluated for their capacity to neutralize HIV-1 strain MN in vitro using a syncytial focus reduction assay (Wang, et al., 1991, Science 245:285). Those sera capable of neutralizing the infectivity of the laboratory adapted strain, HIV-$1_{MN}$, are tested for their capacity to block infection of primary lymphocytes by assorted field virus isolates (White-Scharf et al, 1993, Virology 192:197-206).

TABLE 1

Amino Acid Sequence of Peptides A–E

| Peptide | SEQ ID NO. | Amino Acid Sequence |
|---|---|---|
| A | 10 | Lys—Lys—Lys—Phe—Phe—Leu—Leu—Thr—Arg—Ile—Leu—Thr—Ile—Pro—Gln—Ser—Leu—Asp—Glu—His—Trp—Ser—Tyr—Gly—Leu—Arg—Pro—Gly |
| B | — | [Glu—His—Trp—Ser—Tyr—Gly—Leu—Arg—Pro—Gly—Glu—His—Trp—Ser—Tyr—Gly—Leu—Arg—Pro—Gly—]$_8$—Lys$_4$—Lys$_2$—Lys—Phe—Phe—Leu—Leu—Thr—Arg—Ile—Leu—Thr—Ile—Pro—Gln—Ser—Leu—Asp |
| C | — | [Glu—His—Trp—Ser—Tyr—Gly—Leu—Arq—Pro—Gly—Glu—His—Trp—Ser—Tyr—Gly—Leu—Arg—Pro—Gly—Glu—His—Trp—Ser—Tyr—Gly—Leu—Arg—Pro—Gly—]$_8$—Lys$_4$—Lys$_2$—Lys—Phe—Phe—Leu—Leu—Thr—Arg—Ile—Leu—Thr—Ile—Pro—Gln—Ser—Leu—Asp |
| D | — | [Glu—His—Trp—Ser—Tyr—Gly—Leu—Arg—Pro—Gly—Phe—Phe—Leu—Leu—Thr—Arg—Ile—Leu—Thr—Ile—Pro—Gln—Ser—Leu—Asp—Met]$_8$—Lys$_4$—Lys$_2$—Lys—Ala—Ala |
| E | — | [Glu—His—Trp—Ser—Tyr—Gly—Leu—Arg—Pro—Gly—Glu—His—Trp—Ser—Tyr—Gly—Leu—Arg—Pro—Gly—Phe—Phe—Leu—Leu—Thr—Arg—Ile—Leu—Thr—Ile—Pro—Gln—Ser—Leu—Asp—Met]$_8$—Lys$_4$—Lys$_2$—Lys—Ala—Ala |

TABLE 2

Immunogenicity and Therapeutic Effect after Immunization with Peptides A–E in Rats

| Peptide | α-LHRH[a] | Testosterone[a] | Testes[b] | P + SV[c] |
|---|---|---|---|---|
| A | 3.93 | <0.01 | 0.4 | 0.2 |
| | 2.55 | <0.01 | 0.4 | 0.3 |
| | 2.06 | <0.01 | 0.6 | 0.2 |

TABLE 2-continued

Immunogenicity and Therapeutic Effect after Immunization with Peptides A–E in Rats

| Peptide | α-LHRH[a] | Testosterone[a] | Testes[b] | P + SV[c] |
|---|---|---|---|---|
| | 0.72 | 5.3 | 1.8 | 1.8 |
| | 0.42 | 2.1 | 1.7 | 1.8 |
| B | 0.53 | 14.0 | 1.7 | 1.7 |
| | 0.51 | 16.5 | 1.7 | 1.6 |
| | 0.49 | 12.6 | 1.7 | 1.6 |
| | 0.45 | 4.6 | 1.6 | 1.7 |
| | 0.42 | 10.5 | 1.7 | 2.2 |
| C | 0.78 | 5.6 | 1.6 | 2.3 |
| | 0.45 | 12.3 | 1.8 | 1.6 |
| | 0.41 | 3.9 | 2.1 | 1.6 |
| | 0.41 | 5.3 | 1.6 | 1.8 |
| | 0.39 | 11.2 | 1.7 | 1.8 |
| D | 1.44 | 2.6 | 1.7 | 2.1 |
| | 0.44 | 3.6 | 1.7 | 1.3 |
| | 0.43 | 2.3 | 1.6 | 2.0 |
| | 0.39 | 2.1 | 1.7 | 1.6 |
| | 0.39 | 2.8 | 1.4 | 2.1 |
| E | 1.69 | <0.01 | 1.4 | 2.0 |
| | 0.66 | 0.9 | 1.5 | 1.9 |
| | 0.51 | 3.3 | 1.2 | 1.9 |
| | 0.40 | 4.0 | 1.6 | 2.0 |
| | 0.40 | 13.9 | 1.3 | 0.9 |

[a]nmol/L
[b]Weight of testes in g
[c]Weight of prostate and seminal vesicles (P + SV) in g

TABLE 3

Average Anti-LHRH Titers and Androgen-Dependent Organ Weights in Rats Immunized with Peptides A–E

| Peptide[a] | α-LHRH (nmol/L) | Testes (g) | Epid[b] (g) | P + SV (g) |
|---|---|---|---|---|
| A | 1.94 | 1.0 | 0.4 | 0.9 |
| B | 0.48 | 1.7 | 0.6 | 1.8 |

TABLE 3-continued Average Anti-LHRH Titers and Androgen-Dependent Organ
Weights in Rats Immunized with Peptides A-E

| Peptide[a] | α-LHRH (nmol/L) | Testes (g) | Epid[b] (g) | P + SV (g) |
|---|---|---|---|---|
| C | 0.49 | 1.8 | 0.6 | 1.8 |
| D | 0.62 | 1.6 | 0.6 | 1.8 |
| E | 0.73 | 1.4 | 0.6 | 1.7 |
| Control | 0.45 | 1.6 | 0.7 | 2.0 |

[a]Each peptide was injected in 5 rats.
[b]Abbreviations: Epid., epididymis; P + SV, prostate and seminal vesicles-

TABLE 4

| Peptide | SEQ ID No. | Sequence |
|---|---|---|
| F (PT$_1$Th-LHRH) | 11 | Lys—Lys—Leu—Arg—Arg—Leu—Leu—Tyr—Met—Ile—Tyr—Met—Ser—Gly—Leu—Ala—Val—Arg—Val—His—Val—Ser—Lys—Glu—Glu—Gln—Tyr—Tyr—Asp—Tyr—Glu—His—Trp—Ser—Tyr—Gly—Leu—Arg—Pro—Gly |
| G (PT$_{1A}$Th-LHRH) | 12 | Tyr—Met—Ser—Gly—Leu—Ala—Val—Arg—Val—His—Val—Ser—Lys—Glu—Glu—His—Trp—Ser—Tyr—Gly—Leu—Arg—Pro—Gly |
| H (TT$_1$Th-LHRH) | 13 | Lys—Lys—Gln—Tyr—Ile—Lys—Ala—Asn—Ser—Lys—Phe—Ile—Gly—Ile—Thr—Glu—Leu—Glu—His—Trp—Ser—Tyr—Gly—Leu—Arg—Pro—Gly |
| I (TT$_2$Th-LHRH) | 14 | Lys—Lys—Phe—Asn—Asn—Phe—Thr—Val—Ser—Phe—Trp—Leu—Arg—Val—Pro—Lys—Val—Ser—Ala—Ser—His—Leu—Glu—His—Trp—Ser—Tyr—Gly—Leu—Arg—Pro—Gly |
| J (TT$_3$Th-LHRH) | 15 | Tyr—Asp—Pro—Asn—Tyr—Leu—Arg—Thr—Asp—Ser—Asp—Lys—Asp—Arg—Phe—Leu—Gln—Thr—Met—Val—Lys—Leu—Phe—Asn—Arg—Ile—Lys—Glu—His—Trp—Ser—Tyr—Gly—Leu—Arg—Pro—Gly |
| K (PT$_2$Th-LHRH) | 16 | Gly—Ala—Tyr—Ala—Arg—Cys—Pro—Asn—Gly—Thr—Arg—Ala—Leu—Thr—Val—Ala—Glu—Leu—Arg—Gly—Asn—Ala—Glu—Leu—Glu—His—Trp—Ser—Tyr—Gly—Leu—Arg—Pro—Gly |
| L (MV$_F$Th-LHRH) | 17 | Leu—Ser—Glu—Ile—Lys—Gly—Val—Ile—Val—His—Arg—Leu—Glu—Gly—Val—Glu—His—Trp—Ser—Tyr—Gly—Leu—Arg—Pro—Gly |

TABLE 5

Peptides of the Invention

| Peptide SEQ ID NO: | Sequence[a] |
|---|---|
| 18 (HB$_s$T$_h$-GG-LHRH) | K K K F F L L T R I L T I P Q S L D G<br>G E H W S Y<br>G L R P G |
| 19 (MV$_{F1}$T$_h$-GG-LHRH) | L S E I K G V I V H R L E G V G G<br>E H W S Y G L R P G |
| 20 (MV$_{F1}$T$_h$-MV$_{F1}$T$_h$-GG-LHRH) | L S E I K G V I V H R L E G V L S E I<br>K G V I V H<br>R L E G V G G E H W S Y G L R P G |
| 21 (MV$_{F2}$T$_h$-GG-LHRH) | G I L E S R G I K A R I T H V D T E S<br>Y G G E H W<br>S Y G L R P G |
| 22 (TT$_4$T$_h$-GG-LHRH) | K K W V R D I I D D F T N E S S Q K T<br>G G E H W S<br>Y G L R P G |
| 23 (TT$_5$T$_h$-GG-LHRH) | K K D V S T I V P Y I G P A L N I V G<br>G E H W S Y |

TABLE 5-continued

Peptides of the Invention

| Peptide SEQ ID NO: | Sequence[a] | | | | | | | | | | | | | | | | | |
|---|---|---|---|---|---|---|---|---|---|---|---|---|---|---|---|---|---|---|
| | G | L | R | P | G | | | | | | | | | | | | | |
| 24 (CTT_h-GG-LHRH) | A | L | N | I | W | D | R | F | D | V | F | C | T | L | G | A | T | T | G |
| | Y | L | K | G | N | S | | | | | | | | | | | | |
| | G | G | E | H | W | S | Y | G | L | R | P | G | | | | | | |
| 25 (DT_1T_h-GG-LHRH) | D | S | E | T | A | D | N | L | E | K | T | V | A | A | L | S | I | L | P |
| | G | I | G | C | G | G | | | | | | | | | | | | |
| | E | H | W | S | Y | G | L | R | P | G | | | | | | | | |
| 26 (DT_2T_h-GG-LHRH) | E | E | I | V | A | Q | S | I | A | L | S | S | L | M | V | A | Q | A | I |
| | P | L | V | G | E | L | | | | | | | | | | | | |
| | V | D | I | G | F | A | A | T | N | F | V | E | S | C | G | G | E | H | W |
| | S | Y | G | L | R | P | G | | | | | | | | | | | |
| 27 (PFT_h-GG-LRRH) | D | I | E | K | K | I | A | K | M | E | K | A | S | S | V | F | N | V | V |
| | N | S | G | G | E | H | | | | | | | | | | | | |
| | W | S | Y | G | L | R | P | G | | | | | | | | | | |
| 28 (SMT_h-GG-LHRH) | K | W | F | K | T | N | A | P | N | G | V | D | E | K | I | R | I | G | G |
| | E | H | W | S | Y | G | | | | | | | | | | | | |
| | L | R | P | G | | | | | | | | | | | | | | |
| 29 (TraT_1T_h-GG-LHRH) | G | L | Q | G | K | I | A | D | A | V | K | A | K | G | G | G | E | H | W |
| | S | Y | G | L | R | P | G | | | | | | | | | | | |
| 30 (TraT_2T_h-GG-LHRH) | G | L | A | A | G | L | V | G | M | A | A | D | A | M | V | E | D | V | N |
| | G | G | E | W | W | S | Y | G | L | R | P | G | | | | | | |
| 31 (TraT_3T_h-GG-LHRH) | S | T | E | T | G | N | Q | H | H | Y | Q | T | R | V | V | S | N | A | N |
| | K | G | G | E | H | W | S | Y | G | L | R | P | G | | | | | |
| 32 (Inv-GG-HB_aT_h-GG-LHRH) | T | A | K | S | K | K | F | P | S | Y | T | A | T | Y | Q | F | G | G | F |
| | F | L | L | T | R | I | L | T | G | G | E | H | W | S | Y | G | L | R | P |
| | G | I | P | Q | S | L | D | | | | | | | | | | | |
| 33 (Inv-GG-MV_F1T_h-GG-LHRH) | T | A | K | S | K | K | F | P | S | Y | T | A | T | Y | Q | F | G | G | L |
| | S | E | I | K | G | V | I | V | H | R | L | E | G | V | G | G | E | H | W |
| | S | Y | G | L | R | P | G | | | | | | | | | | | |
| 34 (Inv-GG-PT_2T_h-GG-LHRH) | T | A | K | S | K | K | F | P | S | Y | T | A | T | Y | Q | F | G | G | G |
| | A | Y | A | R | C | P | N | G | T | R | A | L | T | V | E | L | R | G | N |
| | A | E | L | G | G | E | H | W | S | Y | G | L | R | P | G | | | |
| 35 (Inv-GG-TT_1T_h-GG-LHRH) | T | A | K | S | K | K | F | P | S | Y | T | A | T | Y | Q | F | G | G | K |
| | K | Q | Y | I | K | A | N | S | K | F | I | G | I | T | E | L | G | G | E |
| | H | W | S | Y | G | L | R | P | G | | | | | | | | | |
| 36 (Inv-GG-TT_4T_h-GG-LHRH) | T | A | K | S | K | K | F | P | S | Y | T | A | T | Y | Q | F | G | G | K |
| | K | W | V | R | D | I | I | D | D | F | T | N | E | S | S | Q | K | T | G |
| | G | E | H | W | S | Y | G | L | R | P | G | | | | | | | |
| 37 (Inv-GG-TT_5-GG-LHRH) | T | A | K | S | K | K | F | P | S | Y | T | A | T | Y | Q | F | G | G | K |
| | K | D | V | S | T | I | V | P | Y | I | G | P | A | L | N | I | V | G | G |
| | E | H | W | S | Y | G | L | R | P | G | | | | | | | | |
| 38 (SSAL1-GG-LHRH)[b] | D | L | S | E | L | K | G | L | L | L | H | K | L | E | G | L | G | G- | |
| | E | I | | D | I | R | | I | I | I | | R | I | D | | I | | | |
| | | V | | | V | | | V | V | V | | | V | | | V | | | |
| | | F | | | F | | | F | F | F | | | F | | | F | | | |
| 39 (SSAL2-GG-LHRH)[b] | E | H | W | S | Y | G | L | R | P | G | | | | | | | | |
| | K | K | K | L | F | L | L | T | K | L | L | T | L | P | Q | S | L | D- | |
| | R | R | R | I | K | I | I | | R | I | I | | I | | L | | I | R | |
| | | | | V | R | V | V | | | V | V | | V | | V | | V | | |
| | | | | F | F | F | F | | | F | F | | F | | F | | F | | |
| 40 (Inv-GG-SSAL3-GG-LHRH)[b] | G | G | E | H | W | S | Y | G | L | R | P | G | | | | | | |
| | T | A | K | S | K | K | F | P | S | Y | T | A | T | Y | Q | F | G | G | |
| | D | L | S | E | L | K | G | L | L | L | H | K | L | E | G | L- | | | |
| | E | I | | D | I | R | | I | I | I | | R | I | D | | I | | | |
| | | V | | | V | | | V | V | V | | | V | | | V | | | |
| | | F | | | F | | | F | F | F | | | F | | | F | | | |
| 41 (Inv-GG-SSAL4-GG-LHRH)[b] | G | G | E | H | W | S | Y | G | L | R | P | G | | | | | | |
| | T | A | K | S | K | K | F | P | S | Y | T | A | T | Y | Q | F | G | G | |
| | K | K | K | L | F | L | L | T | K | L | L | T | L | P | Q | S | L | D- | |
| | R | R | R | I | K | I | I | | R | I | I | | I | | L | | I | R | |
| | | | | V | | V | V | | | V | V | | V | | I | | V | | |
| | | | | F | | F | F | | | F | F | | F | | F | | F | | |
| | | | | | | | | | | | | | | | V | | | | |
| | G | G | E | H | W | S | Y | G | L | R | P | G | | | | | | |

[a] Sequences are given in the standard one-letter amino acid codes.
[b] For simplicity, the amino acids present at each position of the library are indicated below the main chain. Invariant amino acids are designated a molar value of one, and Variant amino acids are added during synthesis at an equimolar ratio depending on the number of variants at that position, i.e., if a position has 2 amino acids, then each is added in 0.5 ratio relative to the invariant amount, for 3 amino acids the ratio is 0.33, for 4 amino acids the ratio is 0.25, for 5 amino acids, the ratio is 0.20, etc.

TABLE 6

Efficacy of $T_h$: LHRH Synthetic Peptides

| Peptide[a] | Seq ID No. | $T_h$ Epitope | α-LHRH Ab[b] | Reduced S.T.[c] | Testis Atrophy[d] |
|---|---|---|---|---|---|
| A | 10 | HBs | 45 | 40 | 35/90 |
| 18 | 18 | HBs | 100 | 85 | 65/95 |
| 19 | 19 | $MV_{F1}T_h$ | 35 | 85 | 80/95 |
| K | 16 | $PT_2T_h$ | 65 | 50 | 35/90 |
| H | 13 | $TT_1T_h$ | 100 | 100 | 95/— |
| I | 14 | $TT_2T_h$ | 80 | 60 | 40/— |
| 22 | 22 | $TT_4T_h$ | — | — | —/95 |
| 23 | 23 | $TT_5T_h$ | — | — | —/95 |
| LHRH | | None | 0 | 0 | 0 |

[a]In each case, animals received equimolar amounts of peptide equivalent to 100 μg of peptide A. Peptide was administered subcutaneously at weeks 0 (in CFA) and at 3 and 6 weeks (in IFA).
[b]Percentage of animals having LHRH-specific antibody titers of 1.0 nmole/L or greater.
[c]Percentage of animals having serum testosterone levels below 0.5 nmole/L.
[d]Percentage of animals having mean testis weights less than 10% of adjuvant control groups. The first number is for animals receiving subcutaneous administration of the peptide; the second number is for animals receiving intramuscular administration of the peptide.

TABLE 7

Efficacy of $HBsAgT_h$: LHRH Delivery in Microparticles

| Formulation[a] | α-LHRH Ab[b] | Reduced S.T.[c] | Testis Atrophy[d] |
|---|---|---|---|
| Detox | 65 | 15 | 15 |
| Squalene + L121 | 85 | 65 | 65 |
| FCA/IFA | 50 | 0 | 0 |
| IFA/IFA | 15 | 0 | 0 |
| Alum | 15 | 15 | 15 |
| Liposyn | 0 | 0 | 0 |
| Liposyn + Avridine | 65 | 35 | 35 |
| Liposyn + L121 | 50 | 0 | 0 |
| Liposyn + Saponin | 85 | 65 | 65 |
| Emulsigen | 85 | 50 | 50 |
| Emulsigen + DDA | 85 | 65 | 65 |
| Emulsigen + Saponin | 100 | 100 | 100 |
| Saline | 35 | 35 | 35 |
| Free peptide on alum[e] | 20 | 0 | 0 |
| Free peptide in FCA/IFA[f] | 60 | 40 | 40 |

[a]Sprague-Dawley rats were administered 100 μg of peptide A entrapped in rapid release microparticles at 0, 3 and 6 weeks. All immunizations were given subcutaneously. Results are reported as the percentage of animals giving the indicated responses 14 weeks after the commencement of the study.
[b]LHRH-specific antibody titers of 1.0 nmole/L or greater.
[c]Serum testosterone levels below 0.5 nmole/L.
[d]Mean testis weights less than 10% of adjuvant control groups.
[e]Peptide A was administered in its soluble form bound to alum.
[f]Peptide A was administered in its soluble form formulated in Freund's adjuvant.

TABLE 8

Efficacy of $HBsT_h$: LHRH in Emulsion Formulations

| Formulation[1] | α-LHRH Ab[2] | Reduced S.T.[3] | Testis Atrophy[4] |
|---|---|---|---|
| FCA/IFA | 80 | 80 | 60 |
| IFA/IFA[h] | 80 | 60 | 40 |
| DETOX[h] | 60 | 20 | 0 |
| MPL[h] | 60 | 40 | 0 |
| MPL + TDE[h] | 40 | 0 | 0 |
| DEAE DEXTRAN[h] | 20 | 0 | 0 |
| LIPOSYN[h] | 0 | 0 | 0 |
| LIPOSYN + AVRIDINE[h] | 80 | 40 | 40 |
| LIPOSYN + L121[h] | 0 | 0 | 0 |
| ISA 51[h] | 60 | 40 | 40 |
| ISA 720[h] | 80 | 60 | 60 |
| EMULSIGEN[a] | 60 | 60 | 40 |
| EMULSIGEN + DDA[a] | 60 | 40 | 40 |
| EMULSIGEN + SAPONIN[a] | 0 | 0 | 0 |
| EMULSIGEN + L121[a] | 100 | 80 | 80 |
| EMULSIGEN + F127[a] | 60 | 20 | 20 |
| EMULSIGEN + MDP[a] | 60 | 40 | 40 |
| L121 + TWEEN[a] | 60 | 40 | 40 |
| ALUM[h] | 20 | 0 | 0 |

[1]Sprague-Dawley rats were administered 100 μg of peptide I formulated in the above emulsions at 0, 3 & 6 weeks. All immunizations were given subcutaneously. Results are reported as the percentage of animals giving the indicated responses 10 weeks following the commencement of the experiment.
[2]LHRH-specific antibody titers of 1.0 nmole/L or greater.
[3]Serum testosterone levels below 0.5 nmole/L.
[4]Mean testis weights less than 10% of adjuvant control groups.
[a]Adjuvants for use in animals.
[h]Adjuvants for use in humans.

TABLE 9

Efficacy of a Peptide 32-Containing $T_h$: LHRH Immunogen Cocktail

| Formulation[a] | α-LHRH Ab[b] | Reduced S.T.[c] | Testis Atrophy[d] |
|---|---|---|---|
| FIA | 100 | 100 | 100 |
| DETOX | 100 | 100 | 100 |
| MPL + TDE | 100 | 100 | 65 |
| MPL | 100 | 35 | 15 |
| SQUALENE + L121 | 100 | 85 | 85 |
| ISA 51 | 100 | 85 | 80 |
| ISA 720 | 100 | 85 | 85 |
| liposyn + AVRIDINE | 100 | 100 | 100 |
| EMULSIGEN | 100 | 85 | 65 |
| EMULSIGEN + DDA | 100 | 100 | 100 |
| EMULSIGEN + L121 | 100 | 100 | 85 |
| ALUM | 100 | 100 | 100 |
| cocktail w/o pept.32 in IFA[e] | 65 | 35 | 35 |

[a]Sprague-Dawley rats were administered 100 μg of a cocktail composed of equimolar amounts of Inv: GG: HBsAg$T_h$: GG: LHRH (peptide 32) + MVF$T_h$1: GG: LHRH + PTT$_h$2: LHRH + TTT$_h$1: LHRH at 0, 3 & 6 weeks. All immunizations were given intramuscularly. Results are reported as the percentage of animals giving the indicated responses 10 weeks following the commencement of the experiment.
[b]LHRH-specific antibody titers of 1.0 nmole/L or greater.
[c]Serum testosterone levels below 0.5 nmole/L.
[d]Mean testis weights less than 10% of adjuvant control groups.
[e]A cocktail of the same peptides without peptide 32 (at a molar equivalence to the peptide 32-containing cocktail) was formulated in IFA and administered in an identical fashion to the above.

TABLE 10

Examples of Universal Synthetic Immunostimulators with GG Spacers

| Peptide SEQ ID NO: | Sequence |
|---|---|
| 54 (Inv-GG-HB$_s$T$_h$-GG) | T A K S K K F P S Y T A T Y Q F G G F F<br>L L T R I L T I P Q S L D G G |
| 55 (Inv-GG-MV$_{F1}$T$_h$-GG) | T A K S K K F P S Y T A T Y Q F G G L S<br>E I K G V I V H R L E G V G G |
| 56 (InV-GG-PT$_2$T$_h$-GG) | T A K S K K F P S Y T A T Y Q F G G G A<br>Y A R C P N G T R A L T V A E L R G N A<br>E L G G |
| 57 (Inv-GG-TT$_1$T$_h$-GG) | T A K S K K F P S Y T A T Y Q F G G K K<br>Q Y I K A N S K F I G I T E L G G |
| 58 (Inv-GG-TT$_4$T$_h$-GG) | T A K S K K F P S Y T A T Y Q F G G K K<br>W V R D I I D D F T N E S S Q K T G G |
| 59 (Inv-GG-TT$_5$T$_h$-GG) | T A K S K K F P S Y T A T Y Q F G G K K<br>D V S T I V P Y I G P A L N I V G G |
| 60 (GG-HB$_s$T$_h$-GG-Inv) | G G F F L L T R I L T I P Q S L D G G T<br>A K S K K F P S Y T A T Y Q F |
| 61 (GG-MV$_{F1}$T$_h$-GG-Inv) | G G L S E I K G V I V H R L E G V G G T<br>A K S K K F P S Y T A T Y Q F |
| 62 (GG-PT$_2$T$_h$-GG-Inv) | G G G A Y A R C P N G T R A L T V A E L<br>R G N A E L G G T A K S K K F P S Y T A<br>T Y Q F |
| 63 (GG-TT$_1$T$_h$-GG-Inv) | G G K K Q Y I K A N S K F I G I T E L G<br>G T A K S K K F P S Y T A T Y Q F |
| 64 (GG-TT$_4$T$_h$-GG-Inv) | G G K K W V R D I I D D F T N E S S Q K<br>T G G T A K S K K F P S Y T A T Y Q F |
| 65 (GG-TT$_5$-GG-Inv) | G G K K D V S T I V P Y I G P A L N I V<br>G G T A K S K K F P S Y T A T Y Q F |

TABLE 11

Examples of Peptide Haptens

| Peptide SEQ ID NO: | Sequence |
|---|---|
| 66 Human Amylin | K C N T A T C A T Q R L A N F L V H S S<br>N N F G A I L S S T N V G S N T Y-amide |
| 67 Human Amylin N-fragment | K C N T A T C A T Q R L A N F L V H S S |
| 68 Human Amylin C-fragment | S S N N F G A I L S S T N V G S N T Y |
| 69 Gastrin$_{34}$ | Q L G P Q G P P H L V A D P S K K Q G P<br>W L E E E E E A Y G W M D F |
| 70 Gastrin$_{34}$ | Q L G P Q G P P H L V A D P S K K Q G P<br>W L |
| 71 Gastrin$_{34}$ | Q L G P Q G P P H L V A D P S K K Q |
| 72 Gastrin$_{34}$ | Q L G P Q G P P H |
| 73 Gastrin$_{34}$ | Q L G P Q G P P P P |
| 74 Gastrin$_{17}$ | Q G P W L E E E E A Y G W M D F |
| 75 Gastrin$_{17}$ | Q G P W L E E E E A Y |
| 76 Gastrin$_{17}$ | Q G P W L E E E |
| 77 GRP (Gastrin Releasing Peptide) | V P L P A G G T V L T K M Y P R G N H<br>W A V G H L M |
| 78 GRP 10 | G N H W A V G H L M |
| 79 IgE CH4 | K T K G S G F F V F |
| 80 Chlamydia trachomatis MOMP VDI (serovar A C,H,I,J,K & L3)[b] | E F Q M G A A P T T S D T A G L Q N D P T-<br>E N V E D E K V<br>K A S K<br>R<br>T N V A R<br>A<br>V |

TABLE 11-continued

Examples of Peptide Haptens

| Peptide SEQ ID NO: | Sequence | | | | | | | | | | | | | | | | | | | | |
|---|---|---|---|---|---|---|---|---|---|---|---|---|---|---|---|---|---|---|---|---|---|
| 81 Chlamydia trachomatis MOMP VDI (serovar B, Ba,D,E,L1 & L2)[b] | E | F | Q | M | G | A D | K | P | T | T | T A S | T D S | G | N | A S | A T V | A | P | S T | T | L- C |
| | T | A | R | | | | | | | | | | | | | | | | | | |
| 82 Chlamydia trachomatis MOMP VDI (serovar F & G)[b] | E L | F V | E E | M R | G | E | A | L | A | G | A | S | G | N | T | T | S | T | L | S | K |
| 83 Chlamydia trachomatis MOMP VDII (serovar A, C,H,I,J,K & L3)[b] | F | G | T | K | T | Q K | S A Y | S T | N S G D K | F | N D | T | A | K | L N | V I F | P | N | T I A | A | L- |
| | N D | Q R E | A | V | V | | | | | | | | | | | | | | | | |
| 84 Chlamydia trachomatis MOMP VDII (serovar B, Ba & L2)[b] | F | G | N D | N | E | N | Q H | T A | K T | V | S | N D | S G | A T K | F L | V | P | N | M | S | L |
| | D | Q | S | V | V | | | | | | | | | | | | | | | | |
| 85 Chlamydia trachomatis MOMP VDII (serovar D, E,F,G & L1)[b] | F | G | D G | N V | E | N | Q A | K S T | T K Q | V P | K A | A T K | E N D T | S A | V I | P | N | M V | S Q | F L | D- N |
| | Q | S | V | V | | | | | | | | | | | | | | | | | |
| 86 Chlamydia trachomatis MOMP VDIV (serovar A, B,Ba,D,E,I,L1 & L2)[b] | S L | A | T E K S | A T P A G N | I V E | F L G Q N E | D V L A | T | T | L | N | P | T | I | A | G | A K | G | D T E | V- |
| | K V | T A S | S G N | | | | | | | | | | | | | | | | | | |
| 87 Chlamydia trachomatis MOMP VDIV (srovar C, F,G,H,J,K,L3)[b] | L | A V K | E T | A P | I V | L V | D | V I | T | T | L | N | P | T | I | A T | G | K C | G | S T A | V- |
| | V A | A S G | S A | G N | S T | E D | N G | E D Q | L I | A S | | | | | | | | | | | |
| 88 Chlamydia trachomatis MOMP VDIII (serovar A, B,Ba,C,D,E,F,G,H,I,L1 & L3)[b] | K T | G | Y | V | G | A K Q | E | F L | P | L | D A N | I L | T I | A S | G | T | E D | A | A | T | G- |
| | T | K | D A | | | | | | | | | | | | | | | | | | |
| 89 Chlamydia trachomatis MOMP VDIII (serovar L2) | K T | G K | Y D | V | G | A | E | F | P | L | D | L | K | A | G | T | D | G | V | T | G- |
| 90 HIV-1 MN PND | [E P | S G | V R | Q A | I F | N Y | C T | T T | R K | P N | N M]4 | Y K2 | N K | K G | R G | K | R | I | H | I | G |
| 91 Plasmodium berghei | N | N | N | D | D | S | Y | I | P | S | A | E | K | I | L | E | F | V | K | Q | |

[a]Sequences are given in the standard one-letter amino acid codes.
[b]For simplicity, the amino acids present at each position of the library are indicated below the main chain. Invariant amino acids are designated at a molar value of one, and Variant amino acids are added during synthesis at an equimolar ratio depending on the number of variants at that position, i.e., if a position has 2 amino acids, then each is added in 0.5 ratio relative to the invariant amount, for 3 amino acids the ratio is 0.33, for 4 amino acids the ratio is 0.25, for 5 amino acids, the ratio is 0.20, etc.

TABLE 12

Examples of "Universal Synthetic Immunostimulator-Peptide Hapten" Constructs

| Peptide Constructs | Sequence | | | | | | | | | | | | | | | | |
|---|---|---|---|---|---|---|---|---|---|---|---|---|---|---|---|---|---|
| 92 (SEQ ID NO:92) Human Amylin-GG-HBs T$_h$-GG-Inv (No:66–60) | K S G A | C N F K | N N F S | T G L K | A A L K | T I T F | C L R P | A L I S | T S L Y | Q S T T | R T I A | L N P T | A V Q Y | N G S Q | F S L F | L N D | V T G | H Y G | S G T |
| 93 (SEQ ID NO:93) Human Amylin N-fragment-GG-HBsT$_h$-GG-Inv (No:67–60) | K S G | C G T | N G A | T F K | A F S | T L K | C L K | A T F | T R P | Q I S | R L Y | L T T | A I A | N P T | F Q Y | L S Q | V L F | H D | S G |

TABLE 12-continued

Examples of "Universal Synthetic Immunostimulator-Peptide Hapten" Constructs

| Peptide Constructs | Sequence | | | | | | | | | | | | | | | | |
|---|---|---|---|---|---|---|---|---|---|---|---|---|---|---|---|---|---|
| 94 (SEQ ID NO:94) Inv-GG-HBsT$_h$-GG- Human Amylin C-fragment (No:54–68) | T F N | A L N | K L F | S T G | K R A | F I I | P L L | S T S | Y I | T P | A Q | T S | Y L | Q D | F G | G G | G H | F S S |
| 95 (SEQ ID NO:95) Gastrin$_{34}$-GG-HBsT$_h$- GG-Inv(No:69–60) | Q P L K | L W L K | G L T F | P E R P | Q E I S | G E L Y | P E T | P E I A | H A P T | L Y Q Y | V G S Q | A W L F | D M D | P D G | S F G | K G T | K G A | Q F K S |
| 96 (SEQ ID NO:96) Gastrin$_{34}$N-fragment- GG-HBsT$_h$-GG-Inv (No:70–60) | Q P D | L W G | G L G | P G T | Q F A | G F K | P L S | H L K | L T K | V R F | A I P | D L S | P T Y | S I T | K P A | K Q T | Q S | G F L |
| 97 (SEQ ID NO:97) Gastrin$_{34}$N-fragment- GG-HBsT$_h$-GG-Inv (No:71–60) | Q G A | L F K | G F S | P L K | Q L W | G T F | P R P | H I S | L L Y | V T T | A I A | D P T | P Q Y | S S Q | K L F | K D | Q G | G G T |
| 98 (SEQ ID NO:98) Gastrin$_{34}$N-fragment- GG-HBs-T$_h$-GG-Inv (No:72–60) | Q T T | L I A | G P T | P Q Y | Q S Q | G L F | P D | H G | G T | F A | F K | L S | L K | T K | R F | I P | L S | Y |
| 99 (SEQ ID NO:99) Inv-GG-HBsT$_h$-GG- Gastrin$_{17}$ No:54–74) | T F W | A L L | K L E | S T E | K R E | F I E | P L A | S I Y | Y P G | T Q W | A S M | T L D | Y D F | Q G | F G | G Q | G G | F P |
| 100 (SEQ ID NO:100) Inv-GG-HBsT$_h$-GG- Gastrin$_{17}$ N fragment (No:54–75) | T F W | A L L | K L E | S T E | K R E | F I E | P L A | S I Y | Y P | T Q | A S | T L | Y D | Q G | F G | G Q | G G | F P |
| 101 (SEQ ID NO:101) Gastrin releasing peptide HBsT$_h$-GG-Inv (No:77–60) | V H I A | P W P T | L A Q Y | P V S Q | A G L F | G H D | G L G | G M G | T G T | V F A | L F K | T L S | K L K | M T F | Y R P | P I S | R L Y | G T |
| 102 (SEQ ID NO:102) Inv-GG-HBs-GG- Gastrin releasing peptide 10 (No:54–78) | T F W | A L A | K L V | S R G | K I H | F L L | P T M | S I | Y P | T Q | A S | T L | Y D | Q G | F G | G G | G N | F H |
| 103 (SEQ ID NO:103) IgE CH4-GG-HBsT$_h$-GG- Inv (No:79–60) | K L Y | T T T | K I A | G P T | S Q Y | G S Q | F L F | V D | F G | G G | F T | F A | L K | L S | T K | R K | I F | P S |
| 104 (SEQ ID NO:104) Inv-GG-HBsT$_h$-GG- IgECH4 (NO:54–79) | T F G | A L S | K L G | S T F | K R F | F I V | P L F | S I | Y P | T Q | A S | T L | Y D | Q G | F G | G K | G T | F K |
| 105 (SEQ ID NO:105) Chlamydia trachomatis MOMP VDI-GG-HBsT$_h$-GG-Inv (No:80–60) | E P | F T V K | Q T A V | M N | G V | A A R | A E G | P | T G | T F | S N K R | D | T V A | A E | G D | L | Q E S | N K | D- G- |
| | G T | I A | P T | Q Y | S Q | L F | D | G | G | T | A | K | S | K | K | F | P | S | Y- |
| 106 (SEQ ID NO:106) Chlamydia trachomatis MOMP VDI-GG-HBsT$_h$-GG-Inv No:81–60) | E T S Q | F L C L F | Q T D | M A G | G K D G | A S T | P F | T F | T A D S S | T L | G T | N R | A I | A L | A T | P V I | S- P- Q- |
| | | | | | | | | | | | | | | | | | | |
| | | | | | | | | | | | | | | | | | | Y- |
| 107 (SEQ ID NO:107) Chlamydia trachomatis MOMP VDI-GG-HBsT$_h$-GG-Inv (No:82–60) | E S Q Y | F K S Q | E L L F | M V D | G E G | E R G | A G T | L G A | A F K | G L S | S L K | N T K | T R F | S I P | T L S | L T Y | T | L P T |
| 108 (SEQ ID NO:108) Chlamydia trachomatis MOMP VDII-GG-HBsT$_h$-GG-Inv (No:83–60) | F | G | T | K | T | Q K Y | S A T | S G D K | N | F D | T | A | K N | L I | V F | P | N | T- I A |
| | A | L | N D | Q R E | A | V | V | G | G | F | F | L | L | T | R | I | L | T | I- |
| | P T | Q Y | S Q | L F | D | G | G | T | A | K | S | K | K | F | P | S | Y | T | A- |
| 109 (SEQ ID NO:109) Chlamydia | F | G | N N D | E | N | Q H | T A | K T | V | S D | N G | S T | A L | F | V | P | N | M- |

TABLE 12-continued

Examples of "Universal Synthetic Immunostimulator-Peptide Hapten" Constructs

| Peptide Constructs | Sequence |
|---|---|
| trachomatis MOMP VDII-GG-HBsT$_h$-GG-Inv No:84–60) | S L D Q S V V G            K<br>P Q S L D G G T  A K S K K F P S Y T A-<br>Q F<br>F G F L L T R I L T I- |
| 110 (SEQ ID NO:110) Chlamydia trachomatis MOMP VDII-GG-HBsT$_h$-GG-Inv (No:85–60) | F G D N E N Q K T V K A E S V P N M S-<br>    G V    A S K P A T N A I    V Q<br>           T Q   K D<br>F D Q S V V G G F F L L T R I L T I P-<br>L N<br>Q S L D G G T A K S K K F P S Y T A T-<br>Y Q F |
| 111 (SEQ ID NO:111) Chlamydia trachomatis MOMP VDIV-GG-HBsT$_h$-GG-Inv (No:86–60) | S A T A I F D T T T L N P T I A G A G-<br>L  E T V L  V                K<br>  K P<br>D V K T S A E G Q L G G F F L L T R-<br>T  V A G   N E A<br>E   S N<br>I L T I P Q S L D G G T A K S K K F P-<br>S Y T A T Y Q F |
| 112 (SEQ ID NO:112) Chlamydia trachomatis MOMP VDIV-GG-HBsT$_h$-GG-Inv (No:87–60) | L A E A I L D V T T L N P T I A G K G-<br> V T P V V  I             T   C<br>  K<br>S V V A S G S E N E L A G G F F L L T-<br>T A S A N T D G D I S<br>A   G       Q<br>R I L T I P Q S L D G G T A K S K K F-<br>P S Y T A T Y Q F |
| 113 (SEQ ID NO:113) Chlamydia trachomatis MOMP VDIII-GG-HBsT$_h$-GG-Inv (No:88–60) | K G Y V G A E F P L D I T A G T E A A-<br>T     K  L   A L I S    D<br>      Q          N<br>T G T K D G G F F L L T R I L T I P Q-<br>      A<br>S L D G G T A K S K K F P S Y T A T Y-<br>Q F |
| 114 (SEQ ID NO:114) Chlamydia trachomatis MOMP VDIII-GG-HBsT$_h$-GG-Inv (No:89–60) | K G Y V G A E F P L D L K A G T D G V<br>T G T K D G G F F L L T R I L T I P Q<br>S L D G G T A K S K K F P S Y T A T Y<br>Q F |
| 115 HIV-I MN PND-HBsT$_h$-GG-Inv (No:90–60) | [E S V Q I N C T R P N Y N K R P G R<br>A F Y T T K N M]$_4$ K$_2$ K G G G F F L<br>L T R I L T I P Q S L D G G T A K S<br>K K F P S Y T A T Y Q F |

We claim:

1. A peptide represented by the formula
$(A)_n\text{-}(T_h)_m\text{-}(B)_o\text{-LHRH}$
Wherein A is independently an amino acid, an invasin domain or an immunostimulatory analog thereof derived from the outer membrane of variant strains of Yersinia spp.;
B is an amino acid;
Each $T_h$ is independently SEQ ID NO:2, 3, 4, 5, 6, 7, 8, 9, 42, 43, 44, 45, 46, 47, 48, 49, 50, or 51;
LHRH is luteinizing hormone releasing hormone or an immunogenic analog thereof containing a conservative amino acid substitution;
n is 0, 1 or 2;
m is 1 to 4; and
o is 0, 1 or 2.

2. The peptide of claim 1 wherein immunization with said peptide is capable of causing a reduction in serum testosterone to less than 10% of normal values.

3. The peptide of claim 1 wherein immunization with said peptide causes atrophy of or prevents growth of the prostate.

4. The peptide of claim 1 wherein said LHRH has an amino acid sequence of SEQ ID NO:1.

5. The peptide of claim 1 wherein said $T_h$ is SEQ ID NO:2.

6. The peptide of claim 1 wherein said peptide is selected from the group consisting of SEQ ID NOS: 10–19, 22, 23, or 38.

7. The peptide of claim 1 wherein at least one A is an invasin domain.

8. The peptide of claim 7 wherein n is 3, and A is an invasin domain, glycine and glycine in that order.

9. The peptide of claim 1 or 8 wherein said invasin domain has an amino acid sequence of SEQ ID NO:53.

10. A peptide composition comprising a peptide selected from the group consisting of SEQ ID NO:10, 13, 16, 18 19, 32, 33, 34,and 38 or a mixture thereof.

11. A vaccine composition comprising an immunologically effective amount of a peptide of any one of claims, 1, 6, 7 or 10 and a pharmaceutically acceptable carrier.

12. The vaccine composition of claim 11, wherein said immunologically effective amount of said peptide is about 0.5 µg to about 1 mg per kilogram body weight per dose.

13. A peptide composition comprising a mixture of two or more peptides represented by the formula
$(A)_n\text{-}(T_h)_m\text{-}(B)_o\text{-LHRH}$
Wherein A is independently an amino acid, an invasin domain or an immunostimulatory analog thereof derived from the outer membrane of variant strains of Yersinia spp.;
B is an amino acid;
Th is SEQ ID NO:2, 3, 4, 5, 6, 7, 8, 9, 42, 43, 44, 45, 46, 47, 48, 49, 50, or 51;
LHRH is luteinizing hormone releasing hormones or an immunogenic analog thereof containing a conservative amino acid substitution;
n is 0, 1 or 2;
m is 1 to 4; and
o is 0, 1 or 2.

14. The composition of claim 13 wherein said mixture comprises a combination of peptides having amino acid sequences of SEQ ID NOS:13, 16, 18 and 19.

15. The composition of claim 13 wherein said mixture comprises a combination of peptides having amino acid sequences of SEQ ID NOS:13, 16, 19 and 32.

* * * * *

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Glu His Trp Ser Tyr Gly Leu Arg Pro Gly
    1                5                                        10

( 2 ) INFORMATION FOR SEQ ID NO:2:

( i ) SEQUENCE CHARACTERISTICS:
   ( A ) LENGTH: 15 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:2:

Phe Phe Leu Leu Thr Arg Ile Leu Thr Ile Pro Gln Ser Leu Asp
 1               5                  10                  15

( 2 ) INFORMATION FOR SEQ ID NO:3:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Lys Lys Leu Arg Arg Leu Leu Tyr Met Ile Tyr Met Ser Gly Leu Ala
 1               5                  10                  15

Val His Val Ser Lys Glu Glu Gln Tyr Tyr Asp Tyr
              20                  25

( 2 ) INFORMATION FOR SEQ ID NO:4:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Lys Lys Gln Tyr Ile Lys Ala Asn Ser Lys Phe Ile Gly Ile Thr Glu
 1               5                  10                  15

Leu ( 2 ) INFORMATION FOR SEQ ID NO:5:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Lys Lys Phe Asn Asn Phe Thr Val Ser Phe Trp Leu Arg Val Pro Lys
 1               5                  10                  15

Val Ser Ala Ser His Leu
              20

( 2 ) INFORMATION FOR SEQ ID NO:6:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

Tyr Met Ser Gly Leu Ala Val Arg Val His Val Ser Lys Glu Glu
 1               5                  10                  15

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Tyr  Asp  Pro  Asn  Tyr  Leu  Arg  Thr  Asp  Ser  Asp  Lys  Asp  Arg  Phe  Leu
 1                    5                        10                       15
Gln  Thr  Met  Val  Lys  Leu  Phe  Asn  Arg  Ile  Lys
               20                        25
```

( 2 ) INFORMATION FOR SEQ ID NO:8:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Gly  Ala  Tyr  Ala  Arg  Cys  Pro  Asn  Gly  Thr  Arg  Ala  Leu  Thr  Val  Ala
 1                    5                        10                       15
Glu  Leu  Arg  Gly  Asn  Ala  Glu  Leu
               20
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Ser  Glu  Ile  Lys  Gly  Val  Ile  Val  His  Arg  Leu  Glu  Gly  Val  Leu
 1                    5                        10                       15
```

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Lys  Lys  Lys  Phe  Phe  Leu  Leu  Thr  Arg  Ile  Leu  Thr  Ile  Pro  Gln  Ser
 1                    5                        10                       15
Leu  Asp  Glu  His  Trp  Ser  Tyr  Gly  Leu  Arg  Pro  Gly
               20                        25
```

( 2 ) INFORMATION FOR SEQ ID NO:11:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Lys Lys Leu Arg Arg Leu Leu Tyr Met Ile Tyr Met Ser Gly Leu Ala
 1               5                  10                  15
Val His Val Ser Lys Glu Glu Gln Tyr Tyr Asp Tyr Glu His Trp Ser
                20                  25                  30
Tyr Gly Leu Arg Pro Gly
                35
```

( 2 ) INFORMATION FOR SEQ ID NO:12:

( i ) SEQUENCE CHARACTERISTICS:
           ( A ) LENGTH: 25 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:12:

```
Tyr Met Ser Gly Leu Ala Val Arg Val His Val Ser Lys Glu Glu Glu
 1               5                  10                  15
His Trp Ser Tyr Gly Leu Arg Pro Gly
                20                  25
```

( 2 ) INFORMATION FOR SEQ ID NO:13:

( i ) SEQUENCE CHARACTERISTICS:
           ( A ) LENGTH: 27 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:13:

```
Lys Lys Gln Tyr Ile Lys Ala Asn Ser Lys Phe Ile Gly Ile Thr Glu
 1               5                  10                  15
Leu Glu His Trp Ser Tyr Gly Leu Arg Pro Gly
                20                  25
```

( 2 ) INFORMATION FOR SEQ ID NO:14:

( i ) SEQUENCE CHARACTERISTICS:
           ( A ) LENGTH: 32 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:14:

```
Lys Lys Phe Asn Asn Phe Thr Val Ser Phe Trp Leu Arg Val Pro Lys
 1               5                  10                  15
Val Ser Ala Ser His Leu Glu His Trp Ser Tyr Gly Leu Arg Pro Gly
                20                  25                  30
```

( 2 ) INFORMATION FOR SEQ ID NO:15:

( i ) SEQUENCE CHARACTERISTICS:
           ( A ) LENGTH: 37 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:15:

```
Tyr Asp Pro Asn Tyr Leu Arg Thr Asp Ser Asp Lys Asp Arg Phe Leu
 1               5                  10                  15
Gln Thr Met Val Lys Leu Phe Asn Arg Ile Lys Glu His Trp Ser Tyr
```

```
                    2 0                    2 5                         3 0

Gly Leu Arg Pro Gly
         3 5
```

( 2 ) INFORMATION FOR SEQ ID NO:16:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Gly Ala Tyr Ala Arg Cys Pro Asn Gly Thr Arg Ala Leu Thr Val Ala
 1               5                   1 0                      1 5

Glu Leu Arg Gly Asn Ala Glu Leu Glu His Trp Ser Tyr Gly Leu Arg
                2 0                  2 5                  3 0

Pro Gly
```

( 2 ) INFORMATION FOR SEQ ID NO:17:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Ser Glu Ile Lys Gly Val Ile Val His Arg Leu Glu Gly Val Leu Glu
 1               5                   1 0                      1 5

His Trp Ser Tyr Gly Leu Arg Pro Gly
                2 0                  2 5
```

( 2 ) INFORMATION FOR SEQ ID NO:18:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Lys Lys Lys Phe Phe Leu Leu Thr Arg Ile Leu Thr Ile Pro Gln Ser
 1               5                   1 0                      1 5

Leu Asp Gly Gly Glu His Trp Ser Tyr Gly Leu Arg Pro Gly
                2 0                  2 5                  3 0
```

( 2 ) INFORMATION FOR SEQ ID NO:19:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Leu Ser Glu Ile Lys Gly Val Ile Val His Arg Leu Glu Gly Val Gly
 1               5                   1 0                      1 5

Gly Glu His Trp Ser Tyr Gly Leu Arg Pro Gly
                2 0                  2 5
```

( 2 ) INFORMATION FOR SEQ ID NO:20:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Leu Ser Glu Ile Lys Gly Val Ile Val His Arg Leu Glu Gly Val Leu
 1               5                  10                 15

Ser Glu Ile Lys Gly Val Ile Val His Arg Leu Glu Gly Val Gly Gly
            20                  25                 30

Glu His Trp Ser Tyr Gly Leu Arg Pro Gly
        35                  40
```

( 2 ) INFORMATION FOR SEQ ID NO:21:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Gly Ile Leu Glu Ser Arg Gly Ile Lys Ala Arg Ile Thr His Val Asp
 1               5                  10                 15

Thr Glu Ser Tyr Gly Gly Glu His Trp Ser Tyr Gly Leu Arg Pro Gly
            20                  25                 30
```

( 2 ) INFORMATION FOR SEQ ID NO:22:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Lys Lys Trp Val Arg Asp Ile Ile Asp Asp Phe Thr Asn Glu Ser Ser
 1               5                  10                 15

Gln Lys Thr Gly Gly Glu His Trp Ser Tyr Gly Leu Arg Pro Gly
            20                  25                 30
```

( 2 ) INFORMATION FOR SEQ ID NO:23:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
Lys Lys Asp Val Ser Thr Ile Val Pro Tyr Ile Gly Pro Ala Leu Asn
 1               5                  10                 15

Ile Val Gly Gly Glu His Trp Ser Tyr Gly Leu Arg Pro Gly
            20                  25                 30
```

( 2 ) INFORMATION FOR SEQ ID NO:24:

( i ) SEQUENCE CHARACTERISTICS:
        ( A ) LENGTH: 37 amino acids
        ( B ) TYPE: amino acid (D) TOPOLOGY: linear (ii) MOLECULE TYPE: peptide (xi) SEQUENCE DESCRIPTION: SEQ ID NO:24:

```
Ala Leu Asn Ile Trp Asp Arg Phe Asp Val Phe Cys Thr Leu Gly Ala
 1               5                  10                  15
Thr Thr Gly Tyr Leu Lys Gly Asn Ser Gly Gly Glu His Trp Ser Tyr
               20                  25                  30
Gly Leu Arg Pro Gly
               35
```

(2) INFORMATION FOR SEQ ID NO:25:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:25:

```
Asp Ser Glu Thr Ala Asp Asn Leu Glu Lys Thr Val Ala Ala Leu Ser
 1               5                  10                  15
Ile Leu Pro Gly Ile Gly Cys Gly Gly Glu His Trp Ser Tyr Gly Leu
               20                  25                  30
Arg Pro Gly
       35
```

(2) INFORMATION FOR SEQ ID NO:26:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:26:

```
Glu Glu Ile Val Ala Gln Ser Ile Ala Leu Ser Ser Leu Met Val Ala
 1               5                  10                  15
Gln Ala Ile Pro Leu Val Gly Glu Leu Val Asp Ile Gly Phe Ala Ala
               20                  25                  30
Thr Asn Phe Val Glu Ser Cys Gly Gly Glu His Trp Ser Tyr Gly Leu
               35                  40                  45
Arg Pro Gly
       50
```

(2) INFORMATION FOR SEQ ID NO:27:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:27:

```
Asp Ile Glu Lys Lys Ile Ala Lys Met Glu Lys Ala Ser Ser Val Phe
 1               5                  10                  15
Asn Val Val Asn Ser Gly Gly Glu His Trp Ser Tyr Gly Leu Arg Pro
               20                  25                  30
Gly
```

( 2 ) INFORMATION FOR SEQ ID NO:28:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Lys Trp Phe Lys Thr Asn Ala Pro Asn Gly Val Asp Glu Lys Ile Arg
 1               5                  10                  15

Ile Gly Gly Glu His Trp Ser Tyr Gly Leu Arg Pro Gly
             20                  25
```

( 2 ) INFORMATION FOR SEQ ID NO:29:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
Gly Leu Gln Gly Lys Ile Ala Asp Ala Val Lys Ala Lys Gly Gly Gly
 1               5                  10                  15

Glu His Trp Ser Tyr Gly Leu Arg Pro Gly
             20                  25
```

( 2 ) INFORMATION FOR SEQ ID NO:30:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

```
Gly Leu Ala Ala Gly Leu Val Gly Met Ala Ala Asp Ala Met Val Glu
 1               5                  10                  15

Asp Val Asn Gly Gly Glu His Trp Ser Tyr Gly Leu Arg Pro Gly
             20                  25                  30
```

( 2 ) INFORMATION FOR SEQ ID NO:31:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
Ser Thr Glu Thr Gly Asn Gln His His Tyr Gln Thr Arg Val Val Ser
 1               5                  10                  15

Asn Ala Asn Lys Gly Gly Glu His Trp Ser Tyr Gly Leu Arg Pro Gly
             20                  25                  30
```

( 2 ) INFORMATION FOR SEQ ID NO:32:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Thr Ala Lys Ser Lys Lys Phe Pro Ser Tyr Thr Ala Thr Tyr Gln Phe
1               5                   10                  15

Gly Gly Phe Phe Leu Leu Thr Arg Ile Leu Thr Ile Pro Gln Ser Leu
            20                  25                  30

Asp Gly Gly Glu His Trp Ser Tyr Gly Leu Arg Pro Gly
        35                  40                  45

( 2 ) INFORMATION FOR SEQ ID NO:33:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Thr Ala Lys Ser Lys Lys Phe Pro Ser Tyr Thr Ala Thr Tyr Gln Phe
1               5                   10                  15

Gly Gly Leu Ser Glu Ile Lys Gly Val Ile Val His Arg Leu Glu Gly
            20                  25                  30

Val Gly Gly Glu His Trp Ser Tyr Gly Leu Arg Pro Gly
        35                  40                  45

( 2 ) INFORMATION FOR SEQ ID NO:34:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Thr Ala Lys Ser Lys Lys Phe Pro Ser Tyr Thr Ala Thr Tyr Gln Phe
1               5                   10                  15

Gly Gly Gly Ala Tyr Ala Arg Cys Pro Asn Gly Thr Arg Ala Leu Thr
            20                  25                  30

Val Ala Glu Leu Arg Gly Asn Ala Glu Leu Gly Gly Glu His Trp Ser
        35                  40                  45

Tyr Gly Leu Arg Pro Gly
        50

( 2 ) INFORMATION FOR SEQ ID NO:35:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

Thr Ala Lys Ser Lys Lys Phe Pro Ser Tyr Thr Ala Thr Tyr Gln Phe
1               5                   10                  15

Gly Gly Lys Lys Gln Tyr Ile Lys Ala Asn Ser Lys Phe Ile Gly Ile
            20                  25                  30

Thr Glu Leu Gly Gly Glu His Trp Ser Tyr Gly Leu Arg Pro Gly
        35                  40                  45

( 2 ) INFORMATION FOR SEQ ID NO:36:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Thr Ala Lys Ser Lys Lys Phe Pro Ser Tyr Thr Ala Thr Tyr Gln Phe
 1               5                  10                  15
Gly Gly Lys Lys Trp Val Arg Asp Ile Ile Asp Asp Phe Thr Asn Glu
            20                  25                  30
Ser Ser Gln Lys Thr Gly Gly Glu His Trp Ser Tyr Gly Leu Arg Pro
        35                  40                  45
Gly
```

( 2 ) INFORMATION FOR SEQ ID NO:37:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Thr Ala Lys Ser Lys Lys Phe Pro Ser Tyr Thr Ala Thr Tyr Gln Phe
 1               5                  10                  15
Gly Gly Lys Lys Asp Val Ser Thr Ile Val Pro Tyr Ile Gly Pro Ala
            20                  25                  30
Leu Asn Ile Val Gly Gly Glu His Trp Ser Tyr Gly Leu Arg Pro Gly
        35                  40                  45
```

( 2 ) INFORMATION FOR SEQ ID NO:38:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "D0.50;E0.50"

( i x ) FEATURE:
        ( A ) NAME/KEY: Modified-site
        ( B ) LOCATION: 2
        ( D ) OTHER INFORMATION: /note="L0.25;I0.25;V0.25;F0.25"

( i x ) FEATURE:
        ( A ) NAME/KEY: Modified-site
        ( B ) LOCATION: 4
        ( D ) OTHER INFORMATION: /note= "E0.50;D0.50"

( i x ) FEATURE:
        ( A ) NAME/KEY: Modified-site
        ( B ) LOCATION: 5
        ( D ) OTHER INFORMATION: /note="L0.25;I0.25;V0.25;F0.25"

( i x ) FEATURE:
        ( A ) NAME/KEY: Modified-site
        ( B ) LOCATION: 6
        ( D ) OTHER INFORMATION: /note= "K0.50;R0.50"

( i x ) FEATURE:
        ( A ) NAME/KEY: Modified-site

```
        ( B ) LOCATION: 8
        ( D ) OTHER INFORMATION: /note="L0.25;I0.25;V0.25;F0.25"

( i x ) FEATURE:
        ( A ) NAME/KEY: Modified-site
        ( B ) LOCATION: 9
        ( D ) OTHER INFORMATION: /note="L0.25;I0.25;V0.25;F0.25"

( i x ) FEATURE:
        ( A ) NAME/KEY: Modified-site
        ( B ) LOCATION: 10
        ( D ) OTHER INFORMATION: /note="L0.25;I0.25;V0.25;F0.25"

( i x ) FEATURE:
        ( A ) NAME/KEY: Modified-site
        ( B ) LOCATION: 12
        ( D ) OTHER INFORMATION: /note= "K0.50;R0.50"

( i x ) FEATURE:
        ( A ) NAME/KEY: Modified-site
        ( B ) LOCATION: 13
        ( D ) OTHER INFORMATION: /note="L0.25;I0.25;V0.25;F0.25"

( i x ) FEATURE:
        ( A ) NAME/KEY: Modified-site
        ( B ) LOCATION: 14
        ( D ) OTHER INFORMATION: /note= "E0.50;D0.50"

( i x ) FEATURE:
        ( A ) NAME/KEY: Modified-site
        ( B ) LOCATION: 16
        ( D ) OTHER INFORMATION: /note="L0.25;I0.25;V0.25;F0.25"

( x i ) SEQUENCE DESCRIPTION: SEQ ID NO:38:

Asp Leu Ser Glu Leu Lys Gly Leu Leu Leu His Lys Leu Glu Gly Leu
 1               5                   1 0                 1 5

Gly Gly Glu His Trp Ser Tyr Gly Leu Arg Pro Gly
             2 0                 2 5

( 2 ) INFORMATION FOR SEQ ID NO:39:

( i ) SEQUENCE CHARACTERISTICS:
            ( A ) LENGTH: 30 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note= "K0.50;K0.50"

( i x ) FEATURE:
            ( A ) NAME/KEY: Modified-site
            ( B ) LOCATION: 2
            ( D ) OTHER INFORMATION: /note= "K0.50;R0.50"

( i x ) FEATURE:
            ( A ) NAME/KEY: Modified-site
            ( B ) LOCATION: 3
            ( D ) OTHER INFORMATION: /note= "K0.50;R0.50"

( i x ) FEATURE:
            ( A ) NAME/KEY: Modified-site
            ( B ) LOCATION: 4
            ( D ) OTHER INFORMATION: /note="L0.25;I0.25;V0.25;F0.25"

( i x ) FEATURE:
            ( A ) NAME/KEY: Modified-site
            ( B ) LOCATION: 5
            ( D ) OTHER INFORMATION: /note= "F0.34;K0.33;R0.33"

( i x ) FEATURE:
            ( A ) NAME/KEY: Modified-site
            ( B ) LOCATION: 6
            ( D ) OTHER INFORMATION: /note="L0.25;I0.25;V0.25;F0.25"
```

(i x) FEATURE:
  (A) NAME/KEY: Modified-site
  (B) LOCATION: 7
  (D) OTHER INFORMATION: /note="L0.25;I0.25;V0.25;F0.25"

(i x) FEATURE:
  (A) NAME/KEY: Modified-site
  (B) LOCATION: 9
  (D) OTHER INFORMATION: /note= "K0.50;R0.50"

(i x) FEATURE:
  (A) NAME/KEY: Modified-site
  (B) LOCATION: 10
  (D) OTHER INFORMATION: /note="L0.25;I0.25;V0.25;F0.25"

(i x) FEATURE:
  (A) NAME/KEY: Modified-site
  (B) LOCATION: 11
  (D) OTHER INFORMATION: /note="L0.25;I0.25;V0.25;F0.25"

(i x) FEATURE:
  (A) NAME/KEY: Modified-site
  (B) LOCATION: 13
  (D) OTHER INFORMATION: /note="L0.25;I0.25;V0.25;F0.25"

(i x) FEATURE:
  (A) NAME/KEY: Modified-site
  (B) LOCATION: 15
  (D) OTHER INFORMATION: /note=
    " Q0.20;L0.20;I0.20;F0.20V0.20"

(i x) FEATURE:
  (A) NAME/KEY: Modified-site
  (B) LOCATION: 17
  (D) OTHER INFORMATION: /note="L0.25;I0.25;V0.25;F0.25"

(i x) FEATURE:
  (A) NAME/KEY: Modified-site
  (B) LOCATION: 18
  (D) OTHER INFORMATION: /note="D0.50;R0.50"

(x i) SEQUENCE DESCRIPTION: SEQ ID NO:39:

```
Lys Lys Lys Leu Phe Leu Leu Thr Lys Leu Leu Thr Leu Pro Gln Ser
 1               5                  10                   15

Leu Asp Gly Gly Glu His Trp Ser Tyr Gly Leu Arg Pro Gly
              20                  25                  30
```

(2) INFORMATION FOR SEQ ID NO:40:

(i) SEQUENCE CHARACTERISTICS:
    (A) LENGTH: 46 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 19
    (D) OTHER INFORMATION: /note="D0.50;E0.50"

(i x) FEATURE:
    (A) NAME/KEY: Modified-site
    (B) LOCATION: 20
    (D) OTHER INFORMATION: /note="L0.25;I0.25;V0.25;F0.25"

(i x) FEATURE:
    (A) NAME/KEY: Modified-site
    (B) LOCATION: 22
    (D) OTHER INFORMATION: /note="E0.50;D0.50"

(i x) FEATURE:
    (A) NAME/KEY: Modified-site
    (B) LOCATION: 23
    (D) OTHER INFORMATION: /note="L0.25;I0.25;V0.25;F0.25"

( i x ) FEATURE:
    ( A ) NAME/KEY: Modified-site
    ( B ) LOCATION: 24
    ( D ) OTHER INFORMATION: /note="K0.50;R0.50"

( i x ) FEATURE:
    ( A ) NAME/KEY: Modified-site
    ( B ) LOCATION: 26
    ( D ) OTHER INFORMATION: /note="L0.25;I0.25;V0.25;F0.25"

( i x ) FEATURE:
    ( A ) NAME/KEY: Modified-site
    ( B ) LOCATION: 27
    ( D ) OTHER INFORMATION: /note="L0.25;I0.25;V0.25;F0.25"

( i x ) FEATURE:
    ( A ) NAME/KEY: Modified-site
    ( B ) LOCATION: 28
    ( D ) OTHER INFORMATION: /note="L0.25;I0.25;V0.25;F0.25"

( i x ) FEATURE:
    ( A ) NAME/KEY: Modified-site
    ( B ) LOCATION: 30
    ( D ) OTHER INFORMATION: /note="K0.50;R0.50"

( i x ) FEATURE:
    ( A ) NAME/KEY: Modified-site
    ( B ) LOCATION: 31
    ( D ) OTHER INFORMATION: /note="L0.25;I0.25;V0.25;F0.25"

( i x ) FEATURE:
    ( A ) NAME/KEY: Modified-site
    ( B ) LOCATION: 32
    ( D ) OTHER INFORMATION: /note="E0.50;D0.50"

( i x ) FEATURE:
    ( A ) NAME/KEY: Modified-site
    ( B ) LOCATION: 34
    ( D ) OTHER INFORMATION: /note="L0.25;I0.25;V0.25;F0.25"

( x i ) SEQUENCE DESCRIPTION: SEQ ID NO:40:

| Thr | Ala | Lys | Ser | Lys | Lys | Phe | Pro | Ser | Tyr | Thr | Ala | Thr | Tyr | Gln | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gly | Asp | Leu | Ser | Glu | Leu | Lys | Gly | Leu | Leu | Leu | His | Lys | Leu | Glu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Leu | Gly | Gly | Glu | His | Trp | Ser | Tyr | Gly | Leu | Arg | Pro | Gly |
|-----|-----|-----|-----|-----|-----|-----|-----|-----|-----|-----|-----|-----|-----|
|     |     | 35  |     |     |     |     | 40  |     |     |     |     | 45  |     |

( 2 ) INFORMATION FOR SEQ ID NO:41:

( i ) SEQUENCE CHARACTERISTICS:
       ( A ) LENGTH: 48 amino acids
       ( B ) TYPE: amino acid
       ( D ) TOPOLOGY: linear ( i i ) MOLECULE TYPE: peptide ( i x ) FEATURE:
       ( A ) NAME/KEY: Modified-site
       ( B ) LOCATION: 19
       ( D ) OTHER INFORMATION: /note="K0.50;R0.50"

( i x ) FEATURE:
       ( A ) NAME/KEY: Modified-site
       ( B ) LOCATION: 20
       ( D ) OTHER INFORMATION: /note="K0.50;R0.50"

( i x ) FEATURE:
       ( A ) NAME/KEY: Modified-site
       ( B ) LOCATION: 21
       ( D ) OTHER INFORMATION: /note="K0.50;R0.50"

( i x ) FEATURE:
       ( A ) NAME/KEY: Modified-site
       ( B ) LOCATION: 22
       ( D ) OTHER INFORMATION: /note="L0.25;I0.25;V0.25;F0.25"

( i x ) FEATURE:
    ( A ) NAME/KEY: Modified-site
    ( B ) LOCATION: 23
    ( D ) OTHER INFORMATION: /note="F0.34;K0.33;R0.33"

( i x ) FEATURE:
    ( A ) NAME/KEY: Modified-site
    ( B ) LOCATION: 24
    ( D ) OTHER INFORMATION: /note="L0.25;I0.25;V0.25;F0.25"

( i x ) FEATURE:
    ( A ) NAME/KEY: Modified-site
    ( B ) LOCATION: 25
    ( D ) OTHER INFORMATION: /note="L0.25;I0.25;V0.25;F0.25"

( i x ) FEATURE:
    ( A ) NAME/KEY: Modified-site
    ( B ) LOCATION: 27
    ( D ) OTHER INFORMATION: /note="K0.50;R0.50"

( i x ) FEATURE:
    ( A ) NAME/KEY: Modified-site
    ( B ) LOCATION: 28
    ( D ) OTHER INFORMATION: /note="L0.25;I0.25;V0.25;F0.25"

( i x ) FEATURE:
    ( A ) NAME/KEY: Modified-site
    ( B ) LOCATION: 29
    ( D ) OTHER INFORMATION: /note="L0.25;I0.25;V0.25;F0.25"

( i x ) FEATURE:
    ( A ) NAME/KEY: Modified-site
    ( B ) LOCATION: 31
    ( D ) OTHER INFORMATION: /note="L0.25;I0.25;V0.25;F0.25"

( i x ) FEATURE:
    ( A ) NAME/KEY: Modified-site
    ( B ) LOCATION: 33
    ( D ) OTHER INFORMATION: /note=
        "Q0.20;L0.20;I0.20;F0.20;V0.20"

( i x ) FEATURE:
    ( A ) NAME/KEY: Modified-site
    ( B ) LOCATION: 35
    ( D ) OTHER INFORMATION: /note="L0.25;I0.25;V0.25;F0.25"

( i x ) FEATURE:
    ( A ) NAME/KEY: Modified-site
    ( B ) LOCATION: 36
    ( D ) OTHER INFORMATION: /note="D0.50;R0.50"

( x i ) SEQUENCE DESCRIPTION: SEQ ID NO:41:

```
Thr Ala Lys Ser Lys Lys Phe Pro Ser Tyr Thr Ala Thr Tyr Gln Phe
 1               5                  10                  15

Gly Gly Lys Lys Lys Leu Phe Leu Leu Thr Lys Leu Leu Thr Leu Pro
                20                  25                  30

Gln Ser Leu Asp Gly Gly Glu His Trp Ser Tyr Gly Leu Arg Pro Gly
                35                  40                  45
```

( 2 ) INFORMATION FOR SEQ ID NO:42:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

```
Gly Ile Leu Glu Ser Arg Gly Ile Lys Ala Arg Ile Thr His Val Asp
 1               5                  10                  15

Thr Glu Ser Tyr
                20
```

( 2 ) INFORMATION FOR SEQ ID NO:43:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

```
Trp Val Arg Asp Ile Ile Asp Asp Phe Thr Asn Glu Ser Ser Gln Lys
 1               5                  10                  15
Thr
```

( 2 ) INFORMATION FOR SEQ ID NO:44:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

```
Asp Val Ser Thr Ile Val Pro Tyr Ile Gly Pro Ala Leu Asn Ile Val
 1               5                  10                  15
```

( 2 ) INFORMATION FOR SEQ ID NO:45:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

```
Ala Leu Asn Ile Trp Asp Arg Phe Asp Val Phe Cys Thr Leu Gly Ala
 1               5                  10                  15
Thr Thr Gly Tyr Leu Lys Gly Asn Ser
                20                  25
```

( 2 ) INFORMATION FOR SEQ ID NO:46:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

```
Asp Ser Glu Thr Ala Asp Asn Leu Glu Lys Thr Val Ala Ala Leu Ser
 1               5                  10                  15
Ile Leu Pro Gly Ile Gly Cys
                20
```

( 2 ) INFORMATION FOR SEQ ID NO:47:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Glu Glu Ile Val Ala Gln Ser Ile Ala Leu Ser Ser Leu Met Val Ala
1               5                   10                  15

Gln Ala Ile Pro Leu Val Gly Glu Leu Val Asp Ile Gly Phe Ala Ala
            20                  25                  30

Thr Asn Phe Val Glu Ser Cys
            35

( 2 ) INFORMATION FOR SEQ ID NO:48:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

Asp Ile Glu Lys Lys Ile Ala Lys Met Glu Lys Ala Ser Ser Val Phe
1               5                   10                  15

Asn Val Val Asn Ser
            20

( 2 ) INFORMATION FOR SEQ ID NO:49:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Lys Trp Phe Lys Thr Asn Ala Pro Asn Gly Val Asp Glu Lys Ile Arg
1               5                   10                  15

Ile ( 2 ) INFORMATION FOR SEQ ID NO:50:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:

Gly Leu Gln Gly Lys Ile Ala Asp Ala Val Lys Ala Lys Gly
1               5                   10

( 2 ) INFORMATION FOR SEQ ID NO:51:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

Gly Leu Ala Ala Gly Leu Val Gly Met Ala Ala Asp Ala Met Val Glu
1               5                   10                  15

Asp Val Asn ( 2 ) INFORMATION FOR SEQ ID NO:52:

( i ) SEQUENCE CHARACTERISTICS:
: ( A ) LENGTH: 20 amino acids
: ( B ) TYPE: amino acid
: ( D ) TOPOLOGY: linear ( i i ) MOLECULE TYPE: peptide ( x i ) SEQUENCE DESCRIPTION: SEQ ID NO:52:

```
Ser Thr Glu Thr Gly Asn Gln His His Tyr Gln Thr Arg Val Val Ser
  1               5                  10                  15
Asn Ala Asn Lys
         20
```

( 2 ) INFORMATION FOR SEQ ID NO:53:

( i ) SEQUENCE CHARACTERISTICS:
: ( A ) LENGTH: 16 amino acids
: ( B ) TYPE: amino acid
: ( D ) TOPOLOGY: linear ( i i ) MOLECULE TYPE: peptide ( x i ) SEQUENCE DESCRIPTION: SEQ ID NO:53:

```
Thr Ala Lys Ser Lys Lys Phe Pro Ser Tyr Thr Ala Thr Tyr Gln Phe
  1               5                  10                  15
```

( 2 ) INFORMATION FOR SEQ ID NO:54:

( i ) SEQUENCE CHARACTERISTICS:
: ( A ) LENGTH: 35 amino acids
: ( B ) TYPE: amino acid
: ( D ) TOPOLOGY: linear ( i i ) MOLECULE TYPE: peptide ( x i ) SEQUENCE DESCRIPTION: SEQ ID NO:54:

```
Thr Ala Lys Ser Lys Lys Phe Pro Ser Tyr Thr Ala Thr Tyr Gln Phe
  1               5                  10                  15
Gly Gly Phe Phe Leu Leu Thr Arg Ile Leu Thr Ile Pro Gln Ser Leu
                 20                  25                  30
Asp Gly Gly
         35
```

( 2 ) INFORMATION FOR SEQ ID NO:55:

( i ) SEQUENCE CHARACTERISTICS:
: ( A ) LENGTH: 35 amino acids
: ( B ) TYPE: amino acid
: ( D ) TOPOLOGY: linear ( i i ) MOLECULE TYPE: peptide ( x i ) SEQUENCE DESCRIPTION: SEQ ID NO:55:

```
Thr Ala Lys Ser Lys Lys Phe Pro Ser Tyr Thr Ala Thr Tyr Gln Phe
  1               5                  10                  15
Gly Gly Leu Ser Glu Ile Lys Gly Val Ile Val His Arg Leu Glu Gly
                 20                  25                  30
Val Gly Gly
         35
```

( 2 ) INFORMATION FOR SEQ ID NO:56:

( i ) SEQUENCE CHARACTERISTICS:
: ( A ) LENGTH: 44 amino acids
: ( B ) TYPE: amino acid
: ( D ) TOPOLOGY: linear ( i i ) MOLECULE TYPE: peptide ( x i ) SEQUENCE DESCRIPTION: SEQ ID NO:56:

Thr Ala Lys Ser Lys Lys Phe Pro Ser Tyr Thr Ala Thr Tyr Gln Phe
1               5                   10                  15

Gly Gly Gly Ala Tyr Ala Arg Cys Pro Asn Gly Thr Arg Ala Leu Thr
            20                  25                  30

Val Ala Glu Leu Arg Gly Asn Ala Glu Leu Gly Gly
        35                  40

( 2 ) INFORMATION FOR SEQ ID NO:57:

( i ) SEQUENCE CHARACTERISTICS:
( A ) LENGTH: 37 amino acids
( B ) TYPE: amino acid
( D ) TOPOLOGY: linear ( i i ) MOLECULE TYPE: peptide ( x i ) SEQUENCE DESCRIPTION: SEQ ID NO:57:

Thr Ala Lys Ser Lys Lys Phe Pro Ser Tyr Thr Ala Thr Tyr Gln Phe
1               5                   10                  15

Gly Gly Lys Lys Gln Tyr Ile Lys Ala Asn Ser Lys Phe Ile Gly Ile
            20                  25                  30

Thr Glu Leu Gly Gly
        35

( 2 ) INFORMATION FOR SEQ ID NO:58:

( i ) SEQUENCE CHARACTERISTICS:
( A ) LENGTH: 39 amino acids
( B ) TYPE: amino acid
( D ) TOPOLOGY: linear ( i i ) MOLECULE TYPE: peptide ( x i ) SEQUENCE DESCRIPTION: SEQ ID NO:58:

Thr Ala Lys Ser Lys Lys Phe Pro Ser Tyr Thr Ala Thr Tyr Gln Phe
1               5                   10                  15

Gly Gly Lys Lys Trp Val Arg Asp Ile Ile Asp Asp Phe Thr Asn Glu
            20                  25                  30

Ser Ser Gln Lys Thr Gly Gly
        35

( 2 ) INFORMATION FOR SEQ ID NO:59:

( i ) SEQUENCE CHARACTERISTICS:
( A ) LENGTH: 38 amino acids
( B ) TYPE: amino acid
( D ) TOPOLOGY: linear ( i i ) MOLECULE TYPE: peptide ( x i ) SEQUENCE DESCRIPTION: SEQ ID NO:59:

Thr Ala Lys Ser Lys Lys Phe Pro Ser Tyr Thr Ala Thr Tyr Gln Phe
1               5                   10                  15

Gly Gly Lys Lys Asp Val Ser Thr Ile Val Pro Tyr Ile Gly Pro Ala
            20                  25                  30

Leu Asn Ile Val Gly Gly
        35

( 2 ) INFORMATION FOR SEQ ID NO:60:

( i ) SEQUENCE CHARACTERISTICS:

(A) LENGTH: 35 amino acids
(B) TYPE: amino acid
(D) TOPOLOGY: linear (ii) MOLECULE TYPE: peptide (xi) SEQUENCE DESCRIPTION: SEQ ID NO:60:

| Gly | Gly | Phe | Phe | Leu | Leu | Thr | Arg | Ile | Leu | Thr | Ile | Pro | Gln | Ser | Leu |
|---|---|---|---|---|---|---|---|---|---|---|---|---|---|---|---|
| 1 | | | | 5 | | | | | 10 | | | | | 15 | |
| Asp | Gly | Gly | Thr | Ala | Lys | Ser | Lys | Lys | Phe | Pro | Ser | Tyr | Thr | Ala | Thr |
| | | | 20 | | | | | 25 | | | | | 30 | | |
| Tyr | Gln | Phe | | | | | | | | | | | | | |
| | | 35 | | | | | | | | | | | | | |

(2) INFORMATION FOR SEQ ID NO:61:

(i) SEQUENCE CHARACTERISTICS:
(A) LENGTH: 35 amino acids
(B) TYPE: amino acid
(D) TOPOLOGY: linear (ii) MOLECULE TYPE: peptide (xi) SEQUENCE DESCRIPTION: SEQ ID NO:61:

| Gly | Gly | Leu | Ser | Glu | Ile | Lys | Gly | Val | Ile | Val | His | Arg | Leu | Glu | Gly |
|---|---|---|---|---|---|---|---|---|---|---|---|---|---|---|---|
| 1 | | | | 5 | | | | | 10 | | | | | 15 | |
| Val | Gly | Gly | Thr | Ala | Lys | Ser | Lys | Lys | Phe | Pro | Ser | Tyr | Thr | Ala | Thr |
| | | | 20 | | | | | 25 | | | | | 30 | | |
| Tyr | Gln | Phe | | | | | | | | | | | | | |
| | | 35 | | | | | | | | | | | | | |

(2) INFORMATION FOR SEQ ID NO:62:

(i) SEQUENCE CHARACTERISTICS:
(A) LENGTH: 44 amino acids
(B) TYPE: amino acid
(D) TOPOLOGY: linear (ii) MOLECULE TYPE: peptide (xi) SEQUENCE DESCRIPTION: SEQ ID NO:62:

| Gly | Gly | Gly | Ala | Tyr | Ala | Arg | Cys | Pro | Asn | Gly | Thr | Arg | Ala | Leu | Thr |
|---|---|---|---|---|---|---|---|---|---|---|---|---|---|---|---|
| 1 | | | | 5 | | | | | 10 | | | | | 15 | |
| Val | Ala | Glu | Leu | Arg | Gly | Asn | Ala | Glu | Leu | Gly | Gly | Thr | Ala | Lys | Ser |
| | | | 20 | | | | | 25 | | | | | 30 | | |
| Lys | Lys | Phe | Pro | Ser | Tyr | Thr | Ala | Thr | Tyr | Gln | Phe | | | | |
| | | 35 | | | | | 40 | | | | | | | | |

(2) INFORMATION FOR SEQ ID NO:63:

(i) SEQUENCE CHARACTERISTICS:
(A) LENGTH: 37 amino acids
(B) TYPE: amino acid
(D) TOPOLOGY: linear (ii) MOLECULE TYPE: peptide (xi) SEQUENCE DESCRIPTION: SEQ ID NO:63:

| Gly | Gly | Lys | Lys | Gln | Tyr | Ile | Lys | Ala | Asn | Ser | Lys | Phe | Ile | Gly | Ile |
|---|---|---|---|---|---|---|---|---|---|---|---|---|---|---|---|
| 1 | | | | 5 | | | | | 10 | | | | | 15 | |
| Thr | Glu | Leu | Gly | Gly | Thr | Ala | Lys | Ser | Lys | Lys | Phe | Pro | Ser | Tyr | Thr |
| | | | 20 | | | | | 25 | | | | | 30 | | |
| Ala | Thr | Tyr | Gln | Phe | | | | | | | | | | | |
| | | | | 35 | | | | | | | | | | | |

( 2 ) INFORMATION FOR SEQ ID NO:64:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:64:

```
Gly Gly Lys Lys Trp Val Arg Asp Ile Ile Asp Asp Phe Thr Asn Glu
 1               5                  10                  15
Ser Ser Gln Lys Thr Gly Gly Thr Ala Lys Ser Lys Lys Phe Pro Ser
            20                  25                  30
Tyr Thr Ala Thr Tyr Gln Phe
            35
```

( 2 ) INFORMATION FOR SEQ ID NO:65:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:65:

```
Gly Gly Lys Lys Asp Val Ser Thr Ile Val Pro Tyr Ile Gly Pro Ala
 1               5                  10                  15
Leu Asn Ile Val Gly Gly Thr Ala Lys Ser Lys Lys Phe Pro Ser Tyr
            20                  25                  30
Thr Ala Thr Tyr Gln Phe
            35
```

( 2 ) INFORMATION FOR SEQ ID NO:66:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:66:

```
Lys Cys Asn Thr Ala Thr Cys Ala Thr Gln Arg Leu Ala Asn Phe Leu
 1               5                  10                  15
Val His Ser Ser Asn Asn Phe Gly Ala Ile Leu Ser Ser Thr Asn Val
            20                  25                  30
Gly Ser Asn Thr Tyr
            35
```

( 2 ) INFORMATION FOR SEQ ID NO:67:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:67:

```
Lys Cys Asn Thr Ala Thr Cys Ala Thr Gln Arg Leu Ala Asn Phe Leu
 1               5                  10                  15
Val His Ser Ser
            20
```

( 2 ) INFORMATION FOR SEQ ID NO:68:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:68:

Ser Ser Asn Asn Phe Gly Ala Ile Leu Ser Ser Thr Asn Val Gly Ser
1               5                   10                  15
Asn Thr Tyr ( 2 ) INFORMATION FOR SEQ ID NO:69:

( i ) SEQUENCE CHARACTERISTICS:
    ( A ) LENGTH: 34 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:69:

Gln Leu Gly Pro Gln Gly Pro Pro His Leu Val Ala Asp Pro Ser Lys
1               5                   10                  15
Lys Gln Gly Pro Trp Leu Glu Glu Glu Glu Ala Tyr Gly Trp Met
            20                  25                  30
Asp Phe ( 2 ) INFORMATION FOR SEQ ID NO:70:

( i ) SEQUENCE CHARACTERISTICS:
    ( A ) LENGTH: 22 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:70:

Gln Leu Gly Pro Gln Gly Pro Pro His Leu Val Ala Asp Pro Ser Lys
1               5                   10                  15
Lys Gln Gly Pro Trp Leu
            20

( 2 ) INFORMATION FOR SEQ ID NO:71:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:71:

Gln Leu Gly Pro Gln Gly Pro Pro His Leu Val Ala Asp Pro Ser Lys
1               5                   10                  15
Lys Gln ( 2 ) INFORMATION FOR SEQ ID NO:72:

( i ) SEQUENCE CHARACTERISTICS:
    ( A ) LENGTH: 9 amino acids
    ( B ) TYPE: amino acid
    ( D ) TOPOLOGY: linear (  i  i  ) MOLECULE TYPE: peptide (  x  i  ) SEQUENCE DESCRIPTION: SEQ ID NO:72:

Gln Leu Gly Pro Gln Gly Pro Pro His
1                   5

( 2 ) INFORMATION FOR SEQ ID NO:73:

(  i  ) SEQUENCE CHARACTERISTICS:
        ( A ) LENGTH: 11 amino acids
        ( B ) TYPE: amino acid
        ( D ) TOPOLOGY: linear (  i  i  ) MOLECULE TYPE: peptide (  x  i  ) SEQUENCE DESCRIPTION: SEQ ID NO:73:

Gln Leu Gly Pro Gln Gly Pro Pro Pro Pro Pro
1                   5                                  10

( 2 ) INFORMATION FOR SEQ ID NO:74:

(  i  ) SEQUENCE CHARACTERISTICS:
        ( A ) LENGTH: 17 amino acids
        ( B ) TYPE: amino acid
        ( D ) TOPOLOGY: linear (  i  i  ) MOLECULE TYPE: peptide (  x  i  ) SEQUENCE DESCRIPTION: SEQ ID NO:74:

Gln Gly Pro Trp Leu Glu Glu Glu Glu Glu Ala Tyr Gly Trp Met Asp
1                   5                                  10                                 15

Phe ( 2 ) INFORMATION FOR SEQ ID NO:75:

(  i  ) SEQUENCE CHARACTERISTICS:
        ( A ) LENGTH: 12 amino acids
        ( B ) TYPE: amino acid
        ( D ) TOPOLOGY: linear (  i  i  ) MOLECULE TYPE: peptide (  x  i  ) SEQUENCE DESCRIPTION: SEQ ID NO:75:

Gln Gly Pro Trp Leu Glu Glu Glu Glu Glu Ala Tyr
1                   5                                  10

( 2 ) INFORMATION FOR SEQ ID NO:76:

(  i  ) SEQUENCE CHARACTERISTICS:
        ( A ) LENGTH: 8 amino acids
        ( B ) TYPE: amino acid
        ( D ) TOPOLOGY: linear (  i  i  ) MOLECULE TYPE: peptide (  x  i  ) SEQUENCE DESCRIPTION: SEQ ID NO:76:

Gln Gly Pro Trp Leu Glu Glu Glu
1                   5

( 2 ) INFORMATION FOR SEQ ID NO:77:

(  i  ) SEQUENCE CHARACTERISTICS:
        ( A ) LENGTH: 27 amino acids
        ( B ) TYPE: amino acid
        ( D ) TOPOLOGY: linear (  i  i  ) MOLECULE TYPE: peptide ( x i ) SEQUENCE DESCRIPTION: SEQ ID NO:77:

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

( 2 ) INFORMATION FOR SEQ ID NO:78:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:78:

Gly Asn His Trp Ala Val Gly His Leu Met
1               5                   10

( 2 ) INFORMATION FOR SEQ ID NO:79:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:79:

Lys Thr Lys Gly Ser Gly Phe Phe Val Phe
1               5                   10

( 2 ) INFORMATION FOR SEQ ID NO:80:

( i ) SEQUENCE CHARACTERISTICS:
    ( A ) LENGTH: 26 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 7
    ( D ) OTHER INFORMATION: /note= "A0.50;E0.50"

( i x ) FEATURE:
    ( A ) NAME/KEY: Modified-site
    ( B ) LOCATION: 11
    ( D ) OTHER INFORMATION: /note= "S0.25;N0.25;K0.25;R0.25"

( i x ) FEATURE:
    ( A ) NAME/KEY: Modified-site
    ( B ) LOCATION: 13
    ( D ) OTHER INFORMATION: /note= "T0.34;V0.33;A0.33"

( i x ) FEATURE:
    ( A ) NAME/KEY: Modified-site
    ( B ) LOCATION: 14
    ( D ) OTHER INFORMATION: /note= "A0.50;E0.50"

( i x ) FEATURE:
    ( A ) NAME/KEY: Modified-site
    ( B ) LOCATION: 15
    ( D ) OTHER INFORMATION: /note= "G0.50;D0.50"

( i x ) FEATURE:
    ( A ) NAME/KEY: Modified-site
    ( B ) LOCATION: 17
    ( D ) OTHER INFORMATION: /note= "Q0.34;E0.33;S0.33"

( i x ) FEATURE:
    ( A ) NAME/KEY: Modified-site (B) LOCATION: 18
(D) OTHER INFORMATION: /note= "N0.50;K0.50"

(ix) FEATURE:
(A) NAME/KEY: Modified-site
(B) LOCATION: 21
(D) OTHER INFORMATION: /note= "T0.34;V0.33;K0.33"

(ix) FEATURE:
(A) NAME/KEY: Modified-site
(B) LOCATION: 22
(D) OTHER INFORMATION: /note= "T0.34;A0.33;V0.33"

(xi) SEQUENCE DESCRIPTION: SEQ ID NO:80:

```
Glu Phe Gln Met Gly Ala Ala Pro Thr Thr Ser Asp Thr Ala Gly Leu
1               5                   10                  15
Gln Asn Asp Pro Thr Thr Asn Val Ala Arg
            20                  25
```

(2) INFORMATION FOR SEQ ID NO:81:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: Modified-site
(B) LOCATION: 6
(D) OTHER INFORMATION: /note= "A0.50;D0.50"

(ix) FEATURE:
(A) NAME/KEY: Modified-site
(B) LOCATION: 11
(D) OTHER INFORMATION: /note= "T0.34;A0.33;S0.33"

(ix) FEATURE:
(A) NAME/KEY: Modified-site
(B) LOCATION: 12
(D) OTHER INFORMATION: /note= "T0.34;D0.33;S0.33"

(ix) FEATURE:
(A) NAME/KEY: Modified-site
(B) LOCATION: 15
(D) OTHER INFORMATION: /note= "A0.50;S0.50"

(ix) FEATURE:
(A) NAME/KEY: Modified-site
(B) LOCATION: 16
(D) OTHER INFORMATION: /note= "A0.34;T0.33;V0.33"

(ix) FEATURE:
(A) NAME/KEY: Modified-site
(B) LOCATION: 19
(D) OTHER INFORMATION: /note= "S0.50;T0.50"

(ix) FEATURE:
(A) NAME/KEY: Modified-site
(B) LOCATION: 21
(D) OTHER INFORMATION: /note= "L0.50;C0.50"

(xi) SEQUENCE DESCRIPTION: SEQ ID NO:81:

```
Glu Phe Gln Met Gly Ala Lys Pro Thr Thr Thr Gly Asn Ala Ala
1               5                   10                  15
Ala Pro Ser Thr Leu Thr Ala Arg
            20
```

(2) INFORMATION FOR SEQ ID NO:82:

(i) SEQUENCE CHARACTERISTICS:
(A) LENGTH: 25 amino acids
(B) TYPE: amino acid ( D ) TOPOLOGY: linear ( i i ) MOLECULE TYPE: peptide ( x i ) SEQUENCE DESCRIPTION: SEQ ID NO:82:

```
Glu  Phe  Glu  Met  Gly  Glu  Ala  Leu  Ala  Gly  Ala  Ser  Gly  Asn  Thr  Thr
 1              5                        10                        15

Ser  Thr  Leu  Ser  Lys  Leu  Val  Glu  Arg
              20                        25
```

( 2 ) INFORMATION FOR SEQ ID NO:83:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Q0.50;K0.50"

( i x ) FEATURE:
        ( A ) NAME/KEY: Modified-site
        ( B ) LOCATION: 7
        ( D ) OTHER INFORMATION: /note= "S0.34;A0.33;Y0.33"

( i x ) FEATURE:
        ( A ) NAME/KEY: Modified-site
        ( B ) LOCATION: 8
        ( D ) OTHER INFORMATION: /note= "S0.50;T0.50"

( i x ) FEATURE:
        ( A ) NAME/KEY: Modified-site
        ( B ) LOCATION: 9
        ( D ) OTHER INFORMATION: /note=
          " N0.20;S0.20;G0.20;D0.20;K0.20"

( i x ) FEATURE:
        ( A ) NAME/KEY: Modified-site
        ( B ) LOCATION: 11
        ( D ) OTHER INFORMATION: /note= "N0.50;D0.50"

( i x ) FEATURE:
        ( A ) NAME/KEY: Modified-site
        ( B ) LOCATION: 14
        ( D ) OTHER INFORMATION: /note= "K0.50;N0.50"

( i x ) FEATURE:
        ( A ) NAME/KEY: Modified-site
        ( B ) LOCATION: 15
        ( D ) OTHER INFORMATION: /note= "L0.50;I0.50"

( i x ) FEATURE:
        ( A ) NAME/KEY: Modified-site
        ( B ) LOCATION: 16
        ( D ) OTHER INFORMATION: /note= "V0.50;F0.50"

( i x ) FEATURE:
        ( A ) NAME/KEY: Modified-site
        ( B ) LOCATION: 19
        ( D ) OTHER INFORMATION: /note= "T0.34;I0.33;A0.33"

( i x ) FEATURE:
        ( A ) NAME/KEY: Modified-site
        ( B ) LOCATION: 22
        ( D ) OTHER INFORMATION: /note= "N0.50;D0.50"

( i x ) FEATURE:
        ( A ) NAME/KEY: Modified-site
        ( B ) LOCATION: 23
        ( D ) OTHER INFORMATION: /note= "Q0.34;R0.33;E0.33"

( x i ) SEQUENCE DESCRIPTION: SEQ ID NO:83:

```
Phe  Gly  Thr  Lys  Thr  Gln  Ser  Ser  Asn  Phe  Asn  Thr  Ala  Lys  Leu  Val
 1              5                        10                       15

Pro  Asn  Thr  Ala  Leu  Asn  Gln  Ala  Val  Val
          20                        25
```

( 2 ) INFORMATION FOR SEQ ID NO:84:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "N0.50;D0.50"

( i x ) FEATURE:
        ( A ) NAME/KEY: Modified-site
        ( B ) LOCATION: 7
        ( D ) OTHER INFORMATION: /note= "Q0.50;H0.50"

( i x ) FEATURE:
        ( A ) NAME/KEY: Modified-site
        ( B ) LOCATION: 8
        ( D ) OTHER INFORMATION: /note= "T0.50;A0.50"

( i x ) FEATURE:
        ( A ) NAME/KEY: Modified-site
        ( B ) LOCATION: 9
        ( D ) OTHER INFORMATION: /note= "K0.50;T0.50"

( i x ) FEATURE:
        ( A ) NAME/KEY: Modified-site
        ( B ) LOCATION: 12
        ( D ) OTHER INFORMATION: /note= "N0.50;D0.50"

( i x ) FEATURE:
        ( A ) NAME/KEY: Modified-site
        ( B ) LOCATION: 13
        ( D ) OTHER INFORMATION: /note= "S0.50;G0.50"

( i x ) FEATURE:
        ( A ) NAME/KEY: Modified-site
        ( B ) LOCATION: 14
        ( D ) OTHER INFORMATION: /note= "A0.34;T0.33;K0.33"

( i x ) FEATURE:
        ( A ) NAME/KEY: Modified-site
        ( B ) LOCATION: 15
        ( D ) OTHER INFORMATION: /note= "F0.50;L0.50"

( x i ) SEQUENCE DESCRIPTION: SEQ ID NO:84:

```
Phe  Gly  Asn  Asn  Glu  Asn  Gln  Thr  Lys  Val  Ser  Asn  Ser  Ala  Phe  Val
 1              5                        10                       15

Pro  Asn  Met  Ser  Leu  Asp  Gln  Ser  Val  Val
          20                        25
```

( 2 ) INFORMATION FOR SEQ ID NO:85:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note= "N0.50;G0.50"

( i x ) FEATURE:

(A) NAME/KEY: Modified-site
          (B) LOCATION: 5
          (D) OTHER INFORMATION: /note= "E0.50;V0.50"

(ix) FEATURE:
          (A) NAME/KEY: Modified-site
          (B) LOCATION: 7
          (D) OTHER INFORMATION: /note= "Q0.50;A0.50"

(ix) FEATURE:
          (A) NAME/KEY: Modified-site
          (B) LOCATION: 8
          (D) OTHER INFORMATION: /note= "K0.34;S0.33;T0.33"

(ix) FEATURE:
          (A) NAME/KEY: Modified-site
          (B) LOCATION: 9
          (D) OTHER INFORMATION: /note= "T0.34;K0.33;Q0.33"

(ix) FEATURE:
          (A) NAME/KEY: Modified-site
          (B) LOCATION: 10
          (D) OTHER INFORMATION: /note= "V0.50;P0.50"

(ix) FEATURE:
          (A) NAME/KEY: Modified-site
          (B) LOCATION: 11
          (D) OTHER INFORMATION: /note= "K0.50;A0.50"

(ix) FEATURE:
          (A) NAME/KEY: Modified-site
          (B) LOCATION: 12
          (D) OTHER INFORMATION: /note= "A0.34;T0.33;K0.33"

(ix) FEATURE:
          (A) NAME/KEY: Modified-site
          (B) LOCATION: 13
          (D) OTHER INFORMATION: /note= "E0.25;N0.25;D0.25;T0.25"

(ix) FEATURE:
          (A) NAME/KEY: Modified-site
          (B) LOCATION: 14
          (D) OTHER INFORMATION: /note= "S0.50;A0.50"

(ix) FEATURE:
          (A) NAME/KEY: Modified-site
          (B) LOCATION: 15
          (D) OTHER INFORMATION: /note= "V0.50;I0.50"

(ix) FEATURE:
          (A) NAME/KEY: Modified-site
          (B) LOCATION: 18
          (D) OTHER INFORMATION: /note= "M0.50;V0.50"

(ix) FEATURE:
          (A) NAME/KEY: Modified-site
          (B) LOCATION: 19
          (D) OTHER INFORMATION: /note= "S0.50;Q0.50"

(ix) FEATURE:
          (A) NAME/KEY: Modified-site
          (B) LOCATION: 20
          (D) OTHER INFORMATION: /note= "F0.50;L0.50"

(ix) FEATURE:
          (A) NAME/KEY: Modified-site
          (B) LOCATION: 21
          (D) OTHER INFORMATION: /note= "D0.50;N0.50"

(xi) SEQUENCE DESCRIPTION: SEQ ID NO:85:

```
Phe Gly Asp Asn Glu Asn Gln Lys Thr Val Lys Ala Glu Ser Val Pro
 1               5                  10                  15

Asn Met Ser Phe Asp Gln Ser Val Val
            20                  25
```

(2) INFORMATION FOR SEQ ID NO:86:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "S0.50;L0.50"

( i x ) FEATURE:
    ( A ) NAME/KEY: Modified-site
    ( B ) LOCATION: 3
    ( D ) OTHER INFORMATION: /note= "T0.34;E0.33;K0.33"

( i x ) FEATURE:
    ( A ) NAME/KEY: Modified-site
    ( B ) LOCATION: 4
    ( D ) OTHER INFORMATION: /note= "A0.34;T0.33;P0.33"

( i x ) FEATURE:
    ( A ) NAME/KEY: Modified-site
    ( B ) LOCATION: 5
    ( D ) OTHER INFORMATION: /note= "I0.50;V0.50"

( i x ) FEATURE:
    ( A ) NAME/KEY: Modified-site
    ( B ) LOCATION: 6
    ( D ) OTHER INFORMATION: /note= "F0.50;L0.50"

( i x ) FEATURE:
    ( A ) NAME/KEY: Modified-site
    ( B ) LOCATION: 8
    ( D ) OTHER INFORMATION: /note= "T0.50;V0.50"

( i x ) FEATURE:
    ( A ) NAME/KEY: Modified-site
    ( B ) LOCATION: 18
    ( D ) OTHER INFORMATION: /note= "A0.50;K0.50"

( i x ) FEATURE:
    ( A ) NAME/KEY: Modified-site
    ( B ) LOCATION: 20
    ( D ) OTHER INFORMATION: /note= "D0.34;T0.33;E0.33"

( i x ) FEATURE:
    ( A ) NAME/KEY: Modified-site
    ( B ) LOCATION: 22
    ( D ) OTHER INFORMATION: /note= "K0.50;V0.50"

( i x ) FEATURE:
    ( A ) NAME/KEY: Modified-site
    ( B ) LOCATION: 23
    ( D ) OTHER INFORMATION: /note= "T0.34;A0.33;S0.33"

( i x ) FEATURE:
    ( A ) NAME/KEY: Modified-site
    ( B ) LOCATION: 24
    ( D ) OTHER INFORMATION: /note= "S0.34;G0.33;N0.33"

( i x ) FEATURE:
    ( A ) NAME/KEY: Modified-site
    ( B ) LOCATION: 27
    ( D ) OTHER INFORMATION: /note= "G0.50;N0.50"

( i x ) FEATURE:
    ( A ) NAME/KEY: Modified-site
    ( B ) LOCATION: 28
    ( D ) OTHER INFORMATION: /note= "Q0.50;E0.50"

( i x ) FEATURE:
    ( A ) NAME/KEY: Modified-site
    ( B ) LOCATION: 30
    ( D ) OTHER INFORMATION: /note= "G0.50;A0.50"

( x i ) SEQUENCE DESCRIPTION: SEQ ID NO:86:

Ser Ala Thr Ala Ile Phe Asp Thr Thr Thr Leu Asn Pro Thr Ile Ala

```
              1               5              10              15
Gly Ala Gly Asp Val Lys Thr Ser Ala Glu Gly Gln Leu Gly
             20              25              30
```

( 2 ) INFORMATION FOR SEQ ID NO:87:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "E0.34;T0.33;K0.33"

( i x ) FEATURE:
        ( A ) NAME/KEY: Modified-site
        ( B ) LOCATION: 4
        ( D ) OTHER INFORMATION: /note= "A0.50;P0.50"

( i x ) FEATURE:
        ( A ) NAME/KEY: Modified-site
        ( B ) LOCATION: 5
        ( D ) OTHER INFORMATION: /note= "I0.50;V0.50"

( i x ) FEATURE:
        ( A ) NAME/KEY: Modified-site
        ( B ) LOCATION: 6
        ( D ) OTHER INFORMATION: /note= "L0.50;V0.50"

( i x ) FEATURE:
        ( A ) NAME/KEY: Modified-site
        ( B ) LOCATION: 8
        ( D ) OTHER INFORMATION: /note= "V0.50;I0.50"

( i x ) FEATURE:
        ( A ) NAME/KEY: Modified-site
        ( B ) LOCATION: 16
        ( D ) OTHER INFORMATION: /note= "A0.50;T0.50"

( i x ) FEATURE:
        ( A ) NAME/KEY: Modified-site
        ( B ) LOCATION: 18
        ( D ) OTHER INFORMATION: /note= "K0.50;C0.50"

( i x ) FEATURE:
        ( A ) NAME/KEY: Modified-site
        ( B ) LOCATION: 20
        ( D ) OTHER INFORMATION: /note= "S0.34;T0.33;A0.33"

( i x ) FEATURE:
        ( A ) NAME/KEY: Modified-site
        ( B ) LOCATION: 22
        ( D ) OTHER INFORMATION: /note= "V0.50;A0.50"

( i x ) FEATURE:
        ( A ) NAME/KEY: Modified-site
        ( B ) LOCATION: 23
        ( D ) OTHER INFORMATION: /note= "A0.34;S0.33;G0.33"

( i x ) FEATURE:
        ( A ) NAME/KEY: Modified-site
        ( B ) LOCATION: 24
        ( D ) OTHER INFORMATION: /note= "S0.50;A0.50"

( i x ) FEATURE:
        ( A ) NAME/KEY: Modified-site
        ( B ) LOCATION: 25
        ( D ) OTHER INFORMATION: /note= "G0.50;N0.50"

( i x ) FEATURE:
        ( A ) NAME/KEY: Modified-site
        ( B ) LOCATION: 26
        ( D ) OTHER INFORMATION: /note= "S0.50;T0.50"

( i x ) FEATURE:
    ( A ) NAME/KEY: Modified-site
    ( B ) LOCATION: 27
    ( D ) OTHER INFORMATION: /note= "E0.50;D0.50"

( i x ) FEATURE:
    ( A ) NAME/KEY: Modified-site
    ( B ) LOCATION: 28
    ( D ) OTHER INFORMATION: /note= "N0.50;G0.50"

( i x ) FEATURE:
    ( A ) NAME/KEY: Modified-site
    ( B ) LOCATION: 29
    ( D ) OTHER INFORMATION: /note= "E0.34;D0.33;Q0.33"

( i x ) FEATURE:
    ( A ) NAME/KEY: Modified-site
    ( B ) LOCATION: 30
    ( D ) OTHER INFORMATION: /note= "L0.50;I0.50"

( i x ) FEATURE:
    ( A ) NAME/KEY: Modified-site
    ( B ) LOCATION: 31
    ( D ) OTHER INFORMATION: /note= "A0.50;S0.50"

( x i ) SEQUENCE DESCRIPTION: SEQ ID NO:87:

```
Leu Ala Glu Ala Ile Leu Asp Val Thr Thr Leu Asn Pro Thr Ile Ala
 1               5                  10                  15
Gly Lys Gly Ser Val Val Ala Ser Gly Ser Glu Asn Glu Leu Ala
             20                  25                  30
```

( 2 ) INFORMATION FOR SEQ ID NO:88:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "K0.50;T0.50"

( i x ) FEATURE:
    ( A ) NAME/KEY: Modified-site
    ( B ) LOCATION: 6
    ( D ) OTHER INFORMATION: /note= "A0.34;K0.33;Q0.33"

( i x ) FEATURE:
    ( A ) NAME/KEY: Modified-site
    ( B ) LOCATION: 8
    ( D ) OTHER INFORMATION: /note= "F0.50;L0.50"

( i x ) FEATURE:
    ( A ) NAME/KEY: Modified-site
    ( B ) LOCATION: 11
    ( D ) OTHER INFORMATION: /note= "D0.34;A0.33;N0.33"

( i x ) FEATURE:
    ( A ) NAME/KEY: Modified-site
    ( B ) LOCATION: 12
    ( D ) OTHER INFORMATION: /note= "I0.50;L0.50"

( i x ) FEATURE:
    ( A ) NAME/KEY: Modified-site
    ( B ) LOCATION: 13
    ( D ) OTHER INFORMATION: /note= "T0.50;I0.50"

( i x ) FEATURE:
    ( A ) NAME/KEY: Modified-site
    ( B ) LOCATION: 14
    ( D ) OTHER INFORMATION: /note= "A0.50;S0.50"

( i x ) FEATURE:
    ( A ) NAME/KEY: Modified-site (B) LOCATION: 17
(D) OTHER INFORMATION: /note= "E0.50;D0.50"

(ix) FEATURE:
(A) NAME/KEY: Modified-site
(B) LOCATION: 24
(D) OTHER INFORMATION: /note= "D0.50;A0.50"

(xi) SEQUENCE DESCRIPTION: SEQ ID NO:88:

| Lys | Gly | Tyr | Val | Gly | Ala | Glu | Phe | Pro | Leu | Asp | Ile | Thr | Ala | Gly | Thr |
|---|---|---|---|---|---|---|---|---|---|---|---|---|---|---|---|
| 1 | | | | 5 | | | | | 10 | | | | | 15 | |

| Glu | Ala | Ala | Thr | Gly | Thr | Lys | Asp |
|---|---|---|---|---|---|---|---|
| | | | 20 | | | | |

(2) INFORMATION FOR SEQ ID NO:89:

(i) SEQUENCE CHARACTERISTICS:
(A) LENGTH: 24 amino acids
(B) TYPE: amino acid
(D) TOPOLOGY: linear (ii) MOLECULE TYPE: peptide (xi) SEQUENCE DESCRIPTION: SEQ ID NO:89:

| Lys | Gly | Tyr | Val | Gly | Ala | Glu | Phe | Pro | Leu | Asp | Leu | Lys | Ala | Gly | Thr |
|---|---|---|---|---|---|---|---|---|---|---|---|---|---|---|---|
| 1 | | | | 5 | | | | | 10 | | | | | 15 | |

| Asp | Gly | Val | Thr | Gly | Thr | Lys | Asp |
|---|---|---|---|---|---|---|---|
| | | | 20 | | | | |

(2) INFORMATION FOR SEQ ID NO:90:

(i) SEQUENCE CHARACTERISTICS:
(A) LENGTH: 32 amino acids
(B) TYPE: amino acid
(D) TOPOLOGY: linear (ii) MOLECULE TYPE: peptide (xi) SEQUENCE DESCRIPTION: SEQ ID NO:90:

| Glu | Ser | Val | Gln | Ile | Asn | Cys | Thr | Arg | Pro | Asn | Tyr | Asn | Lys | Arg | Lys |
|---|---|---|---|---|---|---|---|---|---|---|---|---|---|---|---|
| 1 | | | | 5 | | | | | 10 | | | | | 15 | |

| Arg | Ile | His | Ile | Gly | Pro | Gly | Arg | Ala | Phe | Tyr | Thr | Thr | Lys | Asn | Met |
|---|---|---|---|---|---|---|---|---|---|---|---|---|---|---|---|
| | | | 20 | | | | | 25 | | | | | 30 | | |

(2) INFORMATION FOR SEQ ID NO:91:

(i) SEQUENCE CHARACTERISTICS:
(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO:91:

| Asn | Asn | Asn | Asp | Asp | Ser | Tyr | Ile | Pro | Ser | Ala | Glu | Lys | Ile | Leu | Glu |
|---|---|---|---|---|---|---|---|---|---|---|---|---|---|---|---|
| 1 | | | | 5 | | | | | 10 | | | | | 15 | |

| Phe | Val | Lys | Gln |
|---|---|---|---|
| | | | 20 |

(2) INFORMATION FOR SEQ ID NO:92:

(i) SEQUENCE CHARACTERISTICS:
(A) LENGTH: 72 amino acids
(B) TYPE: amino acid
(D) TOPOLOGY: linear (ii) MOLECULE TYPE: peptide ( x i ) SEQUENCE DESCRIPTION: SEQ ID NO:92:

| Lys | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | 15 | |

| Val | His | Ser | Ser | Asn | Asn | Phe | Gly | Ala | Ile | Leu | Ser | Ser | Thr | Asn | Val |
|---|---|---|---|---|---|---|---|---|---|---|---|---|---|---|---|
| | | | 20 | | | | | 25 | | | | | 30 | | |

| Gly | Ser | Asn | Thr | Tyr | Gly | Gly | Phe | Phe | Leu | Leu | Thr | Arg | Ile | Leu | Thr |
|---|---|---|---|---|---|---|---|---|---|---|---|---|---|---|---|
| | | 35 | | | | | 40 | | | | | 45 | | | |

| Ile | Pro | Gln | Ser | Leu | Asp | Gly | Gly | Thr | Ala | Lys | Ser | Lys | Lys | Phe | Pro |
|---|---|---|---|---|---|---|---|---|---|---|---|---|---|---|---|
| | 50 | | | | | 55 | | | | | 60 | | | | |

| Ser | Tyr | Thr | Ala | Thr | Tyr | Gln | Phe |
|---|---|---|---|---|---|---|---|
| 65 | | | | | 70 | | |

( 2 ) INFORMATION FOR SEQ ID NO:93:

( i ) SEQUENCE CHARACTERISTICS:
    ( A ) LENGTH: 55 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:93:

| Lys | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | 15 | |

| Val | His | Ser | Ser | Gly | Gly | Phe | Phe | Leu | Leu | Thr | Arg | Ile | Leu | Thr | Ile |
|---|---|---|---|---|---|---|---|---|---|---|---|---|---|---|---|
| | | | 20 | | | | | 25 | | | | | 30 | | |

| Pro | Gln | Ser | Leu | Asp | Gly | Gly | Thr | Ala | Lys | Ser | Lys | Lys | Phe | Pro | Ser |
|---|---|---|---|---|---|---|---|---|---|---|---|---|---|---|---|
| | | | 35 | | | | | 40 | | | | | 45 | | |

| Tyr | Thr | Ala | Thr | Tyr | Gln | Phe |
|---|---|---|---|---|---|---|
| | 50 | | | | | 55 |

( 2 ) INFORMATION FOR SEQ ID NO:94:

( i ) SEQUENCE CHARACTERISTICS:
    ( A ) LENGTH: 55 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:94:

| Thr | Ala | Lys | Ser | Lys | Lys | Phe | Pro | Ser | Tyr | Thr | Ala | Thr | Tyr | Gln | Phe |
|---|---|---|---|---|---|---|---|---|---|---|---|---|---|---|---|
| 1 | | | | 5 | | | | | 10 | | | | | 15 | |

| Gly | Gly | Phe | Phe | Leu | Leu | Thr | Arg | Ile | Leu | Thr | Ile | Pro | Gln | Ser | Leu |
|---|---|---|---|---|---|---|---|---|---|---|---|---|---|---|---|
| | | | 20 | | | | | 25 | | | | | 30 | | |

| Asp | Gly | Gly | His | Ser | Ser | Asn | Asn | Phe | Gly | Ala | Ile | Leu | Ser | Ser | Thr |
|---|---|---|---|---|---|---|---|---|---|---|---|---|---|---|---|
| | | 35 | | | | | 40 | | | | | 45 | | | |

| Asn | Val | Gly | Ser | Asn | Thr | Tyr |
|---|---|---|---|---|---|---|
| | 50 | | | | | 55 |

( 2 ) INFORMATION FOR SEQ ID NO:95:

( i ) SEQUENCE CHARACTERISTICS:
    ( A ) LENGTH: 69 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:95:

| Gln | Leu | Gly | Pro | Gln | Gly | Pro | Pro | His | Leu | Val | Ala | Asp | Pro | Ser | Lys | Lys |
|---|---|---|---|---|---|---|---|---|---|---|---|---|---|---|---|---|
| 1 | | | | 5 | | | | | 10 | | | | | 15 | | |

-continued

```
Gln Gly Pro Trp Leu Glu Glu Glu Glu Ala Tyr Gly Trp Met Asp Phe
             20                  25                  30

Gly Gly Phe Phe Leu Leu Thr Arg Ile Leu Thr Ile Pro Gln Ser Leu Asp
         35                  40                  45

Gly Gly Thr Ala Lys Ser Lys Lys Phe Pro Ser Tyr Thr Ala Thr Tyr Gln
     50                  55                  60                  65

Phe
```

( 2 ) INFORMATION FOR SEQ ID NO:96:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:96:

```
Gln Leu Gly Pro Gln Gly Pro Pro His Leu Val Ala Asp Pro Ser Lys
 1               5                  10                  15

Lys Gln Gly Pro Trp Leu Gly Gly Phe Phe Leu Leu Thr Arg Ile Leu
             20                  25                  30

Thr Ile Pro Gln Ser Leu Asp Gly Gly Thr Ala Lys Ser Lys Lys Phe
         35                  40                  45

Pro Ser Tyr Thr Ala Thr Tyr Gln Phe
     50                  55
```

( 2 ) INFORMATION FOR SEQ ID NO:97:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:97:

```
Gln Leu Gly Pro Gln Gly Pro Pro His Leu Val Ala Asp Pro Ser Lys
 1               5                  10                  15

Lys Gln Gly Gly Phe Phe Leu Leu Thr Arg Ile Leu Thr Ile Pro Gln
             20                  25                  30

Ser Leu Asp Gly Gly Thr Ala Lys Ser Lys Lys Phe Pro Ser Tyr Thr
         35                  40                  45

Ala Thr Tyr Gln Phe
     50
```

( 2 ) INFORMATION FOR SEQ ID NO:98:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:98:

```
Gln Leu Gly Pro Gln Gly Pro Pro His Gly Gly Phe Phe Leu Leu Thr
 1               5                  10                  15

Arg Ile Leu Thr Ile Pro Gln Ser Leu Asp Gly Gly Thr Ala Lys Ser
             20                  25                  30

Lys Lys Phe Pro Ser Tyr Thr Ala Thr Tyr Gln Phe
         35                  40
```

( 2 ) INFORMATION FOR SEQ ID NO:99:

( i ) SEQUENCE CHARACTERISTICS:
    ( A ) LENGTH: 52 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:99:

```
Thr Ala Lys Ser Lys Lys Phe Pro Ser Tyr Thr Ala Thr Tyr Gln Phe
 1               5                  10                  15
Gly Gly Phe Phe Leu Leu Thr Arg Ile Leu Thr Ile Pro Gln Ser Leu
            20                  25                  30
Asp Gly Gly Gln Gly Pro Trp Leu Glu Glu Glu Glu Glu Ala Tyr Gly
            35                  40                  45
Trp Met Asp Phe
        50
```

( 2 ) INFORMATION FOR SEQ ID NO:100:

( i ) SEQUENCE CHARACTERISTICS:
    ( A ) LENGTH: 47 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:100:

```
Thr Ala Lys Ser Lys Lys Phe Pro Ser Tyr Thr Ala Thr Tyr Gln Phe
 1               5                  10                  15
Gly Gly Phe Phe Leu Leu Thr Arg Ile Leu Thr Ile Pro Gln Ser Leu
            20                  25                  30
Asp Gly Gly Gln Gly Pro Trp Leu Glu Glu Glu Glu Glu Ala Tyr
            35                  40                  45
```

( 2 ) INFORMATION FOR SEQ ID NO:101:

( i ) SEQUENCE CHARACTERISTICS:
    ( A ) LENGTH: 62 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:101:

```
Val Pro Leu Pro Ala Gly Gly Gly Thr Val Leu Thr Lys Met Tyr Pro
 1               5                  10                  15
Arg Gly Asn His Trp Ala Val Gly His Leu Met Gly Gly Phe Phe Leu
            20                  25                  30
Leu Thr Arg Ile Leu Thr Ile Pro Gln Ser Leu Asp Gly Gly Thr Ala
            35                  40                  45
Lys Ser Lys Lys Phe Pro Ser Tyr Thr Ala Thr Tyr Gln Phe
        50                  55                  60
```

( 2 ) INFORMATION FOR SEQ ID NO:102:

( i ) SEQUENCE CHARACTERISTICS:
    ( A ) LENGTH: 45 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:102:

```
Thr Ala Lys Ser Lys Lys Phe Pro Ser Tyr Thr Ala Thr Tyr Gln Phe
  1               5                   10                  15

Gly Gly Phe Phe Leu Leu Thr Arg Ile Leu Thr Ile Pro Gln Ser Leu
             20                  25                  30

Asp Gly Gly Gly Asn His Trp Ala Val Gly His Leu Met
             35              40                  45
```

( 2 ) INFORMATION FOR SEQ ID NO:103:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:103:

```
Lys Thr Lys Gly Ser Gly Phe Phe Val Phe Gly Gly Phe Phe Leu Leu
  1               5                   10                  15

Thr Arg Ile Leu Thr Ile Pro Gln Ser Leu Asp Gly Gly Thr Ala Lys
             20                  25                  30

Ser Lys Lys Phe Pro Ser Tyr Thr Ala Thr Tyr Gln Phe
             35              40                  45
```

( 2 ) INFORMATION FOR SEQ ID NO:104:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:104:

```
Thr Ala Lys Ser Lys Lys Phe Pro Ser Tyr Thr Ala Thr Tyr Gln Phe
  1               5                   10                  15

Gly Gly Phe Phe Leu Leu Thr Arg Ile Leu Thr Ile Pro Gln Ser Leu
             20                  25                  30

Asp Gly Gly Lys Thr Lys Gly Ser Gly Phe Phe Val Phe
             35              40                  45
```

( 2 ) INFORMATION FOR SEQ ID NO:105:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 7
        ( D ) OTHER INFORMATION: /note= "A0.50;E0.50"

( i x ) FEATURE:
        ( A ) NAME/KEY: Modified-site
        ( B ) LOCATION: 11
        ( D ) OTHER INFORMATION: /note= "S0.25;N0.25;K0.25;R0.25"

( i x ) FEATURE:
        ( A ) NAME/KEY: Modified-site
        ( B ) LOCATION: 13
        ( D ) OTHER INFORMATION: /note= "T0.34;V0.33;A0.33"

( i x ) FEATURE:
        ( A ) NAME/KEY: Modified-site
        ( B ) LOCATION: 14

( D ) OTHER INFORMATION: /note= "A0.50;E0.50"

( i x ) FEATURE:
    ( A ) NAME/KEY: Modified-site
    ( B ) LOCATION: 15
    ( D ) OTHER INFORMATION: /note= "G0.50;D0.50"

( i x ) FEATURE:
    ( A ) NAME/KEY: Modified-site
    ( B ) LOCATION: 17
    ( D ) OTHER INFORMATION: /note= "Q0.34;E0.33;S0.33"

( i x ) FEATURE:
    ( A ) NAME/KEY: Modified-site
    ( B ) LOCATION: 18
    ( D ) OTHER INFORMATION: /note= "N0.50;K0.50"

( i x ) FEATURE:
    ( A ) NAME/KEY: Modified-site
    ( B ) LOCATION: 21
    ( D ) OTHER INFORMATION: /note= "T0.34;V0.33;K0.33"

( i x ) FEATURE:
    ( A ) NAME/KEY: Modified-site
    ( B ) LOCATION: 22
    ( D ) OTHER INFORMATION: /note= "T0.34;A0.33;V0.33"

( x i ) SEQUENCE DESCRIPTION: SEQ ID NO:105:

```
Glu Phe Gln Met Gly Ala Ala Pro Thr Thr Ser Asp Thr Ala Gly Leu
 1               5                  10                 15

Gln Asn Asp Pro Thr Thr Asn Val Ala Arg Gly Gly Phe Phe Leu Leu
            20                  25                 30

Thr Arg Ile Leu Thr Gly Gly Ile Pro Gln Ser Leu Asp Gly Gly Thr
        35                 40                  45

Ala Lys Ser Lys Lys Phe Pro Ser Tyr Thr Ala Thr Tyr Gln Phe
    50                  55                  60
```

( 2 ) INFORMATION FOR SEQ ID NO:106:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "A0.50;D0.50"

( i x ) FEATURE:
        ( A ) NAME/KEY: Modified-site
        ( B ) LOCATION: 11
        ( D ) OTHER INFORMATION: /note= "T0.34;A0.33;S0.33"

( i x ) FEATURE:
        ( A ) NAME/KEY: Modified-site
        ( B ) LOCATION: 12
        ( D ) OTHER INFORMATION: /note= "T0.34;D0.33;S0.33"

( i x ) FEATURE:
        ( A ) NAME/KEY: Modified-site
        ( B ) LOCATION: 15
        ( D ) OTHER INFORMATION: /note= "A0.50;S0.50"

( i x ) FEATURE:
        ( A ) NAME/KEY: Modified-site
        ( B ) LOCATION: 16
        ( D ) OTHER INFORMATION: /note= "A0.34;T0.33;V0.33"

( i x ) FEATURE:
        ( A ) NAME/KEY: Modified-site
        ( B ) LOCATION: 19
        ( D ) OTHER INFORMATION: /note= "S0.50;T0.50"

( i x ) FEATURE:
    ( A ) NAME/KEY: Modified-site
    ( B ) LOCATION: 21
    ( D ) OTHER INFORMATION: /note= "L0.50;C0.50"

( x i ) SEQUENCE DESCRIPTION: SEQ ID NO:106:

| Glu | Phe | Gln | Met | Gly | Ala | Lys | Pro | Thr | Thr | Thr | Thr | Gly | Asn | Ala | Ala |
|---|---|---|---|---|---|---|---|---|---|---|---|---|---|---|---|
| 1 | | | | 5 | | | | | 10 | | | | | 15 | |
| Ala | Pro | Ser | Thr | Leu | Thr | Ala | Arg | Gly | Gly | Phe | Phe | Leu | Leu | Thr | Arg |
| | | | 20 | | | | | 25 | | | | | 30 | | |
| Ile | Leu | Thr | Ile | Pro | Gln | Ser | Leu | Asp | Gly | Gly | Thr | Ala | Lys | Ser | Lys |
| | | 35 | | | | | 40 | | | | | 45 | | | |
| Lys | Phe | Pro | Ser | Tyr | Thr | Ala | Thr | Tyr | Gln | Phe | | | | | |
| | 50 | | | | 55 | | | | | | | | | | |

( 2 ) INFORMATION FOR SEQ ID NO:107:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:107:

| Glu | Phe | Glu | Met | Gly | Glu | Ala | Leu | Ala | Gly | Ala | Ser | Gly | Asn | Thr | Thr |
|---|---|---|---|---|---|---|---|---|---|---|---|---|---|---|---|
| 1 | | | | 5 | | | | | 10 | | | | | 15 | |
| Ser | Thr | Leu | Ser | Lys | Leu | Val | Glu | Arg | Gly | Gly | Phe | Phe | Leu | Leu | Thr |
| | | | 20 | | | | | 25 | | | | | 30 | | |
| Arg | Ile | Leu | Thr | Ile | Pro | Gln | Ser | Leu | Asp | Gly | Gly | Thr | Ala | Lys | Ser |
| | | | 35 | | | | | 40 | | | | | 45 | | |
| Lys | Lys | Phe | Pro | Ser | Tyr | Thr | Ala | Thr | Tyr | Gln | Phe | | | | |
| | 50 | | | | | 55 | | | | | 60 | | | | |

( 2 ) INFORMATION FOR SEQ ID NO:108:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "Q0.50;K0.50"

( i x ) FEATURE:
        ( A ) NAME/KEY: Modified-site
        ( B ) LOCATION: 7
        ( D ) OTHER INFORMATION: /note= "S0.34;A0.33;Y0.33"

( i x ) FEATURE:
        ( A ) NAME/KEY: Modified-site
        ( B ) LOCATION: 8
        ( D ) OTHER INFORMATION: /note= "S0.50;T0.50"

( i x ) FEATURE:
        ( A ) NAME/KEY: Modified-site
        ( B ) LOCATION: 9
        ( D ) OTHER INFORMATION: /note=
            " N0.20;S0.20;G0.20;D0.20;K0.20"

( i x ) FEATURE:
        ( A ) NAME/KEY: Modified-site
        ( B ) LOCATION: 11
        ( D ) OTHER INFORMATION: /note= "N0.50;D0.50"

( i x ) FEATURE:
  ( A ) NAME/KEY: Modified-site
  ( B ) LOCATION: 14
  ( D ) OTHER INFORMATION: /note= "K0.50;N0.50"

( i x ) FEATURE:
  ( A ) NAME/KEY: Modified-site
  ( B ) LOCATION: 15
  ( D ) OTHER INFORMATION: /note= "L0.50;I0.50"

( i x ) FEATURE:
  ( A ) NAME/KEY: Modified-site
  ( B ) LOCATION: 16
  ( D ) OTHER INFORMATION: /note= "V0.50;F0.50"

( i x ) FEATURE:
  ( A ) NAME/KEY: Modified-site
  ( B ) LOCATION: 19
  ( D ) OTHER INFORMATION: /note= "T0.34;I0.33;A0.33"

( i x ) FEATURE:
  ( A ) NAME/KEY: Modified-site
  ( B ) LOCATION: 22
  ( D ) OTHER INFORMATION: /note= "N0.50;D0.50"

( i x ) FEATURE:
  ( A ) NAME/KEY: Modified-site
  ( B ) LOCATION: 23
  ( D ) OTHER INFORMATION: /note= "Q0.34;R0.33;E0.33"

( x i ) SEQUENCE DESCRIPTION: SEQ ID NO:108:

```
Phe Gly Thr Lys Thr Gln Ser Ser Asn Phe Asn Thr Ala Lys Leu Val
 1               5                  10                  15
Pro Asn Thr Ala Leu Asn Gln Ala Val Val Gly Gly Phe Phe Leu Leu
                20                  25                  30
Thr Arg Ile Leu Thr Ile Pro Gln Ser Leu Asp Gly Gly Thr Ala Lys
            35                  40                  45
Ser Lys Lys Phe Pro Ser Tyr Thr Ala Thr Tyr Gln Phe
        50                  55                  60
```

( 2 ) INFORMATION FOR SEQ ID NO:109:

( i ) SEQUENCE CHARACTERISTICS:
    ( A ) LENGTH: 59 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "N0.50;D0.50"

( i x ) FEATURE:
    ( A ) NAME/KEY: Modified-site
    ( B ) LOCATION: 7
    ( D ) OTHER INFORMATION: /note= "Q0.50;H0.50"

( i x ) FEATURE:
    ( A ) NAME/KEY: Modified-site
    ( B ) LOCATION: 8
    ( D ) OTHER INFORMATION: /note= "T0.50;A0.50"

( i x ) FEATURE:
    ( A ) NAME/KEY: Modified-site
    ( B ) LOCATION: 9
    ( D ) OTHER INFORMATION: /note= "K0.50;T0.50"

( i x ) FEATURE:
    ( A ) NAME/KEY: Modified-site
    ( B ) LOCATION: 12
    ( D ) OTHER INFORMATION: /note= "N0.50;D0.50"

( i x ) FEATURE:

(A) NAME/KEY: Modified-site
                (B) LOCATION: 13
                (D) OTHER INFORMATION: /note= "S0.50;G0.50"

(ix) FEATURE:
                (A) NAME/KEY: Modified-site
                (B) LOCATION: 14
                (D) OTHER INFORMATION: /note= "A0.34;T0.33;K0.33"

(ix) FEATURE:
                (A) NAME/KEY: Modified-site
                (B) LOCATION: 15
                (D) OTHER INFORMATION: /note= "F0.50;L0.50"

(xi) SEQUENCE DESCRIPTION: SEQ ID NO:109:

Phe Gly Asn Asn Glu Asn Gln Thr Lys Val Ser Asn Ser Ala Phe Val
 1           5                   10                  15

Pro Asn Met Ser Leu Asp Gln Ser Val Val Gly Gly Phe Phe Leu Leu
            20                  25                  30

Thr Arg Ile Leu Thr Ile Pro Gln Ser Leu Asp Gly Gly Thr Ala Lys
        35              40                      45

Ser Lys Lys Phe Pro Ser Tyr Thr Ala Gln Phe
    50              55

(2) INFORMATION FOR SEQ ID NO:110:

(i) SEQUENCE CHARACTERISTICS:
            (A) LENGTH: 60 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "N0.50;G0.50"

(ix) FEATURE:
            (A) NAME/KEY: Modified-site
            (B) LOCATION: 5
            (D) OTHER INFORMATION: /note= "E0.50;V0.50"

(ix) FEATURE:
            (A) NAME/KEY: Modified-site
            (B) LOCATION: 7
            (D) OTHER INFORMATION: /note= "Q0.50;A0.50"

(ix) FEATURE:
            (A) NAME/KEY: Modified-site
            (B) LOCATION: 8
            (D) OTHER INFORMATION: /note= "K0.34;S0.33;T0.33"

(ix) FEATURE:
            (A) NAME/KEY: Modified-site
            (B) LOCATION: 9
            (D) OTHER INFORMATION: /note= "T0.34;K0.33;Q0.33"

(ix) FEATURE:
            (A) NAME/KEY: Modified-site
            (B) LOCATION: 10
            (D) OTHER INFORMATION: /note= "V0.50;P0.50"

(ix) FEATURE:
            (A) NAME/KEY: Modified-site
            (B) LOCATION: 11
            (D) OTHER INFORMATION: /note= "K0.50;A0.50"

(ix) FEATURE:
            (A) NAME/KEY: Modified-site
            (B) LOCATION: 12
            (D) OTHER INFORMATION: /note= "A0.34;T0.33;K0.33"

(ix) FEATURE:
            (A) NAME/KEY: Modified-site (B) LOCATION: 13
(D) OTHER INFORMATION: /note= "E0.25;N0.25;D0.25;T0.25"

(ix) FEATURE:
(A) NAME/KEY: Modified-site
(B) LOCATION: 14
(D) OTHER INFORMATION: /note= "S0.50;A0.50"

(ix) FEATURE:
(A) NAME/KEY: Modified-site
(B) LOCATION: 15
(D) OTHER INFORMATION: /note= "V0.50;I0.50"

(ix) FEATURE:
(A) NAME/KEY: Modified-site
(B) LOCATION: 18
(D) OTHER INFORMATION: /note= "M0.50;V0.50"

(ix) FEATURE:
(A) NAME/KEY: Modified-site
(B) LOCATION: 19
(D) OTHER INFORMATION: /note= "S0.50;Q0.50"

(ix) FEATURE:
(A) NAME/KEY: Modified-site
(B) LOCATION: 20
(D) OTHER INFORMATION: /note= "F0.50;L0.50"

(ix) FEATURE:
(A) NAME/KEY: Modified-site
(B) LOCATION: 21
(D) OTHER INFORMATION: /note= "D0.50;N0.50"

(xi) SEQUENCE DESCRIPTION: SEQ ID NO:110:

```
Phe Gly Asp Asn Glu Asn Gln Lys Thr Val Lys Ala Glu Ser Val Pro
  1               5                  10                  15
Asn Met Ser Phe Asp Gln Ser Val Val Gly Gly Phe Phe Leu Leu Thr
             20                  25                  30
Arg Ile Leu Thr Ile Pro Gln Ser Leu Asp Gly Gly Thr Ala Lys Ser
         35                  40                  45
Lys Lys Phe Pro Ser Tyr Thr Ala Thr Tyr Gln Phe
         50                  55              60
```

(2) INFORMATION FOR SEQ ID NO:111:

(i) SEQUENCE CHARACTERISTICS:
(A) LENGTH: 65 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "S0.50;L0.50"

(ix) FEATURE:
(A) NAME/KEY: Modified-site
(B) LOCATION: 3
(D) OTHER INFORMATION: /note= "T0.34;E0.33;K0.33"

(ix) FEATURE:
(A) NAME/KEY: Modified-site
(B) LOCATION: 4
(D) OTHER INFORMATION: /note= "A0.34;T0.33;P0.33"

(ix) FEATURE:
(A) NAME/KEY: Modified-site
(B) LOCATION: 5
(D) OTHER INFORMATION: /note= "I0.50;V0.50"

(ix) FEATURE:
(A) NAME/KEY: Modified-site
(B) LOCATION: 6

(D) OTHER INFORMATION: /note= "F0.50;L0.50"

(ix) FEATURE:
    (A) NAME/KEY: Modified-site
    (B) LOCATION: 8
    (D) OTHER INFORMATION: /note= "T0.50;V0.50"

(ix) FEATURE:
    (A) NAME/KEY: Modified-site
    (B) LOCATION: 18
    (D) OTHER INFORMATION: /note= "A0.50;K0.50"

(ix) FEATURE:
    (A) NAME/KEY: Modified-site
    (B) LOCATION: 20
    (D) OTHER INFORMATION: /note= "D0.34;T0.33;E0.33"

(ix) FEATURE:
    (A) NAME/KEY: Modified-site
    (B) LOCATION: 22
    (D) OTHER INFORMATION: /note= "K0.50;V0.50"

(ix) FEATURE:
    (A) NAME/KEY: Modified-site
    (B) LOCATION: 23
    (D) OTHER INFORMATION: /note= "T0.34;A0.33;S0.33"

(ix) FEATURE:
    (A) NAME/KEY: Modified-site
    (B) LOCATION: 24
    (D) OTHER INFORMATION: /note= "S0.34;G0.33;N0.33"

(ix) FEATURE:
    (A) NAME/KEY: Modified-site
    (B) LOCATION: 27
    (D) OTHER INFORMATION: /note= "G0.50;N0.50"

(ix) FEATURE:
    (A) NAME/KEY: Modified-site
    (B) LOCATION: 28
    (D) OTHER INFORMATION: /note= "Q0.50;E0.50"

(ix) FEATURE:
    (A) NAME/KEY: Modified-site
    (B) LOCATION: 30
    (D) OTHER INFORMATION: /note= "G0.50;A0.50"

(xi) SEQUENCE DESCRIPTION: SEQ ID NO:111:

Ser Ala Thr Ala Ile Phe Asp Thr Thr Thr Leu Asn Pro Thr Ile Ala
1               5                   10                  15

Gly Ala Gly Asp Val Lys Thr Ser Ala Glu Gly Gln Leu Gly Gly Gly
            20              25                  30

Phe Phe Leu Leu Thr Arg Ile Leu Thr Ile Pro Gln Ser Leu Asp Gly
        35                  40                  45

Gly Thr Ala Lys Ser Lys Lys Phe Pro Ser Tyr Thr Ala Thr Tyr Gln
    50              55                  60

Phe
65

(2) INFORMATION FOR SEQ ID NO:112:

(i) SEQUENCE CHARACTERISTICS:
        (A) LENGTH: 66 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (C) OTHER INFORMATION: /note=A0.50;V0.50

(ix) FEATURE:

( A ) NAME/KEY: Modified-site
( B ) LOCATION: 3
( D ) OTHER INFORMATION: /note= "E0.34;T0.33;K0.33"

( i x ) FEATURE:
( A ) NAME/KEY: Modified-site
( B ) LOCATION: 4
( D ) OTHER INFORMATION: /note= "A0.50;P0.50"

( i x ) FEATURE:
( A ) NAME/KEY: Modified-site
( B ) LOCATION: 5
( D ) OTHER INFORMATION: /note= "I0.50;V0.50"

( i x ) FEATURE:
( A ) NAME/KEY: Modified-site
( B ) LOCATION: 6
( D ) OTHER INFORMATION: /note= "L0.50;V0.50"

( i x ) FEATURE:
( A ) NAME/KEY: Modified-site
( B ) LOCATION: 8
( D ) OTHER INFORMATION: /note= "V0.50;I0.50"

( i x ) FEATURE:
( A ) NAME/KEY: Modified-site
( B ) LOCATION: 16
( D ) OTHER INFORMATION: /note= "A0.50;T0.50"

( i x ) FEATURE:
( A ) NAME/KEY: Modified-site
( B ) LOCATION: 18
( D ) OTHER INFORMATION: /note= "K0.50;C0.50"

( i x ) FEATURE:
( A ) NAME/KEY: Modified-site
( B ) LOCATION: 20
( D ) OTHER INFORMATION: /note= "S0.34;T0.33;A0.33"

( i x ) FEATURE:
( A ) NAME/KEY: Modified-site
( B ) LOCATION: 22
( D ) OTHER INFORMATION: /note= "V0.50;A0.50"

( i x ) FEATURE:
( A ) NAME/KEY: Modified-site
( B ) LOCATION: 23
( D ) OTHER INFORMATION: /note= "A0.34;S0.33;G0.33"

( i x ) FEATURE:
( A ) NAME/KEY: Modified-site
( B ) LOCATION: 24
( D ) OTHER INFORMATION: /note= "S0.50;A0.50"

( i x ) FEATURE:
( A ) NAME/KEY: Modified-site
( B ) LOCATION: 25
( D ) OTHER INFORMATION: /note= "G0.50;N0.50"

( i x ) FEATURE:
( A ) NAME/KEY: Modified-site
( B ) LOCATION: 26
( D ) OTHER INFORMATION: /note= "S0.50;T0.50"

( i x ) FEATURE:
( A ) NAME/KEY: Modified-site
( B ) LOCATION: 27
( D ) OTHER INFORMATION: /note= "E0.50;D0.50"

( i x ) FEATURE:
( A ) NAME/KEY: Modified-site
( B ) LOCATION: 28
( D ) OTHER INFORMATION: /note= "N0.50;G0.50"

( i x ) FEATURE:
( A ) NAME/KEY: Modified-site
( B ) LOCATION: 29
( D ) OTHER INFORMATION: /note= "E0.34;D0.33;Q0.33"

( i x ) FEATURE:

(A) NAME/KEY: Modified-site
(B) LOCATION: 30
(D) OTHER INFORMATION: /note= "L0.50;I0.50"

( i x ) FEATURE:
(A) NAME/KEY: Modified-site
(B) LOCATION: 31
(D) OTHER INFORMATION: /note= "A0.50;S0.50"

( x i ) SEQUENCE DESCRIPTION: SEQ ID NO:112:

| Leu | Ala | Glu | Ala | Ile | Leu | Asp | Val | Thr | Thr | Leu | Asn | Pro | Thr | Ile | Ala |
|---|---|---|---|---|---|---|---|---|---|---|---|---|---|---|---|
| 1 | | | | 5 | | | | | 10 | | | | | 15 | |
| Gly | Lys | Gly | Ser | Val | Val | Ala | Ser | Gly | Ser | Glu | Asn | Glu | Leu | Ala | Gly |
| | | | 20 | | | | | 25 | | | | | 30 | | |
| Gly | Phe | Phe | Leu | Leu | Thr | Arg | Ile | Leu | Thr | Ile | Pro | Gln | Ser | Leu | Asp |
| | | 35 | | | | 40 | | | | | | 45 | | | |
| Gly | Gly | Thr | Ala | Lys | Ser | Lys | Lys | Phe | Pro | Ser | Tyr | Thr | Ala | Thr | Tyr |
| | 50 | | | | | 55 | | | | | | 60 | | | |
| Gln | Phe | | | | | | | | | | | | | | |
| 65 | | | | | | | | | | | | | | | |

( 2 ) INFORMATION FOR SEQ ID NO:113:

( i ) SEQUENCE CHARACTERISTICS:
(A) LENGTH: 59 amino acids
(B) TYPE: amino acid
(D) TOPOLOGY: linear ( i i ) MOLECULE TYPE: peptide ( i x ) FEATURE:
(A) NAME/KEY: Modified-site
(B) LOCATION: 1
(D) OTHER INFORMATION: /note= "K0.50;T0.50"

( i x ) FEATURE:
(A) NAME/KEY: Modified-site
(B) LOCATION: 6
(D) OTHER INFORMATION: /note= "A0.34;K0.33;Q0.33"

( i x ) FEATURE:
(A) NAME/KEY: Modified-site
(B) LOCATION: 8
(D) OTHER INFORMATION: /note= "F0.50;L0.50"

( i x ) FEATURE:
(A) NAME/KEY: Modified-site
(B) LOCATION: 11
(D) OTHER INFORMATION: /note= "D0.34;A0.33;N0.33"

( i x ) FEATURE:
(A) NAME/KEY: Modified-site
(B) LOCATION: 12
(D) OTHER INFORMATION: /note= "I0.50;L0.50"

( i x ) FEATURE:
(A) NAME/KEY: Modified-site
(B) LOCATION: 13
(D) OTHER INFORMATION: /note= "T0.50;I0.50"

( i x ) FEATURE:
(A) NAME/KEY: Modified-site
(B) LOCATION: 14
(D) OTHER INFORMATION: /note= "A0.50;S0.50"

( i x ) FEATURE:
(A) NAME/KEY: Modified-site
(B) LOCATION: 17
(D) OTHER INFORMATION: /note= "E0.50;D0.50"

( i x ) FEATURE:
(A) NAME/KEY: Modified-site
(B) LOCATION: 24
(D) OTHER INFORMATION: /note= "D0.50;A0.50"

-continued ( x i ) SEQUENCE DESCRIPTION: SEQ ID NO:113:

Lys Gly Tyr Val Gly Ala Glu Phe Pro Leu Asp Ile Thr Ala Gly Thr
1               5                   10                  15

Glu Ala Ala Thr Gly Thr Lys Asp Gly Gly Phe Phe Leu Leu Thr Arg
            20              25                  30

Ile Leu Thr Ile Pro Gln Ser Leu Asp Gly Gly Thr Ala Lys Ser Lys
        35              40                  45

Lys Phe Pro Ser Tyr Thr Ala Thr Tyr Gln Phe
    50              55

( 2 ) INFORMATION FOR SEQ ID NO:114:

( i ) SEQUENCE CHARACTERISTICS:
( A ) LENGTH: 59 amino acids
( B ) TYPE: amino acid
( D ) TOPOLOGY: linear ( i i ) MOLECULE TYPE: peptide ( x i ) SEQUENCE DESCRIPTION: SEQ ID NO:114:

Lys Gly Tyr Val Gly Ala Glu Phe Pro Leu Asp Leu Lys Ala Gly Thr
1               5                   10                  15

Asp Gly Val Thr Gly Thr Lys Asp Gly Gly Phe Phe Leu Leu Thr Arg
            20              25                  30

Ile Leu Thr Ile Pro Gln Ser Leu Asp Gly Gly Thr Ala Lys Ser Lys
        35              40                  45

Lys Phe Pro Ser Tyr Thr Ala Thr Tyr Gln Phe
    50              55